US011225515B2

(12) United States Patent
Lane et al.

(10) Patent No.: US 11,225,515 B2
(45) Date of Patent: Jan. 18, 2022

(54) MACROPHAGE STIMULATING PROTEIN RECEPTOR (OR RON—RECEPTEUR D'ORIGINE NANTAIS) ANTIBODIES AND USES THEREOF

(71) Applicant: AGENCY FOR SCIENCE, TECHNOLOGY AND RESEARCH, Singapore (SG)

(72) Inventors: David Lane, Singapore (SG); Xin Yu Koh, Singapore (SG); Le-Ann Hwang, Signapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 152 days.

(21) Appl. No.: 16/328,711

(22) PCT Filed: Aug. 28, 2017

(86) PCT No.: PCT/SG2017/050424
§ 371 (c)(1),
(2) Date: Feb. 26, 2019

(87) PCT Pub. No.: WO2018/038684
PCT Pub. Date: Mar. 1, 2018

(65) Prior Publication Data
US 2019/0194309 A1 Jun. 27, 2019

(30) Foreign Application Priority Data

| Aug. 26, 2016 | (SG) | ............................ 10201607147P |
| Jan. 17, 2017 | (SG) | ............................ 10201700393P |
| Jan. 20, 2017 | (SG) | ............................ 10201700521V |
| Apr. 19, 2017 | (SG) | ............................ 10201703234U |

(51) Int. Cl.
| *C07K 16/22* | (2006.01) |
| *A61P 35/00* | (2006.01) |
| *G01N 33/574* | (2006.01) |
| *C07K 16/28* | (2006.01) |
| *A61K 47/68* | (2017.01) |
| *A61K 39/00* | (2006.01) |

(52) U.S. Cl.
CPC .......... *C07K 16/22* (2013.01); *A61K 47/6845* (2017.08); *A61P 35/00* (2018.01); *C07K 16/2863* (2013.01); *G01N 33/57492* (2013.01); *A61K 2039/505* (2013.01); *A61K 2039/545* (2013.01); *C07K 2317/31* (2013.01); *C07K 2317/34* (2013.01); *C07K 2317/565* (2013.01); *C07K 2317/73* (2013.01); *C07K 2317/92* (2013.01); *G01N 2333/71* (2013.01); *G01N 2800/085* (2013.01)

(58) Field of Classification Search
CPC .. C07K 16/22; C07K 2317/565; A61K 35/00; A61K 47/6845
See application file for complete search history.

(56) References Cited

U.S. PATENT DOCUMENTS

| 4,741,900 A | 5/1988 | Alvarez et al. |
| 5,219,996 A | 6/1993 | Bodmer et al. |
| 5,585,089 A | 12/1996 | Queen et al. |
| 5,667,425 A | 9/1997 | Pineau et al. |

FOREIGN PATENT DOCUMENTS

| EP | 0392745 A2 | 10/1990 |
| EP | 0948544 A1 | 10/1999 |
| EP | 1090037 A1 | 11/1999 |
| WO | 86/01533 A1 | 3/1986 |
| WO | 89/00195 A1 | 1/1989 |
| WO | 89/01476 A1 | 2/1989 |
| WO | 1991009967 A1 | 7/1991 |
| WO | 92/02551 A1 | 2/1992 |
| WO | 92/22583 A2 | 12/1992 |
| WO | 92/22853 A1 | 12/1992 |
| WO | 93/06231 A1 | 4/1993 |
| WO | 93/09967 A1 | 5/1993 |
| WO | 199820734 A1 | 5/1998 |
| WO | 98/25971 A1 | 6/1998 |
| WO | 03/031581 A2 | 4/2003 |
| WO | 2004/051268 A1 | 6/2004 |

(Continued)

OTHER PUBLICATIONS

Mittal et al, Animal models of human colorectal cancer: Current status, uses and limitations. World J Gastroenterol 21(41): 11854-11861, 2015.*
Paul, Fundamental Immunology, 3rd Edition, 1993, pp. 292-295.*
Vajdos et al., Comprehensive functional maps of the antigen-binding site of an anti-ErbB2 antibody obtained with shotgun scanning mutagenesis. J. Mol. Biol. 320:415-428, 2002.*
Adair, et al., "Therapeutic Antibodies," Drug Design Reviews, Jan. 4, 2005, pp. 209-217, vol. 2, No. 3, UCB Celltech, Berkshire, UK.
Babcook, et al., "A novel strategy for generating monoclonal antibodies from single, isolated lymphocytes producing antibodies of defined specificities," Immunology, Apr. 11, 1996, pp. 7843-7848, vol. 93, Proceedings of the National Academy of Sciences of the United States of America.

(Continued)

*Primary Examiner* — Ruixiang Li
(74) *Attorney, Agent, or Firm* — Womble Bond Dickinson (US) LLP

(57) ABSTRACT

Disclosed are monoclonal antibodies that bind specifically to macrophage stimulating protein receptor (or RON—Recepteur d' Origine Nantais). Also provided are the chimeric antigen receptors, bispecific antibodies, bivalent antibodies and biTE thereof, as well as pharmaceutical compositions and uses of said antibodies for the treatment of cancer and fibrosis and an ex vivo method of evaluating the status of a cancer patient using said antibodies. In particular, two monoclonal antibodies, 7G8 and 6D4, demonstrating good therapeutic efficacy in inhibiting tumour growth in human xenograft mice models and sensitivity in human xenograft mouse tumour imaging models are provided.

11 Claims, 79 Drawing Sheets

Specification includes a Sequence Listing.

(56) References Cited

FOREIGN PATENT DOCUMENTS

| WO | 2004/106377 A1 | 12/2004 |
|---|---|---|
| WO | 2005/003169 A2 | 1/2005 |
| WO | 2005/003170 A2 | 1/2005 |
| WO | 2005/003171 A2 | 1/2005 |
| WO | 2005016346 A1 | 2/2005 |
| WO | 2005/113605 A1 | 12/2005 |
| WO | 2005117984 A2 | 12/2005 |
| WO | 2008/038024 A1 | 4/2008 |
| WO | 2009/070294 A2 | 6/2009 |
| WO | 2010038086 A2 | 4/2010 |
| WO | 2010/093055 A1 | 8/2010 |
| WO | 2011/090762 A1 | 7/2011 |
| WO | 2012/006341 A2 | 1/2012 |
| WO | 2012/006490 A2 | 1/2012 |
| WO | 2013/040557 A2 | 3/2013 |
| WO | 2015/095002 A1 | 6/2015 |

OTHER PUBLICATIONS

Chapman, A., "PEGylated antibodies and antibody fragments for improved therapy: a review," Advanced Drug Delivery Reviews, Jan. 22, 2002, pp. 531-545, vol. 54, Elsevier Science B.V., Berkshire, UK.

Chothia, et al., "Canonical Structures for the Hypervariable Regions of Immunoglobulins," Journal of Molecular Biology, Apr. 23, 1987, pp. 901-917, vol. 196.

Crameri, et al., "DNA shuffling of a family of genes from diverse species accelerates directed evolution," letters to nature, Jan. 15, 1998, pp. 288-291, vol. 391, Macmillan Publishers Ltd., Santa Clara, California.

Dotti, et al., "Fifteen Years of Gene Therapy Based on Chimeric Antigen Receptors: Are We Nearly There Yet?," Human Gene Therapy, Sep. 22, 2009, pp. 1229-1239, vol. 20, Mary Ann Liebert, Inc., Houston, TX.

Dubowchik, et al., "Receptor-mediated and enzyme-dependent targeting of cytotoxic anticancer drugs," Pharmacology & Therapeutics, 1999, pp. 67-123, vol. 83, Elsevier, Wallingford, Connecticut.

Holliger, et al., "Engineered antibody fragments and the rise of single domains," Nature Biotechnology, Sep. 7, 2005, pp. 1126-113, vol. 23, No. 9, Nature Publishing Group.

Kashmiri, et al., "SDR grafting—a new approach to antibody humanization," Methods, Jan. 17, 2005, pp. 25-34, vol. 36, Elsevier, Bethesda, Maryland.

Kohler, et al., "Continuous cultures of fused cells secreting antibody of predefined specificity," Nature, Aug. 7, 1975, pp. 495-497, vol. 256, Nature Publishing Group, Cambridge, UK.

Kozbor, et al., "The production of monoclonal antibodies from human lymphocytes," Immunology Today, 1983, pp. 72-79, vol. 4, No. 3, Elsevier Biomedical Press.

Low, et al., "Mimicking Somatic Hypermutation: Affinity Maturation of Antibodies Displayed on Bacteriophage Using a Bacterial Mutator Strain," Journal of Molecular Biology, Apr. 26, 1996, pp. 359-368, vol. 260, Academic Press Limited.

Marks, et al., "By-Passing Immunization: Building High Affinity Human Antibodies By Chain Shuffling," Biotechnology, Jul. 1992, pp. 779-783, vol. 10, Nature Publishing Group.

O'Toole, et al., "Therapeutic Implications of a Human Neutralizing Antibody to the Macrophage-Stimulating Protein Receptor Tyrosine Kinase (RON), a c-MET Family Member," Cancer Research, Sep. 15, 2006, pp. 9162-9171, vol. 66, No. 18, American Association for Cancer Research.

Patten, et al., "Applications of DNA shuffling to pharmaceuticals and vaccines," Current Opinion in Biotechnology, 1997, pp. 724-733, vol. 8, Current Biology Ltd, Santa Clara, CA.

Retter, et al., "VBASE2, an integrative V gene database," Nucleic Acids Research, 2005, pp. D671-D674, vol. 33, Oxford University Press.

The International Preliminary Report on Patentability for PCT Application No. PCT/SG2017/050424 dated Oct. 23, 2018, 29 pages.

The International Search Report for PCT Application No. PCT/SG2017/050424 dated Nov. 7, 2017, 8 pages.

The Written Opinion of the International Searching Authority for PCT Application No. PCT/SG2017/050424 dated Nov. 7, 2017, 5 pages.

Thompson, et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," Journal of Molecular Biology, 1996, pp. 77-88, vol. 256, Academic Press Limited.

Thorpe, et al., "The Preparation and Cytotoxic Properties of Antibody-Toxin Conjugates," Immunological Review, 1982, pp. 119-158, vol. 62, Munksgaard, Copenhagen, Denmark.

Vaughan, et al., "Human antibodies by design," Nature Biotechnology, Jun. 1998, pp. 535-539, vol. 16, Nature Publishing Group, Cambridgeshire, UK.

Wang, et al., "Potential therapeutics specific to c-MET/RON receptor tyrosine kinases for molecular targeting in cancer therapy," Acta Pharmacologica Sinica, Aug. 9, 2010, pp. 1181-1188, vol. 31, Nature Publishing Group.

Yang, et al., "CDR Walking Mutagenesis for the Affinity Maturation of a Potent Human Anti-HIV-1 Antibody into the Picomolar Range," Journal of Molecular Biology, 1995, pp. 392-403, vol. 254, Academic Press Limited.

Yao, et al., "Agonistic monoclonal antibodies potentiate tumorigenic and invasive activities of splicing variant of the RON receptor tyrosine kinase," Cancer Biology & Therapy, 2006, pp. 1179-1186, vol. 5, No. 9, Landes Bioscience.

Yao, et al., "The monoclonal antibody Zt/f2 targeting RON receptor tyrosine kinase as potential therapeutics against tumor growth-mediated by colon cancer cells," Molecular Cancer, 2011, 12 pgs., vol. 12, No. 82, BioMed Central.

Chapman, "PEGylated antibodies and antibody fragments for improved therapy: a review" Advanced Drug Delivery Reviews, vol. 54 Issue 4, Apr. 18, 2002, pp. 531-545.

Cole, "Monoclonal antibodies" Canadian Family Physician, vol. 33, Feb. 1987, pp. 369-372.

Hellstrom et al., "Cellular immunity against tumor antigens", Advances in Cancer Research, vol. 12, 1969, pp. 167-223.

Yao et al., "MSP-RON signalling in cancer: pathogenesis and therapeutic potential" Nature Reviews Cancer, vol. 13 No. 7, Jun. 24, 2013, pp. 466-481.

Zalipsky et al., "Introduction to Chemistry and Biological Applications of Poly(ethylene glycol)" ACS Symposium Series, vol. 680, Aug. 5, 1997, pp. 1-13.

* cited by examiner

FIGURE 3
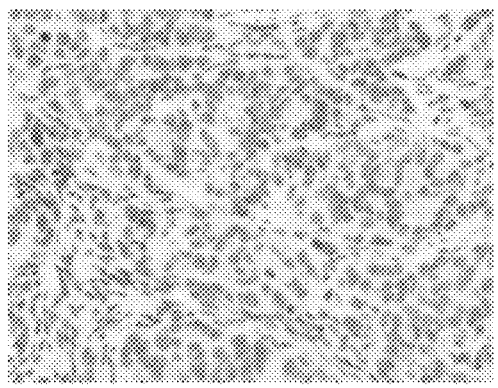
Control goat serum
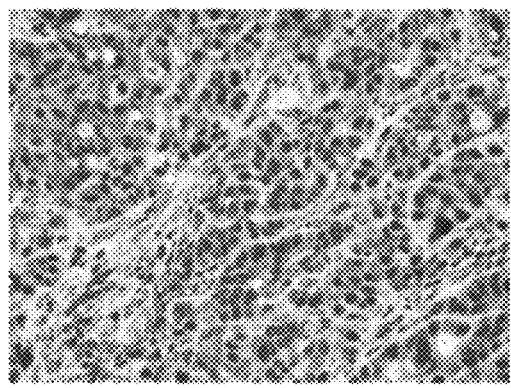
Mouse serum 1:500
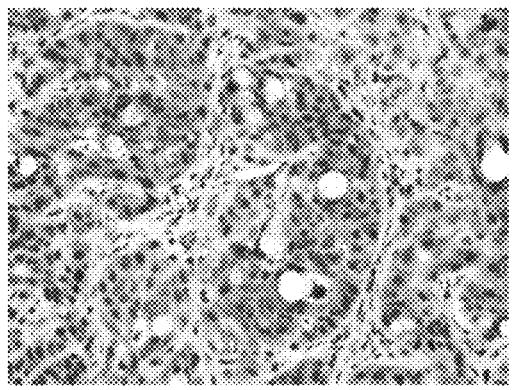
6D4
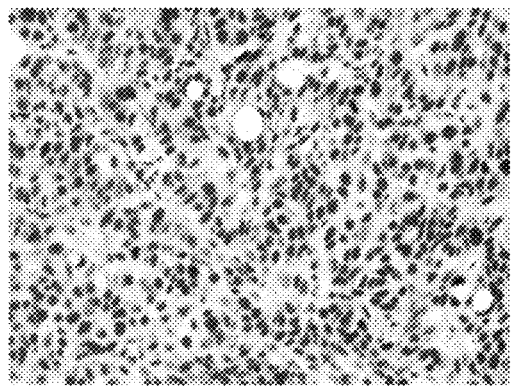
7G8

FIGURE 14

7G8 Heavy chain

```
                       <------------------------------------------- FR1 - IMGT
           1              5                       10                        15
           E   V   Q   L   E   Q   S   G   G       G   L   V   Q   P
7G8H1      gag gtg cag ctg gag cag tct ggg gga ... ggt tta gtg cag cct ------------------------------------------>  _____
                              20                      25                  30
           G   G   S   L   K   L   S   C   A   A   S   G   F   T   F
7G8H1      gga ggg tcc ctg aaa ctc tcc tgt gca gcc tct gga ttc act ttc ___ CDR1 - IMGT _____ <-----------------------------
           ___                    35                  40                  45
                                  N   T   Y   T   M   S   W   V   R   Q   T
7G8H1      ... ... ... ...        aat acc tat acc atg tct tgg gtt cgc cag act FR2 - IMGT ------------------------>  _____ CDR2
                              50                      55                  60
           P   E   K   R   L   E   W   V   A   Y   I   S   N   G
7G8H1      cca gag aag agg ctg gag tgg gtc gca tac att agt aat ggt ...

- IMGT _____ <---------------------------------------------
                              65                      70                  75
                   G   G   S   T   Y   Y   P   D   T   V   K       G   R
7G8H1      ...     ggt ggt agt acc tac tat cca gac act gta aag ... ggc cga -------------------------------- FR3 - IMGT ----------------
                              80                      85                  90
           F   T   I   S   R   D   N   A   K   N   T   L   Y   L   Q
7G8H1      ttc acc atc tcc aga gac aat gcc aag aac acc ctg tac ctg caa ------------------------------------------------------------>
                              95                     100                 104
           M   S   S   L   K   S   E   D   T   A   M   Y   Y   C   A
7G8H1      atg agc agt ctg aag tct gag gac acg gcc atg tat tac tgt gca _____ CDR3 - IMGT _____
           R   G   Y   R   Y   A   A   M   D   Y   W   G   Q   G   T
7G8H1      aga ggc tat agg tac gct gct atg gac tac tgg ggt caa gga acc S   V   T   V   S   S
7G8H1      tca gtc acc gtc tcc tca
```

FIGURE 14 (CONTINUED)

Amino Acid Sequence in FASTA format (7G8H1)

> 7G8H1
EVQLEQSGGGLVQPGGSLKLSCAASGFTFNTYTMSWVRQTPEKRLEWVAYISNGGGSTYYPDTVKGRF
TISRDNAKNTLYLQMSSLKSEDTAMYYCARGYRYAAMDYWGQGTSVTVSS

Nucleotide Sequence in FASTA format (7G8H1)

> 7G8H1
GAGGTGCAGCTGGAGCAGTCTGGGGGAGGTTTAGTGCAGCCTGGAGGGTCCCTGAAACTCTCCTGTGC
AGCCTCTGGATTCACTTTCAATACCTATACCATGTCTTGGGTTCGCCAGACTCCAGAGAAGAGGCTGG
AGTGGGTCGCATACATTAGTAATGGTGGTGGTAGTACCTACTATCCAGACACTGTAAAGGGCCGATTC
ACCATCTCCAGAGACAATGCCAAGAACACCCTGTACCTGCAAATGAGCAGTCTGAAGTCTGAGGACAC
GGCCATGTATTACTGTGCAAGAGGCTATAGGTACGCTGCTATGGACTACTGGGGTCAAGGAACCTCAG
TCACCGTCTCCTCA

Figure 15
7G8 Kappa chain (light chain)

```
                <------------------------------------------ FR1 - IMGT
                1           5                    10                   15
                D   I   V   M   T   Q   T   T   A   T   L   S   V   T   P
7G8K            gat att gtg atg acc cag act aca gcc acc ctg tct gtg act cca ------------------------------------------>  _____
                              20                   25                   30
                G   D   G   V   S   L   S   C   R   A   S   Q   S   I
7G8K            gga gat ggc gtc agt ctt tcc tgc agg gcc agc caa agt att ...

___ CDR1 - IMGT _____  <--------------------------------
                              35                   40                   45
                                          N   N   N   L   H   W   Y   Q   Q   K
7G8K            ... ... ... ...   aac aac aac cta cac tgg tat caa caa aaa FR2 - IMGT --------------------------->  _____ CDR2
                              50                   55                   60
                S   H   E   S   P   R   L   L   I   K   F   A
7G8K            tca cat gag tct cca aga ctt ctc atc aag ttt gct ... ... ...

- IMGT _____  <--------------------------------
                              65                   70                   75
                                S   Q   S   I   S   G   I   P       S   R
7G8K            ... ... ... ... tcc cag tcc atc tct ggg atc ccc ... tcc agg ------------------------------- FR3 - IMGT ----------------
                              80                   85                   90
                F   S   G   S   G           S   G   T   D   F   T   L   S
7G8K            ttc agt ggc agt gga ... ... tca ggg aca gat ttc act ctc agt -------------------------------------------------------> _____
                              95                   100                  104
                I   N   S   V   E   T   E   D   F   G   M   Y   F   C   Q
7G8K            atc aac agt gtg gag act gaa gat ttt gga atg tat ttc tgt caa _____ CDR3 - IMGT _____
                105                  110                  115
                Q   S   N   S   W   P   L   T   F   G   A   G   T   K   L
7G8K            cag agt aac agc tgg cct ctc acg ttc ggt gct ggg acc aag ctg E   L   K
7G8K            gag ctg aaa c
```

Amino Acid Sequence in FASTA format (7G8K)

```
> 7G8K
DIVMTQTTATLSVTPGDGVSLSCRASQSINNNLHWYQQKSHESPRLLIKFASQSISGIPSRFSGSGSG
TDFTLSINSVETEDFGMYFCQQSNSWPLTFGAGTKLELK
```

FIGURE 15 (CONTINUED)

Nucleotide Sequence in FASTA format (7G8K)

```
> 7G8K
GATATTGTGATGACCCAGACTACAGCCACCCTGTCTGTGACTCCAGGAGATGGCGTCAGTCTTTCCTG
CAGGGCCAGCCAAAGTATTAACAACAACCTACACTGGTATCAACAAAAATCACATGAGTCTCCAAGAC
TTCTCATCAAGTTTGCTTCCCAGTCCATCTCTGGGATCCCCTCCAGGTTCAGTGGCAGTGGATCAGGG
ACAGATTTCACTCTCAGTATCAACAGTGTGGAGACTGAAGATTTTGGAATGTATTTCTGTCAACAGAG
TAACAGCTGGCCTCTCACGTTCGGTGCTGGGACCAAGCTGGAGCTGAAAC
```

FIGURE 16

6D4 Heavy chain

```
              <------------------------------------------ FR1 - IMGT
              1           5                  10                  15
              E   V   Q   L   L   E   T   G   G       G   L   V   K   P
    6D4H      gaa gtg cag ctg ttg gag act ggg gga ... ggc tta gtg aag cct --------------------------------------------->
                              20                  25                  30
              G   G   S   L   K   L   S   C   A   A   S   G   F   T   F
    6D4H      gga ggg tcc ctg aaa ctc tcc tgt gca gcc tct gga ttc act ttc CDR1 - IMGT                    <----------------------------
                              35                  40                  45
                              S   N   Y   A   M   S   W   V   R   Q   T
    6D4H      ... ... ... ... agt aac tat gcc atg tct tgg gtt cgc cag act FR2 - IMGT  -------------------------->              CDR2
                              50                  55                  60
              P   E   K   R   L   E   W   G   A   S   I   S   S   G
    6D4H      cca gag aag agg ctg gag tgg ggc gca tcc att agt agt ggt ...

- IMGT              <------------------------------------------
                              65                  70                  75
                      G   S   T   Y   Y   P   D   S   V   K           G   R
    6D4H      ... ... ggt agc acc tac tat cca gac agt gtg aag ... ggc cga ------------------------------------ FR3 - IMGT ----------------
                              80                  85                  90
              F   T   I   S   R   D   N   A   R   N   I   L   Y   L   Q
    6D4H      ttc acc atc tcc aga gat aat gcc agg aac atc ctg tac ctg caa --------------------------------------------------->
                              95                  100                 104
              M   S   S   L   R   S   E   D   T   A   L   Y   Y   C   A
    6D4H      atg agc agt ctg agg tct gag gac acg gcc ctg tat tac tgt gca CDR3 - IMGT
              R   E   G   P   L   Y   Y   G   P   S   Y   G   G   Y   Y
    6D4H      aga gag ggt ccc ctt tac tac ggt cct agc tac gga ggg tac tac F   D   Y   W   G   Q   G   T   T   L   T   V   S   S
    6D4H      ttt gac tac tgg ggc caa ggc acc act ctc aca gtc tcc tca
```

Amino Acid Sequence in FASTA format (6D4H)

>6D4H
EVQLLETGGGLVKPGGSLKLSCAASGFTFSNYAMSWVRQTPEKRLEWGASISSGGSTYYPDSVKG
RFTISRDNARNILYLQMSSLRSEDTALYYCAREGPLYYGPSYGGYYFDYWGQGTTLTVSS

FIGURE 16 (CONTINUED)

Nucleotide Sequence in FASTA format (6D4H)

```
>6D4H
GAAGTGCAGCTGTTGGAGACTGGGGGAGGCTTAGTGAAGCCTGGAGGGTCCCTGAAACTCTCCTGTGC
AGCCTCTGGATTCACTTTCAGTAACTATGCCATGTCTTGGGTTCGCCAGACTCCAGAGAAGAGGCTGG
AGTGGGGCGCATCCATTAGTAGTGGTGGTAGCACCTACTATCCAGACAGTGTGAAGGGCCGATTCACC
ATCTCCAGAGATAATGCCAGGAACATCCTGTACCTGCAAATGAGCAGTCTGAGGTCTGAGGACACGGC
CCTGTATTACTGTGCAAGAGAGGGTCCCCTTTACTACGGTCCTAGCTACGGAGGGTACTACTTTGACT
ACTGGGGCCAAGGCACCACTCTCACAGTCTCCTCA
```

FIGURE 17

6D4 Kappa (Light chain)

```
            <------------------------------------------- FR1 - IMGT
            1           5               10              15
            D   I   V   M   T   Q   S   P   L   S   L   P   V   S   L
6D4K        gac att gtg atg aca cag tct cca ctc tcc ctg cct gtc agt ctt -------------------------------------------> _____
                        20              25                      30
            G   D   Q   A   S   I   S   C   R   S   S   Q   R   L   V
6D4K        gga gat caa gcc tcc atc tct tgc aga tct agt cag agg ctt gta ___ CDR1 - IMGT     _____ <----------------------
                                35              40              45
            Y   S       N   G   N   T   Y   L   H   W   Y   L   Q   K
6D4K        tac agt ... aat gga aac acc tat tta cat tgg tac ctg cag aag FR2 - IMGT  --------------------------> _____ CDR2
                                50              55                   60
            P   G   Q   S   P   K   L   L   I   Y   K   V
6D4K        cca ggc cag tct cca aag ctc ctg atc tac aaa gtt ... ... ...

- IMGT      _____ <-------------------------------
                                65              70              75
                                    S   N   R   F   S   G   V   P     D   R
6D4K        ... ... ... ... tcc aac cga ttt tct ggg gtc cca ... gac agg ---------------------------------- FR3 - IMGT ---------------
                            80              85              90
            F   S   G   S   G           S   G   T   D   F   T   L   K
6D4K        ttc agt ggc agt gga ... ... tca ggg aca gat ttc aca ctc aag -------------------------------------------------> ___
                        95              100             104
            I   S   R   V   E   A   E   D   L   G   V   Y   F   C   S
6D4K        atc agc aga gtg gag gct gag gat ctg gga gtt tat ttc tgc tct _____ CDR3 - IMGT _____
            Q   S   T   H   V   P   W   T   F   G   G   G   T   K   L
6D4K        caa agt aca cat gtt ccg tgg acg ttc ggt gga ggc acc aag ctg E   I   K
6D4K        gaa atc aaa c
```

Amino Acid Sequence in FASTA format (6D4K)

DIVMTQSPLSLPVSLGDQASISCRSSQRLVYSNGNTYLHWYLQKPGQSPKLLIYKVSNRFSGVPDRFS
GSGSGTDFTLKISRVEAEDLGVYFCSQSTHVPWTFGGGTKLEIK

Nucleotide Sequence in FASTA format (6D4K)

> 6D4K
GACATTGTGATGACACAGTCTCCACTCTCCCTGCCTGTCAGTCTTGGAGATCAAGCCTCCATCTCTTG
CAGATCTAGTCAGAGGCTTGTATACAGTAATGGAAACACCTATTTACATTGGTACCTGCAGAAGCCAG
GCCAGTCTCCAAAGCTCCTGATCTACAAAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTGGGAGTTTA
TTTCTGCTCTCAAAGTACACATGTTCCGTGGACGTTCGGTGGAGGCACCAAGCTGGAAATCAAAC

FIGURE 18

3E1 Heavy chain

```
                <---------------------------------------------- FR1 - IMGT
        1                   5                   10                  15
        D   V   M   L   V   E   S   G   G       G   L   V   Q   P
3E1H    gac gtg atg ctg gtg gag tct gga gga ... ggc ttg gtg caa cct ---------------------------------------------->  _____
                            20                  25                  30
        G   G   S   M   K   L   S   C   V   A   S   G   F   S   F
3E1H    gga gga tcc atg aaa ctc tcc tgt gtt gcc tct gga ttc agt ttc ___ CDR1 - IMGT _____ <-------------------------
                            35                  40                  45
                        S   D   Y   W   M   N   W   V   R   Q   S
3E1H    ... ... ... ... agt gac tac tgg atg aac tgg gtc cgc cag tct FR2 - IMGT ---------------------------->  _____ CDR2
                        50                  55                  60
        P   E   K   G   L   E   W   V   A   E   I   R   L   K   S
3E1H    cca gag aag ggg ctt gaa tgg gtt gct gag att aga ttg aaa tct

- IMGT _____ <----------------------------------
                            65                  70                  75
        S   N   Y   A   T   H   Y   A   E   S   V   K       G   R
3E1H    agt aat tat gca aca cat tat gcg gag tct gtg aaa ... ggg agg -------------------------------- FR3 - IMGT ----------------
                            80                  85                  90
        F   T   I   S   R   D   D   S   E   S   S   V   Y   L   Q
3E1H    ttt acc atc tca aga gat gat tcc gaa agt agt gtc tac ctg caa ----------------------------------------------------> ____
                            95                  100             104
        M   N   N   L   R   P   E   D   T   G   F   Y   Y   C   T
3E1H    atg aac aac tta aga cct gaa gac act ggc ttt tat tac tgt acc

CDR3 - IMGT _

R   G   D   Y   W   G   Q   G   T   S   V   T   V   S   S
3E1H    agg ggg gac tat tgg ggt caa gga acc tca gtc acc gtc tct tca
```

Amino Acid Sequence in FASTA format (3E1H)

> 3E1H
DVMLVESGGGLVQPGGSMKLSCVASGFSFSDYWMNWVRQSPEKGLEWVAEIRLKSSNYATHYAES
VKGRFTISRDDSESSVYLQMNNLRPEDTGFYYCTRGDYWGQGTSVTVSS

Nucleotide Sequence in FASTA format (3E1H)

> 3E1H
GACGTGATGCTGGTGGAGTCTGGAGGAGGCTTGGTGCAACCTGGAGGATCCATGAAACTCTCCTG
TGTTGCCTCTGGATTCAGTTTCAGTGACTACTGGATGAACTGGGTCCGCCAGTCTCCAGAGAAGG
GGCTTGAATGGGTTGCTGAGATTAGATTGAAATCTAGTAATTATGCAACACATTATGCGGAGTCT

FIGURE 18 (CONTINUED)

```
GTGAAAGGGAGGTTTACCATCTCAAGAGATGATTCCGAAAGTAGTGTCTACCTGCAAATGAACAACTT
AAGACCTGAAGACACTGGCTTTTATTACTGTACCAGGGGGGACTATTGGGGTCAAGGAACCTCAGTCA
CCGTCTCTTCA
```

FIGURE 19

3E1Kappa chain (light chain)

```
              <---------------------------------------- FR1 - IMGT
        1              5                    10                   15
        D    I    V    M    T    Q    S    P    A    T    L    S    V    T    P
3E1K    gat  att  gtg  atg  acc  cag  tct  cca  gcc  acc  ctg  tct  gtg  act  cca ------------------------------------------->   _____
                       20                   25                             30
        G    D    G    V    S    L    S    C    R    A    S    Q    S    I
3E1K    gga  gat  ggc  gtc  agt  ctt  tcc  tgc  agg  gcc  agc  caa  agt  att  ...

___   CDR1 - IMGT    _____   <-------------------------------
                              35                   40                        45
                              N    N    N    L    H    W    Y    Q    Q    K
3E1K    ... ... ... ... ...  aac  aac  aac  cta  cac  tgg  tat  caa  caa  aaa FR2 - IMGT  ------------------------>   _____    CDR2
                         50                   55                    60
        S    H    E    S    P    R    L    L    I    K    F    A
3E1K    tca  cat  gag  tct  cca  aga  ctt  ctc  atc  aag  ttt  gct  ...  ...  ...

- IMGT    _____   <---------------------------------------
                                65                   70                   75
                                S    Q    S    I    S    G    I    P         S    R
3E1K    ... ... ... ...        tcc  cag  tcc  atc  tct  ggg  atc  ccc  ...  tcc  agg -------------------------------   FR3 - IMGT  -----------------
                             80                   85                    90
        F    S    G    S    G                   S    G    T    D    F    T    L    S
3E1K    ttc  agt  ggc  agt  gga  ...  ...      tca  ggg  aca  gat  ttc  act  ctc  agt ------------------------------------------------------->  ___
                       95                  100              104
        I    N    S    V    E    T    E    D    F    G    M    Y    F    C    Q
3E1K    atc  aac  agt  gtg  gag  act  gaa  gat  ttt  gga  atg  tat  ttc  tgt  caa _____   CDR3 - IMGT    _____
        Q    S    N    S    W    P    L    T    F    G    A    G    T    K    L
3E1K    cag  agt  aac  agc  tgg  cct  ctc  acg  ttc  ggt  gct  ggg  acc  aag  ctg E    L    K
3E1K    gag  ctg  aaa  c
```

Amino Acid Sequence in FASTA format (3E1K )

> 3E1K
DIVMTQSPATLSVTPGDGVSLSCRASQSINNNLHWYQQKSHESPRLLIKFASQSISGIPSRFSGS
GSGTDFTLSINSVETEDFGMYFCQQSNSWPLTFGAGTKLELK

Nucleotide Sequence in FASTA format (3E1K )

```
GATATTGTGATGACCCAGTCTCCAGCCACCCTGTCTGTGACTCCAGGAGATGGCGTCAGTCTTTC
CTGCAGGGCCAGCCAAAGTATTAACAACAACCTACACTGGTATCAACAAAAATCACATGAGTCTC
CAAGACTTCTCATCAAGTTTGCTTCCCAGTCCATCTCTGGGATCCCCTCCAGGTTCAGTGGCAGT
GGATCAGGGACAGATTTCACTCTCAGTATCAACAGTGTGGAGACTGAAGATTTTGGAATGTATTT
CTGTCAACAGAGTAACAGCTGGCCTCTCACGTTCGGTGCTGGGACCAAGCTGGAGCTGAAAC
```

FIGURE 20

3G4 Heavy chain

```
          <---------------------- F  R  1  -  I  M  G  T -
          1                    5                          10
          E   V   Q   L   E   E   S   G   T       V   L
3G4H      GAA GTG CAG CTG GAG GAG TCA GGG ACT ... GTG CTG

------------------------------------------------>
                    15                      20                      25
          A   R   P   G   A   S   V   K   M   S   C   K   A   S
3G4H      GCA AGG CCT GGG GCT TCA GTG AAG ATG TCC TGC AAG GCT TCT

CDR1 - IMGT
                            30                      35
          G   Y   I   F   T   S   Y   W
3G4H      GGC TAC ATT TTT ACC AGC TAC TGG ... ... ... ...
          <-------------------- F  R  2  -  I  M  G  T
                40                      45                      50
          M   H   W   I   K   Q   R   P   G   Q   G   L   E   W
3G4H      ATG CAC TGG ATA AAA CAG AGG CCT GGA CAG GGT CTG GAA TGG

-----------> _____ CDR2 - IMGT _____
                      55                      60
          I   G   A   I   Y   P   G   N   S   D   T
          ATT GGC GCT ATT TAT CCT GGA AAT AGT GAT ACT ... ...
3G4H      <--------------------------------------------------
                65                      70                      75
          S   T   N   Q   K   F   K       D   K   A   K   L
          AGT ACT AAT CAG AAG TTC AAG ... GAC AAG GCC AAA CTG

-------- F  R  3  -  I  M  G  T --------------------
                      80                      85                      90
          T   A   V   T   S   T   S   T   A   Y   L   E
3G4H      ACT GCA GTC ACA TCC ACC AGC ACT GCC TAT TTG GAA
          ------------------------------------------------>
                    95                      100
          L   S   S   L   T   N   E   D   S   A   V   F   Y   C
3G4H      CTC AGC AGC CTG ACA AAT GAG GAC TCA GCG GTC TTT TAC TGT

CDR3 - IMGT _____ <------
          105               109 113       115
          T   R   D   G   Y   Y   P   F   A   Y   W   G
3G4H      ACA AGA GAT GGT TAC TAC CCG TTT GCT TAC TGG GGC
          --------- FR4 - IMGT ---------------->
                120                     125
          Q   G   T   L   V   T   V   S   A
          CAA GGG ACT CTG GTC ACT GTC TCT GCA
```

FIGURE 20 (CONTINUED)

Amino Acid Sequence in FASTA format (3G4H)

> 3G4H
EVQLEESGTVLARPGASVKMSCKASGYIFTSYWMHWIKQRPGQGLEWIGAIYPGNSDTSTNQKFKDKA
KLTAVTSTSTAYLELSSLTNEDSAVFYCTRDGYYPFAYWGQGTLVTVSA

Nucleotide Sequence in FASTA format (3G4H)

> 3G4H
GAAGTGCAGCTGGAGGAGTCAGGGACTGTGCTGGCAAGGCCTGGGGCTTCAGTGAAGATGTCCTGCAA
GGCTTCTGGCTACATTTTTACCAGCTACTGGATGCACTGGATAAAACAGAGGCCTGGACAGGGTCTGG
AATGGATTGGCGCTATTTATCCTGGAAATAGTGATACTAGTACTAATCAGAAGTTCAAGGACAAGGCC
AAACTGACTGCAGTCACATCCACCAGCACTGCCTATTTGGAACTCAGCAGCCTGACAAATGAGGACTC
AGCGGTCTTTTACTGTACAAGAGATGGTTACTACCCGTTTGCTTACTGGGGCCAAGGGACTCTGGTCA
CTGTCTCTGCA

FIGURE 21

3G4 Kappa chain (light chain)

```
                <---------------------------------------------- FR1 - IMGT
          1              5                    10                      15
          D    I    V    L    T    Q    S    P    L    S    L    P    V    S    L
3G4K      gac  att  gtg  ctg  acc  caa  tct  cca  ctc  tcc  ctg  cct  gtc  agt  ctt ---------------------------------------->  _____
                              20                       25                      30
          G    D    Q    A    S    I    S    C    R    S    S    Q    S    L    V
3G4K      gga  gat  caa  gcc  tcc  atc  tct  tgc  aga  tct  agt  cag  agc  ctt  gta ____ CDR1 - IMGT _____  <-----------------------------
                              35                       40                      45
          Y    I         N    G    D    T    Y    F    H    W    Y    L    Q    K
3G4K      tat  att  ...  aat  gga  gac  acc  tat  ttt  cat  tgg  tac  ttg  cag  aag FR2 - IMGT  ------------------------>  _____  CDR2
                              50                       55                      60
          P    G    Q    S    P    K    L    L    I    Y    R    V
3G4K      cca  ggc  cag  tct  cca  aag  ctc  ctg  atc  tac  aga  gtt  ... ... ...

- IMGT _____  <-----------------------------------------
                              65                       70                      75
                                   S    N    R    F    S    G    V    P         D    R
3G4K      ... ... ... ...  tcc  aac  cga  ttt  tct  ggg  gtc  cca  ...  gac  agg ------------------------------------- FR3 - IMGT ----------------
                              80                       85                      90
          F    S    G    S    G              S    G    T    D    F    T    L    K
3G4K      ttc  agt  ggc  agt  gga  ... ...  tca  ggg  aca  gat  ttc  aca  ctc  aag ---------------------------------------------------->  _____
                              95                       100                     104
          I    S    R    V    E    A    E    D    L    G    V    Y    F    C    S
3G4K      atc  agc  aga  gtg  gag  gct  gag  gat  ctg  gga  gtt  tat  ttc  tgc  tct

_____ CDR3 - IMGT _____

Q    T    K    H    V    P    Y    T    F    G    G    G    T    K    L
3G4K      caa  act  aaa  cat  gtt  ccg  tac  acg  ttc  gga  ggg  ggg  acc  aag  ctg E    M    K
3G4K      gaa  atg  aaa  cg
```

Amino Acid Sequence in FASTA format (3G4K)

DIVLTQSPLSLPVSLGDQASISCRSSQSLVYINGDTYFHWYLQKPGQSPKLLIYRVSNRFSGVPDRFS
GSGSGTDFTLKISRVEAEDLGVYFCSQTKHVPYTFGGGTKLEMKR

Nucleotide Sequence in FASTA format (3G4K)

> 3G4K
GACATTGTGCTGACCCAATCTCCACTCTCCCTGCCTGTCAGTCTTGGAGATCAAGCCTCC
ATCTCTTGCAGATCTAGTCAGAGCCTTGTATATATTAATGGAGACACCTATTTTCATTGGT
ACTTGCAGAAGCCAGGCCAGTCTCCAAAGCTCCTGATCTACAGAGTTTCCAACCGATTTT
CTGGGGTCCCAGACAGGTTCAGTGGCAGTGGATCAGGGACAGATTTCACACTCAAGATC
AGCAGAGTGGAGGCTGAGGATCTGGGAGTTTATTTCTGCTCTCAAACTAAACATGTTCCG
TACACGTTCGGAGGGGGGACCAAGCTGGAAATGAAACG

FIGURE 22

5B9 Heavy chain

```
            <------------------------------------------- FR1 - IMGT
              1           5                   10                  15
              E   V   Q   L   Q   Q   P   G   A       E   L   V   R   P
5B9H          gag gtc cag ctg cag cag cct ggg gct ... gag ctg gtg agg cct ------------------------------------------>
                          20                  25                  30
              G   S   S   V   K   I   S   C   K   A   S   G   Y   E   F
5B9H          ggg tcc tca gtg aag att tcc tgc aag gct tct ggc tat gaa ttc CDR1 - IMGT                     <--------------------------
                          35                  40                  45
                              S   K   Y   W   M   N   W   V   K   Q   R
5B9H          ... ... ... ... agt aag tac tgg atg aac tgg gtg aag cag agg FR2 - IMGT  -------------------------->              CDR2
                          50                  55                  60
              P   G   Q   G   L   E   W   I   G   Q   I   F   P   G
5B9H          cct gga cag ggt ctt gag tgg att gga cag att ttt cca gga ...

- IMGT              <---------------------------------------
                          65                  70                  75
              D   G   D   I   N   Y   N   G   K   F   K       G   K
5B9H          ... gac ggt gat att aat tac aat gga aaa ttc aag ... ggt aaa -------------------------------- FR3 - IMGT ----------------
                          80                  85                  90
              A   T   L   T   A   D   K   S   S   S   T   A   Y   M   Q
5B9H          gcc aca ctg act gca gac aaa tcc tcc agc aca gcc tac atg cag ---------------------------------------------------------->
                          95                  100                 104
              L   S   S   L   T   S   E   E   S   A   V   Y   F   C   A
5B9H          ctc agc agc cta aca tct gag gaa tct gcg gtc tat ttc tgt gca CDR3 - IMGT
              R   W   Y   Y   G   S   N   Y   A   M   D   Y   W   G   Q
5B9H          aga tgg tac tac ggt agt aac tat gct atg gac tac tgg ggt caa G   T   S   V   T   V   S   S
5B9H          gga acc tca gtc acc gtc tcc tca
```

Amino Acid Sequence in FASTA format (5B9H)

EVQLQQPGAELVRPGSSVKISCKASGYEFSKYWMNWVKQRPGQGLEWIGQIFPGDGDINYNGKFKGKA
TLTADKSSSTAYMQLSSLTSEESAVYFCARWYYGSNYAMDYWGQGTSVTVSS

Nucleotide Sequence in FASTA format (5B9H)

```
> 5B9H
GAGGTCCAGCTGCAGCAGCCTGGGGCTGAGCTGGTGAGGCCTGGGTCCTCAGTGAAGATTTCCTGCAA
GGCTTCTGGCTATGAATTCAGTAAGTACTGGATGAACTGGGTGAAGCAGAGGCCTGGACAGGGTCTTG
AGTGGATTGGACAGATTTTTCCAGGAGACGGTGATATTAATTACAATGGAAAATTCAAGGGTAAAGCC
ACACTGACTGCAGACAAATCCTCCAGCACAGCCTACATGCAGCTCAGCAGCCTAACATCTGAGGAATC
TGCGGTCTATTTCTGTGCAAGATGGTACTACGGTAGTAACTATGCTATGGACTACTGGGGTCAAGGAA
CCTCAGTCACCGTCTCCTCA
```

FIGURE 23

5B9 Kappa chain (light chain)

```
             <------------------------------------------- FR1 - IMGT
          1              5                    10                       15
             D   I   V   M   T   Q   T   P   S   S   L   A   V   S   V
5B9K        gac att gtg atg acc cag act cca tcc tcc cta gct gtg tca gtt ------------------>  _____
                            20                   25                          30
              G   E   K   I   T   M   S   C   K   S   S   Q   S   L   L
5B9K         gga gag aag att act atg agc tgc aag tcc agt cag agc ctt tta ___ CDR1 - IMGT _____            <------------------------
                            35                   40                        45
               Y   S   S   N   Q   K   N   Y   L   A   W   Y   Q   Q   K
5B9K          tat agt agc aat caa aag aac tac ttg gcc tgg tac cag cag aaa FR2 - IMGT ----------------------------->  _____ CDR2
                            50                   55                        60
               P   G   Q   S   P   K   L   L   I   Y   W   A
5B9K          cca ggg cag tct cct aaa ctg ctg att tac tgg gca ... ... ...

- IMGT _____            <------------------------------------
                            65                   70                        75
                                   S   T   R   E   S   G   V   P       D   R
5B9K         ... ... ... ... tcc act agg gaa tct ggg gtc cct ... gat cgc ------------------------------ FR3 - IMGT ----------------
                            80                   85                        90
               F   T   G   S   G           S   G   T   D   F   T   L   T
5B9K          ttc aca ggc agt gga ... ... tct ggg aca gat ttc act ctc acc ------>  _____
                            95                  100                       104
               I   S   S   V   K   A   E   D   L   A   V   Y   Y   C   Q
5B9K          atc agc agt gtg aag gct gaa gac ctg gca gtt tat tac tgt cag

_____ CDR3 - IMGT _____

Q   Y   Y   A   Y   R   T   F   G   G   G   T   K   L   E
5B9K          caa tat tat gcc tat cgg acg ttc ggt gga ggc acc aag ctg gaa I   K
5B9K          atc aaa c
```

Amino Acid Sequence in FASTA format (5B9K)

DIVMTQTPSSLAVSVGEKITMSCKSSQSLLYSSNQKNYLAWYQQKPGQSPKLLIYWASTRESGVPDRF
TGSGSGTDFTLTISSVKAEDLAVYYCQQYYAYRTFGGGTKLEIK

Nucleotide Sequence in FASTA format (5B9K)

>5B9K

GACATTGTGATGACCCAGACTCCATCCTCCCTAGCTGTGTCAGTTGGAGAGAAGATTACTATGAG
CTGCAAGTCCAGTCAGAGCCTTTTATATAGTAGCAATCAAAAGAACTACTTGGCCTGGTACCAGC
AGAAACCAGGGCAGTCTCCTAAACTGCTGATTTACTGGGCATCCACTAGGGAATCTGGGGTCCCT
GATCGCTTCACAGGCAGTGGATCTGGGACAGATTTCACTCTCACCATCAGCAGTGTGAAGGCTGA
AGACCTGGCAGTTTATTACTGTCAGCAATATTATGCCTATCGGACGTTCGGTGGAGGCACCAAGC
TGGAAATCAAAC

FIGURE 24

6E6 Heavy chain

```
           <------------------------------------------------ FR1 - IMGT
            1               5                  10                    15
            E   V   K   L   Q   Q   S   G   T       V   L   A   R   P
   6E6H    gag gtt aag ctg cag cag tct ggg act ... gtg ctg gca agg cct ---------------------------->
                            20                  25                    30
            G   T   S   V   K   M   S   C   K   A   S   G   Y   I   F
   6E6H    ggg act tca gtg aag atg tct tgc aag gct tct ggc tac att ttt ___ CDR1 - IMGT           <---------------------------
                            35                  40                    45
                            T   S   Y   W   M   H   W   I   K   E   R
   6E6H    ... ... ... ... acc agc tac tgg atg cat tgg ata aaa gag agg FR2 - IMGT   ---------------------->            CDR2
                            50                  55                    60
            P   G   Q   G   L   E   W   I   G   A   I   Y   P   G
   6E6H    cct gga cag ggt ctg gaa tgg att ggc gct att tat cct gga ...

- IMGT       <---------------------------------------------
                            65                  70                    75
                N   N   D   T   S   T   N   Q   K   F   K       G   K
   6E6H    ... aat aat gat act agt act aat cag aag ttc aag ... ggc aag ------------------------------- FR3 - IMGT ----------------
                            80                  85                    90
            A   K   L   T   A   V   T   S   T   S   T   A   Y   L   E
   6E6H    gcc aaa ctg act gca gtc aca tcc acc agc act gcc tat ttg gaa --------------------->
                            95                  100                  104
            L   S   S   L   T   N   E   D   S   A   V   Y   Y   C   T
   6E6H    ctc agc agc ctg aca aat gag gac tca gcg gtc tat tac tgt aca CDR3 - IMGT
            R   D   G   F   Y   P   F   A   Y   W   G   Q   G   T   L
   6E6H    aga gat ggt ttt tac ccg ttt gct tac tgg ggc caa ggg act ctg V   T   V   S   A
   6E6H    gtc act gtc tct gca
```

Amino Acid Sequence in FASTA format (6E6H)

FIGURE 24 (CONTINUED)

>6E6H
EVKLQQSGTVLARPGTSVKMSCKASGYIFTSYWMHWIKERPGQGLEWIGAIYPGNNDTSTNQKFKGKA
KLTAVTSTSTAYLELSSLTNEDSAVYYCTRDGFYPFAYWGQGTLVTVSA

Nucleotide Sequence in FASTA format (6E6H)

>6E6H
GAGGTTAAGCTGCAGCAGTCTGGGACTGTGCTGGCAAGGCCTGGGACTTCAGTGAAGATGTCTTGCAA
GGCTTCTGGCTACATTTTTACCAGCTACTGGATGCATTGGATAAAAGAGAGGCCTGGACAGGGTCTGG
AATGGATTGGCGCTATTTATCCTGGAAATAATGATACTAGTACTAATCAGAAGTTCAAGGGCAAGGCC
AAACTGACTGCAGTCACATCCACCAGCACTGCCTATTTGGAACTCAGCAGCCTGACAAATGAGGACTC
AGCGGTCTATTACTGTACAAGAGATGGTTTTTACCCGTTTGCTTACTGGGGCCAAGGGACTCTGGTCA
CTGTCTCTGCA

FIGURE 25

6E6 Kappa chain (light chain)

```
                <----------------------------------------- FR1 - IMGT
         1              5                    10                   15
         D    I    V    L    T    Q    T    P    L    S    L    P    V    S    L
6E6K     gat  att  gtg  ctg  acc  cag  act  cca  ctc  tcc  ctg  cct  gtc  agt  ctt ----------------------------------------------->
                          20                   25                   30
         G    D    Q    A    S    I    S    C    R    S    S    Q    S    L    V
6E6K     gga  gat  caa  gcc  tcc  atc  tct  tgc  aga  tct  agt  cag  agc  ctt  gta ___ CDR1 - IMGT _____         <-----------------------------
                          35                   40                   45
         Y    I         N    G    D    T    Y    F    H    W    Y    L    Q    K
6E6K     tat  att  ...  aat  gga  gac  acc  tat  ttt  cat  tgg  tac  ctg  cag  aag FR2 - IMGT  ------------------------>  _____     CDR2
                          50                   55                   60
         P    G    Q    S    P    K    L    L    I    Y    R    V
6E6K     cca  ggc  cag  tct  cca  aag  ctc  ctg  atc  tac  aga  gtt  ...  ...  ...

- IMGT _____      <-------------------------------------------
                          65                   70                   75
                                     S    N    R    F    S    G    V    P         D    R
6E6K     ...  ...  ...  ...  tcc  aac  cga  ttt  tct  ggg  gtc  cca  ...  gac  agg -----------------------------  FR3 - IMGT  ----------------
                          80                   85                   90
         F    S    G    S    G              S    G    T    D    F    T    L    K
6E6K     ttc  agt  ggc  agt  gga  ...  ...  tca  ggg  aca  gat  ttc  aca  ctc  aag
```

FIGURE 25 (CONTINUED)

```
              ----------------------------------------------------------->
                              95                 100              104
              I   S   R   V   E   A   E   D   L   G   V   Y   F   C   S
6E6K          atc agc aga gtg gag gct gag gat ctg gga gtt tat ttc tgc tct

_____  CDR3 - IMGT  _____

Q   T   K   H   V   P   Y   T   F   G   G   G   T   K   L
6E6K          caa act aaa cat gtt ccg tac acg ttc gga ggg ggg acc aag ctg E   M   K
6E6K          gaa atg aaa cg
```

Amino Acid Sequence in FASTA format (6E6K)

> 6E6K

DIVLTQTPLSLPVSLGDQASISCRSSQSLVYINGDTYFHWYLQKPGQSPKLLIYRVSNRFSGVPDRFS
GSGSGTDFTLKISRVEAEDLGVYFCSQTKHVPYTFGGGTKLEMKR

Nucleotide Sequence in FASTA format (6E6K)

>6E6K

GATATTGTGCTGACCCAGACTCCACTCTCCCTGCCTGTCAGTCTTGGAGATCAAGCCTCCATCTC
TTGCAGATCTAGTCAGAGCCTTGTATATATTAATGGAGACACCTATTTTCATTGGTACCTGCAGA
AGCCAGGCCAGTCTCCAAAGCTCCTGATCTACAGAGTTTCCAACCGATTTTCTGGGGTCCCAGAC
AGGTTCAGTGGCAGTGGATCAGGGACAGATTTCACACTCAAGATCAGCAGAGTGGAGGCTGAGGA
TCTGGGAGTTTATTTCTGCTCTCAAACTAAACATGTTCCGTACACGTTCGGAGGGGGGACCAAGC
TGGAAATGAAACG

FIGURE 26

2F1 Heavy chain

```
            <------------------------------------------------ FR1 - IMGT
            1              5                   10                      15
            Q    V    Q    L    K    E    S    G    A         E    L    V    K    P
2F1H        cag  gtg  cag  ctg  aag  gag  tca  ggg  gct  ...  gaa  ctg  gtg  aaa  cct ------------------------------------------>
                                20                  25                      30
            G    T    S    V    K    L    S    C    K    A    S    G    Y    T    F
2F1H        ggg  act  tca  gtg  aag  ttg  tcc  tgc  aag  gct  tct  ggc  tac  acc  ttc ___ CDR1 - IMGT _____   <----------------------------------
                                35                  40                      45
                                T    S    Y    Y    M    Y    W    L    K    Q    R
2F1H        ... ... ... ...    acc  agc  tac  tat  atg  tac  tgg  ttg  aag  cag  agg FR2 - IMGT ------------------------------>  _____ CDR2
                            50                  55                      60
            P    G    Q    G    L    E    W    I    G    G    I    N    P    T
2F1H        cct  gga  caa  ggc  ctt  gag  tgg  att  ggg  ggg  att  aat  cct  acc  ...

- IMGT _____  <----------------------------------------
                            65                  70                      75
                 T    G    G    T    D    F    N    E    N    F    K         N    K
2F1H        ... act  ggt  ggt  act  gac  ttc  aat  gag  aac  ttc  aag  ...  aac  aag ------------------------------------- FR3 - IMGT ----------------
                            80                  85                      90
            A    T    L    T    L    A    T    S    S    S    T    A    Y    I    Q
2F1H        gcc  aca  ctg  act  ttg  gcc  aca  tcc  tcc  agc  aca  gcc  tac  ata  caa ------------------------------------------>  _____
                            95                  100                     104
            L    S    S    L    T    S    E    D    S    A    V    Y    F    C    A
2F1H        ctc  agc  agc  ctg  aca  tct  gag  gac  tct  gcg  gtc  tat  ttc  tgt  gca

_____ CDR3 - IMGT _____

R    M    G    R    D    A    M    D    Y    W    G    Q    G    T    S
2F1H        aga  atg  gga  cgg  gat  gct  atg  gac  tac  tgg  ggt  caa  gga  acc  tca V    T    V    S    S
2F1H        gtc  acc  gtc  tcc  tca
```

Amino Acid Sequence in FASTA format (2F1H)

QVQLKESGAELVKPGTSVKLSCKASGYTFTSYYMYWLKQRPGQGLEWIGGINPTTGGTDFNENFKNKA
TLTLATSSSTAYIQLSSLTSEDSAVYFCARMGRDAMDYWGQGTSVTVSS

Nucleotide Sequence in FASTA format (2F1H)

> 2F1H
CAGGTGCAGCTGAAGGAGTCAGGGGCTGAACTGGTGAAACCTGGGACTTCAGTGAAGTTGTCCTGCAA
GGCTTCTGGCTACACCTTCACCAGCTACTATATGTACTGGTTGAAGCAGAGGCCTGGACAAGGCCTTG
AGTGGATTGGGGGGATTAATCCTACCACTGGTGGTACTGACTTCAATGAGAACTTCAAGAACAAGGCC
ACACTGACTTTGGCCACATCCTCCAGCACAGCCTACATACAACTCAGCAGCCTGACATCTGAGGACTC
TGCGGTCTATTTCTGTGCAAGAATGGGACGGGATGCTATGGACTACTGGGGTCAAGGAACCTCAGTCA
CCGTCTCCTCA

FIGURE 27

2F1 Kappa (light chain)

```
                <-------------------------------------------- FR1 - IMGT
                1               5                   10                  15
                D   I   V   L   T   Q   S   P   A   S   L   A   V   S   L
        2F1K    gac att gtg ctg aca cag tct cct gct tcc tta gct gta tct ctg -------------------------------------------->
                        20                  25                  30
                G   Q   R   A   T   I   S   Y   R   A   S   K   S   V   S
        2F1K    ggg cag agg gcc acc atc tca tac agg gcc agc aaa agt gtc agt CDR1 - IMGT                     <-----------------------
                                    35                  40                  45
                T               S   G   Y   S   Y   M   H   W   N   Q   Q   K
        2F1K    aca ... ... tct ggc tat agt tat atg cac tgg aac caa cag aaa FR2 - IMGT  ------------------------->                  CDR2
                            50                  55                      60
                P   G   Q   P   P   R   L   L   I   Y   L   V
        2F1K    cca gga cag cca ccc aga ctc ctc atc tat ctt gta ... ... ...

- IMGT              <---------------------------------
                            65                  70                  75
                                S   N   L   E   S   G   V   P       A   R
        2F1K    ... ... ... ... tcc aac cta gaa tct ggg gtc cct ... gcc agg ------------------------------  FR3 - IMGT  ----------------
                                80                  85                  90
                F   S   G   S   G               S   G   T   D   F   T   L   N
        2F1K    ttc agt ggc agt ggg ... ... tct ggg aca gac ttc acc ctc aac --------------------------------------------->
                            95                  100                 104
                I   H   P   V   E   E   E   D   A   A   T   Y   Y   C   Q
        2F1K    atc cat cct gtg gag gag gag gat gct gca acc tat tac tgt cag

CDR3 - IMGT

H   I   R   E   L   T   R   S   E   G   G   P   S   W   K
        2F1K    cac att agg gag ctt aca cgt tcg gag ggg gga cca agc tgg aaa
```

Amino Acid Sequence in FASTA format (2F1K)

```
> 2F1K
DIVLTQSPASLAVSLGQRATISYRASKSVSTSGYSYMHWNQQKPGQPPRLLIYLVSNLESGVPARFSG
SGSGTDFTLNIHPVEEEDAATYYCQHIRELTRSEGGPSWK
```

Nucleotide Sequence in FASTA format (2F1K)

FIGURE 27 (CONTINUED)

```
> 2F1K
GACATTGTGCTGACACAGTCTCCTGCTTCCTTAGCTGTATCTCTGGGGCAGAGGGCCACCATCTCATA
CAGGGCCAGCAAAAGTGTCAGTACATCTGGCTATAGTTATATGCACTGGAACCAACAGAAACCAGGAC
AGCCACCCAGACTCCTCATCTATCTTGTATCCAACCTAGAATCTGGGGTCCCTGCCAGGTTCAGTGGC
AGTGGGTCTGGGACAGACTTCACCCTCAACATCCATCCTGTGGAGGAGGAGGATGCTGCAACCTATTA
CTGTCAGCACATTAGGGAGCTTACACGTTCGGAGGGGGGACCAAGCTGGAAA
```

FIGURE 28

1D2 Heavy Chain

```
                <---------------------------------------- FR1 - IMGT
        1           5                       10                  15
        E   V   Q   L   Q   Q   S   G   S       E   L   V   K   P
1D2H    gag gtt cag ctg cag cag tct ggg tct ... gaa ctg gtg aaa cct ------------------------------------------>  _____
                        20                  25                  30
        G   A   S   V   K   L   S   C   K   A   S   G   Y   I   F
1D2H    ggg gct tca gtg aag ttg tcc tgc aag gct tct ggc tac atc ttc ___  CDR1 - IMGT _____    <----------------------------
                        35                  40                  45
                        T   S   Y   Y   M   Y   W   V   K   Q   R
1D2H    ... ... ... ... acc agc tac tat atg tac tgg gtg aag cag agg FR2 - IMGT  ------------------------------>  _____  CDR2
                        50                  55                  60
        P   G   Q   G   L   E   W   I   G   G   I   N   P   I
1D2H    cct gga caa ggc ctt gag tgg att ggg ggg att aat cct atc ...

- IMGT  _____    <----------------------------
                        65                  70                  75
            T   G   G   T   D   F   N   E   K   F   K       N   K
1D2H    ... act ggt ggt act gac ttc aat gag aag ttc aag ... aac aag ------------------------------- FR3 - IMGT ----------------
                        80                  85                  90
        A   T   L   T   L   A   T   S   S   S   T   A   Y   I   H
1D2H    gcc aca ctg act ctg gcc aca tcc tcc agc aca gcc tac ata cat ------------------------------------------>  _____
                        95                  100                 104
        L   S   S   L   T   S   E   D   S   A   V   Y   F   C   A
1D2H    ctc agc agc ctg aca tct gag gac tct gcg gtc tat ttc tgt gca _____  CDR3 - IMGT _____
        R   M   G   R   D   A   M   D   Y   W   G   Q   G   T   S
1D2H    aga atg gga cgg gat gct atg gac tac tgg ggt caa gga acc tca V   T   V   S
1D2H    gtc acc gtc tcc
```

Amino Acid Sequence in FASTA format (1D2H)
> 1D2H
EVQLQQSGSELVKPGASVKLSCKASGYIFTSYYMYWVKQRPGQGLEWIGGINPITGGTDFNEKFKN
KATLTLATSSSTAYIHLSSLTSEDSAVYFCARMGRDAMDYWGQGTSVTVS

FIGURE 28 (CONTINUED)

Nucleotide Sequence in FASTA format (1D2H)

```
> 1D2H
GAGGTTCAGCTGCAGCAGTCTGGGTCTGAACTGGTGAAACCTGGGGCTTCAGTGAAGTTGTCCTGCAA
GGCTTCTGGCTACATCTTCACCAGCTACTATATGTACTGGGTGAAGCAGAGGCCTGGACAAGGCCTTG
AGTGGATTGGGGGGATTAATCCTATCACTGGTGGTACTGACTTCAATGAGAAGTTCAAGAACAAGGCC
ACACTGACTCTGGCCACATCCTCCAGCACAGCCTACATACATCTCAGCAGCCTGACATCTGAGGACTC
TGCGGTCTATTTCTGTGCAAGAATGGGACGGGATGCTATGGACTACTGGGGTCAAGGAACCTCAGTCA
CCGTCTCC
```

FIGURE 29A

2B3 Heavy Chain

```
                <----------------------------------------- FR1 - IMGT
        1               5                       10                      15
          Q    V    Q    L    K    Q    S    G    S         E    L    V    K    P
2B3H    cag  gtg  cag  ctg  aag  cag  tca  ggg  tct  ...  gaa  ctg  gtg  aaa  cct ------------------------------------------>    _____
                              20                      25                      30
          G    A    S    V    K    L    S    C    K    A    S    G    Y    I    F
2B3H    ggg  gct  tca  gtg  aag  ttg  tcc  tgc  aag  gct  tct  ggc  tac  atc  ttc ___   CDR1 - IMGT  _____    <----------------------------
                              35                      40                      45
                                     T    S    Y    Y    M    Y    W    V    K    Q    R
2B3H    ... ... ... ...  acc  agc  tac  tat  atg  tac  tgg  gtg  aag  cag  agg FR2 - IMGT  ------------------------>  _____    CDR2
                              50                      55                      60
          P    G    Q    G    L    E    W    I    G    G    I    N    P    I
2B3H    cct  gga  caa  ggc  ctt  gag  tgg  att  ggg  ggg  att  aat  cct  atc  ...

- IMGT  _____  <---------------------------
                              65                      70                      75
                T    G    G    T    D    F    N    E    K    F    K         D    K
2B3H    ...  act  ggt  ggt  act  gac  ttc  aat  gag  aag  ttc  aag  ...  gac  aag ---------------------------------  FR3 - IMGT  ----------------
                              80                      85                      90
          A    T    L    T    L    A    A    S    S    S    T    A    Y    I    Q
2B3H    gcc  aca  ctg  act  ctg  gcc  gca  tcc  tcc  agc  aca  gcc  tac  ata  caa ------------------------------------------>  _____
                              95                     100                     104
          L    S    S    L    T    S    E    D    S    A    V    Y    F    C    A
2B3H    ctc  agc  agc  ctg  aca  tct  gag  gac  tct  gcg  gtc  tat  ttc  tgt  gca _____    CDR3 - IMGT   _____
          R    M    G    R    D    A    M    D    Y    W    G    Q    G    T    S
2B3H    aga  atg  gga  cgg  gat  gct  atg  gac  tac  tgg  ggt  caa  gga  acc  tca V    T    V    S
2B3H    gtc  acc  gtc  tcc  tc
```

Amino Acid Sequence in FASTA format (2B3H)

> 2B3H
QVQLKQSGSELVKPGASVKLSCKASGYIFTSYYMYWVKQRPGQGLEWIGGINPITGGTDFNEKFKDKA
TLTLAASSSTAYIQLSSLTSEDSAVYFCARMGRDAMDYWGQGTSVTVSS

Nucleotide Sequence in FASTA format (2B3H)

```
CAGGTGCAGCTGAAGCAGTCAGGGTCTGAACTGGTGAAACCTGGGGCTTCAGTGAAGTTGTCCTGCAA
GGCTTCTGGCTACATCTTCACCAGCTACTATATGTACTGGGTGAAGCAGAGGCCTGGACAAGGCCTTG
AGTGGATTGGGGGGATTAATCCTATCACTGGTGGTACTGACTTCAATGAGAAGTTCAAGGACAAGGCC
ACACTGACTCTGGCCGCATCCTCCAGCACAGCCTACATACAACTCAGCAGCCTGACATCTGAGGACTC
TGCGGTCTATTTCTGTGCAAGAATGGGACGGGATGCTATGGACTACTGGGGTCAAGGAACCTCAGTCA
CCGTCTCCTC
```

Figure 29B

2B3 Kappa Chain

```
              <------------------- F   R   1   -   I   M   G   T  -
               1               5                      10
               D    I    V    L    T    Q    S    P    A    S    L    A
2B3K           GAC  ATT  GTG  CTG  ACA  CAG  TCT  CCT  GCT  TCC  TTA  GCT
              ------------------------------------------------->
                              15                  20                  25
               V    S    L    G    Q    R    A    T    I    S    Y    R    A    S
2B3K           GTA  TCT  CTG  GGG  CAG  AGG  GCC  ACC  ATC  TCA  TAC  AGG  GCC  AGC
              _____    CDR1 - IMGT  _____  <--------
                              30                  35
               K    S    V    S    T    S    G    Y    S    Y
2B3K           AAA  AGT  GTC  AGT  ACA  TCT  GGC  TAT  AGT  TAT  ...  ...

-----------       F   R   2   -   I   M   G   T
                    40                      45                       50
               M    H    W    N    Q    Q    K    P    G    Q    P    P    R    L
2B3K           ATG  CAC  TGG  AAC  CAA  CAG  AAA  CCA  GGA  CAG  CCA  CCC  AGA  CTC

-----------> _____   CDR2 - IMGT  _____ <----
                         55                      60
               L    I    Y    L    V    S
2B3K           CTC  ATC  TAT  CTT  GTA  TCC  ...  ...  ...  ...  ...  ...  ...

--------------------------------------------------
                   65                  70                  75
               N    L    E    S    G    V    P         A    R    F    S    G
2B3K           AAC  CTA  GAA  TCT  GGG  GTC  CCT  ...  GCC  AGG  TTC  AGT  GGC
              -------- F   R   3   -   I   M   G   T   --------------------
                        80                  85                  90
               S    G                   S    G    T    D    F    T    L    N
2B3K           AGT  GGG  ...  ...  TCT  GGG  ACA  GAC  TTC  ACC  CTC  AAC
              ------------------------------------------------->
                              95                 100
               I    H    P    V    E    E    D    A    A    T    Y    Y    C
               ATC  CAT  CCT  GTG  GAG  GAG  GAG  GAT  GCT  GCA  ACC  TAT  TAC  TGT

_____   CDR3 - IMGT  _____ <---------------
                    105              108  114                      120
               Q    H    I    R    E    L    Y    T    F    G    G    G
2B3K           CAG  CAC  ATT  AGG  GAG  CTT  TAC  ACG  TTC  GGA  GGG  GGG  ACC
               FR4 - IMGT ------------>
                                125
               T    K    L    E    I    K
               AAG  CTG  GAA  ATA  AAA
```

FIGURE 29B (CONTINUED)

Amino Acid Sequence in FASTA format (2B3)

> 2B3
DIVLTQSPASLAVSLGQRATISYRASKSVSTSGYSYMHWNQQKPGQPPRLLIYLVSNLESGVPARFSGSGSGTDF
TLNIHPVEEEDAATYYCQHIRELYTFGGGTKLEIK

Nucleotide Sequence in FASTA format (2B3)

> 2B3
GACATTGTGCTGACACAGTCTCCTGCTTCCTTAGCTGTATCTCTGGGGCAGAGGGCCACCATCTCATACAGGGCC
AGCAAAAGTGTCAGTACATCTGGCTATAGTTATATGCACTGGAACCAACAGAAACCAGGACAGCCACCCAGACTC
CTCATCTATCTTGTATCCAACCTAGAATCTGGGGTCCCTGCCAGGTTCAGTGGCAGTGGGTCTGGGACAGACTTC
ACCCTCAACATCCATCCTGTGGAGGAGGAGGATGCTGCAACCTATTACTGTCAGCACATTAGGGAGCTTTACACG
TTCGGAGGGGGGACCAAGCTGGAAATAAAAC

FIGURE 30

1B9 Heavy chain

```
                <-------------------------------------------- FR1 - IMGT
                1            5                      10                    15
                E   V   Q   L   Q   Q   S   G   A       E   L   V   K   P
    1B9H        gag gtt cag ctg cag cag tct ggg gct ... gaa ctg gtg aaa cct ----------------------------------------->  _____
                                  20                      25                    30
                G   T   S   V   K   L   S   C   K   A   S   G   Y   T   F
    1B9H        ggg act tca gtg aag ttg tcc tgc aag gct tct ggc tac acc ttc ___ CDR1 - IMGT _____           <--------------------------
                                  35                      40                    45
                                  T   S   Y   Y   M   Y   W   L   K   Q   R
    1B9H        ... ... ... ... acc agc tac tat atg tac tgg ttg aag cag agg FR2 - IMGT --------------------------->  _____  CDR2
                                  50                      55                    60
                P   G   Q   G   L   E   W   I   G   G   I   N   P   T
    1B9H        cct gga caa ggc ctt gag tgg att ggg ggg att aat cct acc ...

- IMGT           <-----------------------------------------
                                  65                      70                    75
                            T   G   G   T   D   F   N   E   N   F   K       N   K
    1B9H        ... act ggt ggt act gac ttc aat gag aac ttc aag ... aac aag ----------------------------- FR3 - IMGT ----------------
                                  80                      85                    90
                A   T   L   T   L   A   T   S   S   T   A   Y   I   Q
    1B9H        gcc aca ctg act ttg gcc aca tcc tcc agc aca gcc tac ata caa ----------------------------------------->  _____
                                  95                     100              104
                L   S   S   L   T   S   E   D   S   A   V   Y   F   C   A
    1B9H        ctc agc agc ctg aca tct gag gac tct gcg gtc tat ttc tgt gca

_____ CDR3 - IMGT _____

R   M   G   R   D   A   M   D   Y   W   G   Q   G   T   S
    1B9H        aga atg gga cgg gat gct atg gac tac tgg ggt caa gga acc tca V   T   V   S   S
    1B9H        gtc acc gtc tcc tca
```

Amino Acid Sequence in FASTA format (1B9H)

EVQLQQSGAELVKPGTSVKLSCKASGYTFTSYYMYWLKQRPGQGLEWIGGINPTTGGTDFNENFKNKA
TLTLATSSSTAYIQLSSLTSEDSAVYFCARMGRDAMDYWGQGTSVTVSS

Nucleotide Sequence in FASTA format (1B9H)

> 1B9H
GAGGTTCAGCTGCAGCAGTCTGGGGCTGAACTGGTGAAACCTGGGACTTCAGTGAAGTTGTCCTGCAA
GGCTTCTGGCTACACCTTCACCAGCTACTATATGTACTGGTTGAAGCAGAGGCCTGGACAAGGCCTTG
AGTGGATTGGGGGGATTAATCCTACCACTGGTGGTACTGACTTCAATGAGAACTTCAAGAACAAGGCC
ACACTGACTTTGGCCACATCCTCCAGCACAGCCTACATACAACTCAGCAGCCTGACATCTGAGGACTC
TGCGGTCTATTTCTGTGCAAGAATGGGACGGGATGCTATGGACTACTGGGGTCAAGGAACCTCAGTCA
CCGTCTCCTCA

FIGURE 31A
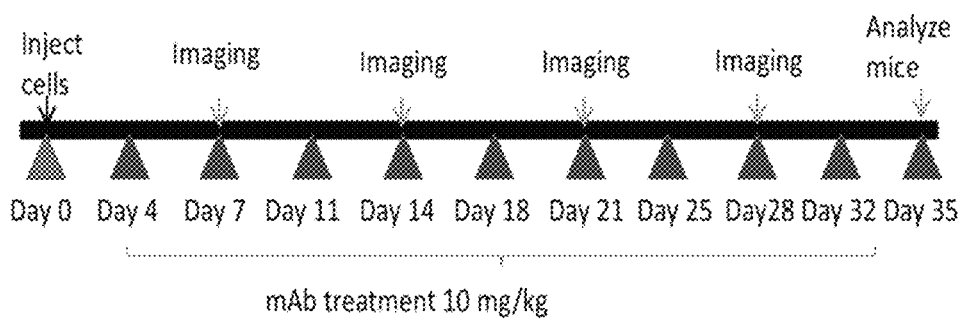
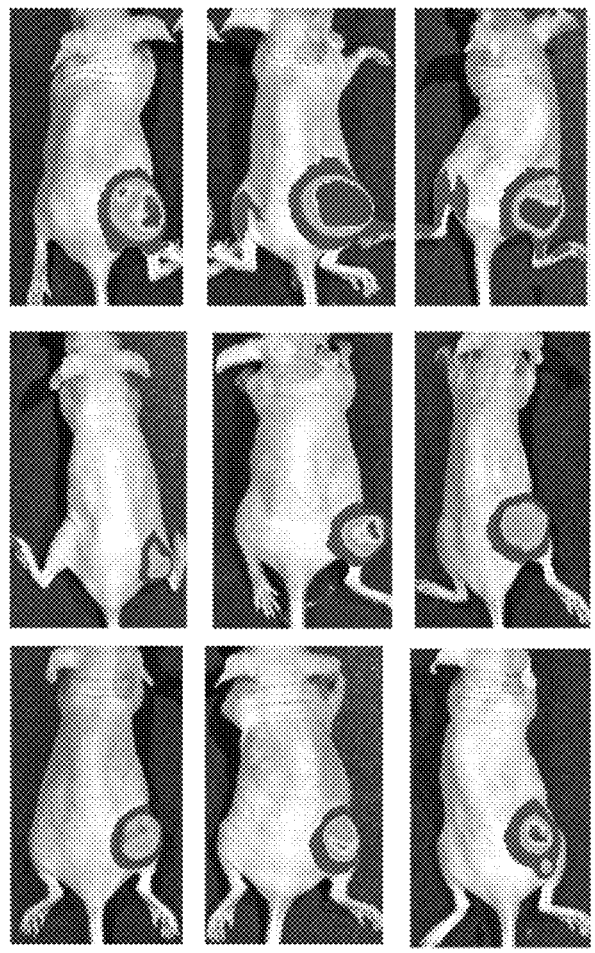
Control
Pt/s: 1.50 X 10¹⁰ ± 0.60
Inhibition (%): 0.00
6D4
Pt/s: 6.14 X 10⁹ ± 3.35
Inhibition (%): 50.19
7G8
Pt/s: 3.54 X 10⁹ ± 0.463
Inhibition (%): 76.45
Antibodies inhibit tumour growth in HT29 human xenograft mouse model at 21 days FIGURE 42
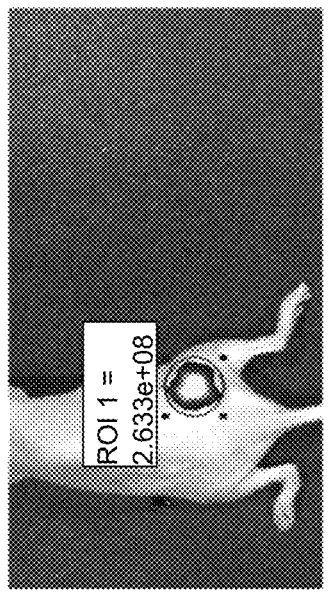
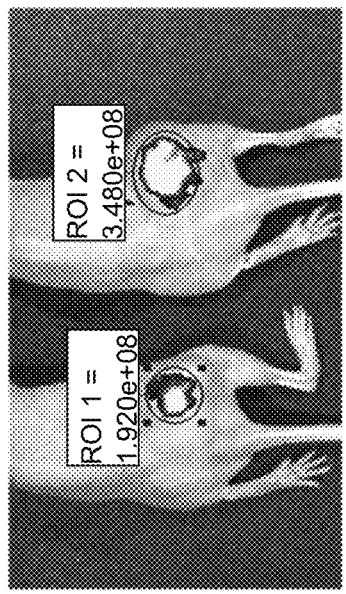
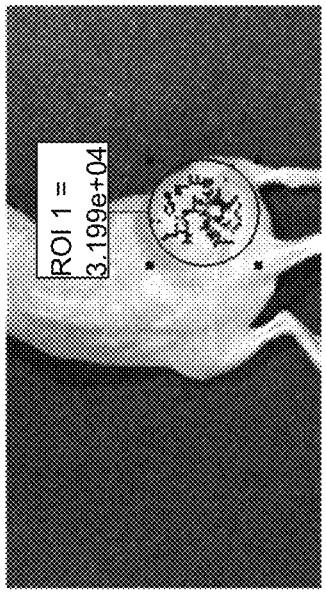
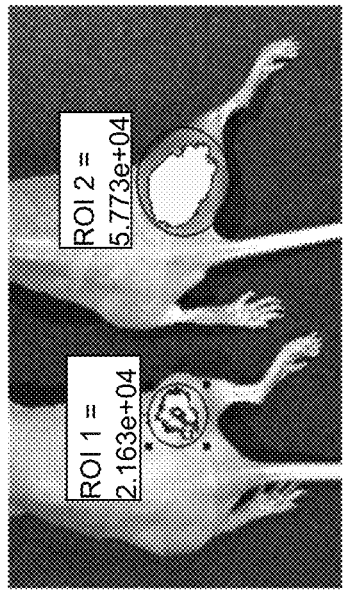
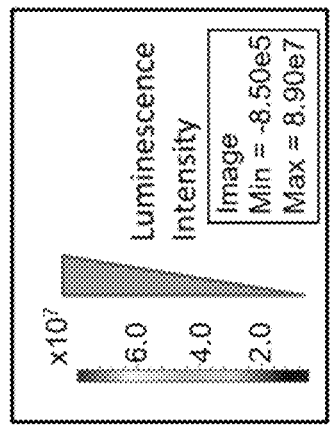

FIGURE 45
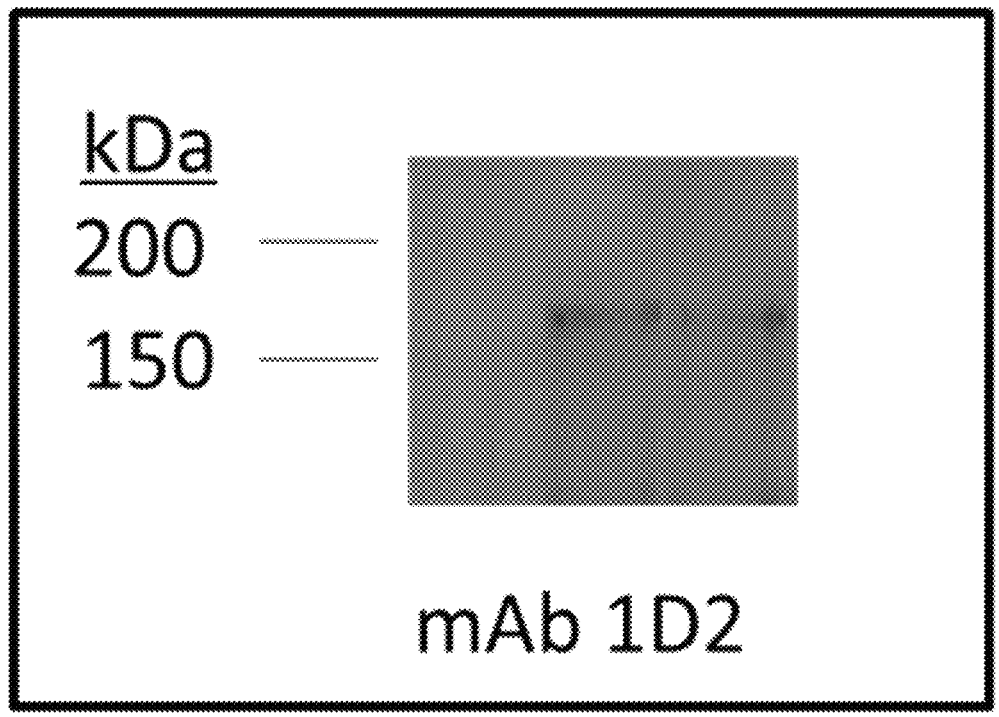
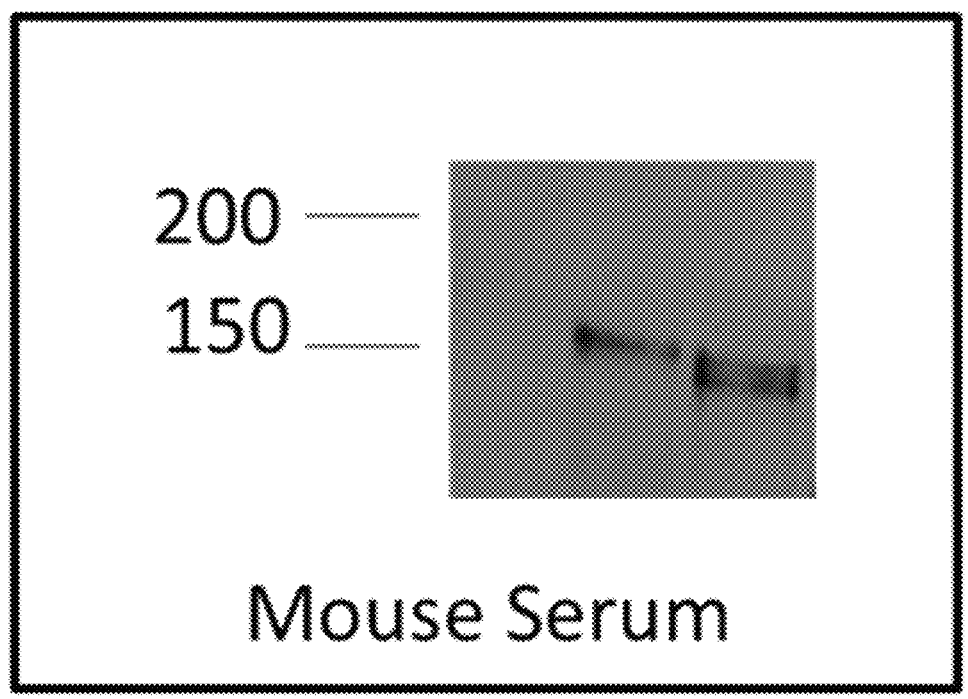
1st Lane: 3T3
2nd Lane: HCT116
3rd Lane: HT29

FIGURE 46
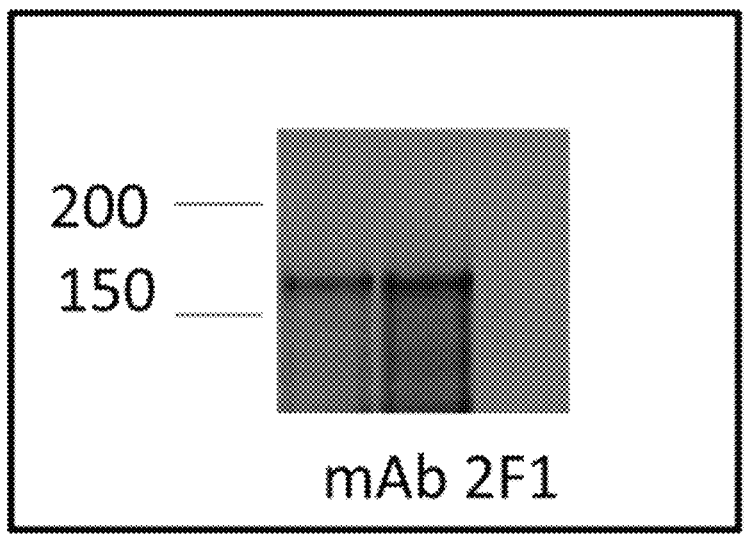
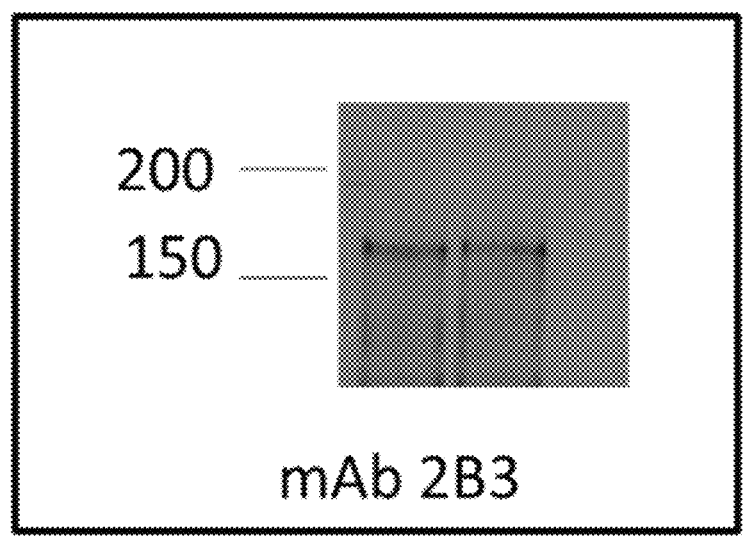
1st lane: HCT116
2nd Lane: HT29
3rd Lane: 3T3
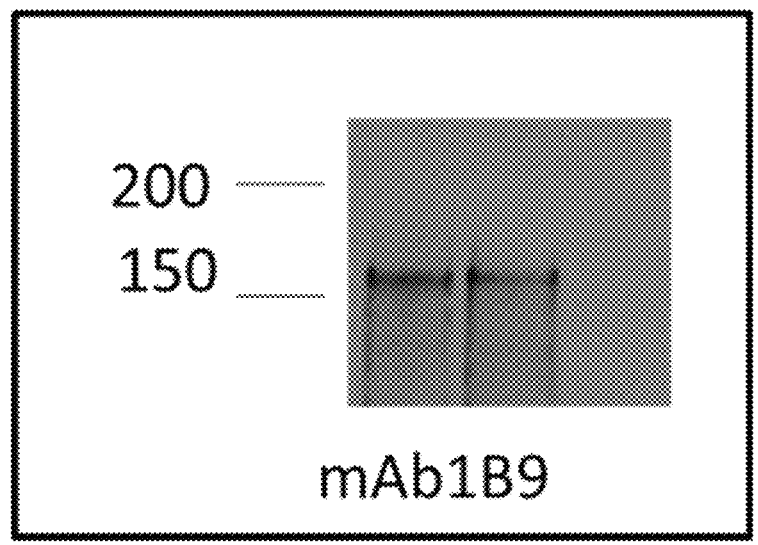

FIGURE 48B

| 2F1 | | |
|---|---|---|
| 1 | SSPYHNSHPHNSS | 0.655 |
| 2 | VHNHPQHPHIR | 0.725 |
| 3 | NIKRPDHPHPNR | 0.643 |
| 4 | GLDPSRHPHGSW | 0.599 |
| 5 | GLIYHPHSYHAP | 0.595 |
| 6 | GLNHTHHPHSNC | 0.639 |

| 1B9 | | |
|---|---|---|
| 1 | WLKDPHNIRGK | 0.305 |
| 2 | VSRHPHTFFVDT | 0.532 |
| 3 | DNLSMPRHPHS | 0.367 |
| 4 | IPHQHPHHILQM | 0.319 |
| 5 | DVRHPHNELWMQ | 0.396 |
| 6 | DNLSMSRHPHSY | 0.362 |
| 7 | ELPQSQHPHTL | 0.407 |
| 8 | SSYMSHPHNAPL | 0.412 |
| 9 | DNLSMSRHPHSY | 0.389 |
| 10 | HNYHHHHHPHRQ | 0.424 |

| 1D2 | | |
|---|---|---|
| 1 | GSWSSHPHSLVR | 0.247 |
| 2 | AFMVHPHNLGLH | 0.323 |
| 3 | TLHPHSSRLLTP | 0.215 |
| 4 | SSWHPHGRLAIK | 0.694 |
| 5 | GRQHPRHPHGNW | 0.538 |
| 6 | DVSYHPHHLSLR | 0.333 |
| 7 | ALLKHPHNHPGL | 0.423 |
| 8 | AFKHPHVAPMPV | 0.291 |
| 9 | NLHPHPQNARSR | 0.611 |
| 10 | TTWHPHSHYRFN | 0.229 |

12mer library- Multiple sequence alignment

```
Clone 1     -TTNSWHPHNRVL---
Clone 2      -RPLEIHPHSREM---
Clone 3      ---GKNHPHPGPLFR-
Clone 4      -ASIWSHPHSPLY---
Clone 5      -AGPSYHPHHYHY---
Clone 6         ----SPHPHAPSFLRL
Clone 7     NIKRPDHPHPNR---
Clone 8     GLNHTHHPHSNC----
Clone 9     GRRAPRHPHHSW----
Clone 10    GLEASRHPHGSW----
                   ***
Consensus   KLTEFHPHSGPLRGS
```

565  PPKLTEF HPH SGPLRGST  585

2B3 epitope

FIGURE 49A
mAb 5A5
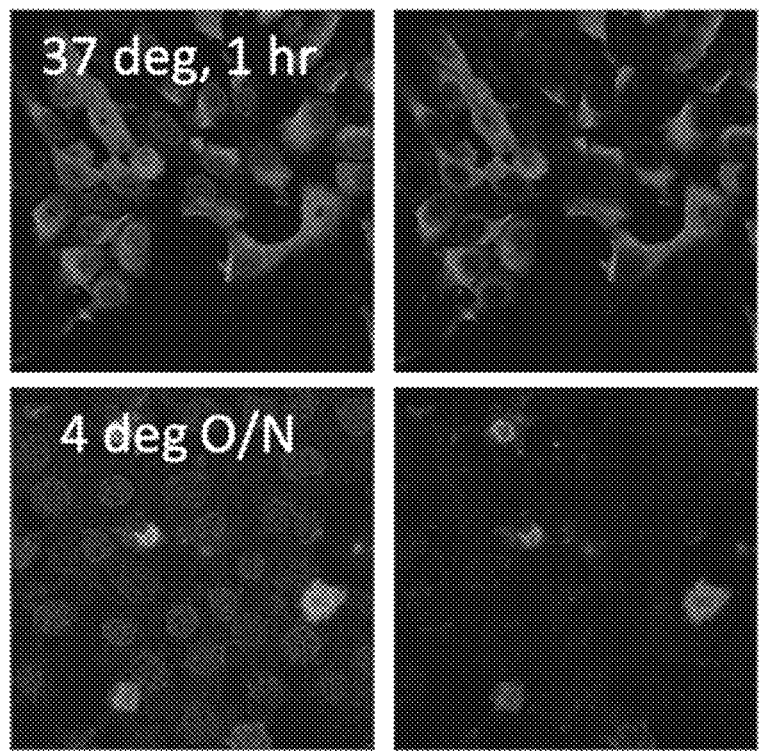
mAb 6B5
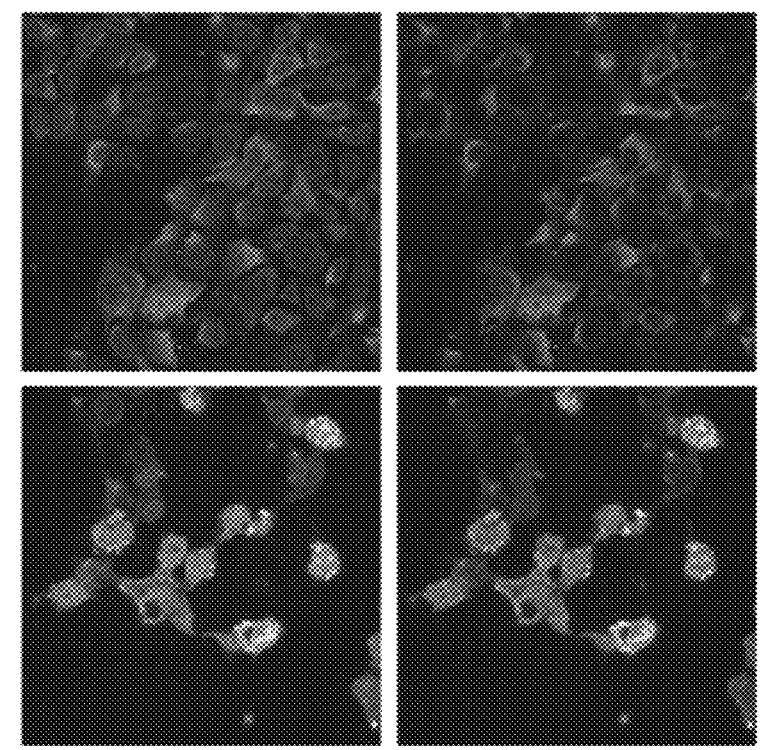

mAb 6D4

FIGURE 50A

5A5 Heavy Chain

```
              <------------------------ F  R  1  -  I  M  G  T
              1              5                       10
              L    E    V    K    L    E    Q    S    G    P    G    L    V    K
    5A5H      CTT  GAG  GTT  AAG  CTG  GAG  CAG  TCA  GGA  CCT  GGC  CTG  GTG  AAA
              ------------------------------------------------->
              15                      20                           25
              P    S    Q    S    L    S    L    T    C    T    V    T
    5A5H      CCT  TCT  CAG  TCT  CTG  TCC  CTC  ACC  TGC  ACT  GTC  ACT

CDR1  -  IMGT                     <-----
                              30                        35                    40
              D    Y    S    I    T    S    D    Y    A                   W    N
    5A5H      GAC  TAC  TCA  ATC  ACC  AGT  GAT  TAT  GCC  ... ... ...  TGG  AAC

----------------    F    R    2    -    I    M    G    T
                              45                       50
              W    I    R    Q    F    P    G    N    K    L    E    W
    5A5H      TGG  ATC  CGG  CAA  TTT  CCA  GGA  AAC  AAA  CTG  GAG  TGG

---------->             CDR2  -  IMGT                       <-
                      55                       60                         65
              M    G    Y    I    L    Y    S    G    S    T                   T
    5A5H      ATG  GGT  TAC  ATA  CTC  TAC  AGT  GGT  TCC  ACT  ... ... ...  ACG
              ----------------------------------------------------------
                              70                        75
              Y    N    P    S    L    K         S    R    V    S    I
    5A5H      TAC  AAT  CCG  TCT  CTC  AAA  ...  AGT  CGA  GTC  TCT  ATC

-------  F    R    3    -    I    M    G    T    ------------------
                      80                        85                        90
              T    R    D    T    S    K    N    Q    F    F    L    H    L    D
    5A5H      ACT  CGA  GAC  ACA  TCC  AAG  AAC  CAG  TTC  TTC  CTG  CAC  TTG  GAT
              ------------------------------------------------->
                              95                        100
              S    V    T    T    E    D    A    A    T    Y    Y    C
    5A5H      TCT  GTG  ACT  ACT  GAG  GAC  GCT  GCC  ACA  TAT  TAC  TGT
                         CDR3  -  IMGT                <---------------  FR4 -
              A    S    L    G    R    G    G    S    W    G    Q    G    T    T
              105            108  114                                120
    5A5H      GCA  AGC  CTC  GGG  CGT  GGG  GGG  TCC  TGG  GGC  CAG  GGC  ACC  ACT
              IMGT ----------------->
                      125
              L    A    V    S    S
    5A5H      CTC  GCA  GTC  TCC  TCA
```

FIGURE 50A (CONTINUED)

Amino Acid Sequence in FASTA format (5A5H)

> 5A5H
LEVKLEQSGPGLVKPSQSLSLTCTVTDYSITSDYAWNWIRQFPGNKLEWMGYILYSGSTTYNPSLKSR
VSITRDTSKNQFFLHLDSVTTEDAATYYCASLGRGGSWGQGTTLAVSS

Nucleotide Sequence in FASTA format (5A5H)

> 5A5H
CTTGAGGTTAAGCTGGAGCAGTCAGGACCTGGCCTGGTGAAACCTTCTCAGTCTCTGTCCCTCACCTG
CACTGTCACTGACTACTCAATCACCAGTGATTATGCCTGGAACTGGATCCGGCAATTTCCAGGAAACA
AACTGGAGTGGATGGGTTACATACTCTACAGTGGTTCCACTACGTACAATCCGTCTCTCAAAAGTCGA
GTCTCTATCACTCGAGACACATCCAAGAACCAGTTCTTCCTGCACTTGGATTCTGTGACTACTGAGGA
CGCTGCCACATATTACTGTGCAAGCCTCGGGCGTGGGGGTCCTGGGGCCAGGGCACCACTCTCGCAG
TCTCCTCA

FIGURE 50B

```
                  <------------------- F   R   1   -   I   M   G   T
                  1               5                           10
                  D   I   L   M   T   Q   T   P   L   S   L   P
5A5K              GAT ATT TTG ATG ACC CAA ACT CCT CTC TCC CTG CCT
                  ------------------------------------------------->
                          15                  20                  25
                  V   S   L   G   D   Q   A   S   I   S   C   R   S   S
5A5K              GTC AGT CTT GGA GAT CAA GCC TCC ATC TCT TGC AGA TCT AGT

_____ CDR1 - IMGT _____
                          30                          35
                  Q   S   I   V   H   S   N   G   N   T   Y
5A5K              CAG AGC ATT GTA CAT AGT AAT GGA AAC ACC TAT ...
                  <------------------- F   R   2   -   I   M   G   T
                          40                  45                  50
                  L   E   W   Y   L   Q   K   P   G   Q   S   P   K   L
5A5K              TTG GAA TGG TAC CTG CAG AAA CCA GGC CAG TCT CCA AAG CTC

---------->  _____ CDR2 - IMGT _____
                                  55                  60
                  L   I   Y   K   V   S
5A5K              CTT ATC TAC AAA GTT TCC ... ... ... ... ... ... ...
                  <---------------------------------------------------------
                          65                  70                  75
                  N   R   F   S   G   V   P       D   R   F   T   G
5A5K              AAC CGA TTT TCT GGG GTC CCA ... GAC AGG TTC ACT GGC

-------- F   R   3   -   I   M   G   T   ------------------
                          80                  85                  90
                  S   G           S   G   T   D   F   T   L   K
5A5K              AGT GGA ... ... TCA GGG ACA GAT TTC ACA CTC AAG

--------------------------------------------------------->
                                  95                          100
                  I   S   R   V   E   A   E   D   L   G   I   Y   Y   C
5A5K              ATC AGC AGA GTG GAG GCT GAG GAT CTG GGA ATT TAT TAC TGC

_____ CDR3 - IMGT _____  <-------------- FR4
                  105                 109 114                 120
                  F   Q   G   S   H   A   P   W   T   F   G   G
5A5K              TTT CAA GGT TCA CAT GCT CCG TGG ACG TTC GGT GGA
                  - IMGT ------------->
                                  125
                  G   T   K   L   E   I   R
5A5K              GGC ACC AAG CTG GAA ATC AGA C
```

FIGURE 50B (CONTINUED)

Amino Acid Sequence in FASTA format (5A5K)

> 5A5K
DILMTQTPLSLPVSLGDQASISCRSSQSIVHSNGNTYLEWYLQKPGQSPKLLIYKVSNRFSGVPDRFT
GSGSGTDFTLKISRVEAEDLGIYYCFQGSHAPWTFGGGTKLEIR

Nucleotide Sequence in FASTA format (5A5K)

> 5A5K
GATATTTTGATGACCCAAACTCCTCTCTCCCTGCCTGTCAGTCTTGGAGATCAAGCCTCCATCTCTTG
CAGATCTAGTCAGAGCATTGTACATAGTAATGGAAACACCTATTTGGAATGGTACCTGCAGAAACCAG
GCCAGTCTCCAAAGCTCCTTATCTACAAAGTTTCCAACCGATTTTCTGGGGTCCCAGACAGGTTCACT
GGCAGTGGATCAGGGACAGATTTCACACTCAAGATCAGCAGAGTGGAGGCTGAGGATCTGGGAATTTA
TTACTGCTTTCAAGGTTCACATGCTCCGTGGACGTTCGGTGGAGGCACCAAGCTGGAAATCAGAC

2B3 binding affinity as measured by Proteon

|  | Ka (1/Ms) | Kd (1/s) | KD (M) | Rmax (RU) | Chi2 (RU) |
|---|---|---|---|---|---|
| 2B3 | 3.48E5 | 5.15E-5 | 1.48E-10 | 619.55 | 60.87 |

MACROPHAGE STIMULATING PROTEIN RECEPTOR (OR RON—RECEPTEUR D'ORIGINE NANTAIS) ANTIBODIES AND USES THEREOF

CROSS-REFERENCE TO RELATED APPLICATIONS

This patent application is a U.S. National Phase Application Under 35 U.S.C. § 371 of International Application No. PCT/SG2017/050424, filed 28 Aug. 2017, entitled MACROPHAGE STIMULATING PROTEIN RECEPTOR (OR RON RECEPTEUR D' ORIGINE NANTAIS) ANTIBODIES AND USES THEREOF, which claims the benefit of priority of Singapore patent application No. 10201607147P, filed 26 Aug. 2016, Singapore patent application No. 10201700393P, filed on 17 Jan. 2017, Singapore patent application No. 10201700521V, filed on 20 Jan. 2017, and Singapore patent application No. 10201703234U, filed on 19 Apr. 2017, the contents of which were incorporated by reference in the entirety for all purposes.

FIELD OF THE INVENTION

The present invention relates to a preparation for medical purpose or specific therapeutic activity of a preparation. In particular, the present invention relates to antibodies and other agents that bind to RON (i.e. Macrophage stimulating protein receptor or RON-Recepteur d' Origine Nantais), as well as to methods of using the antibodies or other agents for the treatment of diseases.

BACKGROUND OF THE INVENTION

Cancer treatments have advanced enormously in recent times, especially with the availability of immunotherapeutics, such as Herceptin®. However, there are a large number of cancers for which no effective treatment is available. Furthermore, there are other cancers for which treatments are available but for which resistance develops during treatment. In the context of immunotherapeutics one approach to improve efficacy is to prepare an antibody drug conjugate. In other contexts combinations of chemotherapy have been employed to try and address tumour resistance. These approaches have provided limited success.

Thus, there is presently an unmet medical need for alternative cancer therapies.

SUMMARY OF THE INVENTION

In one aspect there is provided an antigen specific binding domain comprising the heavy chain CDRs of CDRH1, CDRH2, and CDRH3 and/or the light chain CDRs of CDRL1, CDRL2, and CDRL3, wherein
  (a) CDRH1 is selected from the group consisting of SEQ ID NO: 1, SEQ ID NO: 27, SEQ ID NO: 45, SEQ ID NO: 56, SEQ ID NO: 73, SEQ ID NO: 89, SEQ ID NO: 100, SEQ ID NO: 116, and SEQ ID NO: 135 or a CDRH1 sequence differing 1 or 2 amino acids therefrom;
  (b) CDRH2 is selected from the group consisting of SEQ ID NO: 2, SEQ ID NO: 28, SEQ ID NO: 46, SEQ ID NO: 57, SEQ ID NO: 74, SEQ ID NO: 90, SEQ ID NO: 101, SEQ ID NO: 117, and SEQ ID NO: 136; or a CDRH2 sequence differing 1 or 2 amino acids therefrom;
  (c) CDRH3 is selected from the group consisting of SEQ ID NO: 3, SEQ ID NO: 29, SEQ ID NO: 47, SEQ ID NO: 58, SEQ ID NO: 75, SEQ ID NO: 91, SEQ ID NO: 102, and SEQ ID NO: 137; or a CDRH3 sequence differing 1 or 2 amino acids therefrom;
  (d) CDRL1 is selected from the group consisting of SEQ ID NO: 18, SEQ ID NO: 36, SEQ ID NO: 65, SEQ ID NO: 81, SEQ ID NO: 108, and SEQ ID NO: 144; or a CDRL1 sequence differing 1 or 2 amino acids therefrom;
  (e) CDRL2 is selected from the group consisting of SEQ ID NO: 19, SEQ ID NO: 37, SEQ ID NO: 66, SEQ ID NO: 82, and SEQ ID NO: 109; or a CDRL2 sequence differing 1 or 2 amino acids therefrom; and
  (f) CDRL3 is selected from the group consisting of SEQ ID NO: 20, SEQ ID NO: 38, SEQ ID NO: 67, SEQ ID NO: 83, SEQ ID NO: 220, SEQ ID NO: 123, and SEQ ID NO: 145; or a CDRL2 sequence differing 1 or 2 amino acids therefrom.

In another aspect there is provided an antigen specific binding domain comprising CDRH1, CDRH2, CDRH3, CDRL1, CDRL2, and CDRL3, wherein:
  (a) CDRH1 is selected from the group consisting of SEQ ID NO: 1, SEQ ID NO: 27, SEQ ID NO: 45, SEQ ID NO: 56, SEQ ID NO: 73, SEQ ID NO: 89, and SEQ ID NO: 100, SEQ ID NO: 116, SEQ ID NO: 135 and a CDRH1 differing from any one of the same in that 1 or 2 amino acids are replaced, deleted or added;
  (b) CDRH2 is selected from the group consisting of SEQ ID NO: 2, SEQ ID NO: 28, SEQ ID NO: 46, SEQ ID NO: 57, SEQ ID NO: 74, SEQ ID NO: 90, and SEQ ID NO: 101, SEQ ID NO: 117, SEQ ID NO: 136 and a CDRH2 differing from any one of the same in that 1 or 2 amino acids are replaced, deleted or added;
  (c) CDRH3 is selected from the group consisting of SEQ ID NO: 3, SEQ ID NO: 29, SEQ ID NO: 47, SEQ ID NO: 58, SEQ ID NO: 75, SEQ ID NO: 91, and SEQ ID NO: 102, SEQ ID NO: 137 and a CDRH3 differing from any one of the same in that 1 or 2 amino acids are replaced, deleted or added;
  (d) CDRL1 is selected from the group consisting of SEQ ID NO: 18, SEQ ID NO: 36, SEQ ID NO: 65, SEQ ID NO: 81, SEQ ID NO: 108, SEQ ID NO: 144 and a CDRL1 differing from any one of the same in that 1 or 2 amino acids are replaced, deleted or added;
  (e) CDRL2 is selected from the group consisting of SEQ ID NO: 19, SEQ ID NO: 37, SEQ ID NO: 66, SEQ ID NO: 82, SEQ ID NO: 109 and a CDRL2 differing from any one of the same in that 1 or 2 amino acids are replaced, deleted or added; and
  (f) CDRL3 is selected from the group consisting of SEQ ID NO: 20, SEQ ID NO: 38, SEQ ID NO: 67, SEQ ID NO: 83, SEQ ID NO: 110, SEQ ID NO: 123, SEQ ID NO: 145 and a CDRL3 differing from any one of the same in that 1 or 2 amino acids are replaced, deleted or added.

In some examples, the antigen specific binding domain as described herein may have CDRH1 that is SEQ ID NO: 1, CRDH2 is SEQ ID NO: 2, and CDRH3 is SEQ ID NO: 3 or a RON specific binding domain wherein one or more modified sequences 1, 2, and 3 are employed and the modification(s) is independently selected from replacement, deletion or addition of 1 or 2 amino acids.

In some examples, the antigen specific binding domain as described herein may have the heavy chain CDRs are selected from the group consisting of (i) the CDRH1 is SEQ ID NO: 1, the CRDH2 is SEQ ID NO: 2, the CRDH3 is SEQ ID NO: 3;
(ii) the CDRH1 is SEQ ID NO: 27, the CRDH2 is SEQ ID NO: 28, the CRDH3 is SEQ ID NO: 29;
(iii) the CDRH1 is SEQ ID NO: 45, the CRDH2 is SEQ ID NO: 46, the CRDH3 is SEQ ID NO: 47;
(iv) the CDRH1 is SEQ ID NO: 56, the CRDH2 is SEQ ID NO: 57, the CRDH3 is SEQ ID NO: 58;
(v) the CDRH1 is SEQ ID NO: 73, the CRDH2 is SEQ ID NO: 74, the CRDH3 is SEQ ID NO: 75;
(vi) the CDRH1 is SEQ ID NO: 89, the CRDH2 is SEQ ID NO: 90, the CRDH3 is SEQ ID NO: 91;
(vii) the CDRH1 is SEQ ID NO: 100, the CRDH2 is SEQ ID NO: 101, the CRDH3 is SEQ ID NO: 102; and
(viii) the CDRH1 is SEQ ID NO: 135, the CRDH2 is SEQ ID NO: 136, the CRDH3 is SEQ ID NO: 137.

In some examples, the antigen specific binding domain as described herein may have the light chain CDRs are selected from the group consisting of
(i) the CDRL1 is SEQ ID NO: 18, the CDRL2 is SEQ ID NO: 19, the CDRL3 is SEQ ID NO: 20;
(ii) the CDRL1 is SEQ ID NO: 36, the CDRL2 is SEQ ID NO: 37, the CDRL3 is SEQ ID NO: 38;
(iii) the CDRL1 is SEQ ID NO: 18, the CDRL2 is SEQ ID NO: 19, the CDRL3 is SEQ ID NO: 20;
(iv) the CDRL1 is SEQ ID NO: 65, the CDRL2 is SEQ ID NO: 66, the CDRL3 is SEQ ID NO: 67;
(v) the CDRL1 is SEQ ID NO: 81, the CDRL2 is SEQ ID NO: 82, the CDRL3 is SEQ ID NO: 83;
(vi) the CDRL1 is SEQ ID NO: 108, the CDRL2 is SEQ ID NO: 109, the CDRL3 is SEQ ID NO: 110; and
(vii) the CDRL1 is SEQ ID NO: 144, the CDRL2 is SEQ ID NO: 37, the CDRL3 is SEQ ID NO: 145.

In some examples, the antigen specific binding domain as described herein, wherein the variable heavy domain has a sequence selected from the group consisting of:
(i) SEQ ID NO: 8;
(ii) SEQ ID NO: 34;
(iii) SEQ ID NO: 51;
(iv) SEQ ID NO: 63;
(v) SEQ ID NO: 79;
(vi) SEQ ID NO: 95;
(vii) SEQ ID NO: 106; and
(viii) SEQ ID NO: 142.

In some examples, the antigen specific binding domain as described herein, wherein the variable light domain has a sequence selected from the group consisting of
(i) SEQ ID NO: 25;
(ii) SEQ ID NO: 43;
(iii) SEQ ID NO: 54;
(iv) SEQ ID NO: 71;
(v) SEQ ID NO: 87;
(vi) SEQ ID NO: 98;
(vii) SEQ ID NO: 114; and
(viii) SEQ ID NO: 150.

In another aspect, there is provided a chimeric antigen receptor comprising a binding domain as described herein.

In another aspect, there is provided an isolated antibody or antibody comprising a binding domain as described herein.

In some examples, the isolated antibody or antibody as described herein may be selected from a group consisting of multispecific antibody, a full-length antibody, and an antibody binding fragment.

In some examples, the isolated antibody or antibody as described herein, where the multispecific antibody is bispecific antibody.

In some examples, the isolated antibody or antibody as described herein, wherein the bispecific antibody is a bispecific T cell engager (Bite®).

In some examples, the isolated antibody or antibody as described herein, wherein the bispecific antibody comprises one binding domain specifically binding to a first RON epitope, and a second binding domain specifically binding to a second RON epitope which is different from the first RON epitope.

In some examples, the isolated antibody or antibody as described herein, wherein a first RON binding domain comprising CDRH1, H2 and H3 as shown in SEQ ID NO: 1, 2, 3 respectively and CDRL1, L2 and L3 show in SEQ ID NO: 18, 19 and 20.

In some examples, the isolated antibody or antibody as described herein comprising a second RON binding domain comprising CDRH1, H2 and H3 as shown in SEQ ID NO: 27, 28, 29 respectively and CDRL1, L2 and L3 show in SEQ ID NO: 36, 37 and 38.

In some examples, the isolated antibody or antibody as described herein wherein the antibody molecule comprises an effector function.

In some examples, the isolated antibody or antibody as described herein wherein the antibody is conjugated to a payload. In some examples, the payload is selected from a wherein the payload is selected from a group consisting of toxin, a polymer, biologically active proteins, nucleic acids and fragments thereof radionuclides chelated metals, nanoparticles and reporter groups.

In some examples, wherein the toxin in selected from a group consisting of an auristatin, MMAF (monomethyl auristatin F), pyrrolobenzodiazepine (PBD), doxorubicin, duocarmycin, a maytansinoid, calocheamicin, dolastatin, Maytansine, α-Amanitin, and a Tubulysin.

In yet another aspect, there is provided a pharmaceutical composition comprising an antibody as described herein and an excipient, diluent and/or carrier.

In some examples, the pharmaceutical composition as described herein comprises at least two antigen specific antibody as described herein. In some examples, one of the at least two antigen specific antibody comprises CDRH1, H2 and H3 as shown in SEQ ID NO: 1, 2, 3 respectively and CDRL1, L2 and L3 show in SEQ ID NO: 18, 19 and 20; optionally where a second antibody of the at least two antibodies comprises CDRH1, H2 and H3 as shown in SEQ ID NO: 27, 28, 29 respectively and CDRL1, L2 and L3 show in SEQ ID NO: 36, 37 and 38.

In yet another aspect, there is provided an antigen binding domain as described herein, or a chimeric antigen receptor as described herein, or an antibody as described herein, or a pharmaceutical composition as described herein, for use in therapy or treatment.

In yet another aspect, there is provided a method of preventing or treating cancer or fibrosis in a patient comprising administering a therapeutic effective amount of an antigen binding domain as described herein, or a chimeric antigen receptor as described herein, or an antibody as described herein, or a pharmaceutical composition as described herein to the patient in need thereof.

In some examples, the patient is a patient population characterised in that patients making up the population have a RON positive tumour. In some examples, the patients making up the population have a RON positive and C-MET positive tumour.

In some examples, the method as described herein, comprises the step of identifying the patient to have a RON positive tumour before treatment.

In yet another aspect, there is provided the use of an antigen binding domain as described herein, or a chimeric antigen receptor as described herein, or an antibody as described herein, or a pharmaceutical composition as described herein in the manufacture of a medicament for the treatment of cancer or fibrosis.

In yet another aspect, there is provided an antibody which cross-blocks or binds the same epitope as an antibody comprising a variable heavy region (VH) of SEQ ID NO: 8, SEQ ID NO: 34, SEQ ID NO: 51, SEQ ID NO: 63, SEQ ID NO: 79, SEQ ID NO: 95, SEQ ID NO: 106, SEQ ID NO: 121, SEQ ID NO: 130, SEQ ID NO: 133 or 142.

In yet another aspect, there is provided antibody, which cross-blocks or binds the same epitope as an antibody comprising a variable heavy region/variable light region (VH/VL) pair selected from a group consisting of SEQ ID NO: 8 and 25, SEQ ID NO: 34 and 43, SEQ ID NO: 51 and 54, SEQ ID NO: 63 and 71, SEQ ID NO: 79 and 87, SEQ ID NO: 95 and 98, SEQ ID NO: 106 and 114, SEQ ID NO: 121 and 130 or SEQ ID NO: 142 and 150.

In yet another aspect, there is provided an ex vivo method of evaluating the status of a cancer; wherein the method comprises: a) scanning a patient or a specific site of the patient known to comprise a tumor of the cancer, wherein the patient had been administered with a labelled form of an antibody at a first time point, wherein the antibody is as defined herein, b) repeating a) at one or more further time points, and comparing the results from two or more time points to evaluate the status of the cancer.

BRIEF DESCRIPTION OF THE FIGURES

FIG. 1 shows anti-RON Antibodies as described herein binds to RON-GST with minimal background binding to GST protein.

FIG. 2 shows anti-RON Antibodies as described herein binds to truncated RON proteins can stain human colorectal cells (such as HCT116 cells). In addition, staining is specific for RON as anti-RON Antibodies do not stain RON negative cell lines such as mouse embryonic fibroblast (named TKO).

FIG. 3 shows immunohistochemistry staining of xenograft mouse tumour tissues using exemplary anti-RON Antibodies (6D4 and 7G4 antibodies). Serums from mice were injected with recombinant RON protein was used as a positive control. Thus, FIG. 3 shows anti-RON antibodies as described herein can be used in immunohistochemistry.

FIG. 4 was extracted from Yao, Hang-Ping et al. "MSP-RON signalling in cancer: pathogenesis and therapeutic potential." *Nature reviews. Cancer* 13 7 (2013): 466-81.

FIG. 5 shows that exemplary anti-RON Antibodies as described herein does not bind to triple-knockout cells (i.e. negative control). In contrast, the anti-RON Antibodies as described herein binds to human breast cancer cells. Thus, FIG. 5 shows the anti-RON Antibodies as described herein is specific to cancer cells.

FIG. 6 shows dose dependent (1.25 µg/ml to 12.5 µg/ml) suppression of cell proliferation by antibodies as described herein.

FIG. 7 shows 7G8 antibody provides significant inhibition of HT29 cell migration. Inhibition of migration of cancer cells is a desirable quality as RON overexpression leads to uncontrolled cell migration in tumours.

FIG. 8 shows 7G8 antibody provides significant inhibition of HT29 cell migration.

FIG. 9 shows treatment with anti-RON Antibodies (6D4 and 7G8) leads to decrease in the amount of RON detected, and lower levels of phosphorylated targets downstream of RON signalling. Thus, FIG. 9 shows treatment with anti-RON Antibodies (6D4 and 7G8) can lead to degradation of RON and abrogation of its downstream signalling pathways (Ras/Raf pathway and PI3K/Akt pathway).

FIG. 10 shows the antibodies as described herein induce cell lysis in breast cancer cell lines in the presence of effector cells.

Thus, FIG. 11 shows both 6D4 and 7G8 are endocytosed into live cells, allowing for efficient targeting of live cancer cells expressing RON on the surface.

FIG. 12 shows 7G8 antibody can cause cell death in human colon carcinoma cell lines (HCT116 cells).

FIG. 13A shows the antibodies as described herein, when coupled with antibody drug conjugate, retards cancer cell growth in RON positive cells and not in RON negative cell lines.

FIG. 13B shows the antibodies (5A5, 5B9, 6D4 and 7G8) as described herein, when coupled with antibody drug conjugate, reduces cancer cell viability as seen from the decrease in luminescence readings of HCT116 cells treated with 5A5, 5B9, 6D4 and 7G8.

FIG. 13C shows the antibodies as described herein (5A5, 5B9, 6D4 and 7G8), when coupled with antibody drug conjugate, reduces cancer cell viability.

FIG. 14 shows 7G8 heavy chain 1 amino acid and nucleotide sequences, and 7G8 heavy chain 1 framework and CDR sequences.

FIG. 15 shows 7G8 kappa chain (light chain) amino acid and nucleotide sequences, and 7G8 kappa chain framework and CDR sequences.

FIG. 16 shows 6D4 heavy chain amino acid and nucleotide sequences, and 6D4 heavy chain framework and CDR sequences.

FIG. 17 shows 6D4 kappa chain (light chain) amino acid and nucleotide sequences, and 6D4 kappa framework and CDR sequences.

FIG. 18 shows 3E1 heavy chain amino acid and nucleotide sequences, and 3E1 heavy chain framework and CDR sequences.

FIG. 19 shows 3E1 kappa chain (light chain) amino acid and nucleotide sequences, and 3E1 kappa chain framework and CDR sequences.

FIG. 20 shows 3G4 heavy chain amino acid and nucleotide sequence, and 3G4 heavy chain framework and CDR sequences.

FIG. 21 shows 3G4 kappa chain (light chain) amino acid and nucleotide sequence, and 3 G4 kappa chain framework and CDR sequences.

FIG. 22 shows 5B9 heavy chain amino acid and nucleotide sequence, and 5B9 heavy chain framework and CDR sequences.

FIG. 23 shows 5B9 kappa chain (light chain) amino acid and nucleotide sequence, and 5B9 kappa chain framework and CDR sequences.

FIG. 24 shows 6E6 heavy chain amino acid and nucleotide sequence, and 6E6 heavy chain framework and CDR sequences.

FIG. 25 shows 6E6 kappa chain (light chain) amino acid and nucleotide sequence, and 6E6 kappa chain framework and CDR sequences.

FIG. 26 shows 2F1 heavy chain amino acid and nucleotide sequence, and 2F1 kappa chain framework and CDR sequences.

FIG. 27 shows 2F1 kappa chain (light chain) amino acid and nucleotide sequence, and 2F1 kappa chain framework and CDR sequences.

FIG. 28 shows 1D2 heavy chain amino acid and nucleotide sequence, and 1D2 heavy chain framework and CDR sequences.

FIG. 29A shows 2B3 heavy chain amino acid and nucleotide sequence, and 2B3 heavy chain framework and CDR sequences.

FIG. 29B shows 2B3 light chain amino acid and nucleotide sequence, and 2B3 light chain framework and CDR sequences.

FIG. 30 shows 1B9 heavy chain amino acid and nucleotide sequence, and 1B9 heavy chain framework and CDR sequences.

FIG. 31 shows the antibodies as described herein inhibits tumor growth in vivo.

FIG. 32 shows mice treated with an exemplary antibody as described herein has reduced tumour volume.

FIG. 42 shows photographical images of the results of experiments employing 6D4 and 7G8 antibodies as in vivo imaging agents 21 days after administration and measures the tumour volume by measuring the photons reflected by expression of luciferase genes in the tumour cells.

FIG. 45 shows Western Blots showing immunoprecipitation results for antibody 1D2 against mouse embryo fibroblast cell line (e.g. 3T3), human colorectal carcinoma cell line (e.g. HCT116) and mouse hybridoma (e.g. HT29) cell lines. Thus, FIG. 45 shows that RON (MW 180 kDa) can be immunoprecipitated by 1D2 in RON-positive HT29 and HCT116 cells but not in RON negative 3T3 cells.

FIG. 46 shows Western Blots showing immunoprecipitation results for antibodies 2F1, 2B3 and 1B9 against 3T3, HCT116 and HT29 cell lines. Thus, FIG. 45 shows that RON (MW 180 kDa) can be immunoprecipitated by 2F1, 2B3 and 1B9 in RON-positive HT29 and HCT116 cells but not in RON negative 3T3 cells.

FIG. 48B shows results of epitope mapping by phage display.

FIG. 49A shows immunofluorescence images showing the endocytosis of anti-RON antibodies 5A5 and 6B5. Thus, FIG. 49A shows that 5A5 and 6B5 are endocytosed into live cells, allowing for use as therapeutic drugs-delivering vehicles that target live cancer cells expressing RON on the surface.

FIG. 49B shows the antibody 6D4 is endocytosed, thus allowing the antibody to be used as therapeutic drugs-delivering vehicles that target live cancer cells expressing RON on the surface.

FIG. 50A shows variable 5A5 heavy chain amino acid and nucleotide sequence, and 5A5 heavy chain framework and CDR sequences.

FIG. 50B shows variable 5A5 kappa chain (light chain) amino acid and nucleotide sequence, and 5A5 kappa chain framework and CDR sequences.

FIG. 51 indicates that antibody 2B3 has a strong affinity for RON3.

TABLE 1

Peptides Associated with FIG. 58A

Figure 1A:
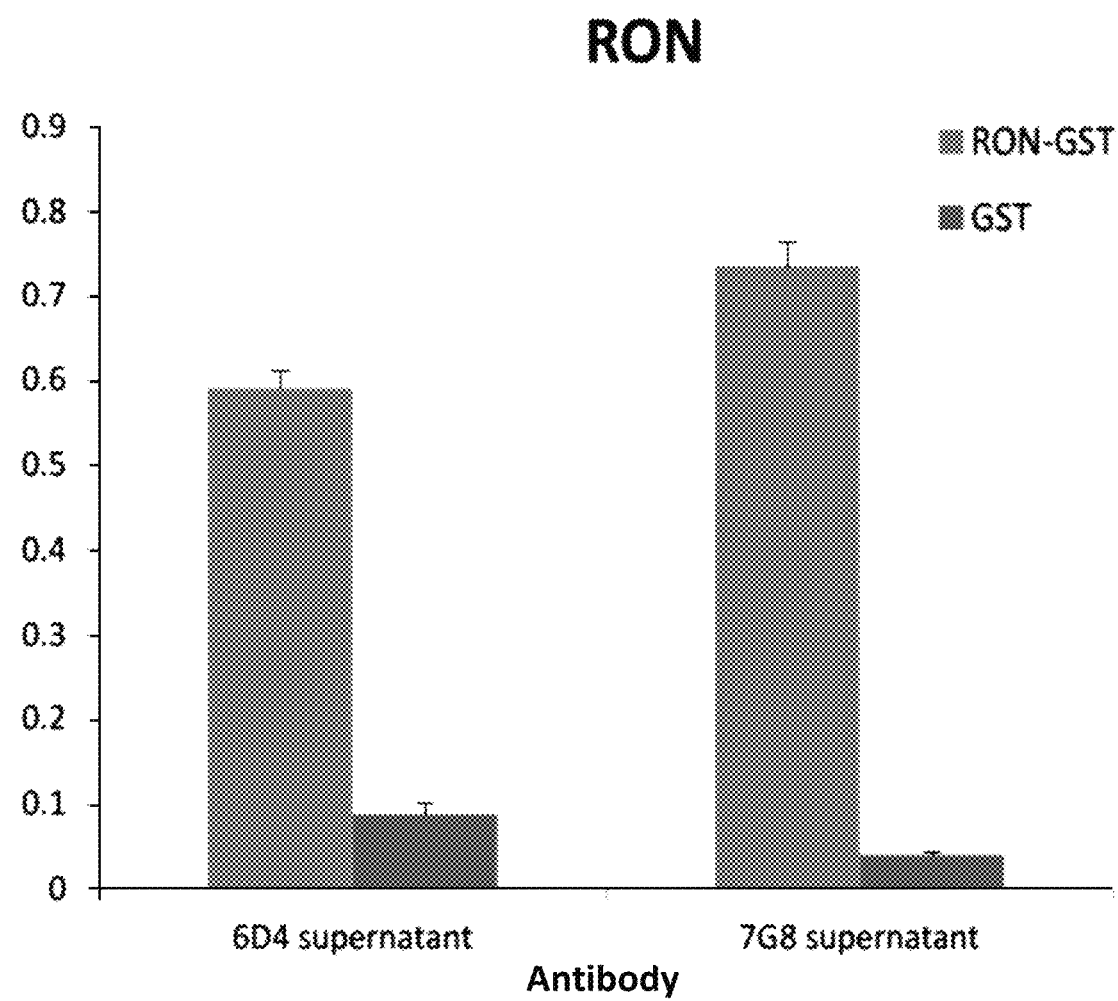
FIG. 1A shows a bar graph illustrating the results of an ELISA-Based Binding Assay of exemplary anti-RON Antibodies (such as 6D4 and 7G8 clones) to Coated Recombinant Truncated RON Proteins as well as GST Protein. Proteins were coated at 0.1 µg/ml. Antibody supernatants were tested and absorbance was observed at 650 nm.
Figure 1B:
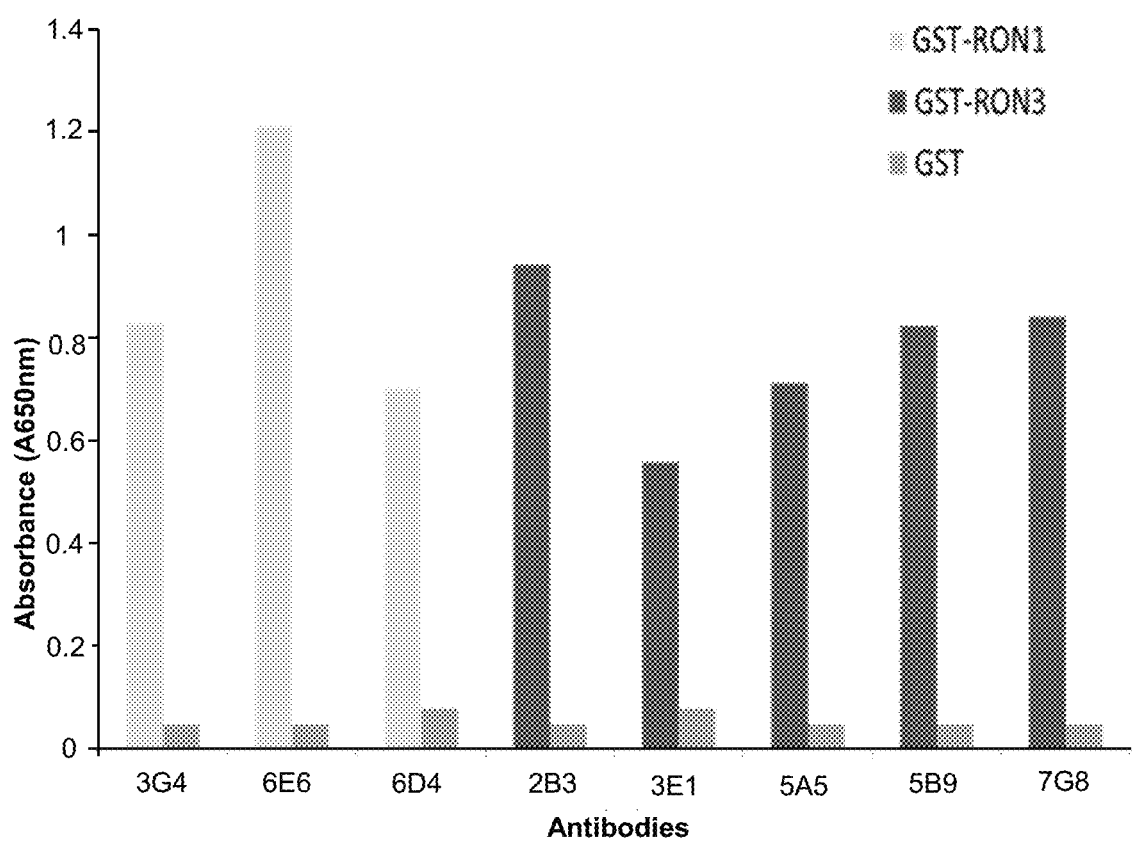
FIG. 1B shows a bar graph illustrating the results of an ELISA-Based Binding Assay of exemplary anti-RON Antibodies to Coated Recombinant Truncated RON Proteins (GST-RON1 and GST-RON3) as well as GST Protein. Proteins were coated at 0.1 µg/ml. Antibody supernatants were tested and absorbance was observed at 650 nm. Thus.
Figure 2:
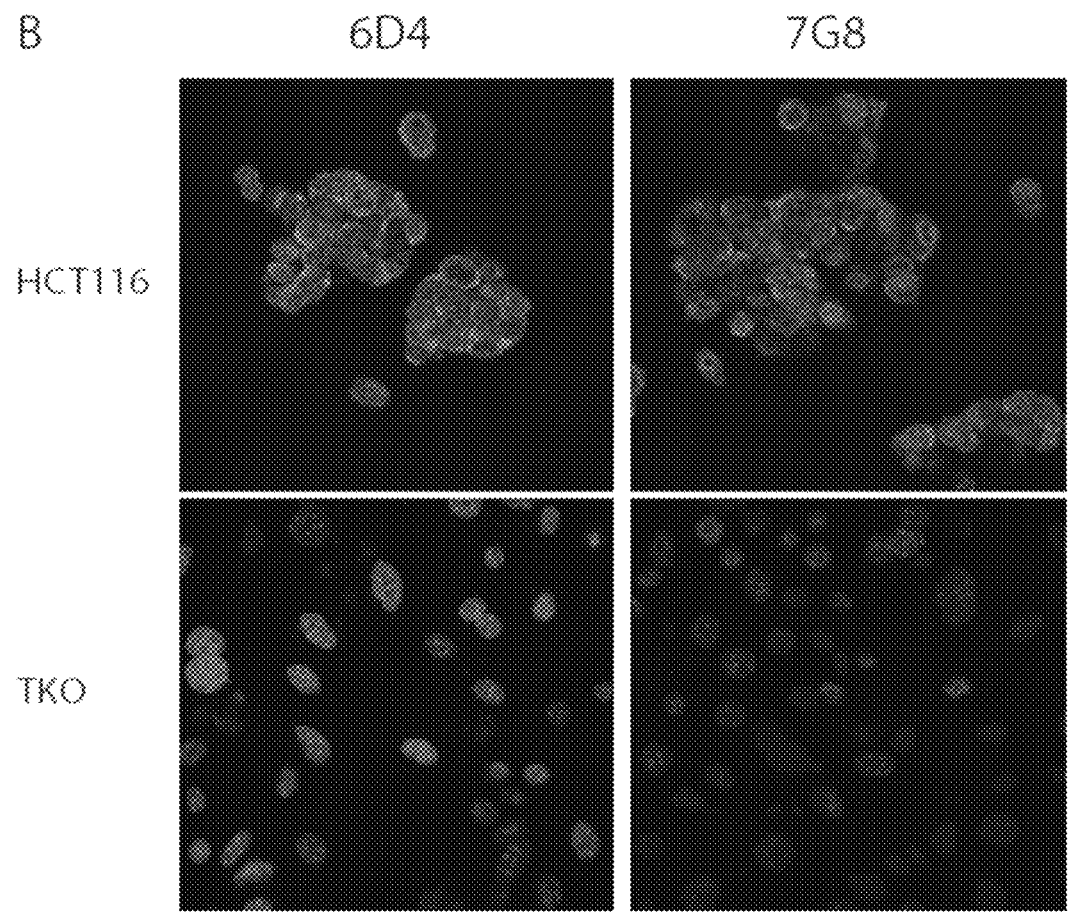
FIG. 2 shows immunofluorescence staining of exemplary anti-RON Antibodies (6D4 and 7G8 antibodies) on PFA fixed HCT116 cells (human colorectal carcinoma). Cells were stained with DAPI for nuclear visualization and anti-mouse conjugate to 488 was used as a secondary mouse antibody. Thus.
Figure 4:
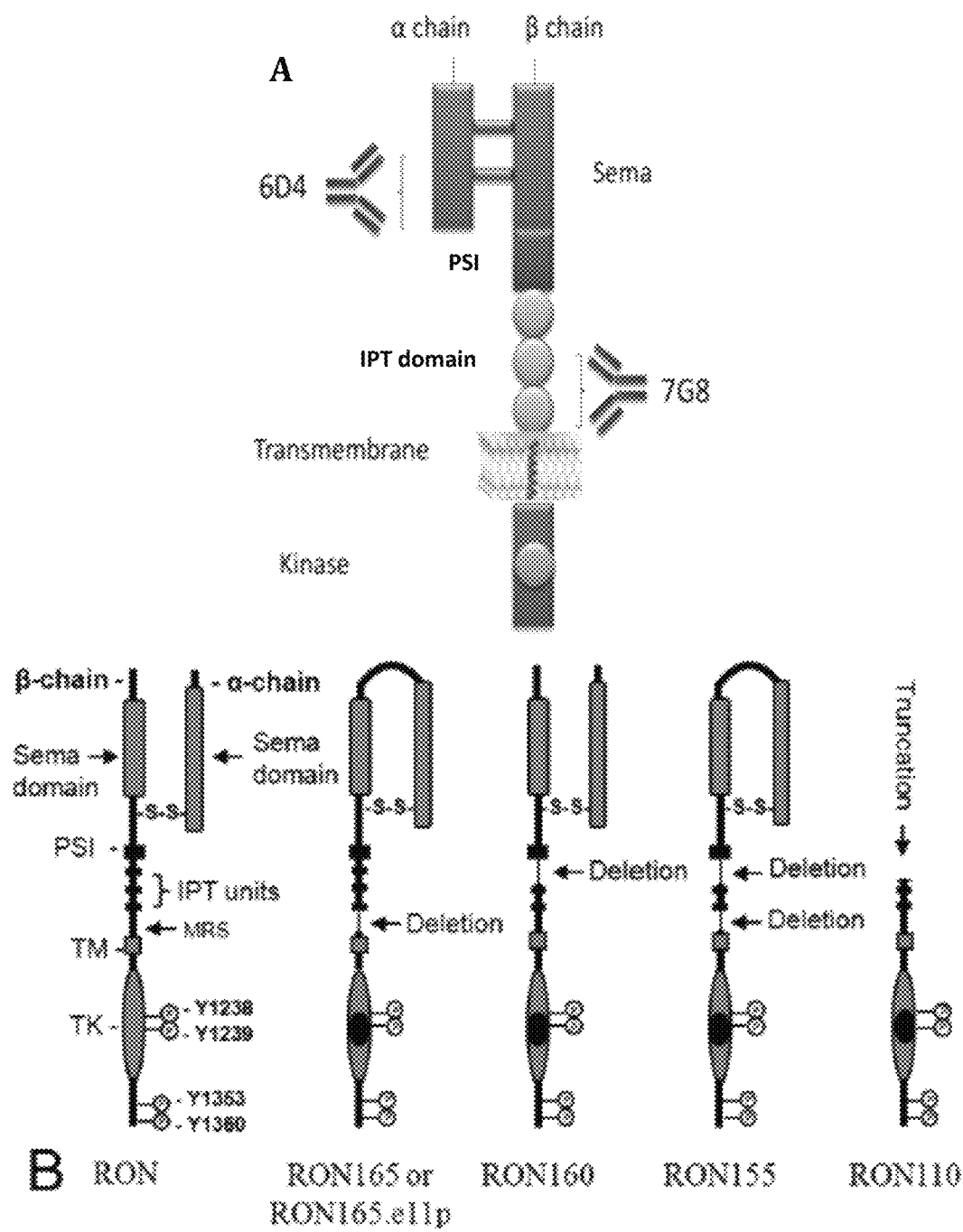
FIG. 4 shows schematic representations of RON protein domains. A shows the RON protein domains which 6D4 and 7G8 antibodies bind to; B shows various isoforms of RON protein.
Figure 5:
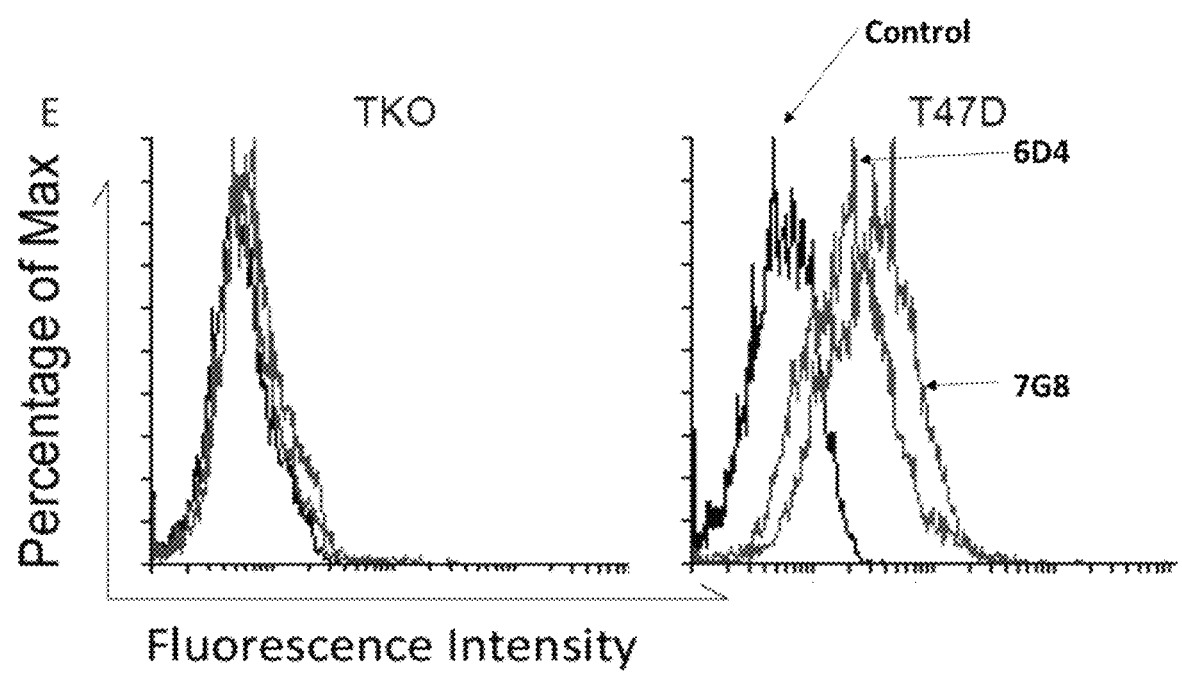
FIG. 5 shows flow cytometry data for exemplary anti-RON Antibodies (6D4 and 7G8 antibodies) on triple-knockout (TKO) cells (left) and human breast cancer cells (T47D cells) (right).
Figure 6:
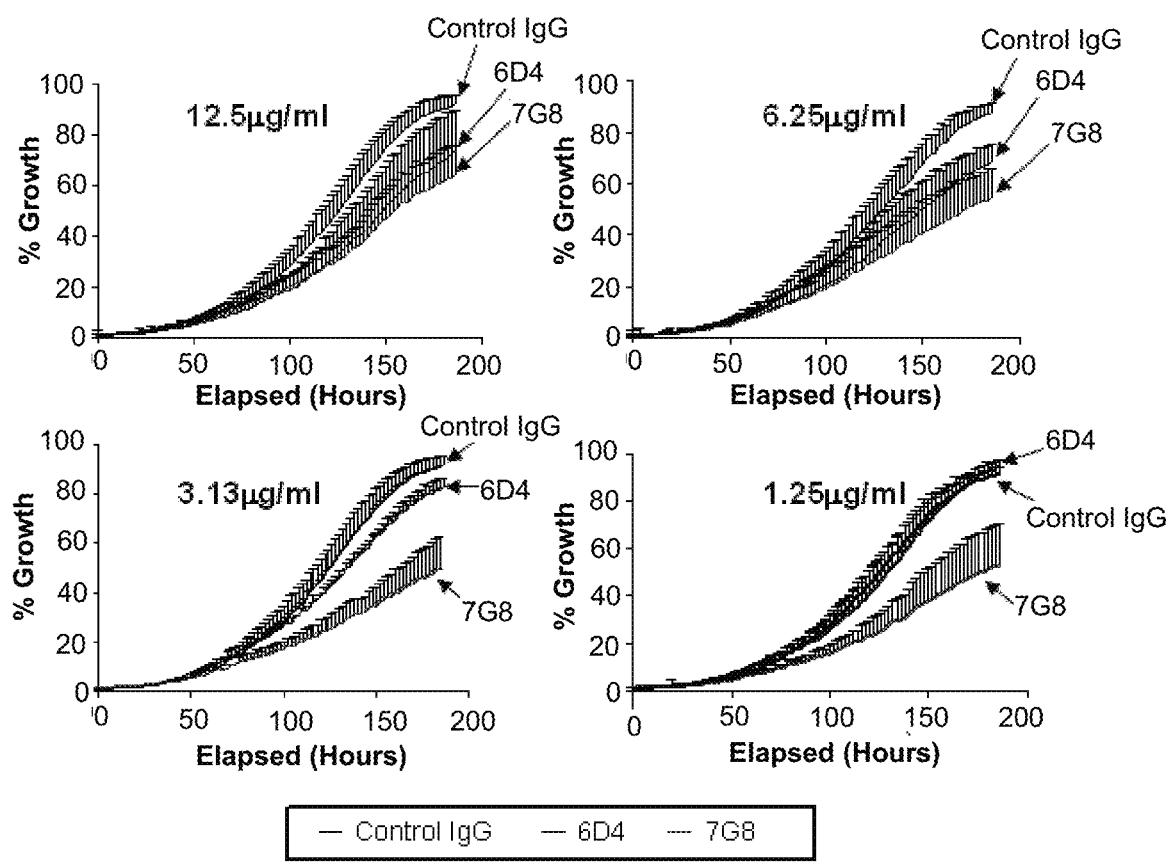
FIG. 6 shows a curve illustrating the cell proliferation of mouse hybridoma cell line (HT29 cells) in complete media in vitro which were monitored over 7 days in the presence of control IgG, and anti-RON Antibodies as described herein (e.g. 6D4 and 7G8 antibodies), via IncuCyte Live Cell Analysis System (Essen BioScience).
Figure 7:
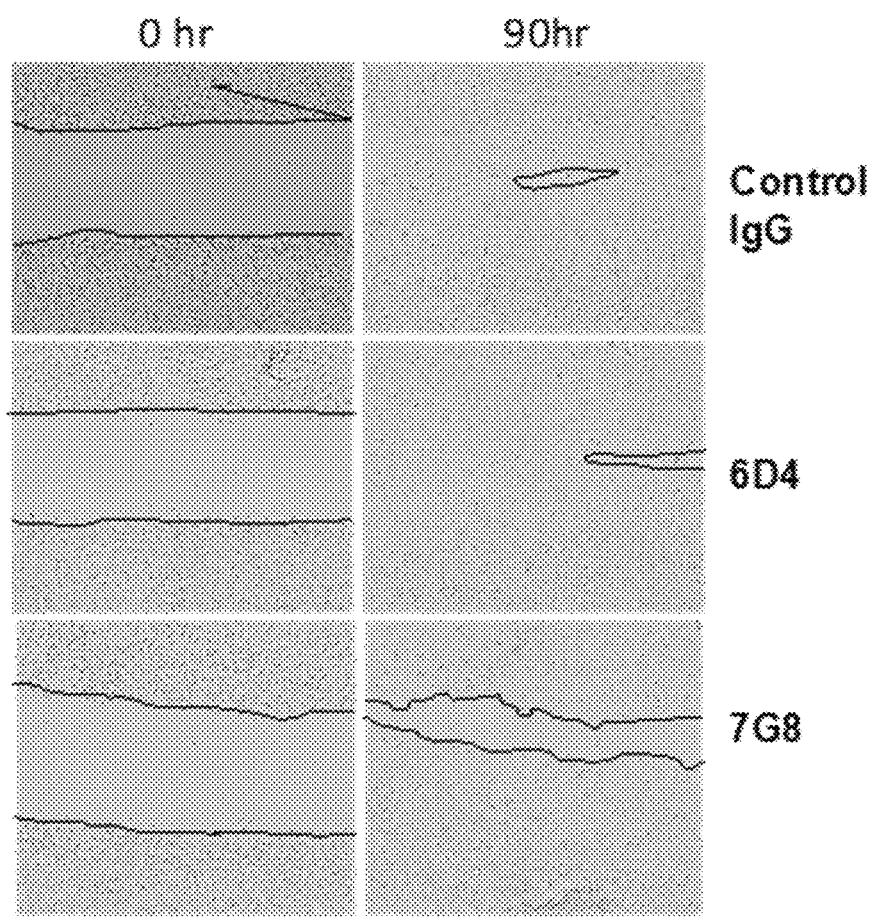
FIG. 7 shows a clear microscope image of the result of a scratch wound inhibition assay of mouse hybridoma (HT29 cell) in presence of control IgG, anti-RON Antibodies as described herein (6D4 or 7G8 antibodies) in scratch wound assay at 0 and 90 hours.
Figure 8:
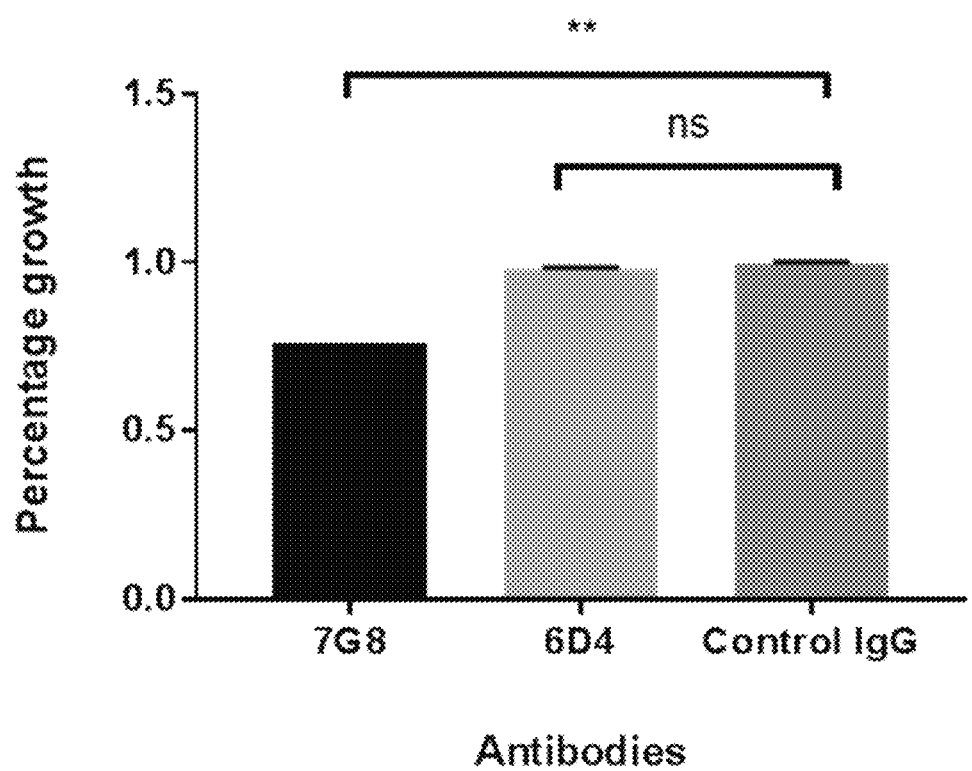
FIG. 8 shows a bar graph of the percentage inhibition of wound healing of mouse hybridoma (HT29 cells) in the presence of control IgG and anti-RON Antibodies as described herein (6D4 or 7G8 antibodies) in scratch wound assay. Percentages were calculated based on remaining wound healing area estimated by Image J software.
Figure 9:
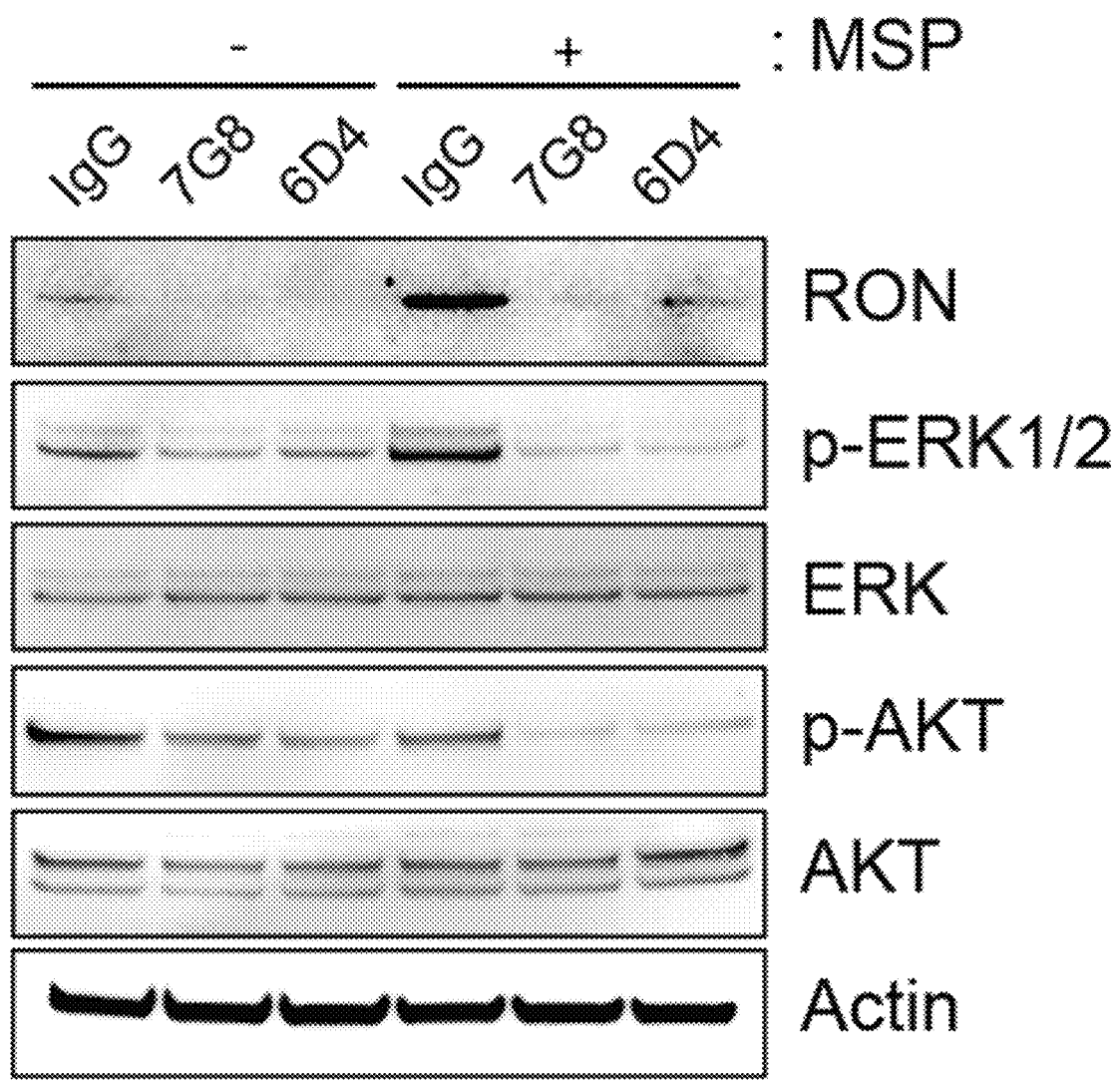
FIG. 9 shows an immunoblot showing the relative protein levels of HT29 cells treated with examplary RON-neutralising antibodies (7G8 or 6D4), or control IgG, in the presence and absence of 10 ng/ml of MSP. Cells were harvested at 48 hours post-treatment.
Figure 10:
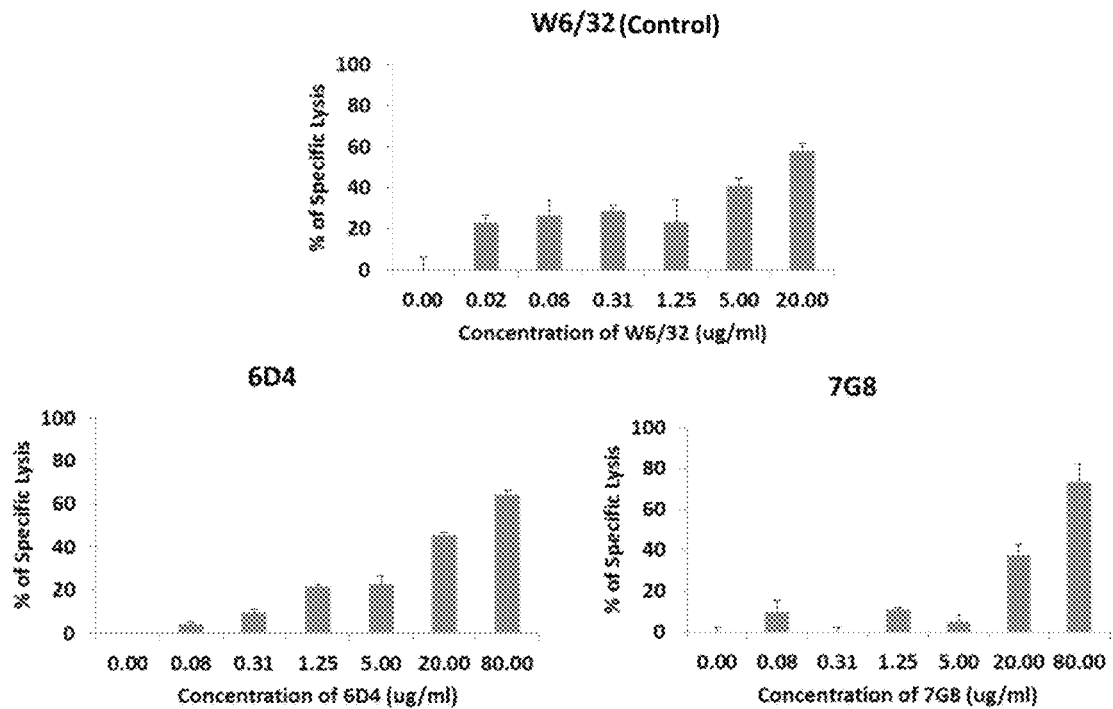
FIG. 10 shows percentage of specific cell lysis in human breast cancer cell lines (T47D cells) measured by europium-TDA (TDA, i.e. 2,2':6',2"-terpyridine-6,6"-dicarboxylic acid) in Antibody-Dependent Cell-Mediated Cytotoxicity (ADCC) assay (Positive Control IgG W6/32 has ADCC functions). Percentage lysis was detected in europium-TDA release assay after co-incubation of antibodies with mouse splenocytes (effector cells) and T47D cells (target) at an effector:target ratio of 150:1 overnight at 37° C. Thus.
Figure 11:
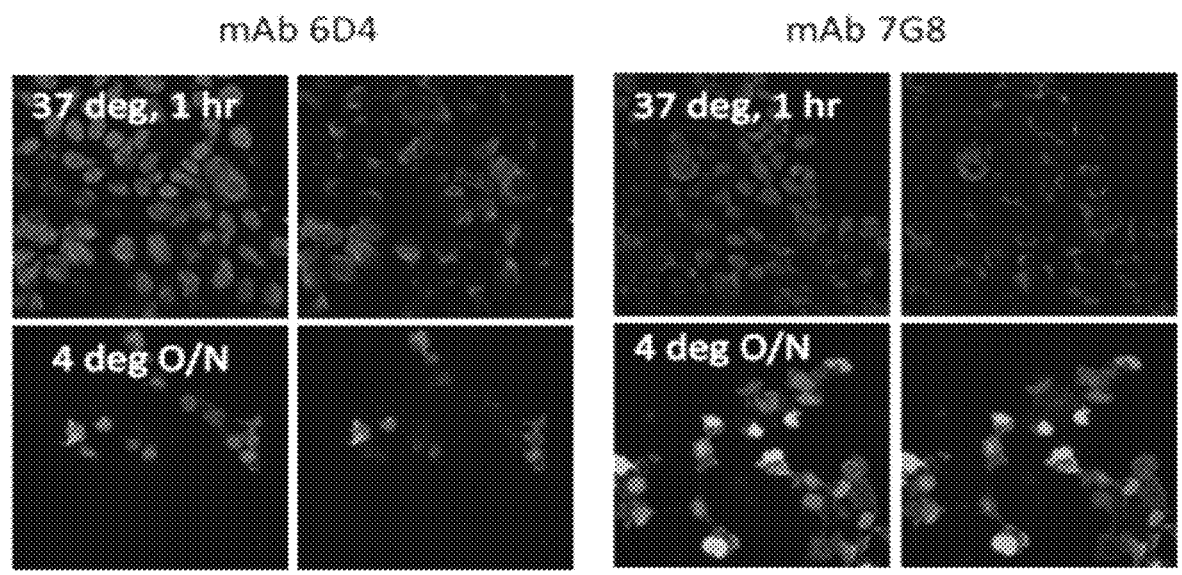
FIG. 11 shows exemplary immunofluorescence staining of anti-RON Antibodies (6D4 and 7G8) antibodies on live HCT116 cells. The two antibodies were incubated with human colon carcinoma cell lines (HCT116 cells) for 1 hour at 37° C. or overnight at 4° C., with serum. Antibody binding was detected using a secondary anti-mouse-FITC antibody.
Figure 12:
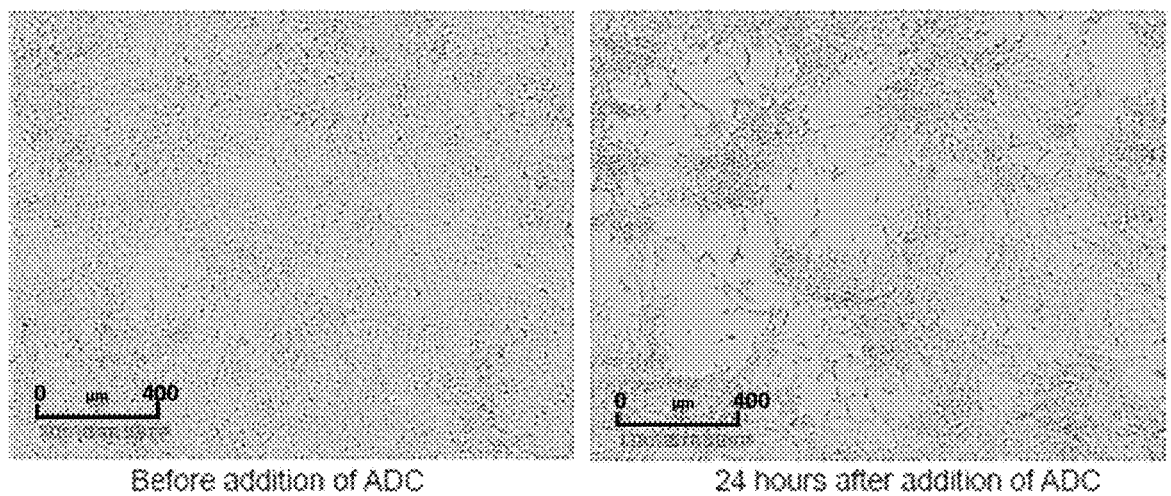
FIG. 12 shows IncuCyte image showing cell death 2 hours after addition of anti-mouse IgG-DM1 (2°ADC) with 7G8 antibody. Thus.
Figure 13A:
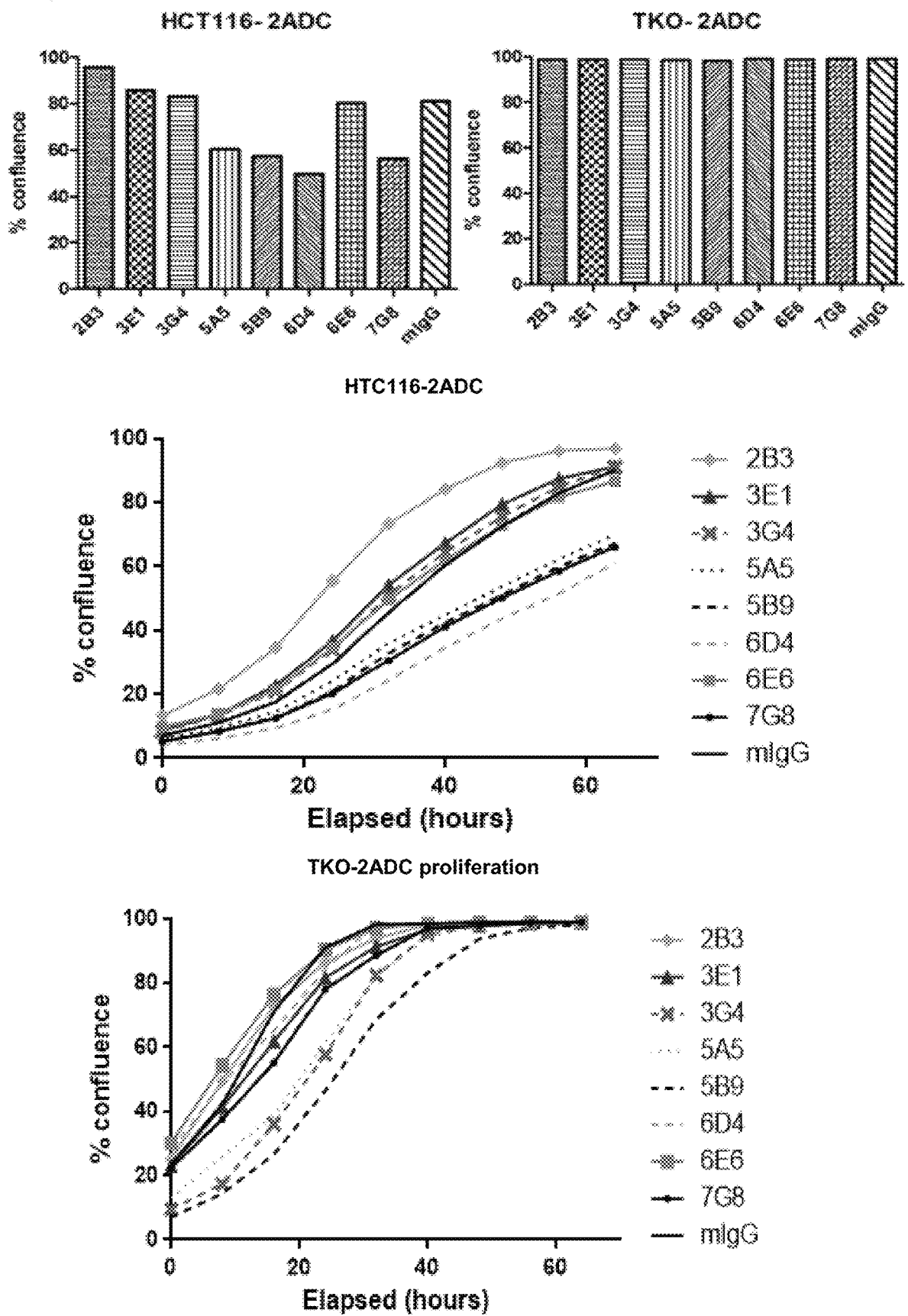
FIG. 13A shows bar graphs of percentage cell growth of human colon carcinoma cell lines (HCT116 cell) and P53, P21 and MDM2 triple knockout mouse embryonic fibroblast (TKO cells), when incubated with the panel of anti-RON Antibodies with 2°ADC (antibody drug conjugate) for 72 hours under image monitoring by IncuCyte to measure cell growth. Thus.
Figure 13:
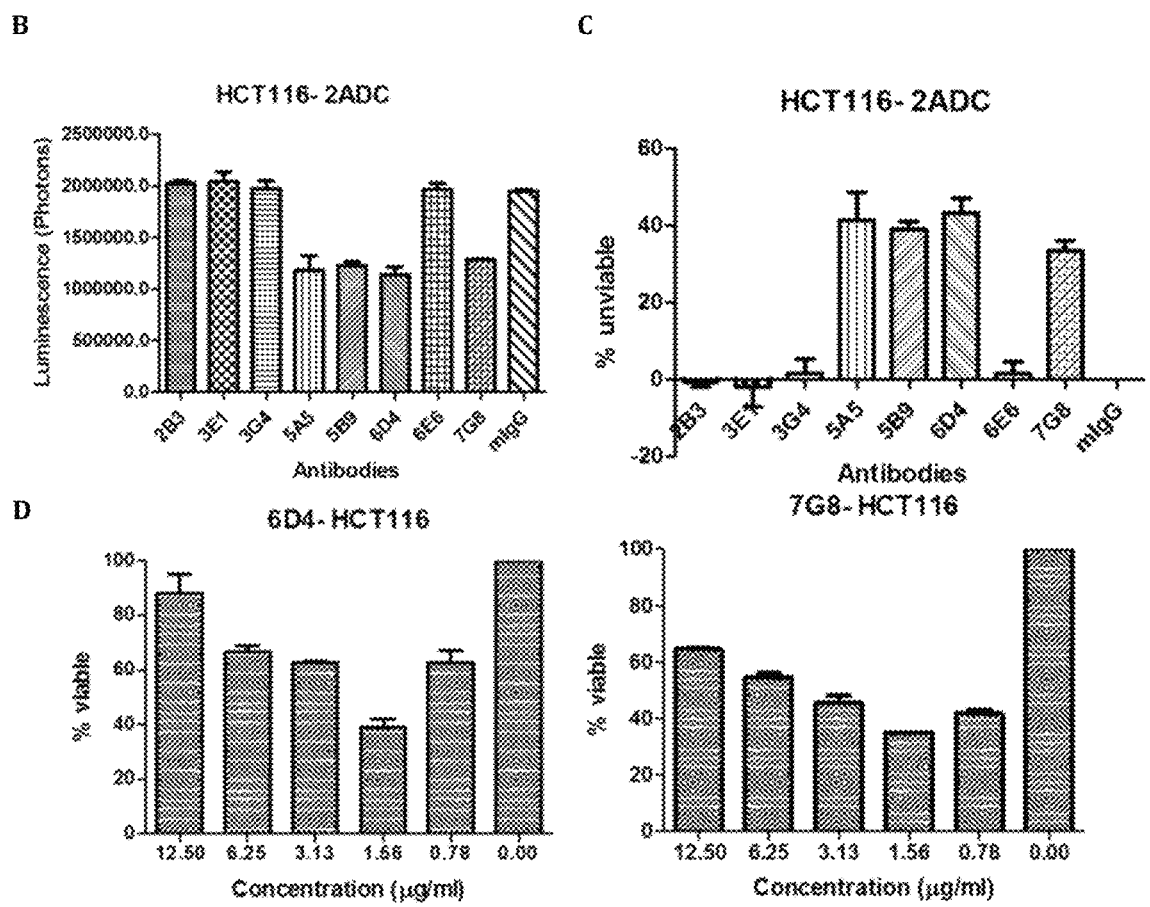
FIG. 13B shows bar graphs of percentage cell viability of human colon carcinoma cell lines (HCT116 cells) when incubated with the panel of anti-RON Antibodies with 2°ADC (antibody drug conjugate) for 72 hours and cell viability investigated using Celltitre Glo Luminescent cell viability assay. Thus.
FIG. 13C shows bar graphs of percentage cell viability of human colon carcinoma cell lines (HCT116 cell) with 2°ADC and treated with the panel of anti-RON Antibodies. Cell viabilities are plotted as percentage of unviable cells in FIG. 13C. Thus.
FIG. 13D shows the cytotoxic profiles of anti-RON Antibodies as described herein (6D4 and 7G8) in a dose dependent manner in the presence of 1 µg/ml of 2°ADC (antibody drug conjugate), on the RON positive human colorectal cancer cells (HCT116 cells). Thus, it can be seen that 6D4 and 7G8 display potent cytotoxicity against human colorectal cancer cells, although killing of HCT116 cells are limited by antibody: antibody drug conjugate ratio.

| No. | Antibody | Peptide Number | Epitope | SEQ ID NO: |
|---|---|---|---|---|
| 1 | 5A5 | 48 | HCPPKLTEFHPHSGP | 10 |
|   |     | 49 | PHSGPLRGSTRLTLC | 11 |
| 2 | 2B3 | 48 | HCPPKLTEFHPHSGP | 10 |
| 3 | 3E1 | 67 | AQVPGSWTFQYREDP | 12 |
|   |     | 68 | YREDPVVLSISPNCG | 13 |
|   |     | 69 | LHTRLARLSATEPEL | 14 |
| 4 | 6E6 | 29 | DPALPALVSCGSSLQ | 15 |
|   |     | 31 | HDLEPQGTAVHLAAP | 16 |
| 5 | 3G4 | 29 | DPALPALVSCGSSLQ | 15 |

DETAILED DESCRIPTION OF THE DISCLOSURE

Macrophage stimulating protein receptor (or RON—Recepteur d' Origine Nantais) is a c-MET-related tyrosine kinase receptor which transduces signals from the extracellular matrix into the cytoplasm when engaged by the ligand MSP. This signalling stimulates the intracellular domain of RON and provides active sites for engaging downstream signalling molecules, such as PIK3R1, PLCG1 or GAB1. Thus, RON is part of the signalling cascade. The human RON receptor tyrosine kinase has the UniProt number Q04912 and the murine protein has the UniProt number Q62190. The receptor is encoded in humans by gene MST1R.

Macrophage stimulating protein receptor (RON) is a c-MET-related tyrosine kinase receptor which the present inventors believe may be an important therapeutic target, in particular for the treatment of cancer. It may be that overexpression of RON is a factor which induces tumorgenesis and it appears to be a hallmark of many human cancers. Cancer patients with RON overexpression also seem to have a worse prognosis in comparison to patients without said overexpression.

Patients with RON positive tumours have a significantly worse 10-year disease-free survival rate than those patients with RON negative tumours (30.3% versus 58.6%, respectively; P=0.009). Patients with both RON positive and MET positive tumours have the lowest 10-year disease-free survival (11.8%), and those with both RON negative and MET negative tumours have the highest 10-year disease-free survival (79.3%; P=0.008). RON expression may also be used as a prognostic biomarker for disease progression and patient survival in some cancers.

In view of the statistics relating RON positivity with survival and progression of cancer patients, the inventors of the present disclosure set out to provide an antibody that recognizes and/or can bind to RON. In particular, various antibodies have been isolated and characterised to recognise cell surface expressed receptor tyrosine kinase RON.

Thus, in one aspect, there is provided a RON specific binding domain comprising the heavy chain CDRs of CDRH1, CDRH2, and CDRH3 and/or the light chain CDRs of CDRL1, CDRL2, and CDRL3, wherein (a) CDRH1 is selected from the group consisting of SEQ ID NO: 1, SEQ ID NO: 27, SEQ ID NO: 45, SEQ ID NO: 56, SEQ ID NO: 73, SEQ ID NO: 89, SEQ ID NO: 100, SEQ ID NO: 116, and SEQ ID NO: 135 or a CDRH1 sequence differing 1 or 2 amino acids therefrom;

(b) CDRH2 is selected from the group consisting of SEQ ID NO: 2, SEQ ID NO: 28, SEQ ID NO: 46, SEQ ID NO: 57, SEQ ID NO: 74, SEQ ID NO: 90, SEQ ID NO: 101, SEQ ID NO: 117, and SEQ ID NO: 136; or a CDRH2 sequence differing 1 or 2 amino acids therefrom;

(c) CDRH3 is selected from the group consisting of SEQ ID NO: 3, SEQ ID NO: 29, SEQ ID NO: 47, SEQ ID NO: 58, SEQ ID NO: 75, SEQ ID NO: 91, SEQ ID NO: 102, and SEQ ID NO: 137; or a CDRH3 sequence differing 1 or 2 amino acids therefrom;

(d) CDRL1 is selected from the group consisting of SEQ ID NO: 18, SEQ ID NO: 36, SEQ ID NO: 65, SEQ ID NO: 81, SEQ ID NO: 108, and SEQ ID NO: 144; or a CDRL1 sequence differing 1 or 2 amino acids therefrom;

(e) CDRL2 is selected from the group consisting of SEQ ID NO: 19, SEQ ID NO: 37, SEQ ID NO: 66, SEQ ID NO: 82, and SEQ ID NO: 109; or a CDRL2 sequence differing 1 or 2 amino acids therefrom; and (f) CDRL3 is selected from the group consisting of SEQ ID NO: 20, SEQ ID NO: 38, SEQ ID NO: 67, SEQ ID NO: 83, SEQ ID NO: 220, SEQ ID NO: 123, and SEQ ID NO: 145; or a CDRL2 sequence differing 1 or 2 amino acids therefrom.

Also disclosed is an antigen binding domain comprising (or consisting of) the heavy chain CDRs of CDRH1, CDRH2, and CDRH3 and/or the light chain CDRs of CDRL1, CDRL2, and CDRL3, wherein (a) CDRH1 is selected from the group consisting of SEQ ID NO: 1, SEQ ID NO: 27, SEQ ID NO: 45, SEQ ID NO: 56, SEQ ID NO: 73, SEQ ID NO: 89, SEQ ID NO: 100, SEQ ID NO: 116, and SEQ ID NO: 135;

(b) CDRH2 is selected from the group consisting of SEQ ID NO: 2, SEQ ID NO: 28, SEQ ID NO: 46, SEQ ID NO: 57, SEQ ID NO: 74, SEQ ID NO: 90, SEQ ID NO: 101, SEQ ID NO: 117, and SEQ ID NO: 136;

(c) CDRH3 is selected from the group consisting of SEQ ID NO: 3, SEQ ID NO: 29, SEQ ID NO: 47, SEQ ID NO: 58, SEQ ID NO: 75, SEQ ID NO: 91, SEQ ID NO: 102, and SEQ ID NO: 137;

(d) CDRL1 is selected from the group consisting of SEQ ID NO: 18, SEQ ID NO: 36, SEQ ID NO: 65, SEQ ID NO: 81, SEQ ID NO: 108, and SEQ ID NO: 144;

(e) CDRL2 is selected from the group consisting of SEQ ID NO: 19, SEQ ID NO: 37, SEQ ID NO: 66, SEQ ID NO: 82, and SEQ ID NO: 109; and (f) CDRL3 is selected from the group consisting of SEQ ID NO: 20, SEQ ID NO: 38, SEQ ID NO: 67, SEQ ID NO: 83, SEQ ID NO: 220, SEQ ID NO: 123, and SEQ ID NO: 145.

Also provided is an isolated antibody, or fragment thereof, wherein the antibody, or fragment thereof, comprises (or consists of) the heavy chain CDRs of CDRH1, CDRH2, and CDRH3 and/or the light chain CDRs of CDRL1, CDRL2, and CDRL3, wherein (a) CDRH1 is selected from the group consisting of SEQ ID NO: 1, SEQ ID NO: 10, SEQ ID NO: 27, SEQ ID NO: 45, SEQ ID NO: 56, SEQ ID NO: 73, SEQ ID NO: 89, SEQ ID NO: 116, S and SEQ ID NO: 100; or a CDRH1 sequence differing 1 or 2 amino acids therefrom;

(b) CDRH2 is selected from the group consisting of SEQ ID NO: 2, SEQ ID NO: 11, SEQ ID NO: 28, SEQ ID NO: 46, SEQ ID NO: 57, SEQ ID NO: 74, SEQ ID NO: 90, and SEQ ID NO: 101; or SEQ ID NO: 117 or a CDRH2 sequence differing 1 or 2 amino acids therefrom;

(c) CDRH3 is selected from the group consisting of SEQ ID NO: 3, SEQ ID NO: 12, SEQ ID NO: 29, SEQ ID NO: 47, SEQ ID NO: 58, SEQ ID NO: 75, SEQ ID NO: 91, and SEQ ID NO: 102; or a CDRH3 sequence differing 1 or 2 amino acids therefrom;

(d) CDRL1 is selected from the group consisting of SEQ ID NO: 18, SEQ ID NO: 36, SEQ ID NO: 65, SEQ ID NO: 81, and SEQ ID NO: 108; or a CDRL1 sequence differing 1 or 2 amino acids therefrom;

(e) CDRL2 is selected from the group consisting of SEQ ID NO: 19, SEQ ID NO: 37, SEQ ID NO: 66, SEQ ID NO: 82, and SEQ ID NO: 109; or a CDRL2 sequence differing 1 or 2 amino acids therefrom; and (f) CDRL3 is selected from the group consisting of SEQ ID NO: 20, SEQ ID NO: 38, SEQ ID NO: 67, SEQ ID NO: 83, and SEQ ID NO: 123; or a CDRL2 sequence differing 1 or 2 amino acids therefrom.

In some examples, the antibody as described herein has the heavy chain CDRs that are selected from the group consisting of:

(a) a CDRH1 having the sequence SEQ ID NO: 1, a CDRH2 having the sequence SEQ ID NO: 2, and a CDRH3 having the sequence SEQ ID NO: 3, and/or a CDRH1 having the sequence SEQ ID NO: 10, a CDRH2 having the sequence SEQ ID NO: 11, and a CDRH3 having the sequence SEQ ID NO: 12; or a CDRH1, CDRH2, or CDRH3 sequence differing 1 or 2 amino acids therefrom;

(b) a CDRH1 having the sequence SEQ ID NO: 27, a CDRH2 having the sequence SEQ ID NO: 28, and a CDRH3 having the sequence SEQ ID NO: 29; or a CDRH1, CDRH2, or CDRH3 sequence differing 1 or 2 amino acids therefrom;

(c) a CDRH1 having the sequence SEQ ID NO: 45, a CDRH2 having the sequence SEQ ID NO: 46, and a CDRH3 having the sequence SEQ ID NO: 47; or a CDRH1, CDRH2, or CDRH3 sequence differing 1 or 2 amino acids therefrom;

(d) a CDRH1 having the sequence SEQ ID NO: 56, a CDRH2 having the sequence SEQ ID NO: 57, and a CDRH3 having the sequence SEQ ID NO: 58; or a CDRH1, CDRH2, or CDRH3 sequence differing 1 or 2 amino acids therefrom;

(e) a CDRH1 having the sequence SEQ ID NO: 73, a CDRH2 having the sequence SEQ ID NO: 74, and a CDRH3 having the sequence SEQ ID NO: 75; or a CDRH1, CDRH2, or CDRH3 sequence differing 1 or 2 amino acids therefrom;

(f) a CDRH1 having the sequence SEQ ID NO: 89, a CDRH2 having the sequence SEQ ID NO: 90, and a CDRH3 having the sequence SEQ ID NO: 101; or a CDRH1, CDRH2, or CDRH3 sequence differing 1 or 2 amino acids therefrom;

(g) a CDRH1 having the sequence SEQ ID NO: 116, a CDRH2 having the sequence SEQ ID NO: 117, and a CDRH3 having the sequence SEQ ID NO: 102; or a CDRH1, CDRH2, or CDRH3 sequence differing 1 or 2 amino acids therefrom;

(h) a CDRH1 having the sequence SEQ ID NO: 116, a CDRH2 having the sequence SEQ ID NO: 117, and a CDRH3 having the sequence SEQ ID NO: 102; or a CDRH1, CDRH2, or CDRH3 sequence differing 1 or 2 amino acids therefrom;

(i) a CDRH1 having the sequence SEQ ID NO: 116, a CDRH2 having the sequence SEQ ID NO: 101, and a CDRH3 having the sequence SEQ ID NO: 102; or a CDRH1, CDRH2, or CDRH3 sequence differing 1 or 2 amino acids therefrom; and (a) a CDRH1 having the sequence SEQ ID NO: 100, a CDRH2 having the sequence SEQ ID NO: 101, and a CDRH3 having the sequence SEQ ID NO: 102 or a CDRH1, CDRH2, or CDRH3 sequence differing 1 or 2 amino acids therefrom; and (j) a CDRH1, a CDRH2, and a CDRH3 as recited in Table 1, or CDRH1 or CDRH2 or CDRH3 differing 1 or 2 amino acids therefrom.

In some examples, the antibodies as described herein has light chain CDRs are selected from the group consisting of:

(b) a CDRL1 having the sequence SEQ ID NO: 18, a CDRL2 having the sequence SEQ ID NO: 19, and a CDRL3 having the sequence SEQ ID NO: 20; or a CDRL1, CDRL2, or CDRL3 sequence differing 1 or 2 amino acids therefrom;

(c) a CDRL1 having the sequence SEQ ID NO: 36, a CDRL2 having the sequence SEQ ID NO: 37, and a CDRL3 having the sequence SEQ ID NO: 38; or a CDRL1, CDRL2, or CDRL3 sequence differing 1 or 2 amino acids therefrom;

(d) a CDRL1 having the sequence SEQ ID NO: 18, a CDRL2 having the sequence SEQ ID NO: 19, and a CDRL3 having the sequence SEQ ID NO: 20; or a CDRL1, CDRL2, or CDRL3 sequence differing 1 or 2 amino acids therefrom;

(e) a CDRL1 having the sequence SEQ ID NO: 65, a CDRL2 having the sequence SEQ ID NO: 66, and a CDRL3 having the sequence SEQ ID NO: 67; or a CDRL1, CDRL2, or CDRL3 sequence differing 1 or 2 amino acids therefrom;

(f) a CDRL1 having the sequence SEQ ID NO: 81, a CDRL2 having the sequence SEQ ID NO: 82, and a CDRL3 having the sequence SEQ ID NO: 83; or a CDRL1, CDRL2, or CDRL3 sequence differing 1 or 2 amino acids therefrom;

(g) a CDRL1 having the sequence SEQ ID NO: 65, a CDRL2 having the sequence SEQ ID NO: 66, and a CDRL3 having the sequence SEQ ID NO: 67; or a CDRL1, CDRL2, or CDRL3 sequence differing 1 or 2 amino acids therefrom;

(h) a CDRL1 having the sequence SEQ ID NO: 108, a CDRL2 having the sequence SEQ ID NO: 109, and a CDRL3 having the sequence SEQ ID NO:123; or a CDRL1, CDRL2, or CDRL3 sequence differing 1 or 2 amino acids therefrom; and (i) a CDRL1, a CDRL2, and a CDRL3 as recited in Table 1, or CDRL1 or CDRL2 or CDRL3 differing 1 or 2 amino acids therefrom.

In some examples, the antibodies as described herein has the heavy chain CDRs and light chain CDRs are selected from the group consisting of:

(a) a CDRH1 having the sequence SEQ ID NO: 1, a CDRH2 having the sequence SEQ ID NO: 2, and a CDRH3 having the sequence SEQ ID NO: 3, and/or a CDRH1 having the sequence SEQ ID NO: 10, a CDRH2 having the sequence SEQ ID NO: 11, and a CDRH3 having the sequence SEQ ID NO: 12, and a CDRL1 having the sequence SEQ ID NO: 18, a CDRL2 having the sequence SEQ ID NO: 19, and a CDRL3 having the sequence SEQ ID NO: 20;

(b) a CDRH1 having the sequence SEQ ID NO: 27, a CDRH2 having the sequence SEQ ID NO: 28, and a CDRH3 having the sequence SEQ ID NO: 29, and a CDRL1 having the sequence SEQ ID NO: 36, a CDRL2 having the sequence SEQ ID NO: 37, and a CDRL3 having the sequence SEQ ID NO: 38;

(c) a CDRH1 having the sequence SEQ ID NO: 45, a CDRH2 having the sequence SEQ ID NO: 46, and a CDRH3 having the sequence SEQ ID NO: 47, and a CDRL1 having the sequence SEQ ID NO: 18, a CDRL2 having the sequence SEQ ID NO: 19, and a CDRL3 having the sequence SEQ ID NO: 20;

(d) a CDRH1 having the sequence SEQ ID NO: 56, a CDRH2 having the sequence SEQ ID NO: 57, and a CDRH3 having the sequence SEQ ID NO: 58, and a CDRL1 having the sequence SEQ ID NO: 65, a CDRL2 having the sequence SEQ ID NO: 66, and a CDRL3 having the sequence SEQ ID NO: 67;

(e) a CDRH1 having the sequence SEQ ID NO: 73, a CDRH2 having the sequence SEQ ID NO: 74, and a CDRH3 having the sequence SEQ ID NO: 75, and a CDRL1 having the sequence SEQ ID NO: 81, a CDRL2 having the sequence SEQ ID NO: 82, and a CDRL3 having the sequence SEQ ID NO: 83;

(f) a CDRH1 having the sequence SEQ ID NO: 89, a CDRH2 having the sequence SEQ ID NO: 90, and a CDRH3 having the sequence SEQ ID NO: 91, and a CDRL1 having the sequence SEQ ID NO: 65, a CDRL2 having the sequence SEQ ID NO: 66, and a CDRL3 having the sequence SEQ ID NO:67;

(g) a CDRH1 having the sequence SEQ ID NO: 116, a CDRH2 having the sequence SEQ ID NO: 117, and a CDRH3 having the sequence SEQ ID NO: 102, and a CDRL1 having the sequence SEQ ID NO: 108, a CDRL2 having the sequence SEQ ID NO: 109, and a CDRL3 having the sequence SEQ ID NO: 123; and (h) a CDRH1, a CDRH2, a CDRH3 having a sequence as recited in Table 1, and a CDRL1, a CDRL2, a CDRL3 as recited in Table 1.

In some examples, the antibodies as described herein comprises (or consists of) a heavy chain variable region encoded by a nucleotide sequence having at least 80%, or at least 85% or at least 90%, or at least 95%, or at least 96%, or at least 97%, or at least 98%, or at least 99% sequence identity to one of the nucleotide sequence recited in Table 1 or selected from the group consisting of SEQ ID NO: 9, SEQ ID NO: 35, SEQ ID NO: 52 SEQ ID NO: 64, SEQ ID NO: 80, SEQ ID NO: 96, SEQ ID NO: 122, SEQ ID NO: 131, SEQ ID NO: 134, and SEQ ID NO: 107.

In some examples, the antibody as described herein comprises (or consists of) a light chain variable region encoded by a nucleotide sequence having at least 80%, or at least 85% or at least 90%, or at least 95%, or at least 96%, or at least 97%, or at least 98%, or at least 99% sequence identity to one of the nucleotide sequence recited in Table 1 or selected from the group consisting of SEQ ID NO: 26, SEQ ID NO: 44, SEQ ID NO: 55, SEQ ID NO: 72, SEQ ID NO: 88, SEQ ID NO: 99, and SEQ ID NO: 128.

In some examples, the antibody as described herein comprises (or consists of) a heavy chain variable region encoded by a nucleotide sequence to one of selected from the group consisting of SEQ ID NO: 9, SEQ ID NO: 35, SEQ ID NO: 52, SEQ ID NO: 64, SEQ ID NO: 80, SEQ ID NO: 96, SEQ ID NO: 122, SEQ ID NO; 131, SEQ ID NO: 134, SEQ ID NO: 107.

In some examples, the antibody as described herein comprises (or consists of) a light chain variable region encoded by a nucleotide sequence to one of selected from the group consisting of SEQ ID NO: 26, SEQ ID NO: 44, SEQ ID NO: 55, SEQ ID NO: 72, SEQ ID NO: 88, SEQ ID NO: 99, and SEQ ID NO: 128.

In some examples, the antibody as described herein comprises (or consists of) a heavy chain variable region selected from the group consisting of:
(a) an amino acid sequence of SEQ ID NO: 8;
(b) an amino acid sequence SEQ ID NO: 34;
(c) an amino acid sequence SEQ ID NO: 51;
(d) an amino acid sequence SEQ ID NO: 63;
(e) an amino acid sequence SEQ ID NO: 79;
(f) an amino acid sequence SEQ ID NO: 95;
(g) an amino acid sequence SEQ ID NO: 121;
(h) an amino acid sequence SEQ ID NO: 130;
(i) an amino acid sequence SEQ ID NO: 132;
(j) an amino acid sequence SEQ ID NO: 106; and
(k) an amino acid sequence having a sequence identity of at least 85%, or at least 90%, or at least 95%, or at least 96%, or at least 97%, or at least 98%, or at least 99%, or at least 99.95%, or 100% of (a) to (k).

In some examples, the antibody as described herein comprises (or consists of) a light chain variable region selected from the group consisting of:
(a) an amino acid sequence of SEQ ID NO: 25;
(b) an amino acid sequence SEQ ID NO: 43;
(c) an amino acid sequence SEQ ID NO: 54;
(d) an amino acid sequence SEQ ID NO: 71;
(e) an amino acid sequence SEQ ID NO: 87;
(f) an amino acid sequence SEQ ID NO: 98;
(g) an amino acid sequence SEQ ID NO: 127; and
(h) an amino acid sequence having a sequence identity of at least 85%, or at least 90%, or at least 95%, or at least 96%, or at least 97%, or at least 98%, or at least 99%, or at least 99.95%, or 100% of (a) to (h).

In some examples, the antibody as described herein may further comprises (or consists of) a framework sequence.

In some examples, the antibody as described herein may comprise the heavy chain framework sequence comprising (or consisting of) at least 90%, or at least 95%, or at least 96%, or at least 97%, or at least 98%, or at least 99%, or 100% sequence identity to framework selected from the group consisting of:
(a) an FR1 having the sequence SEQ ID NO: 4, an FR2 having the sequence SEQ ID NO: 5, an FR3 having the sequence SEQ ID NO: 6, and an FR4 having the sequence SEQ ID NO: 7, an FR2 having the sequence SEQ ID NO: 14, and an FR3 having the sequence SEQ ID NO: 15;
(b) an FR1 having the sequence SEQ ID NO: 30, an FR2 having the sequence SEQ ID NO: 31, an FR3 having the sequence SEQ ID NO: 32, and an FR4 having the sequence SEQ ID NO: 33;
(c) an FR1 having the sequence SEQ ID NO: 48, an FR2 having the sequence SEQ ID NO: 49, an FR3 having the sequence SEQ ID NO: 50, and an FR4 having the sequence SEQ ID NO: 7;
(d) an FR1 having the sequence SEQ ID NO: 59, an FR2 having the sequence SEQ ID NO: 60, an FR3 having the sequence SEQ ID NO: 61, and an FR4 having the sequence SEQ ID NO: 62;
(e) an FR1 having the sequence SEQ ID NO: 76, an FR2 having the sequence SEQ ID NO: 77, an FR3 having the sequence SEQ ID NO: 86, and an FR4 having the sequence SEQ ID NO: 7;
(f) an FR1 having the sequence SEQ ID NO: 92, an FR2 having the sequence SEQ ID NO: 93, an FR3 having the sequence SEQ ID NO: 94, and an FR4 having the sequence SEQ ID NO: 62;
(g) an FR1 having the sequence SEQ ID NO: 118, an FR2 having the sequence SEQ ID NO: 119, an FR3 having the sequence SEQ ID NO: 120, and an FR4 having the sequence SEQ ID NO: 7;
(h) an FR1 having the sequence SEQ ID NO: 129, an FR2 having the sequence SEQ ID NO: 119, an FR3 having the sequence SEQ ID NO: 120, and an FR4 having the sequence SEQ ID NO: 7;
(i) an FR1 having the sequence SEQ ID NO: 129, an FR2 having the sequence SEQ ID NO: 119, an FR3 having the sequence SEQ ID NO: 120, and an FR4 having the sequence SEQ ID NO: 132;
(j) an FR1 having the sequence SEQ ID NO: 103, an FR2 having the sequence SEQ ID NO: 104, an FR3 having the sequence SEQ ID NO: 105; and
(k) an FR as recited in Table 1.

In some examples, the antibody as described herein may comprise (or consist of) the light chain framework sequence comprising at least 90%, or at least 95%, or at least 96%, or at least 97%, or at least 98%, or at least 99%, or 100% sequence identity to framework selected from the group consisting of:
(a) an FR1 having the sequence SEQ ID NO: 21, an FR2 having the sequence SEQ ID NO: 22, an FR3 having the sequence SEQ ID NO: 23, and an FR4 having the sequence SEQ ID NO: 24;
(b) an FR1 having the sequence SEQ ID NO: 39, an FR2 having the sequence SEQ ID NO: 40, an FR3 having the sequence SEQ ID NO: 41, and an FR4 having the sequence SEQ ID NO: 42;
(c) an FR1 having the sequence SEQ ID NO: 53, an FR2 having the sequence SEQ ID NO: 22, an FR3 having the sequence SEQ ID NO: 23, and an FR4 having the sequence SEQ ID NO: 24;
(d) an FR1 having the sequence SEQ ID NO: 68, an FR2 having the sequence SEQ ID NO: 69, an FR3 having the sequence SEQ ID NO: 41, and an FR4 having the sequence SEQ ID NO: 70;
(e) an FR1 having the sequence SEQ ID NO: 84, an FR2 having the sequence SEQ ID NO: 85, an FR3 having the sequence SEQ ID NO: 86, and an FR4 having the sequence SEQ ID NO: 42;
(f) an FR1 having the sequence SEQ ID NO: 97, an FR2 having the sequence SEQ ID NO: 69, an FR3 having the sequence SEQ ID NO: 41, and an FR4 having the sequence SEQ ID NO: 70; and
(g) an FR1 having the sequence SEQ ID NO: 124, an FR2 having the sequence SEQ ID NO: 125, and an FR3 having the sequence SEQ ID NO: 126, (and optionally an FR4 having the sequence SEQ ID NO: 42); and
(h) an FR as recited in Table 1.

In some examples, the antibody as described herein binds to a receptor tyrosine kinase RON (Recepteur d' Origine Nantais (RON), or Macrophage Stimulating Protein Receptor (MSP R, or MST1-R)).

In some examples, the antibody as described herein binds specifically to a human and/or a mouse RON.

In some examples, the antibody as described herein binds to a cell surface expressed RON.

In some examples, the antibody as described herein is capable of being (or is) endocytosed by a target cell. This may be particular advantageous when the antibody molecule is conjugated to a payload because the payload may be delivered into the cell (not just to the exterior of the cell). Thus the use of payloads that are activated by enzymes inside the cancer cell are envisaged.

In some examples, the antibody as described herein may be a monoclonal antibody.

In some examples, the antibody as described herein may be a chimeric antibody and/or multispecific antibody.

In some examples, the antibody as described herein may be a humanized antibody.

In some examples, the antibody as described herein may be a fragment, such as, but is not limited to, a Fab fragment, a Fab' fragment, a F(ab')2 fragment, a Fv fragment, a diabody, a single chain antibody molecule, and the like.

In some examples, the antibody as described herein may be an IgG1 antibody, an IgG2 antibody, an IgG3 antibody, or an IgG4 antibody.

In some examples, the antibody as described herein may be transferred to a human IgG scaffold.

In some examples, the antibody as described herein may be conjugated to a chemical moiety selected from the group consisting of a therapeutic agent, an immunoadhesion molecule, and a detection label (such as an imaging label).

In some examples, the detection label may include, but is not limited to a radiolabel, an enzyme, a fluorescent label, a luminescent label, a bioluminescent label, a magnetic label, a biotin, and the like.

In some examples, the therapeutic agent may be an anti-cancer treatment.

In some examples, there is provided a pharmaceutical composition comprising the antibody or fragment thereof as described herein.

In some example, wherein the pharmaceutical composition may further comprise a pharmaceutically acceptable carrier, excipient, and/or stabilizer.

In some example, there is provided a kit, comprising the RON specific binding domain, chimeric antigen receptor, antibody, or composition as described herein.

In some example, there is provided an isolated nucleic acid comprising any one selected from the group consisting of:
(g) a nucleotide sequence encoding the antibody or fragment thereof as described herein;
(h) a nucleotide sequence encoding:
a heavy chain region having at least 80%, or at least 90%, or at least 95%, or at least 96%, or at least 97%, or at least 98%, or at least 99%, or 100% of one of heavy region recited in Table 1, or one selected from the group consisting of SEQ ID NO: 9, SEQ ID NO: 35, SEQ ID NO: 52, SEQ ID NO: 64, SEQ ID NO: 80, SEQ ID NO: 96, SEQ ID NO: 122, SEQ ID NO: 131, SEQ ID NO: 134,and SEQ ID NO: 107; and/or
a light chain region having at least 80%, or at least 90%, or at least 95%, or at least 96%, or at least 97%, or at least 98%, or at least 99%, or 100% of one light region recited in Table 1, or one selected from the group consisting of SEQ ID NO: 26, SEQ ID NO: 44, SEQ ID NO: 55, SEQ ID NO: 72, SEQ ID NO: 88, SEQ ID NO: 99, and SEQ ID NO: 128.
(i) a nucleic acid complementary to any one of the sequences in (a) or (b); and
(j) a nucleic acid sequence capable of hybridizing to (a), (b), or (c) under stringent conditions.

In some examples, there is provided an expression vector comprising the nucleic acid as described herein.

In some examples, there is provided a host cell comprising the expression vector as described herein.

In some examples, there is provided method of producing a polypeptide comprising an immunoglobulin heavy chain variable region and/or an immunoglobulin light chain variable region, the method comprising: growing the host cell as described herein under conditions so that the host cell expresses the polypeptide comprising the immunoglobulin heavy chain variable region and/or the immunoglobulin heavy chain variable region.

In some examples, the method of producing the polypeptide as described herein further comprises the step of purifying the polypeptide comprising the immunoglobulin heavy chain variable region and/or the immunoglobulin light chain variable region.

In some examples, the isolated antibody or fragment thereof as described herein, or pharmaceutical composition as described herein for use in medicine.

In some examples, the isolated antibody or fragment thereof as described herein to 140, or pharmaceutical composition as described herein, for use in treating cancer.

In some examples, there is provided a method of treating cancer in a subject in need thereof, comprising administering an isolated antibody, or fragment thereof, as described herein to the subject.

In some examples, the method of treating cancer as described herein further include administering a therapeutic agent selected from the group consisting of an anti-cancer agent (such as a second anti-cancer antibody), and a chemotherapeutic agent.

In some examples, the therapeutic agent may be an anti-cancer agent such as, but is not limited to, a drug conjugate (such as mertansine or DM1(N2'-deacetyl-N2'-(3-mercapto-1-oxopropyl)-maytansine).

In some examples, the cancer may be a RON expressing cancer such as, but is not limited to colorectal cancer, non-small cell lung cancer, breast cancer, ovarian cancer, prostate cancer, cervical cancer, lung cancer, renal cancer, bladder cancer, gastrointestinal tumors, liver cancer, pancreatic cancer, gastric cancer, head and neck cancers, and the like.

In some examples, the isolated antibody or fragment thereof, may be administered in a pharmaceutically effective amount.

In some examples, there is provided a method of detecting a tumor cell in a subject, comprising detecting the expression of RON in a sample obtained from the subject using an antibody as described herein.

In some examples, the tumor cell may be a cancer cell.

In some examples, wherein the cancer is a RON expressing cancer, such as, but is not limited to colorectal cancer, non-small cell lung cancer, breast cancer, ovarian cancer, prostate cancer, cervical cancer, lung cancer, renal cancer, bladder cancer, gastrointestinal tumors, liver cancer, pancreatic cancer, gastric cancer, head and neck cancers, and the like.

RON is expressed and may be over-expressed by many cancers, in particular many epithelial cancers.

The binding domains of the present disclosure can target the surface expressed RON. However, the data generated by the present inventions suggests that the antibody molecules comprising said binding domains are taken into the cell (expressing the RON) by a process involving active transport known as endocytosis. Once in the cells the antibody molecule may be localised in the cytoplasm or a cell nucleus. This is likely to be really beneficial in that the toxins or biological molecule conjugated to the antibody molecule may be internalized into the cancerous cell. Thus it may be possible to minimise the systemic toxicity and off target effects, for example by employing a toxin that is only activated inside the cell.

In particular wherein the binding domain is part of an antibody or binding fragment thereof. The disclosure also extends to pharmaceutical compositions comprising the binding domain (or an entity, such as an antibody or binding fragment, containing the binding domain), polynucleotides encoding the binding domain (or encoding an entity such as an antibody or binding fragment, containing the binding domain). In a further aspect there is provided a binding domain or an entity comprising the same or a pharmaceutical composition of any one of the same for use in treatment, in particular the treatment of cancer. In one example the binding domain according to the present disclosure is employed in a combination therapy with a further therapeutic agent. The entities, such as antibodies and binding fragments thereof may also be employed as research a tool, a reagent, a diagnostic or part-thereof and/or a prognostic agent or part thereof.

As mentioned above, RON is expressed and may be over-expressed by many cancers, in particular many epithelial cancers. As illustrated in the Figures generated from the Experimental section of the present disclosure, the binding domains of the present disclosure can target the surface expressed RON. Further, the data generated by the present inventions suggests that the antibody molecules comprising said binding domains are taken into the cell (expressing the RON) by a process involving active transport known as endocytosis. Once in the cells the antibody molecule may be localised in the cytoplasm or a cell nucleus. This is likely to be really beneficial in that the toxins or biological molecule conjugated to the antibody molecule may be internalized into the cancerous cell. Thus it may be possible to minimise the systemic toxicity and off target effects, for example by employing a toxin that is only activated inside the cell.

The binding domains (and antibody molecules) of the present disclosure are specific for human RON. However, they also recognise (i.e. are cross-reactive with) at least one non-human RON protein, for example murine RON. Thus the antibodies cross react with mouse and human protein. This is a very useful unexpected property as it allows easy preclinical analysis of potential toxicity to normal tissue and organs in a mouse therapeutic module allowing determination of the therapeutic index. Thus cross-reactivity is beneficial because it allows preliminary toxicology and in vivo analysis to be performed to evaluate the safety of the molecule before it is administered to a human.

Thus, in another aspect, there is provided an antigen specific binding domain comprising (or consisting of) CDRH1, CDRH2, CDRH3, CDRL1, CDRL2, and CDRL3, wherein:
  (a) CDRH1 is selected from the group consisting of SEQ ID NO: 1, SEQ ID NO: 27, SEQ ID NO: 45, SEQ ID NO: 56, SEQ ID NO: 73, SEQ ID NO: 89, and SEQ ID NO: 100, SEQ ID NO: 116, SEQ ID NO: 135 and a CDRH1 differing from any one of the same in that 1 or 2 amino acids are replaced (with an alternative amino acid), deleted or added;
  (b) CDRH2 is selected from the group consisting of SEQ ID NO: 2, SEQ ID NO: 28, SEQ ID NO: 46, SEQ ID NO: 57, SEQ ID NO: 74, SEQ ID NO: 90, and SEQ ID NO: 101, SEQ ID NO: 117, SEQ ID NO: 136 and a CDRH2 differing from any one of the same in that 1 or 2 amino acids are replaced (with an alternative amino acid), deleted or added;
  (c) CDRH3 is selected from the group consisting of SEQ ID NO: 3, SEQ ID NO: 29, SEQ ID NO: 47, SEQ ID NO: 58, SEQ ID NO: 75, SEQ ID NO: 91, and SEQ ID NO: 102, SEQ ID NO: 137 and a CDRH3 differing from any one of the same in that 1 or 2 amino acids are replaced (with an alternative amino acid), deleted or added;
  (d) CDRL1 is selected from the group consisting of SEQ ID NO: 18, SEQ ID NO: 36, SEQ ID NO: 65, SEQ ID NO: 81, SEQ ID NO: 108, SEQ ID NO: 144 and a CDRL1 differing from any one of the same in that 1 or 2 amino acids are replaced (with an alternative amino acid), deleted or added;
  (e) CDRL2 is selected from the group consisting of SEQ ID NO: 19, SEQ ID NO: 37, SEQ ID NO: 66, SEQ ID NO: 82, SEQ ID NO: 109 and a CDRL2 differing from any one of the same in that 1 or 2 amino acids are replaced (with an alternative amino acid), deleted or added; and
  (f) CDRL3 is selected from the group consisting of SEQ ID NO: 20, SEQ ID NO: 38, SEQ ID NO: 67, SEQ ID NO: 83, SEQ ID NO: 110, SEQ ID NO: 123, SEQ ID NO: 145 and a CDRL3 differing from any one of the same in that 1 or 2 amino acids are replaced (with an alternative amino acid), deleted or added.

In some examples, the CDRH1 may be SEQ ID NO: 1, CRDH2 is SEQ ID NO: 2, and CDRH3 is SEQ ID NO: 3 or an antigen specific binding domain wherein one or more modified sequences 1, 2, and 3 are employed and the modification(s) is independently selected from replacement, deletion or addition of 1 or 2 amino acids.

In some examples, the antigen specific binding domain as described herein may have heavy chain CDRs including:
  (a) the CDRH1 is SEQ ID NO: 1, the CRDH2 is SEQ ID NO: 2, the CRDH3 is SEQ ID NO: 3; or
  (b) the CDRH1 is SEQ ID NO: 27, the CRDH2 is SEQ ID NO: 28, the CRDH3 is SEQ ID NO: 29; or
  (c) the CDRH1 is SEQ ID NO: 45, the CRDH2 is SEQ ID NO: 46, the CRDH3 is SEQ ID NO: 47; or
  (d) the CDRH1 is SEQ ID NO: 56, the CRDH2 is SEQ ID NO: 57, the CRDH3 is SEQ ID NO: 58; or
  (e) the CDRH1 is SEQ ID NO: 73, the CRDH2 is SEQ ID NO: 74, the CRDH3 is SEQ ID NO: 75; or
  (f) the CDRH1 is SEQ ID NO: 89, the CRDH2 is SEQ ID NO: 90, the CRDH3 is SEQ ID NO: 91; or
  (g) the CDRH1 is SEQ ID NO: 100, the CRDH2 is SEQ ID NO: 101, the CRDH3 is SEQ ID NO: 102; or
  (h) the CDRH1 is SEQ ID NO: 135, the CRDH2 is SEQ ID NO: 136, the CRDH3 is SEQ ID NO: 137.

In some examples, the antigen specific binding domain may have the light chain CDRs including:
  (a) the CDRL1 is SEQ ID NO: 18, the CDRL2 is SEQ ID NO: 19, the CDRL3 is SEQ ID NO: 20;
  (b) the CDRL1 is SEQ ID NO: 36, the CDRL2 is SEQ ID NO: 37, the CDRL3 is SEQ ID NO: 38;
  (c) the CDRL1 is SEQ ID NO: 18, the CDRL2 is SEQ ID NO: 19, the CDRL3 is SEQ ID NO: 20;
  (d) the CDRL1 is SEQ ID NO: 65, the CDRL2 is SEQ ID NO: 66, the CDRL3 is SEQ ID NO: 67;
  (e) the CDRL1 is SEQ ID NO: 81, the CDRL2 is SEQ ID NO: 82, the CDRL3 is SEQ ID NO: 83;
  (f) the CDRL1 is SEQ ID NO: 108, the CDRL2 is SEQ ID NO: 109, the CDRL3 is SEQ ID NO: 110; and
  (g) the CDRL1 is SEQ ID NO: 144, the CDRL2 is SEQ ID NO: 37, the CDRL3 is SEQ ID NO: 145.

In some examples, the antigen specific binding domain as described herein may have the variable heavy domain such as:
  (i) SEQ ID NO: 8;
  (ii) SEQ ID NO: 34;
  (iii) SEQ ID NO: 51;
  (iv) SEQ ID NO: 63;
  (v) SEQ ID NO: 79;
  (vi) SEQ ID NO: 95;

(vii) SEQ ID NO: 106; and
(viii) SEQ ID NO: 142.

In some examples, the antigen specific binding domain as described herein may have the variable light domain such as:
(i) SEQ ID NO: 25;
(ii) SEQ ID NO: 43;
(iii) SEQ ID NO: 54;
(iv) SEQ ID NO: 71;
(v) SEQ ID NO: 87;
(vi) SEQ ID NO: 98;
(vii) SEQ ID NO: 114; and
(viii) SEQID NO: 150.

In some examples, the antigen specific binding domain as described herein may have CDRH1 that is SEQ ID NO: 1 or a sequence differing therefrom in that 1 or 2 amino acids are independently replaced (with an alternative amino acid), deleted or added.

In some examples, the antigen specific binding domain as described herein may have CRDH2 that is SEQ ID NO: 2 or a sequence differing therefrom in that 1 or 2 amino acids are independently replaced (with an alternative amino acid), deleted or added.

In some examples, the antigen specific binding domain as described herein may have CRDH3 that is SEQ ID NO: 3 or a sequence differing therefrom in that 1 or 2 amino acids are independently replaced (with an alternative amino acid), deleted or added.

In some examples, the antigen specific binding domain as described herein may have CDRL1 that is SEQ ID NO: 18 or a sequence differing therefrom in that 1 or 2 amino acids are independently replaced (with an alternative amino acid), deleted or added.

In some examples, the antigen specific binding domain as described herein may have CDRL2 that is SEQ ID NO: 19 or a sequence differing therefrom in that 1 or 2 amino acids are independently replaced (with an alternative amino acid), deleted or added.

In some examples, the antigen specific binding domain as described herein may have CDRL3 that is SEQ ID NO: 20 or a sequence differing therefrom in that 1 or 2 amino acids are independently replaced (with an alternative amino acid), deleted or added.

In some examples, the antigen specific binding domain as described herein may have the variable heavy domain has a sequence: as shown in SEQ ID NO: 8, or a sequence derived from SEQ ID NO: 8 wherein 1, 2, 3, 4, 5, 6, 7, 8, 9 or 10 amino acids are independently replaced (with an alternative amino acid), deleted or added, in an independent aspect of the disclosure there is provided a derivative of SEQ ID NO: 8 with at least 95% identity thereto.

In some examples, the antigen specific binding domain as described herein may include the variable light domain has a sequence: as shown in SEQ ID NO: 25; a sequence derived from SEQ ID NO: 25 wherein 1, 2, 3, 4, 5, 6, 7, 8, 9 or 10 amino acids are independently replaced (with an alternative amino acid), deleted or added, in an independent aspect of the disclosure there is provided a derivative of SEQ ID NO: 25 with at least 95% identity thereto;

In some examples, the antigen specific binding domain as described herein may have CDRH1 that is SEQ ID NO: 27 or a sequence differing therefrom in that 1 or 2 amino acids are independently replaced (with an alternative amino acid), deleted or added.

In some examples, the antigen specific binding domain as described herein may have CDRH2 that is SEQ ID NO: 28 or a sequence differing therefrom in that 1 or 2 amino acids are independently replaced (with an alternative amino acid), deleted or added.

In some examples, the antigen specific binding domain as described herein may have CDRH3 that is SEQ ID NO: 29 or a sequence differing therefrom in that 1 or 2 amino acids are independently replaced (with an alternative amino acid), deleted or added.

In some examples, the antigen specific binding domain as described herein may have CDRL1 that is SEQ ID NO: 36 or a sequence differing therefrom in that 1 or 2 amino acids are independently replaced (with an alternative amino acid), deleted or added.

In some examples, the antigen specific binding domain as described herein may have CDRL2 that is SEQ ID NO: 37 or a sequence differing therefrom in that 1 or 2 amino acids are independently replaced (with an alternative amino acid), deleted or added.

In some examples, the antigen specific binding domain as described herein may have CDRL3 that is SEQ ID NO: 38 or a sequence differing therefrom in that 1 or 2 amino acids are independently replaced (with an alternative amino acid), deleted or added.

In some examples, the antigen specific binding domain as described herein may have the heavy chain variable domain having a sequence: as shown in SEQ ID NO: 34; or a sequence derived from SEQ ID NO: 34 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO; 34 with at least 95% identical thereto.

In some examples, the antigen specific binding domain as described herein, wherein the light chain variable domain has a sequence: as shown in SEQ ID NO: 43; a sequence derived from SEQ ID NO: 43 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO; 43 with at least 95% identical thereto.

In some examples, the antigen specific binding domain as described herein, wherein CDRH1 is SEQ ID NO: 45 or a sequence differing therefrom in that 1 or 2 amino acids are independently replaced [with an alternative amino acid], deleted or added.

In some examples, the antigen specific binding domain as described herein, wherein CDRH2 is SEQ ID NO: 46 or a sequence differing therefrom in that 1 or 2 amino acids are independently replaced (with an alternative amino acid), deleted or added.

In some examples, the antigen specific binding domain as described herein, wherein CDRH3 is SEQ ID NO: 47 or a sequence differing therefrom in that 1 or 2 amino acids are independently replaced (with an alternative amino acid), deleted or added.

In some examples, the antigen specific binding domain as described herein, wherein CDRL1 is SEQ ID NO: 18 or a sequence differing therefrom in that 1 or 2 amino acids are independently replaced (with an alternative amino acid), deleted or added.

In some examples, the antigen specific binding domain as described herein, wherein CDRL2 is SEQ ID NO: 19 or a sequence differing therefrom in that 1 or 2 amino acids are independently replaced (with an alternative amino acid), deleted or added.

In some examples, the antigen specific binding domain as described herein, wherein CDRL3 is SEQ ID NO: 20 or a sequence differing therefrom in that 1 or 2 amino acids are independently replaced (with an alternative amino acid), deleted or added.

In some examples, the antigen specific binding domain as described herein, wherein the heavy chain variable domain has a sequence: as shown in SEQ ID NO: 51; a sequence derived from SEQ ID NO: 51 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO; 51 with atleast 95% identical thereto.

In some examples, antigen specific binding domain as described herein, wherein the light chain variable domain has a sequence: shown in SEQ ID NO: 54; or a sequence derived from SEQ ID NO: 54 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO; 54 with at least 95% identical thereto.

In some examples, the antigen specific binding domain as described herein, wherein CDRH1 is SEQ ID NO: 56 or a sequence differing therefrom in that 1 or 2 amino acids are independently replaced (with an alternative amino acid), deleted or added.

In some examples, the antigen specific binding domain as described herein, wherein CDRH2 is SEQ ID NO: 57 or a sequence differing therefrom in that 1 or 2 amino acids are independently replaced (with an alternative amino acid), deleted or added.

In some examples, the antigen specific binding domain as described herein wherein CDRH3 is SEQ ID NO: 58 or a sequence differing therefrom in that 1 or 2 amino acids are independently replaced [with an alternative amino acid], deleted or added.

In some examples, the antigen specific binding domain as described herein, wherein CDRL1 is SEQ ID NO: 65 or a sequence differing therefrom in that 1 or 2 amino acids are independently replaced (with an alternative amino acid), deleted or added.

In some examples, the antigen specific binding domain as described herein, wherein CDRL2 is SEQ ID NO: 66 or a sequence differing therefrom in that 1 or 2 amino acids are independently replaced (with an alternative amino acid), deleted or added.

In some examples, the antigen specific binding domain as described herein, wherein CDRL3 is a SEQ ID NO: 67 or a sequence differing therefrom in that 1 or 2 amino acids are independently replaced (with an alternative amino acid), deleted or added.

In some examples, the antigen specific binding domain as described herein, wherein the heavy chain variable domain has sequence: shown in SEQ ID NO: 63; or a sequence derived from SEQ ID NO: 63 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 63 with at least 95% identical thereto.

In some examples, the antigen specific binding domain as described herein, wherein the light chain variable domain has a sequence: show in SEQ ID NO: 71; a sequence derived from SEQ ID NO: 71 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 71 with at least 95% identical thereto.

In some examples, the antigen specific binding domain as described herein, wherein CDRH1 is SEQ ID NO: 73 or a sequence differing therefrom in that 1 or 2 amino acids are independently replaced (with an alternative amino acid), deleted or added.

In some examples, the antigen specific binding domain as described herein, wherein CDRH2 is SEQ ID NO: 74 or a sequence differing therefrom in that 1 or 2 amino acids are independently replaced (with an alternative amino acid), deleted or added.

In some examples, the antigen specific binding domain as described herein wherein CDRH3 is SEQ ID NO: 75 or a sequence differing therefrom in that 1 or 2 amino acids are independently replaced (with an alternative amino acid), deleted or added.

In some examples, the antigen specific binding domain as described herein, wherein CDRL1 is SEQ ID NO: 81 or a sequence differing therefrom in that 1 or 2 amino acids are independently replaced (with an alternative amino acid), deleted or added.

In some examples, the antigen specific binding domain as described herein, wherein CDRL2 is SEQ ID NO: 82 or a sequence differing therefrom in that 1 or 2 amino acids are replaced (with an alternative amino acid), deleted or added.

In some examples, the antigen specific binding domain as described herein, wherein CDRL3 is SEQ ID NO: 83 or a sequence differing therefrom in that 1 or 2 amino acids are independently replaced (with an alternative amino acid), deleted or added.

In some examples, the antigen specific binding domain as described herein, wherein the heavy chain variable domain has sequence: shown in SEQ ID NO: 79; a sequence derived from SEQ ID NO: 79 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 79 with at least 95% identical thereto.

In some examples, the antigen specific binding domain as described herein, wherein the light chain variable domain has a sequence: as show in SEQ ID NO: 87; a sequence derived from SEQ ID NO: 87 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 87 with at least 95% identical thereto.

In some examples, the antigen specific binding domain as described herein, wherein CDRH1 is SEQ ID NO: 89 or a sequence differing therefrom in that 1 or 2 amino acids are independently replaced (with an alternative amino acid), deleted or added.

In some examples, the antigen specific binding domain as described herein, wherein CDRH2 is SEQ ID NO: 90 or a sequence differing therefrom in that 1 or 2 amino acids are independently replaced (with an alternative amino acid), deleted or added.

In some examples, the antigen specific binding domain as described herein wherein CDRH3 is SEQ ID NO: 91 or a sequence differing therefrom in that 1 or 2 amino acids are independently replaced (with an alternative amino acid), deleted or added.

In some examples, the antigen specific binding domain as described herein, wherein CDRL1 is SEQ ID NO: 65 or a sequence differing therefrom in that 1 or 2 amino acids are independently replaced (with an alternative amino acid), deleted or added.

In some examples, the antigen specific binding domain as described herein, wherein CDRL2 is SEQ ID NO: 66 or a sequence differing therefrom in that 1 or 2 amino acids are independently replaced (with an alternative amino acid), deleted or added.

In some examples, the antigen specific binding domain as described herein, wherein CDRL3 is SEQ ID NO: 67 or a sequence differing therefrom in that 1 or 2 amino acids are independently replaced (with an alternative amino acid), deleted or added.

In some examples, the antigen specific binding domain as described herein, wherein the heavy chain variable domain has sequence: as shown in SEQ ID NO: 95; a sequence derived from SEQ ID NO: 95 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 95 with at least 95% identical thereto.

In some examples, the antigen specific binding domain as described herein, wherein the light chain variable domain has a sequence: show in SEQ ID NO: 98; a sequence derived from SEQ ID NO: 98 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 98 with at least 95% identical thereto.

In some examples, the antigen specific binding domain as described herein, wherein CDRH1 is SEQ ID NO: 100 or a sequence differing therefrom in that 1 or 2 amino acids are independently replaced (with an alternative amino acid), deleted or added.

In some examples, the antigen specific binding domain as described herein, wherein CDRH2 is SEQ ID NO: 101 or a sequence differing therefrom in that 1 or 2 amino acids are independently replaced (with an alternative amino acid), deleted or added.

In some examples, the antigen specific binding domain as described herein wherein CDRH3 is SEQ ID NO: 102 or a sequence differing therefrom in that 1 or 2 amino acids are independently replaced (with an alternative amino acid), deleted or added.

In some examples, the antigen specific binding domain as described herein, wherein CDRL1 is SEQ ID NO: 108 or a sequence differing therefrom in that 1 or 2 amino acids are independently replaced (with an alternative amino acid), deleted or added.

In some examples, the antigen specific binding domain as described herein, wherein CDRL2 is SEQ ID NO: 109 or a sequence differing therefrom in that 1 or 2 amino acids are independently replaced (with an alternative amino acid), deleted or added.

In some examples, the antigen specific binding domain as described herein, wherein CDRL3 is SEQ ID NO: 110 or a sequence differing therefrom in that 1 or 2 amino acids are independently replaced (with an alternative amino acid), deleted or added.

In some examples, the antigen specific binding domain as described herein wherein the heavy chain variable domain has sequence: shown in SEQ ID NO: 106; a sequence derived from SEQ ID NO: 106 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 106 with at least 95% identical thereto.

In some examples, the antigen specific binding domain as described herein, wherein the light chain variable domain has a sequence: show in SEQ ID NO: 114; a sequence derived from SEQ ID NO: 114 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 114 with atleast 95% identical thereto.

In some examples, the antigen specific binding domain as described herein, wherein CDRH1 is SEQ ID NO: 116 or a sequence differing therefrom in that 1 or 2 amino acids are independently replaced (with an alternative amino acid), deleted or added.

In some examples, the antigen specific binding domain as described herein, wherein CDRH2 is SEQ ID NO: 117 or a sequence differing therefrom in that 1 or 2 amino acids are independently replaced (with an alternative amino acid), deleted or added.

In some examples, the antigen specific binding domain as described herein wherein CDRH3 is SEQ ID NO: 102 or a sequence differing therefrom in that 1 or 2 amino acids are independently replaced (with an alternative amino acid), deleted or added.

In some examples, the antigen specific binding domain as described herein, wherein CDRL1 is SEQ ID NO: 108 or a sequence differing therefrom in that 1 or 2 amino acids are independently replaced (with an alternative amino acid), deleted or added.

In some examples, the antigen specific binding domain as described herein, wherein CDRL2 is SEQ ID NO: 109 or a sequence differing therefrom in that 1 or 2 amino acids are independently replaced (with an alternative amino acid), deleted or added.

In some examples, the antigen specific binding domain as described herein wherein CDRL3 is SEQ ID NO: 123 or a sequence differing therefrom in that 1 or 2 amino acids are independently replaced (with an alternative amino acid), deleted or added.

In some examples, the antigen specific binding domain as described herein, wherein the heavy chain variable domain has sequence: as shown in SEQ ID NO: 121; a sequence derived from SEQ ID NO: 121 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 121 with at least 95% identical thereto.

In some examples, the antigen specific binding domain as described herein, wherein the light chain variable domain has sequence: as shown in SEQ ID NO: 127; a sequence derived from SEQ ID NO: 127 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 127 with at least 95% identical thereto.

In some examples, the antigen specific binding domain as described herein, wherein CDRH1 is SEQ ID NO: 116 or a sequence differing therefrom in that 1 or 2 amino acids are independently replaced (with an alternative amino acid), deleted or added.

In some examples, the antigen specific binding domain as described herein, wherein CDRH2 is SEQ ID NO: 117 or a sequence differing therefrom in that 1 or 2 amino acids are independently replaced (with an alternative amino acid), deleted or added.

In some examples, the antigen specific binding domain as described herein wherein CDRH3 is SEQ ID NO: 102 or a sequence differing therefrom in that 1 or 2 amino acids are independently replaced [with an alternative amino acid], deleted or added.

In some examples, the antigen specific binding domain as described herein, wherein the heavy chain variable domain has sequence: shown in SEQ ID NO: 130; or a sequence derived from SEQ ID NO: 130 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 130 with at least 95% identical thereto.

In some examples, the antigen specific binding domain as described herein, wherein CDRH1 is SEQ ID NO: 116 or a sequence differing therefrom in that 1 or 2 amino acids are independently replaced (with an alternative amino acid), deleted or added.

In some examples, the antigen specific binding domain as described herein, wherein CDRH2 is SEQ ID NO: 101 or a sequence differing therefrom in that 1 or 2 amino acids are independently replaced (with an alternative amino acid), deleted or added.

In some examples, the antigen specific binding domain as described herein wherein CDRH3 is SEQ ID NO: 102 or a sequence differing therefrom in that 1 or 2 amino acids are independently replaced (with an alternative amino acid), deleted or added.

In some examples, the antigen specific binding domain as described herein, wherein the heavy chain variable domain has sequence: shown in SEQ ID NO: 133; a sequence derived from SEQ ID NO: 133 wherein 1, 2, 3, 4, 5, 6, 7, 8, 9 or 10 amino acids are independently replaced (with an alternative amino acid), deleted or added, or in an independent aspect of the disclosure there is provided a derivative of SEQ ID NO: 133 with at least 95% identical thereto.

In some examples, the antigen specific binding domain as described herein wherein CDRH1 is SEQ ID NO: 135.

In some examples, the antigen specific binding domain as described herein, wherein CDRH2 is SEQ ID NO: 136.

In some examples, the antigen specific binding domain as described herein wherein CDRH3 is SEQ ID NO: 137.

In some examples, the antigen specific binding domain as described herein, wherein the heavy chain variable domain has sequence shown in SEQ ID NO: 142.

In some examples, the antigen specific binding domain as described herein, wherein CDRL1 is SEQ ID NO: 144.

In some examples, the antigen specific binding domain as described herein, wherein CDRL2 is SEQ ID NO: 37.

In some examples, the antigen specific binding domain as described herein, wherein CDRL3 is SEQ ID NO: 145.

In some examples, the antigen specific binding domain as described herein, wherein the heavy chain variable domain has sequence shown in SEQ ID NO: 150.

In yet another aspect, there is provided a chimeric antigen receptor comprising the binding domain as described herein.

In some examples, the chimeric antigen receptor as described herein, wherein the chimeric antigen receptor is expressed on a cell surface. In some examples, the chimeric antigen receptor as described herein, wherein the cell is includes a T cell (such as a cytotoxic T cell), an NK cell and a NKT cell. In some examples, the chimeric antigen receptor as described herein, which comprises an intracellular signalling domain. In some examples, the chimeric antigen receptor as described herein, wherein the intracellular signalling domain is from CD3-zeta, for example described in WO2013/040557 incorporated herein by reference.

In some examples, the chimeric antigen receptor as described herein which further comprises a co-stimulator domain. In some examples, the chimeric antigen receptor as described herein, wherein the co-stimulator domain is independently selected from a group consisting of CD28, 4-1BB or OX40, and combinations thereof, such as CD28 and 4-1BB or CD28 and OX40.

In yet another aspect there is provided an isolated antibody or antibody comprising a binding domain as described herein. In some examples, the isolated antibody or antibody as described herein, wherein the antibody may include, but is not limited to, a multispecific antibody (such as a bispecific antibody), a full-length antibody or an antibody binding fragment.

In some examples, the isolated antibody or antibody as described herein, wherein the multispecific antibody is bispecific antibody. In some examples, the isolated antibody or antibody as described herein, where the multispecific antibody is a bispecific T cell engager (BiTe®).

In some examples, the isolated antibody or antibody as described herein, wherein the multispecific antibody comprises two different RON binding domains. In some examples, the antibody as described herein, wherein the two different RON binding domains are specific for different epitopes.

Figure 48A:
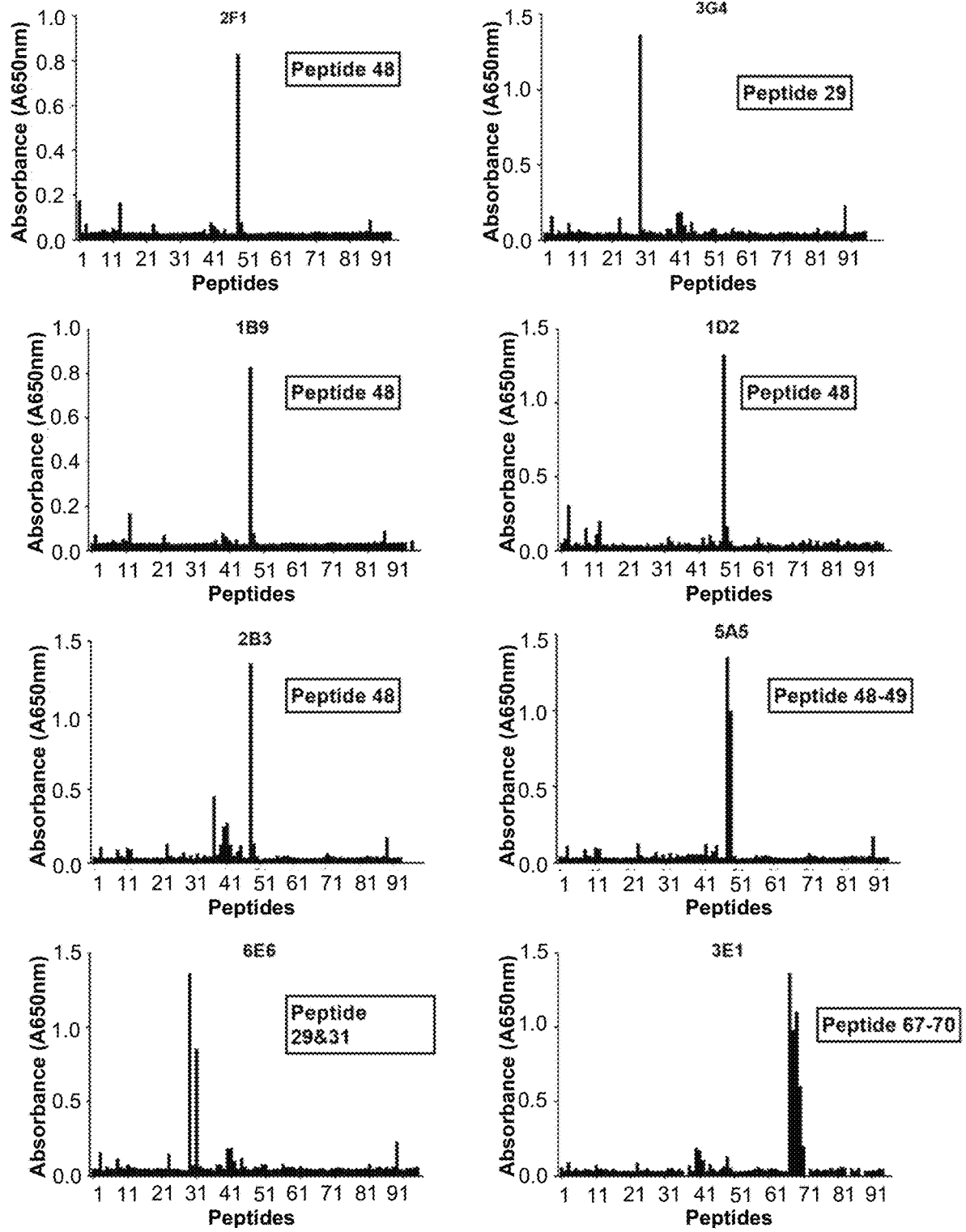
FIG. 48A shows the results of epitope mapping by Pepscan.
Figure 49B:
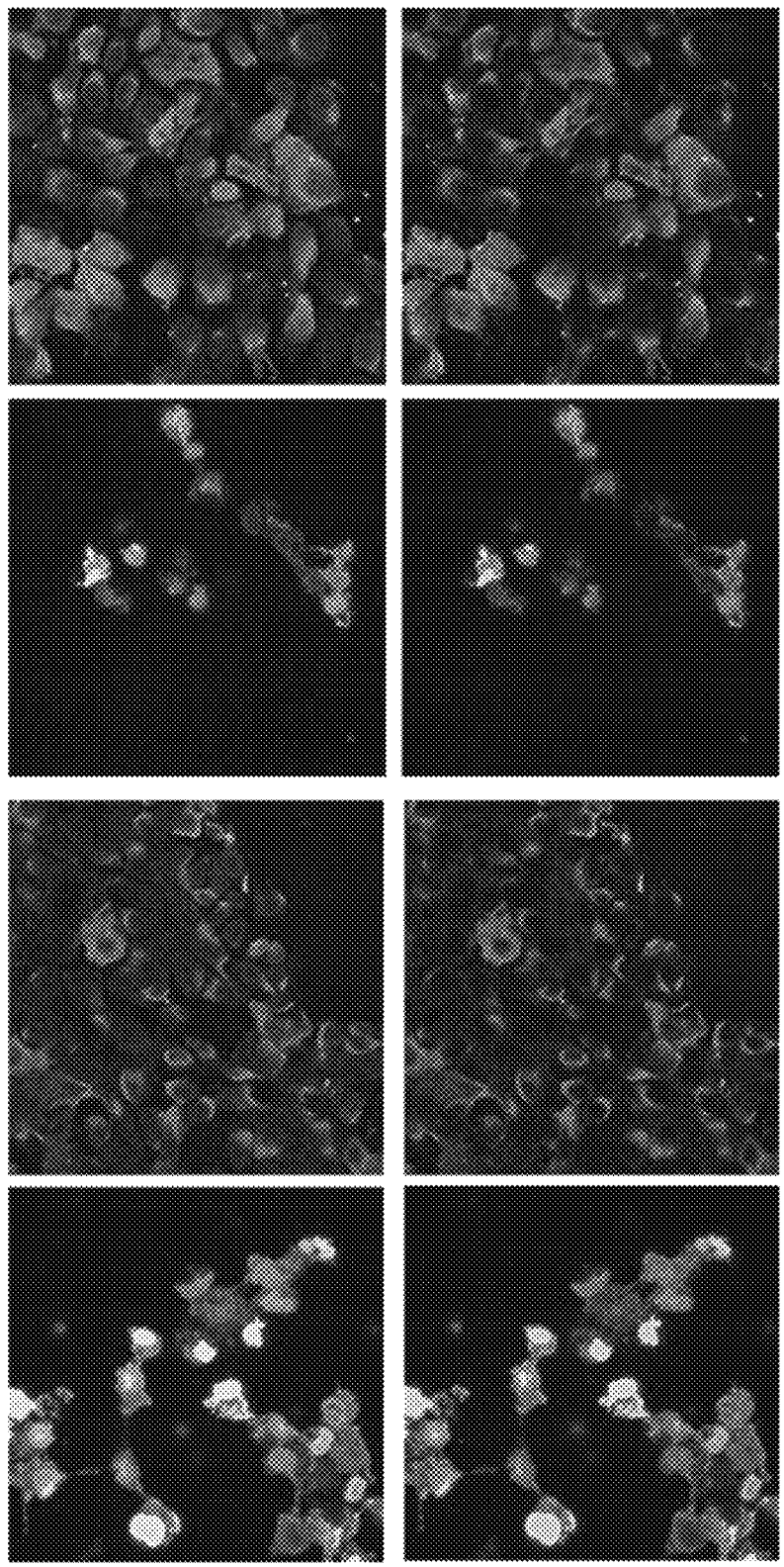
FIG. 49B shows immunofluorescence images showing the endocytosis of anti-RON antibody 6D4. Thus.
Figure 51:
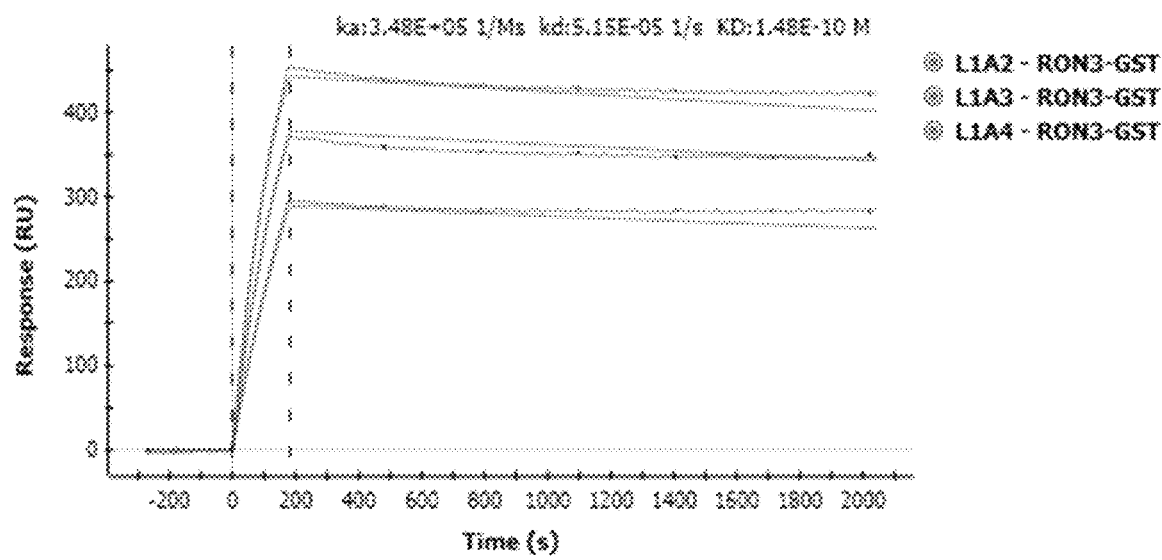
FIG. 51 shows a line graph showing the study into the binding affinity of an example of the antibody as described herein (i.e. 2B3) as measured by Proteon.

In some examples, the isolated antibody or antibody as described herein is capable of binding (or binds) to an epitope within RON as described within FIG. 48A, FIG. 48B, and Table 1. In some example, the antibody as described herein is capable of binding (or binds) to an epitope within RON having sequences including, but is not limited to, SEQ ID NO: 10, SEQ ID NO: 11, SEQ ID NO: 12, SEQ ID NO: 13, SEQ ID NO: 14, SEQ ID NO: 15, and SEQ ID NO: 16.

In some examples, the isolated antibody or antibody as described herein, wherein a first RON binding domain comprising CDRH1, H2 and H3 as shown in SEQ ID NO: 1, 2, 3 respectively and CDRL1, L2 and L3 shown in SEQ ID NO: 18, 19 and 20 respectively (in particular employed in variable regions shown in SEQ ID NO: 8 and 25, or a variant of the VH and/or VL domain with at least 95% identity to said sequence).

In some examples, the isolated antibody or antibody as described herein comprising a second RON binding domain comprising CDRH1, H2 and H3 as shown in SEQ ID NO: 27, 28, 29 respectively and CDRL1, L2 and L3 show in SEQ ID NO: 36, 37 and 38 respectively (in particular employed in variable regions shown in SEQ ID NO: 34 and 43 or a variant of the VH and/or VL with at least 95% identity thereto).

In some examples, the isolated antibody or antibody as described herein, wherein the antibody binding fragment may include, but is not limited to, a Fab, a modified Fab, a Fab', a modified Fab', a F(ab')2, an Fv, ds-FV, Fab-Fv, Fab-dsFv, a single domain antibody (e.g. VH or VL or VHH), a scFv, and a ds-scFv.

In some examples, the isolated antibody or antibody as described herein, wherein the antibody molecule comprises an effector function.

In some examples, the isolated antibody or antibody as described herein, wherein the effector function is provided by an antibody constant region (such as the Fc region). In some examples, the antibody molecule as described herein, wherein the effector function is provided by an antibody constant region or an active fragment thereof, for example a full-length IgG isotype, such as IgG1, IgG2, IgG3 or IgG4 (in particular IgG1 or IgG4).

In some examples, the isolated antibody or antibody as described herein, wherein the antibody is conjugated to a payload. In some examples, the antibody as described herein, wherein the payload includes, but is not limited to, a toxin, a polymer (for example synthetic or naturally occurring polymers), biologically active proteins (for example enzymes, other antibody or antibody fragments), nucleic acids and fragments thereof (for example DNA, RNA and fragments thereof) radionuclides (particularly radioiodide, radioisotopes) chelated metals, nanoparticles and reporter groups such as fluorescent or luminescent labels or compounds which may be detected by NMR or ESR spectroscopy.

In some examples, wherein the toxin in selected from an auristatin (for example MMAE (monomethyl auristatin E-CAS number: 474645-27-7), MMAF (monomethyl auristatin F-CAS number: 745017-94-1)), pyrrolobenzodiazepine (PBD), doxorubicin (CAS number: 23214-92-8), duocarmycin, a maytansinoid (for example N2'-deacetyl-N2'-(3-mercapto-1-oxopropyl)-maytansine (DM1; CAS number: 139504-50-0), N2'-deacetyl-N2'-(4-mercapto-1-oxopentyl)-maytansine (DM3) and N2'-deacetyl-N2'(4-methyl-4-mercapto-1-oxopentyl)-maytansine (DM4; CAS number: 796073-69-3)), calocheamicin (CAS number: 108212-75-5), dolastatin, maytansine (CAS number: 35846-53-8), α-amanitin (CAS number: 23109-05-9), and a tubulysin (CAS number: 205304-86-5). In some example, the toxin may include, but is not limited to, wherein the toxin is selected from a group consisting of an auristatin, MMAF (monomethyl auristatin F), pyrrolobenzodiazepine (PBD), doxorubicin, duocarmycin, a maytansinoid, calocheamicin, dolastatin, maytansine, α-amanitin, and a tubulysin.

In yet another aspect there is provided a pharmaceutical composition comprising an antibody as described herein and an excipient, diluent and/or carrier.

In some examples, the pharmaceutical composition as described herein, comprising at least two monoclonal antibody in admixture, for example two antigen specific antibody as described herein.

In some examples, the pharmaceutical composition comprises one of the at least two antigen specific antibody comprises CDRH1, H2 and H3 as shown in SEQ ID NO: 1, 2, 3 respectively and CDRL1, L2 and L3 show in SEQ ID NO: 18, 19 and 20; optionally wherein a second antibody of the at least two antibodies comprises CDRH1, H2 and H3 as shown in SEQ ID NO: 27, 28, 29 respectively and CDRL1, L2 and L3 as shown in SEQ ID NO: 36, 37 and 38. In some examples, the pharmaceutical composition comprises one of the at least two antigen specific antibody comprises CDRH1, H2 and H3 as shown in SEQ ID NO: 27, 28, 29 respectively and CDRL1, L2 and L3 as shown in SEQ ID NO: 36, 37 and 38; optionally wherein a second antibody of the at least two antibodies comprises CDRH1, H2 and H3 as shown in SEQ ID NO: 1, 2, 3 respectively and CDRL1, L2 and L3 show in SEQ ID NO: 18, 19 and 20.

In some examples, the pharmaceutical composition as described herein, wherein the least one antigen specific antibody comprises CDRH1, H2 and H3 as shown in SEQ ID NO: 1, 2, 3 respectively and CDRL1, L2 and L3 show in SEQ ID NO: 18, 19 and 20 respectively (in particular employed in variable regions shown in SEQ ID NO: 8 and 25, or a variant of the VH and/or VL with at least 95% identity thereto).

In some examples, the pharmaceutical composition as described herein, wherein the least one antigen comprising a second RON binding domain comprising CDRH1, H2 and H3 as shown in SEQ ID NO: 27, 28, 29 respectively and CDRL1, L2 and L3 show in SEQ ID NO: 36, 37 and 38 (in particular employed in variable regions shown in SEQ ID NO: 34 and 43, or a variant of the VH and/or VL with at least 95% identity thereto).

In some examples, the pharmaceutical composition as described herein, wherein the formulation is a parenteral.

In yet another aspect, there is provided a RON binding domain as described herein, or a chimeric antigen receptor as described herein, or a composition as described herein, or an antibody as described herein, or a pharmaceutical composition as described herein, for use in treatment (or therapy).

In yet another aspect there is provided a RON binding domain as described herein, for use in treatment (or therapy).

In yet another aspect there is provided a chimeric antigen receptor as described herein or a pharmaceutical composition as described herein for use in treatment (or therapy).

In yet another aspect there is provided an antibody molecule as described herein, or a composition as described herein for use in treatment (or therapy).

In yet another aspect, there is provided the use of an antigen binding domain as described herein, or a chimeric antigen receptor as described herein, or an antibody as described herein, or a pharmaceutical composition as described herein in the manufacture of a medicament for the treatment of cancer or fibrosis (in particular in cancer). In some example, the cancer is a RON positive cancer.

In yet another aspect there is provided a use of an antigen binding domain as described herein, in the manufacture of a medicament for the treatment of cancer or fibrosis (in particular cancer).

In yet another aspect there is provided a use of a chimeric antigen receptor as described herein or a pharmaceutical composition as described herein for the manufacture of a medicament for the treatment of cancer or fibrosis (in particular cancer).

In yet another aspect there is provided a use of an antibody as described herein, or a composition as described herein for the manufacture of medicament for the treatment of tumor, cancer or fibrosis (in particular cancer, such as a solid cancer mass and/or metastatic cancer). In some example, the cancer is a RON expressing cancer.

In yet another aspect, there is provided a method of preventing or treating cancer or fibrosis in a patient comprising administering a therapeutic effective amount of an antigen binding domain as described herein, or a chimeric antigen receptor as described herein, or an antibody as described herein, or a pharmaceutical composition as described herein to the patient in need thereof.

In some examples, the patient is (or forms part of) a patient population characterised in that patients making up the population have a RON positive tumour. In some examples, the patients making up the population have a RON positive and C-MET positive tumour.

In some examples, the method as described herein, comprises the step of identifying the patient to have a RON positive tumour before treatment.

In yet another example, there is provided a method of treating a patient for cancer or fibrosis comprising administering a therapeutic amount of an RON binding domain as described herein, or a chimeric antigen receptor as described herein, or a composition as described herein, or an antibody as described herein, or a pharmaceutical composition as described herein.

In yet another example there is provided a method of treating a patient for cancer or fibrosis comprising administering a therapeutic amount of an RON binding domain as described herein.

In yet another example there is provided a method of treating a patient for cancer or fibrosis comprising administering a therapeutic amount of an chimeric antigen receptor as described herein or a composition as described herein.

In yet another example there is provided a method of treating a patient for cancer or fibrosis comprising administering a therapeutic amount of an antibody as described herein or a composition as described herein.

In yet another example, there is provided a method of treating a patient population with an RON binding domain as described herein, or a chimeric antigen receptor as described herein, or a composition as described herein, or an antibody as described herein, wherein the population is characterised in that patients making up the population have a RON positive tumour. In some examples, the patients making up the population have a RON positive and C-MET positive tumour.

In yet another example there is provided a method of treating a patient population with a chimeric antigen receptor as described herein, a composition comprising the same as described herein, antibody molecule as described herein or a composition comprising the same as described herein, wherein the population is characterised in that patients making up the population have a RON positive tumour.

In yet another example there is provided a method of treating a patient population as described herein, wherein the patients making up the population have a RON positive and MET positive tumour.

In yet another example there is provided a method of treating a patient population as described herein, which comprises the step of identifying the patient as in the population before treatment according to the present disclosure is administered.

In yet another example, there is provided a use of a composition as described herein, or an antibody as described herein for use as diagnostic or prognostic agent. In yet another aspect there is provided a use of an antibody molecule as described herein, or a composition as described herein for use as diagnostic or prognostic agent, for example wherein the antibody molecule is conjugated to a imaging agent, which is visualizable in vivo.

In some examples there is provided a method of downregulating RON expression in a patient by administering a therapeutically effective amount of a binding domain according to the present disclosure (in particular an antibody molecule as disclosed herein).

In yet another aspect there is provided an antibody which cross-blocks or binds the same epitope as an antibody comprising a VH of SEQ ID NO: 8, SEQ ID NO: 34, SEQ ID NO: 51, SEQ ID NO: 63, SEQ ID NO: 79, SEQ ID NO: 95, SEQ ID NO: 106, SEQ ID NO: 121, SEQ ID NO: 130 or SEQ ID NO: 132.

In yet another aspect there is provided an antibody, which cross-blocks or binds the same epitope as an antibody comprising a VH/VL pair selected from SEQ ID NO: 8 and 25, SEQ ID NO: 34 and 43, SEQ ID NO: 51 and 54, SEQ ID NO: 63 and 71, SEQ ID NO: 79 and 87, SEQ ID NO: 95 and 98, SEQ ID NO: 106 and 114 or SEQ ID NO: 121 and 130.

In some examples, the antibody as described herein cross-blocks or binds to the epitope as defined in FIG. 48A, FIG. 48B, or Table 1.

In yet another aspect, there is provided an ex vivo method of evaluating the status of a cancer; wherein the method comprises: a) scanning a patient or a specific site of the patient known to comprise a tumor of the cancer, wherein the patient had been administered with a labelled form of an antibody at a first time point, wherein the antibody is as defined herein, b) repeating a) at one or more further time points, and comparing the results from two or more time points to evaluate the status of the cancer.

In yet another example there is provided a method of monitor a cancer patient using an antibody molecule as defined herein, wherein the method comprises the steps of: using a labelled form of the antibody molecule to access the cancer, in particular a tumour, at a first time point, using a labelled form of the antibody molecule to access the cancer, in particular a tumour, at least a second time point, and comparing the results from the two or more time points to evaluate the status of the cancer. In some examples, in the method of monitoring a cancer patient as described herein, decreases in RON expression by the tumour between the first time point and a subsequent time point correlates with an improved prognosis.

In one example the epitope bound by an antibody of the present disclosure binds a conformational epitope.

In one example the epitope bound by an antibody of the present disclosure binds a linear epitope.

In one example there is provided an antibody which specifically binds at least 5 amino acids, such as 6, 7, 8, 9, 10, 11, 12, 13, 14 or 15 amino acids in peptide sequence In some examples, the epitope bound by (recognised by) an antibody or antigen binding domain as described herein includes the peptides as described in FIG. 48A, FIG. 48B, and Table 1.

In one example there is provided a binding domain comprises SEQ ID NO: 8 or a sequence at least 95% identical thereto, and SEQ ID NO: 25 or a sequence at least 95% identical thereto.

In one example the binding domain of the present disclosure comprises SEQ ID NO: 34 or a sequence at least 95% identical thereto, and SEQ ID NO: 43 or a sequence at least 95% identical thereto.

In one example the binding domain of the present disclosure comprises SEQ ID NO: 51 or a sequence at least 95% identical thereto, and SEQ ID NO: 54 or a sequence at least 95% identical thereto.

In one example the binding domain of the present disclosure comprises SEQ ID NO: 63 or a sequence at least 95% identical thereto, and SEQ ID NO: 71 or a sequence at least 95% identical thereto.

In one example the binding domain of the present disclosure comprises SEQ ID NO: 79 or a sequence at least 95% identical thereto, and SEQ ID NO: 97 or a sequence at least 95% identical thereto.

In one example the binding domain of the present disclosure comprises SEQ ID NO: 95 or a sequence at least 95% identical thereto, and SEQ ID NO: 98 or a sequence at least 95% identical thereto.

In one example the binding domain of the present disclosure comprises SEQ ID NO: 106 or a sequence at least 95% identical thereto, and SEQ ID NO: 114 or a sequence atleast 95% identical thereto.

In one example the binding domain of the present disclosure comprises SEQ ID NO: 121 or a sequence at least 95% identical thereto, and SEQ ID NO: 130 or a sequence atleast 95% identical thereto.

In one example the binding domain of the present disclosure comprises SEQ ID NO: 8 or a sequence at least 95% identical thereto, and SEQ ID NO: 43 or a sequence at least 95% identical thereto.

In one example the binding domain of the present disclosure comprises SEQ ID NO: 8 or a sequence at least 95% identical thereto, and SEQ ID NO: 54 or a sequence at least 95% identical thereto.

In one example the binding domain of the present disclosure comprises SEQ ID NO: 8 or a sequence at least 95% identical thereto, and SEQ ID NO: 71 or a sequence at least 95% identical thereto.

In one example the binding domain of the present disclosure comprises SEQ ID NO: 8 or a sequence at least 95% identical thereto, and SEQ ID NO: 87 or a sequence at least 95% identical thereto.

In one example the binding domain of the present disclosure comprises SEQ ID NO: 8 or a sequence at least 95% identical thereto, and SEQ ID NO: 98 or a sequence at least 95% identical thereto.

In one example the binding domain of the present disclosure comprises SEQ ID NO: 8 or a sequence at least 95% identical thereto, and SEQ ID NO: 114 or a sequence at least 95% identical thereto.

In one example the binding domain of the present disclosure comprises SEQ ID NO: 8 or a sequence at least 95% identical thereto, and SEQ ID NO: 127 or a sequence at least 95% identical thereto.

In one example the binding domain of the present disclosure comprises SEQ ID NO: 34 or a sequence at least 95% identical thereto, and SEQ ID NO: 71 or a sequence at least 95% identical thereto.

In one example the binding domain of the present disclosure comprises SEQ ID NO: 34 or a sequence at least 95% identical thereto, and SEQ ID NO: 87 or a sequence at least 95% identical thereto.

In one example the binding domain of the present disclosure comprises SEQ ID NO: 34 or a sequence at least 95% identical thereto, and SEQ ID NO: 98 or a sequence at least 95% identical thereto.

In one example the binding domain of the present disclosure comprises SEQ ID NO: 34 or a sequence at least 95% identical thereto, and SEQ ID NO: 114 or a sequence at least 95% identical thereto.

In one example the binding domain of the present disclosure comprises SEQ ID NO: 34 or a sequence at least 95% identical thereto, and SEQ ID NO: 127 or a sequence at least 95% identical thereto.

In one example the binding domain of the present disclosure comprises SEQ ID NO: 51 or a sequence at least 95% identical thereto, and SEQ ID NO: 70 or a sequence at least 95% identical thereto.

In one example the binding domain of the present disclosure comprises SEQ ID NO: 51 or a sequence at least 95% identical thereto, and SEQ ID NO: 86 or a sequence at least 95% identical thereto.

In one example the binding domain of the present disclosure comprises SEQ ID NO: 51 or a sequence at least 95% identical thereto, and SEQ ID NO: 102 or a sequence at least 95% identical thereto.

In one example the binding domain of the present disclosure comprises SEQ ID NO: 51 or a sequence at least 95% identical thereto, and SEQ ID NO: 118 or a sequence at least 95% identical thereto.

In one example the binding domain of the present disclosure comprises SEQ ID NO: 62 or a sequence at least 95% identical thereto, and SEQ ID NO: 54 or a sequence at least 95% identical thereto.

In one example the binding domain of the present disclosure comprises SEQ ID NO: 62 or a sequence at least 95% identical thereto, and SEQ ID NO: 86 or a sequence at least 95% identical thereto.

In one example the binding domain of the present disclosure comprises SEQ ID NO: 62 or a sequence at least 95% identical thereto, and SEQ ID NO: 102 or a sequence at least 95% identical thereto.

In one example the binding domain of the present disclosure comprises SEQ ID NO: 62 or a sequence at least 95% identical thereto, and SEQ ID NO: 118 or a sequence at least 95% identical thereto.

In one example the binding domain of the present disclosure comprises SEQ ID NO: 78 or a sequence at least 95% identical thereto, and SEQ ID NO: 54 or a sequence at least 95% identical thereto.

In one example the binding domain of the present disclosure comprises SEQ ID NO: 78 or a sequence at least 95% identical thereto, and SEQ ID NO: 70 or a sequence at least 95% identical thereto.

In one example the binding domain of the present disclosure comprises SEQ ID NO: 78 or a sequence at least 95% identical thereto, and SEQ ID NO: 102 or a sequence at least 95% identical thereto.

In one example the binding domain of the present disclosure comprises SEQ ID NO: 78 or a sequence at least 95% identical thereto, and SEQ ID NO: 118 or a sequence at least 95% identical thereto.

In one example the binding domain of the present disclosure comprises SEQ ID NO: 96 or a sequence at least 95% identical thereto, and SEQ ID NO: 54 or a sequence at least 95% identical thereto.

In one example the binding domain of the present disclosure comprises SEQ ID NO: 96 or a sequence at least 95% identical thereto, and SEQ ID NO: 70 or a sequence at least 95% identical thereto.

In one example the binding domain of the present disclosure comprises SEQ ID NO: 96 or a sequence at least 95% identical thereto, and SEQ ID NO: 86 or a sequence at least 95% identical thereto.

In one example the binding domain of the present disclosure comprises SEQ ID NO: 96 or a sequence at least 95% identical thereto, and SEQ ID NO: 118 or a sequence at least 95% identical thereto.

In one example the binding domain of the present disclosure comprises SEQ ID NO: 110 or a sequence at least 95% identical thereto, and SEQ ID NO: 54 or a sequence at least 95% identical thereto.

In one example the binding domain of the present disclosure comprises SEQ ID NO: 110 or a sequence at least 95% identical thereto, and SEQ ID NO: 70 or a sequence at least 95% identical thereto.

In one example the binding domain of the present disclosure comprises SEQ ID NO: 110 or a sequence at least 95% identical thereto, and SEQ ID NO: 86 or a sequence at least 95% identical thereto.

In one example the binding domain of the present disclosure comprises SEQ ID NO: 110 or a sequence at least 95% identical thereto, and SEQ ID NO: 102 or a sequence at least 95% identical thereto.

In one example the binding domain according to the present disclosure, such as an antibody molecule, which is humanized.

In one example there is provided a polynucleotide (such as DNA) encoding a binding domain, chimeric receptor, or an antibody molecule according to the present disclosure, for example where heavy and light chains are encoded in the same polynucleotide (such as DNA) molecule or on different polynucleotide (such as DNA) molecules.

In one example there is provided a vector comprising a polynucleotide (such as DNA) according to the present disclosure.

A cell comprising a polynucleotide (such as DNA) according to the present disclosure or a vector as defined herein, for example a mammalian cell. In one example the cell is a host cell, simply designed for expression of the encoded protein, for example a CHO, HEK, PerC6, *E. coli* or similar cells. In one example the cell is a therapeutic mammalian cell, which is engineered to express a binding domain according to the present disclosure, for example T cell (such as a cytotoxic T cell), an NK cell or an NKT cell.

In one example there is provide a mammalian lymphocyte cell (in particular an NKT cell or a T cell), such as cytotoxic T cell with an engineered T cell receptor, wherein said receptor comprises 6 CDRs from an antibody as disclosed herein.

Thus in one example there is provided a method for the treatment of human cancer comprising administering a monoclonal antibody that binds to the RON protein; the antibody having the CDR sequences listed.

In one example there is provided a cell according to the present disclosure for use in treatment, in particular for the treatment of cancer.

In one example the binding domains of the present disclosure, such as an antibody molecule, downregulates RON expression on a tumour cells. This may for example render the cancer more susceptible or sensitive to a cancer treatment, such as sensitising the patient to chemotherapy.

Thus in one independent aspect there is provided a method of changing the prognosis of a cancer patient comprising converting the patient from a RON positive patient population to a RON negative patient population by administering an antibody molecule treatment according to the present disclosure.

Advantageously the off-target effects of the antibody molecule of the present disclosure seem to be minimal, as RON has limited expression in non-cancerous cells, while being highly overexpressed in cancer tissues.

In one example the antibody molecule is a RON inhibitor (ant-agonist). A RON inhibitor as employed herein refers to an entity, such as an antibody or binding fragment, which reduces or cancels or blocks a relevant biological activity of RON receptor tyrosine kinase (also known as MST1R), in particular inhibits the human protein. The inhibitor effects on cancer cells may include one or more the following, inhibition of cancer cell proliferation, inhibition of cancer cell migration, reduced expression of RON (which may lead to an improved response to treatment and a better prognosis).

In one example the inhibitor reduces a relevant biological activity, for example by 5, 10, 15, 20, 25, 30, 35, 40, 45, 50, 55, 60, 65, 70, 75, 80, 85, 90, 95 or 100%, such as when measured in a relevant in vitro assay.

In one example the inhibitor according to the present disclosure is a direct inhibitor. Direct inhibition is where the inhibitor binds directly to or physically blocks a binding interaction to inhibit a biological activity.

Antibody molecule as employed herein refers to a complete antibody molecule having full length heavy and light chains, or a fragment thereof (which may be, but is not limited to Fab, modified Fab, Fab', modified Fab', F(ab')2, Fv, Fab-Fv, Fab-dsFv, single domain antibodies (e.g. VH or VL or VHH), scFv and a multispecific antibody format, for example comprising a binding domain according to the present disclosure (including as part of a full length antibody or antibody fragment), such as bi, tri or tetra-valent antibodies, Bis-scFv, diabodies, triabodies, tetrabodies and epitope-binding fragments of any of the above.

In the context of the antibodies specifically referred to herein it will be clear to the skilled person that the disclosure includes use of the variable domains, in particular as a pair from the said antibody in any antibody or fragment format, including a multispecific antibody. In one example 6 CDRs are employed from an antibody disclosed herein in combination with an alternative framework, such as a human framework.

Antibody as employed herein refers to a complete antibody having full length heavy and light chains or a multivalent antibody comprising at least a complete antibody and which may comprise multiple specificities e.g. bispecific or may be monospecific (see for example WO92/22853 and WO05/113605). Bispecific and multispecific antibody variants are especially relevant as the role of the therapeutic molecules of the present disclosure in one example as the therapeutic objective is to inhibit two independent target proteins, namely RON receptor tyrosine kinase and for example second therapeutic target, such as a protein in the PD-1 pathway (in particular PD-1 or PD-L1).

In one example antibody molecule of the present disclosure is multivalent.

Multivalent as employed herein refers to an antibody molecule, which binds a given target (including the same target) more than once. Multivalent antibody molecules can cross-link targets and, for example induce complement pathways or the like.

In one example the antibody molecule of the present disclosure is monovalent. Monovalent as employed herein refers to an antibody molecule which is designed or engineered to bind a target only once.

In one example an antibody molecule according to the present disclosure is chimeric.

In one example an antibody molecule according to the present disclosure, in particular a binding domain therein is humanised.

In one example an antibody molecule according to the present disclosure is monoclonal.

"Multispecific molecule" as employed herein refers to a molecule with the ability to specifically bind at least two distinct antigens, for example different antigens. In one example the multispecific molecule is a bispecific, trispecific or tetraspecific molecule, in particular a bispecific or trispecific molecule. Multi-valent antibodies may comprise multiple specificities e.g bispecific or may be monospecific (see for example WO92/22853 and WO05/113605).

"Antibody fragment" as employed herein refers to an antibody binding fragment including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217).

"Epitope" as employed herein refers to a portion or portions of a macromolecule which is capable of being bound by a specific antibody, in the present disclosure, a portion of a polypeptide, in particular RON. Epitopes generally consist of chemically active surface groups and have specific three dimensional structural characteristics, as well as specific charge characteristics.

The term "cross-block", "cross-blocked" and "cross-blocking" are used interchangeably herein to mean the ability of an amino acid sequence or other binding agents (such as the antigen binding domain as described herein) to interfere with the binding of other amino acid sequences or antigen binding domain as described herein to a given target (for example epitope as defined herein). The extent to which an amino acid sequence or the antigen binding domain as described herein is able to interfere with the binding of another to the target epitope, and therefore whether it can be said to cross-block according to the present disclosure, can be determined using competition binding assays known in the art.

One particularly suitable quantitative assay uses a Biacore machine which can measure the extent of interactions using surface plasmon resonance technology. Another suitable quantitative cross-blocking assay uses an ELISA-based approach to measure competition between amino acid sequence or antigen binding domain as described herein in terms of their binding to the target epitope.

The following generally describes a suitable Biacore assay for determining whether an amino acid sequence or antigen binding domain as described herein cross-blocks or is capable of cross-blocking. It will be appreciated that the assay can be used with any of the amino acid sequence or antigen binding domain as described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or antigen binding domain as described herein is one which will bind to the target in the above Biacore cross-blocking assay such that during the assay and in the presence of a second amino acid sequence or antigen binding domain as described herein the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or antigen binding domain as described herein in combination. The Biacore assay described above is a primary assay used to determine if amino acid sequences or antigen binding domain as described herein cross-block each other according to the present disclosure.

The following generally describes an ELISA assay for determining whether an amino acid sequence or antigen binding domain as described herein directed against a target cross-blocks or is capable of cross-blocking as defined herein. It will be appreciated that the assay can be used with any of the amino acid sequences (or antigen binding domain as described herein) described herein. The general principal of the assay is to have an amino acid sequence or antigen binding domain that is directed against the target epitope coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y [target] binding sites per well are at least 10 fold higher than the moles of Ab-X [target] binding sites that were used, per well, during the coating of the ELISA plate, [target] is then added such that the moles of [target] added per well are at least 25-fold lower than the moles of Ab-X [target] binding sites that were used for coating each well. Following a suitable incubation period the ELISA plate is washed and a reagent for detecting the target is added to measure the amount of target specifically bound by the coated anti-[target]amino acid sequence (in this case Ab-X). The background signal for the assay is defined as the signal obtained in wells with the coated amino acid sequence (in this case Ab-X), second solution phase amino acid sequence (in this case Ab-Y), [target] buffer only (i.e. no target), and target detection reagents. The positive control signal for the assay is defined as the signal obtained in wells with the coated amino acid sequence (in this case Ab-X), second solution phase amino acid sequence buffer only (i.e. no second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for [target]) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal (i.e. the amount of target bound by the coated amino acid sequence) as compared to the target detection signal obtained in the absence of the solution phase anti-target amino acid sequence (i.e. the positive control wells).

The term "cross-block" is in contrast with "binding", which when used herein, refers to the selective affinities between a pair of species that chemically bind together. In the present case, binding refers to the specific recognition of the antigen binding domain to the epitopes as described herein. Therefore, this is in contrast with "cross-block" which interfere with the binding of the antigen binding domain as described herein to the RON epitope as described herein.

Other antibody fragments for use in the present invention include the Fab and Fab' fragments described in International patent applications WO2005/003169, WO2005/003170 and WO2005/003171.

A "binding fragment" as employed herein refers to an antibody fragment capable of binding a target peptide or antigen with sufficient specificity to characterise the fragment as specific for the peptide or antigen.

Specific as employed herein refers to an antibody molecule that only recognises the antigen to which it is specific or an antibody molecule that has significantly higher binding affinity for the antigen to which it is specific compared to the binding affinity for antigens to which it is non-specific, for example 5, 6, 7, 8, 9, 10 or more times higher binding affinity.

The term "Fab fragment" as used herein refers to an antibody fragment comprising a light chain fragment comprising a $V_L$ (variable light) domain and a constant domain of a light chain ($C_L$), and a $V_H$ (variable heavy) domain and a first constant domain ($CH_1$) of a heavy chain.

The Fv refers to two variable domains, for example co-operative variable domains, such as a cognate pair or affinity matured variable domains, such as a $V_H$ and $V_L$ pair.

Co-operative variable domains as employed herein are variable domains that complement each other and/or both contribute to antigen binding to render the Fv ($V_H/V_L$ pair) specific for the antigen in question.

Binding domain as employed herein refers to two co-operative variable regions, such as a VH and VL each comprising 3 CDRs, wherein the binding domain is specific to a particular (target) antigen.

In one example the antibody molecules of the present disclosure have high affinity, for example affinity of 500 nM or higher affinity, such as 400, 300, 200, 150, 125, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 nM or higher affinity.

Higher binding affinity as employed herein refers to a lower numerical affinity value, for example InM affinity is higher affinity (also referred to as increased affinity) than 10 nM affinity.

Binding affinity (affinity) may be measured by a number of standard assays, for example surface plasmon resonance, such as BIAcore.

The affinity of the original antibody may be increased by employing an affinity maturation protocols including mutating the CDRs (Yang et al J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al Nature, 391, 288-291, 1998). Vaughan et al. (supra) discusses these methods of affinity maturation. Increased affinity as employed herein in this context refers to an improvement over the starting molecule.

In one example the antibody molecule of the present disclosure comprises an amino acid sequence at least 95% identical to a sequence disclosed herein. This example also extends to sequences 96, 97, 98 or 99% to a given sequence disclosed herein.

The methods for creating and manufacturing these antibodies and antibody fragments are well known in the art. Antibodies for use in the present disclosure may be obtained using any suitable method known in the art. The polypeptide/protein including: fusion proteins, for example polypeptide-Fc fusions proteins; or cells, recombinantly or naturally, expressing the polypeptide (as activated T cells), can be used to, for example immunise a host and produce antibodies which specifically recognise the target polypeptide/protein. The polypeptide may be the full length polypeptide or a biologically active fragment or derivative thereof.

Polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The antigen polypeptide may in some instances be part of a larger protein such as a fusion protein for example fused to an affinity tag.

Antibodies generated against the antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al Monoclonal Antibodies and Cancer Therapy, pp 77-96, Alan R Liss, Inc., 1985).

Antibodies for use in the disclosure may also be generated using single lymphocyte antibody methods by cloning and expressing immunoglobulin variable region cDNAs generated from single lymphocytes selected for the production of specific antibodies by, for example, the methods described by Babcook, J. et al 1996, Proc. Natl. Acad. Sci. USA 93(15):7843-78481; WO92/02551; WO2004/051268 and WO2004/106377.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term 'humanised antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one example rather than the entire CDR being transferred, only one or more of the specificity determining residues from any one of the CDRs described herein above are transferred to the human antibody framework (see for example, Kashmiri et al., 2005, Methods, 36, 25-34). In one example only the specificity determining residues from one or more of the CDRs described herein above are transferred to the human antibody framework. In another example only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

CDRs as referred to herein are defined by the VBASE2 software: Retter I, Althaus H H, Münch R, Müller W: VBASE2, an integrative V gene database. Nucleic Acids Res. 2005 Jan. 1; 33 (Database issue):D671-4.

In an alternative independent there is provided the CDRs defined in each of the a variable domains disclosed herein wherein the CDRs are defined by Kabat/Clothia numbering as a defined below.

CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The term "antibody effector function(s)" or "effector function" as used herein refers to a function contributed by the constant region of an antibody (e.g. the Fc effector domain(s) of an immunoglobulin). Such function can be effected by, for example, binding of an Fc effector domain(s) to an Fc receptor on an immune cell with pathogenic or lytic activity or by binding of an Fc effector domain(s) to components of the complement system. examples of effector functions include, but is not limited to, antibody-dependent cell-mediated cytotoxicity (ADCC), antibody-dependent cellular phagocytosis (ADCP), and complement dependent cytotoxicity (CDC).

In one example an antibody molecule according to the present disclosure may induce (or increase) antibody-dependent cell-mediated cytotoxicity (ADCC) of target (cancer) cells. ADCC is an immune mechanism leading to the lysis of antibody-coated target cells by immune effector cells. The target cells are cells to which antibodies or fragments thereof comprising an Fc region specifically bind, generally via the protein part that is N-terminal to the Fc region. An exemplary method of determining ADCC can be found in the Experimental section of the present disclosure.

In one example an antibody molecule according to the present disclosure may be conjugated to at least one payload. It will be appreciated that the payload may comprise a single molecule or two or more such molecules so linked as to form a single moiety that can be attached to the antibodies of the present invention. Where it is desired to obtain an antibody fragment linked to an molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al Controlled Drug Delivery, 2nd Ed., Robinson et al eds., 1987, pp. 623-53; Thorpe et al., 1982, Immunol. Rev., 62:119-58 and Dubowchik et al 1999, Pharmacology and Therapeutics, 83, 67-123). Particular chemical procedures include, for example, those described in WO 93/06231, WO 92/22583, WO 89/00195, WO89/01476 and WO03031581. Alternatively, where the molecule is a protein or polypeptide the linkage may be achieved using recombinant DNA procedures, for example as described in WO 86/01533 and EP0392745.

The term payloads as used herein includes, for example, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Other payloads may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other payloads include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other payloads may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the payload may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545).

Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures.

Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one example, the antibody is a modified Fab fragment or diFab which is PEGylated, i.e. has PEG (poly(ethyleneglycol)) covalently attached thereto, e.g. according to the method disclosed in EP 0948544 or EP1090037 [see also "Poly(ethyleneglycol] Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

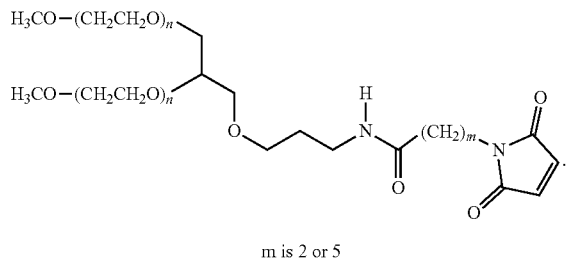

m is 2 or 5

That is to say each PEG is about 20,000 Da.

Further alternative PEG effector molecules of the following type:

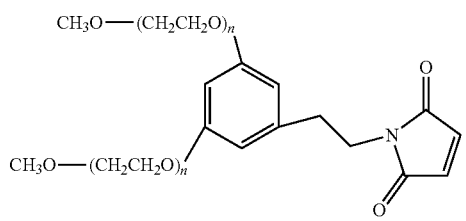

are available from Dr Reddy, NOF and Jenkem.

In one example there is provided an antibody which is PEGylated (for example with a PEG described herein), attached through a cysteine amino acid residue at or about amino acid 226 in the chain, for example amino acid 226 of the heavy chain (by sequential numbering).

T Cell Receptor and Chimeric Antigen Receptors

A comparison and review of T cell receptor and chimeric antigen receptor technology is provided in Dotti et al 2009 (Human Gene Therapy 20: 1229-1239 (November 2009).

In one example a chimeric antigen receptor according to the present disclosure comprises the technology disclosed in WO2013/040557, incorporated herein by reference. In brief, as used herein, the term "chimeric antigen receptor" refers to molecules that combine antibody-based specificity for an antigen with cell receptor-activating intracellular domains with specific cellular immune activity. For example, the chimeric antigen receptor may combine the antigen binding domain as described herein with a cell receptor-activating intracellular domain (e.g. T cell receptor-activating intracellular domain) with specific anti-tumor cellular immune activity. The chimeric antigen receptor would then allow a T cell to achieve MHC-independent primary activation through a single chain Fv (scFv) antigen-specific extracellular region fused to intracellular domains that provide T cell activation and co-stimulatory signals.

Pharmaceutical Compositions

In one aspect a pharmaceutical formulation or composition according to the invention comprises an antibody molecule according to the present disclosure and a pharmaceutically acceptable excipient, diluent and/or carrier.

Such carriers enable the pharmaceutical compositions to be formulated as tablets, pills, dragees, capsules, liquids, gels, syrups, slurries and suspensions, for ingestion by the patient.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions.

The pharmaceutical compositions of this invention may be administered by any number of routes including but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form (such as lyophilised), for reconstitution before use with an appropriate sterile liquid, such as glycose, saline, water for injection or a combination of two or more of the same.

Thus in one example the formulation is provided for parenteral administration, in particular for intravenous or subcutaneous injection.

Once formulated, the compositions of the invention can be administered directly to the subject. The subjects to be treated can be animals. However, in one or more examples the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one example the pH of a liquid formulation according to the present disclosure is in range pH 5.5 to 8, such as pH 6, 6.5, 7, 7.1, 7.2, 7.3, 7.4, 7.5, 7.6, 7.7, 7.8 or 7.9.

In one example the formulation is provide is isotonic or is isotonic after constitution.

In one example the composition or formulation of the present disclosure comprises 1-200 mg/mL of an antibody molecule according to the present disclosure, for example 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198 or 199 mg/ml.

Evaluation

As illustrated in the Experimental Section, the antibodies of the present disclosure can be used to track the growth of tumor in vivo. Thus, it is envisaged that the antibody as defined herein may be used to evaluate the status of a cancer in a patient.

The term "status" as used herein, refers to the situation or state of the tumor or cancerous mass at a given time point Thus, as used herein, the status of a cancer patient may be defined by the size of the tumour, the location (or number of locations) of the tumor, and the stage of tumour observed. Thus, depending on the type of cancer, the status of the patient may be the same as the stage of tumour observed. In some examples, the status may be "nodal status", "local", "distant", or "recurrence".

Treatment

Thus one example there is provided an antibody molecule or a composition according to the present disclosure for use in therapy, in particular the treatment of cancer or fibrosis.

The term "fibrosis" as used herein refers to the formation of excess fibrous connective tissue in an organ or tissue, for example, in reparative or reactive process. This is as opposed to formation of fibrous tissue as a normal constituent of an organ or tissue. Thus, in the present disclosure, the term "fibrosis" is used to distinguish abnormal from normal healing processes. In some examples, the term "fibrosis" is limited to fibrosis relating to cancer, for example solid cancer mass or metastatic cancer).

In one example the treatment of the present disclosure is administered for epithelial cancer, for example is selected from liver cancer (such as hepatocellular carcinoma), biliary duct cancer, breast cancer (such as non ER+ breast cancer), prostate cancer, colorectal cancer, ovarian cancer, endometrial cancer, cervical cancer, lung cancer, gastric cancer, oesophageal cancer, pancreatic cancer, bone cancer, bladder cancer, head and neck cancer, thyroid cancer, skin cancer, renal cancer, and oesophagus cancer and combinations thereof, for example gastric cancer.

In one example the cancer is selected from selected from the group comprising hepatocellular carcinoma, biliary duct cancer, breast cancer, prostate cancer, colorectal cancer, ovarian cancer, lung cancer, gastric cancer, pancreatic and oesophagus cancer.

In one example the biliary duct cancer is in a location selected from intrahepatic bile ducts, left hepatic duct, right hepatic duct, common hepatic duct, cystic duct, common bile duct, Ampulla of Vater and combinations thereof.

In one example the biliary duct cancer is in an intrahepatic bile duct. In one example the biliary duct cancer is in a left hepatic duct. In one example the biliary duct cancer is in a right hepatic duct. In one example the biliary duct cancer is in a common hepatic duct. In one example the biliary duct cancer is in a cystic duct. In one example the biliary duct cancer is in a common bile duct. In one example the biliary duct cancer is in an Ampulla of Vater.

In one example the epithelial cancer is a carcinoma.

In one example the cancer is tumour, for example a solid tumour, a liquid tumour or a combination of the same.

In one example the treatment according to the disclosure is adjuvant therapy, for example after surgery.

In one example the therapy according to the disclosure is neoadjuvant treatment, for example to shrink a tumour before surgery.

In one example the tumour is a solid tumour. In one example the cancer is a primary cancer, secondary cancer, metastasis or combination thereof. In one example the treatment according to the present disclosure is suitable for the treatment of secondary tumours. In one example the cancer is metastatic cancer. In one example the treatment according to the present disclosure is suitable for the treatment of primary cancer and metastases. In one example the treatment according to the present disclosure is suitable for the treatment of secondary cancer and metastases. In one example the treatment according to the present disclosure is suitable for the treatment of primary cancer, secondary cancer and metastases.

In one example the treatment according to the present disclosure is suitable for the treatment of cancerous cells in a lymph node, for a cancer of the present disclosure.

In one example the liver cancer is primary liver cancer. In one example the liver cancer is secondary liver cancer. In one example the liver cancer is stage 1, 2, 3A, 3B, 3C, 4A or 4B.

In one example the gastric cancer is stage 0, I, II, III or IV.

In one example the cancer is a RON positive. In one example the cancer is Met positive. In one example the cancer is RON positive and Met positive.

In one example the cancer is refractory or resistant to one or more available cancer treatments.

In one example the therapy of the present disclosure is first line therapy. In one example the therapy according to the present disclosure is second line or subsequent line therapy.

In one example the antibody molecule according to the present disclosure is employed in a combination therapy.

In one example the combination therapy comprises a checkpoint inhibitor, such as a CTLA4 inhibitor, a PD-1 inhibitor or a PD-L1 inhibitor, in particular an antibody or binding fragment thereof.

In one example the combination therapy of the present disclosure comprises or further comprises a chemotherapeutic agent.

In one example the combination therapy comprises a HER inhibitor, for example herceptin or the pan-HER inhibitor varlitinib [(R]-N4-[3-Chloro-4-(thiazol-2-ylmethoxy)-phenyl]-N6-(4-methyl-4,5,-dihydro-oxazol-2-yl)-quinazoline-4,6-diamine (Varlitinib Example 52 disclosed in WO2005/016346)] for example administered once or twice daily at a dose in the range 10 mg to 500 mg, such as 200 mg, 300 mg or 400 mg.

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, taxanes, topoisomerase inhibitors, parp inhibitors and other antitumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent, nitrogen mustards, nitrosoureas, tetrazines, aziridines, platins and derivatives, and non-classical alkylating agents.

Examples of platinum containing chemotherapeutic agents (also referred to as platins), include cisplatin, carboplatin, oxaliplatin, satraplatin, picoplatin, nedaplatin, triplatin and lipoplatin (a liposomal version of cisplatin), in particular cisplatin, carboplatin and oxaliplatin.

The dose for cisplatin ranges from about 20 to about 270 mg/m$^2$ depending on the exact cancer. Often the dose is in the range about 70 to about 100 mg/m$^2$.

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil (5-FU) and prodrugs thereof such as capecitabine [Xeloda®]), floxuridine, gemcitabine, cytarabine, decitabine, raltitrexed (tomudex) hydrochloride, cladribine and 6-azauracil.

Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currently are used only to treat bladder cancer and mitoxantrone an anthracycline analog, in particular doxorubicin.

Examples of anti-microtubule agents, which may be employed in the method of the present disclosure, include include vinca alkaloids and taxanes.

Vinca alkaloids include completely natural chemicals for example vincristine and vinblastine and also semi-synthetic vinca alkaloids, for example vinorelbine, vindesine, and vinflunine.

Taxanes include paclitaxel, docetaxel, abraxane, carbazitaxel and derivatives of thereof. Derivatives of taxanes as employed herein includes reformulations of taxanes like taxol, for example in a micelluar formulaitons, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

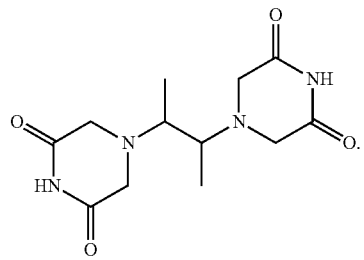 [SMILES: CC(C(C)N1CC(=O)NC(=O)C1)N1CC(=O)NC(=O)C1]

Type II poisons include amsacrine, etoposide, etoposide phosphate, teniposide and doxorubicin and fluoroquinolones.

In one example the chemotherapeutic is a PARP inhibitor.

In one example a combination of chemotherapeutic agents employed is, for example a platin and 5-FU or a prodrug thereof, for example cisplatin or oxaplatin and capecitabine or gemcitabine, such as FOLFOX.

In one example the chemotherapy comprises a combination of chemotherapy agents, in particular cytotoxic chemotherapeutic agents.

In one example the chemotherapy combination comprises a platin, such as cisplatin and fluorouracil or capecitabine.

In one example the chemotherapy combination is capecitabine and oxaliplatin (XELOX).

In one example the chemotherapy is a combination of folinic acid and 5-FU, optionally in combination with oxaliplatin (FOLFOX).

In one example the chemotherapy is a combination of folinic acid, 5-FU and irinotecan (FOLFIRI), optionally in combination with oxaliplatin (FOLFIRINOX). The regimen, for example includes: irinotecan (180 mg/m$^2$ IV over 90 minutes) concurrently with folinic acid (400 mg/m$^2$ [or 2×250 mg/m$^2$] IV over 120 minutes); followed by fluorouracil (400-500 mg/m$^2$ IV bolus) then fluorouracil (2400-3000 mg/m$^2$ intravenous infusion over 46 hours). This cycle is typically repeated every two weeks. The dosages shown above may vary from cycle to cycle.

In one example the chemotherapy combination employs a microtubule inhibitor, for example vincristine sulphate, epothilone A, N-[2-[(4-Hydroxyphenyl)amino]-3-pyridinyl]-4-methoxybenzenesulfonamide (ABT-751), a taxol derived chemotherapeutic agent, for example paclitaxel, abraxane, or docetaxel or a combination thereof.

In one example the chemotherapy combination employs an mTor inhibitor. Examples of mTor inhibitors include:

everolimus (RAD001), WYE-354, KU-0063794, papamycin (Sirolimus), Temsirolimus, Deforolimus (MK-8669), AZD8055 and BEZ235(NVP-BEZ235).

In one example the chemotherapy combination employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one example the chemotherapy combination employs an AKT inhibitor. Examples of AKT inhibitors include: MK-2206 and AT7867.

In one example the combination employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one example the chemotherapy combination employs a p38 inhibitor, for example as disclosed in WO2010/038086, such as N-[4-({4-[3-(3-tert-Butyl-1-p-tolyl-1H-pyrazol-5-yl)ureido]naphthalen-1-yloxy}methyl)pyridin-2-yl]-2-methoxyacetamide.

In one example the combination employs a Bcl-2 inhibitor. Examples of Bcl-2 inhibitors include: obatoclax mesylate, ABT-737, ABT-263(navitoclax) and TW-37.

In one example the chemotherapy combination comprises an antimetabolite such as capecitabine (xeloda), fludarabine phosphate, fludarabine (fludara), decitabine, raltitrexed (tomudex), gemcitabine hydrochloride and/or cladribine.

In one example the chemotherapy combination comprises ganciclovir, which may assist in controlling immune responses and/or tumour vasculation.

"Administering a combination therapy" as employed herein does not require the therapies employed in the combination to be administered at the same time. Combination therapy as employed herein refers to two or more modes of therapy being employing over the same treatment period, i.e. the opposite of sequential therapy. Two or more modes of therapy as employed herein refers to at least two therapies which have different modes of action and/or different activities and/or different routes of administration.

Terms such as "treating" or "treatment" or "to treat" as employed herein refers to therapeutic measures that: cure, slow down, ameliorate symptoms of, and/or halt progression of a diagnosed pathologic condition or disorder; or prophylactic or preventative measures that prevent and/or slow the development of a targeted pathologic condition or disorder. Thus, those in need of treatment include those already with the disorder; those prone to have the disorder; and those in whom the disorder is to be prevented and those in whom reoccurrence of the disorder needs to be prevented (e.g. those in remission). In certain aspects, a subject is successfully "treated" for a disease or condition, for example cancer if the patient shows, e.g. total, partial, or transient remission of the disease or condition.

A therapeutically effective amount as employed herein refers to an amount suitable to elicit the requisite therapeutic effect. In the combination therapy of the present disclosure the RON inhibitor may be employed at a dose which is the same or lower than the monotherapy dose with said inhibitor. In one example the dose of thePD-1 pathway inhibitor employed is the same or lower than the monotherapy dose with said inhibitor. In one example the dose on the RON inhibitor is the same as the dose employed in monotherapy and the dose of the PD-1 pathway inhibitor is the same as the dose employed in monotherapy. In one example the dose on the RON inhibitor is lower than the dose employed in monotherapy and the dose of the PD-1 pathway inhibitor is the same as the dose employed in monotherapy. In one example the dose on the RON inhibitor is the same as the dose employed in monotherapy and the dose of the PD-1 pathway inhibitor is lower than the dose employed in monotherapy. In one example the dose on the RON inhibitor is lower the dose employed in monotherapy and the dose of the PD-1 pathway inhibitor is lower than the dose employed in monotherapy. A suitable dose can be established by those skilled in the art.

Cancer Types In more Detail

In one example the gastric cancer is selected from the group comprising adenocarcinoma of the stomach, squamous cell carcinomas, lymphoma of the stomach, gastric stromal tumour, and neuroendocrine tumours.

In one example the liver cancer is, for example selected from the group hepatocellular carcinoma, cholangiocarcinoma, angiosarcoma, and hepatoblastoma, in particular hepatocellular carcinoma. In one example the primary liver cancer is stage 1, 2, 3 or 4. In one example the liver cancer is secondary or metastasized liver cancer.

Lung cancers are classified according to histological type and are categorized by the size and appearance of the malignant cells seen by a histopathologist under a microscope. For therapeutic purpose, two broad classes are distinguished: non-small cell lung carcinoma and small cell lung carcinoma.

In one example the epithelial cancer is lung cancer, for example small-cell lung cancer (SCLC) and non-small-cell lung cancer (NSCLC).

Non-Small-Cell Lung Carcinoma—

The three main subtypes of NSCLC are adenocarcinoma, squamous-cell carcinoma and large-cell carcinoma.

Nearly 40% of lung cancers are adenocarcinoma, which usually originates in peripheral lung tissue. A subtype of adenocarcinoma, the bronchioloalveolar carcinoma, is more common in female never-smokers, and may have a better long term survival.

Squamous-cell carcinoma accounts for about 30% of lung cancers. They typically occur close to large airways. A hollow cavity and associated cell death are commonly found at the center of the tumor. About 9% of lung cancers are large-cell carcinoma. These are so named because the cancer cells are large, with excess cytoplasm, large nuclei and conspicuous nucleoli.

Small-Cell Lung Carcinoma—

In small-cell lung carcinoma (SCLC), the cells contain dense neurosecretory granules (vesicles containing neuroendocrine hormones), which give this tumor an endocrine/paraneoplastic syndrome association. Most cases arise in the larger airways (primary and secondary bronchi). These cancers grow quickly and spread early in the course of the disease. Sixty to seventy percent have metastatic disease at presentation.

In one example the cancer is non-small lung carcinoma.

In one example the cancer is liver cancer, for example a liver metastasis from a primary cancer, for example colon cancer, which has spread to the liver. In one example the liver cancer is HCC hepatocellular carcinoma.

In one example there is provided treatment of renal cancer, for example renal cell carcinoma and/or urothelial cell carcinoma. Other examples of renal cancer include squamous cell carcinoma, juxtaglomerular cell tumor (reninoma), angiomyolipoma, renal oncocytoma, Bellini duct carcinoma, clear-cell sarcoma of the kidney, mesoblastic nephroma, Wilms' tumor, mixed epithelial stromal tumor, clear cell adenocarcinoma, transitional cell carcinoma, inverted papilloma, renal lymphoma, teratoma, carcinosarcoma, and carcinoid tumor of the renal pelvis.

In one example the cancer is bladder cancer, for example is any of several types of malignancy arising from the epithelial lining (i.e., the urothelium) of the urinary bladder. About 90% of bladder cancers are transitional cell carcinoma. The other 10% are squamous cell carcinoma, adenocarcinoma, sarcoma, small cell carcinoma, and secondary deposits from cancers elsewhere in the body. The staging of is given below.

T (Primary tumour)
TX Primary tumour cannot be assessed
T0 No evidence of primary tumour
Ta Non-invasive papillary carcinoma
Tis Carcinoma in situ ('flat tumour')
T1 Tumour invades subepithelial connective tissue
T2a Tumour invades superficial muscle (inner half)
T2b Tumour invades deep muscle (outer half)
T3 Tumour invades perivesical tissue:
T3a Microscopically
T3b Macroscopically (extravesical mass)
T4a Tumour invades prostate, uterus or vagina
T4b Tumour invades pelvic wall or abdominal wall
N (Lymph nodes)
NX Regional lymph nodes cannot be assessed
N0 No regional lymph node metastasis
N1 Metastasis in a single lymph node 2 cm or less in greatest dimension
N2 Metastasis in a single lymph node more than 2 cm but not more than 5 cm in greatest dimension, or multiple lymph nodes, none more than 5 cm in greatest dimension
N3 Metastasis in a lymph node more than 5 cm in greatest dimension
M (Distant metastasis)
MX Distant metastasis cannot be assessed
M0 No distant metastasis
M1 Distant metastasis.
Bladder Cancer The current disclosure extends to any stage of bladder cancer.

Ovarian Cancer

There are more than 30 different types of ovarian cancer which are classified according to the type of cell from which they start. Cancerous ovarian tumors can start from three common cell types:

Surface Epithelium—cells covering the lining of the ovaries

Germ Cells—cells that are destined to form eggs

Stromal Cells—Cells that release hormones and connect the different structures of the ovaries The present disclosure relates to treatment of ovarian cancer from any source, for example as described herein, in particular epithelium cells. Epithelial ovarian carcinomas (EOCs) account for 85 to 90 percent of all cancers of the ovaries.

Common Epithelial Tumors—Epithelial ovarian tumors develop from the cells that cover the outer surface of the ovary. Most epithelial ovarian tumors are benign (noncancerous). There are several types of benign epithelial tumors, including serous adenomas, mucinous adenomas, and Brenner tumors. Cancerous epithelial tumors are carcinomas—meaning they begin in the tissue that lines the ovaries. These are the most common and most dangerous of all types of ovarian cancers. Unfortunately, almost 70 percent of women with the common epithelial ovarian cancer are not diagnosed until the disease is advanced in stage.

There are some ovarian epithelial tumors whose appearance under the microscope does not clearly identify them as cancerous. These are called borderline tumors or tumors of low malignant potential (LMP tumors). The method of the present disclosure includes treatment of the latter.

Germ Cell Tumors—Ovarian germ cell tumors develop from the cells that produce the ova or eggs. Most germ cell tumors are benign (non-cancerous), although some are cancerous and may be life threatening. The most common germ cell malignancies are maturing teratomas, dysgerminomas, and endodermal sinus tumors. Germ cell malignancies occur most often in teenagers and women in their twenties. Today, 90 percent of patients with ovarian germ cell malignancies can be cured and their fertility preserved.

Stromal Tumors—Ovarian stromal tumors are a rare class of tumors that develop from connective tissue cells that hold the ovary together and those that produce the female hormones, estrogen and progesterone. The most common types are granulosa-theca tumors and Sertoli-Leydig cell tumors. These tumors are quite rare and are usually considered low-grade cancers, with approximately 70 percent presenting as Stage I disease (cancer is limited to one or both ovaries).

Primary Peritoneal Carcinoma—The removal of one's ovaries eliminates the risk for ovarian cancer, but not the risk for a less common cancer called Primary Peritoneal Carcinoma. Primary Peritoneal Carcinoma is closely rated to epithelial ovarian cancer (most common type). It develops in cells from the peritoneum (abdominal lining) and looks the same under a microscope. It is similar in symptoms, spread and treatment.

Stages of Ovarian Cancer

Once diagnosed with ovarian cancer, the stage of a tumor can be determined during surgery, when the doctor can tell if the cancer has spread outside the ovaries. There are four stages of ovarian cancer—Stage I (early disease) to Stage IV (advanced disease). The treatment plan and prognosis (the probable course and outcome of your disease) will be determined by the stage of cancer you have.

Following is a description of the various stages of ovarian cancer:

Stage I—Growth of the cancer is limited to the ovary or ovaries.

Stage IA—Growth is limited to one ovary and the tumor is confined to the inside of the ovary. There is no cancer on the outer surface of the ovary. There are no ascites present containing malignant cells. The capsule is intact.

Stage IB—Growth is limited to both ovaries without any tumor on their outer surfaces. There are no ascites present containing malignant cells. The capsule is intact.

Stage IC—The tumor is classified as either Stage IA or IB and one or more of the following are present: (1) tumor is present on the outer surface of one or both ovaries; (2) the capsule has ruptured; and (3) there are ascites containing malignant cells or with positive peritoneal washings.

Stage II—Growth of the cancer involves one or both ovaries with pelvic extension.

Stage IIA—The cancer has extended to and/or involves the uterus or the fallopian tubes, or both.

Stage IIB—The cancer has extended to other pelvic organs.

Stage IIC—The tumor is classified as either Stage IIA or IIB and one or more of the following are present: (1) tumor is present on the outer surface of one or both ovaries; (2) the capsule has ruptured; and (3) there are ascites containing malignant cells or with positive peritoneal washings.

Stage III—Growth of the cancer involves one or both ovaries, and one or both of the following are present: (1) the cancer has spread beyond the pelvis to the lining of the abdomen; and (2) the cancer has spread to lymph nodes. The tumor is limited to the true pelvis but with histologically proven malignant extension to the small bowel or omentum.

Stage IIIA—During the staging operation, the practitioner can see cancer involving one or both of the ovaries, but no cancer is grossly visible in the abdomen and it has not spread to lymph nodes. However, when biopsies are checked under a microscope, very small deposits of cancer are found in the abdominal peritoneal surfaces.

Stage IIIB—The tumor is in one or both ovaries, and deposits of cancer are present in the abdomen that are large enough for the surgeon to see but not exceeding 2 cm in diameter. The cancer has not spread to the lymph nodes.

Stage IIIC—The tumor is in one or both ovaries, and one or both of the following is present: (1) the cancer has spread to lymph nodes; and/or (2) the deposits of cancer exceed 2 cm in diameter and are found in the abdomen.

Stage IV—This is the most advanced stage of ovarian cancer. Growth of the cancer involves one or both ovaries and distant metastases (spread of the cancer to organs located outside of the peritoneal cavity) have occurred. Finding ovarian cancer cells in pleural fluid (from the cavity which surrounds the lungs) is also evidence of stage IV disease.

In one example the ovarian cancer is: type I, for example IA, IB or IC; type II, for example IIA, IIB or IIC; type III, for example IIIA, IIIB or IIIC; or type IV.

In one example the breast cancer is one selected from the group comprising ductal carcinoma in situ, lobular carcinoma in situ, invasive breast cancer, invasive lobular breast cancer, Paget's disease, angiosarcoma of the breast, medullary breast cancer, mucinous breast cancer, tubular breast cancer, adenoid cystic carcinoma of the breast, metaplastic breast cancer, lymphoma of the breast, basal type breast cancer, phyllodes or cystosarcoma phyllodes and papillary breast cancer.

In one example the prostate cancer is selected from the group comprising ductal adenocarcinoma, transitional cell (urothelial) cancer, squamous cell cancer, carcinoid, small cell cancer, sarcomas and sarcomatoid cancers.

TABLE 2

Summary of RON antibody sequences

| | SEQ ID NO: | Sequence |
|---|---|---|
| 7G8 (Heavy chain 1) | | |
| CDRH1 | 1 | GFTFNTYT |
| CDRH2 | 2 | ISNGGGST |
| CDRH3 | 3 | ARGYRYAAMDY |
| FR1 | 4 | EVQLEQSGGGLVQPGGSLKLSCAAS |
| FR2 | 5 | MSWVRQTPEKRLEWVAY |
| FR3 | 6 | YYPDTVKGRFTISRDNAKNTLYLQMSSLKSEDTAMYYC |
| FR4 | 7 | WGQGTSVTVSS |
| Heavy chain variable (amino acid) | 8 | EVQLEQSGGGLVQPGGSLKLSCAASGFTFNTYTMSWVRQTPEKRLEWV AYISNGGGSTYYPDTVKGRFTISRDNAKNTLYLQMSSLKSEDTAMYYCA RGYRYAAMDYWGQGTSVTVSS |
| Heavy chain variable (nucleotide sequence) | 9 | GAGGTGCAGCTGGAGCAGTCTGGGGGAGGTTTAGTGCAGCCTGGAGGGT CCCTGAAACTCTCCTGTGCAGCCTCTGGATTCACTTTCAATACCTATACC ATGTCTTGGGTTCGCCAGACTCCAGAGAAGAGGCTGGAGTGGGTCGCAT ACATTAGTAATGGTGGTGGTAGTACCTACTATCCAGACACTGTAAAGGG CCGATTCACCATCTCCAGAGACAATGCCAAGAACACCCTGTACCTGCAA ATGAGCAGTCTGAAGTCTGAGGACACGGCCATGTATTACTGTGCAAGAG GCTATAGGTACGCTGCTATGGACTACTGGGGTCAAGGAACCTCAGTCAC CGTCTCCTCA |
| 7G8 (Kappa/light chain) | | |
| CDRL1 | 18 | QSINNN |
| CDRL2 | 19 | FAS |
| CDRL3 | 20 | QQSNSWPLT |
| FR1 | 21 | DIVMTQTTATLSVTPGDGVSLSCRAS |
| FR2 | 22 | LHWYQQKSHESPRLLIK |
| FR3 | 23 | QSISGIPSRFSGSGSGTDFTLSINSVETEDFGMYFC |
| FR4 | 24 | FGAGTKLELK |

TABLE 2-continued

Summary of RON antibody sequences

| | SEQ ID NO: | Sequence |
|---|---|---|
| Light chain variable (amino acid) | 25 | DIVMTQTTATLSVTPGDGVSLSCRASQSINNNLHWYQQKSHESPRLLIKF ASQSISGIPSRFSGSGSGTDFTLSINSVETEDFGMYFCQQSNSWPLTFGAG TKLELK |
| Light chain variable (nucleotide sequence) | 26 | GATATTGTGATGACCCAGACTACAGCCACCCTGTCTGTGACTCCAGGAG ATGGCGTCAGTCTTTCCTGCAGGGCCAGCCAAAGTATTAACAACAACCT ACACTGGTATCAACAAAAATCACATGAGTCTCCAAGACTTCTCATCAAG TTTGCTTCCCAGTCCATCTCTGGGATCCCCTCCAGGTTCAGTGGCAGTGG ATCAGGGACAGATTTCACTCTCAGTATCAACAGTGTGGAGACTGAAGAT TTTGGAATGTATTTCTGTCAACAGAGTAACAGCTGGCCTCTCACGTTCG GTGCTGGGACCAAGCTGGAGCTGAAAC |

6D4 (Heavy chain)

| | SEQ ID NO: | Sequence |
|---|---|---|
| CDRH1 | 27 | GFTFSNYA |
| CDRH2 | 28 | ISSGGST |
| CDRH3 | 29 | AREGPLYYGPSYGGYYFDY |
| FR1 | 30 | EVQLLETGGGLVKPGGSLKLSCAAS |
| FR2 | 31 | MSWVRQTPEKRLEWGAS |
| FR3 | 32 | YYPDSVKGRFTISRDNARNILYLQMSSLRSEDTALYYC |
| FR4 | 33 | WGQGTTLTVSS |
| Heavy chain variable (amino acid) | 34 | EVQLLETGGGLVKPGGSLKLSCAASGFTFSNYAMSWVRQTPEKRLEWGA SISSGGSTYYPDSVKGRFTISRDNARNILYLQMSSLRSEDTALYYCAREGP LYYGPSYGGYYFDYWGQGTTLTVSS |
| Heavy chain variable (nucleotide sequence) | 35 | GAAGTGCAGCTGTTGGAGACTGGGGGAGGCTTAGTGAAGCCTGGAGGGT CCCTGAAACTCTCCTGTGCAGCCTCTGGATTCACTTTCAGTAACTATGCC ATGTCTTGGGTTCGCCAGACTCCAGAGAAGAGGCTGGAGTGGGGCGCAT CCATTAGTAGTGGTGGTAGCACCTACTATCCAGACAGTGTGAAGGGCCG ATTCACCATCTCCAGAGATAATGCCAGGAACATCCTGTACCTGCAAATG AGCAGTCTGAGGTCTGAGGACACGGCCCTGTATTACTGTGCAAGAGAGG GTCCCCTTTACTACGGTCCTAGCTACGGAGGGTACTACTTTGACTACTG GGGCCAAGGCACCACTCTCACAGTCTCCTCA |

6D4 (Kappa/light chain)

| | SEQ ID NO: | Sequence |
|---|---|---|
| CDRL1 | 36 | QRLVYSNGNTY |
| CDRL2 | 37 | KVS |
| CDRL3 | 38 | SQSTHVPWT |
| FR1 | 39 | DIVMTQSPLSLPVSLGDQASISCRSS |
| FR2 | 40 | LHWYLQKPGQSPKLLIY |
| FR3 | 41 | NRFSGVPDRFSGSGSGTDFTLKISRVEAEDLGVYFC |
| FR4 | 42 | FGGGTKLEIK |
| Light chain variable (amino acid) | 43 | DIVMTQSPLSLPVSLGDQASISCRSSQRLVYSNGNTYLHWYLQKPGQSPK LLIYKVSNRFSGVPDRFSGSGSGTDFTLKISRVEAEDLGVYFCSQSTHVP WTFGGGTKLEIK |
| Light chain variable (nucleotide sequence) | 44 | GACATTGTGATGACACAGTCTCCACTCTCCCTGCCTGTCAGTCTTGGAG ATCAAGCCTCCATCTCTTGCAGATCTAGTCAGAGGCTTGTATACAGTAA TGGAAACACCTATTTACATTGGTACCTGCAGAAGCCAGGCCAGTCTCCA AAGCTCCTGATCTACAAAGTTTCCAACCGATTTTCTGGGGTCCCAGACA GGTTCAGTGGCAGTGGATCAGGGACAGATTTCACACTCAAGATCAGCAG AGTGGAGGCTGAGGATCTGGGAGTTTATTTCTGCTCTCAAAGTACACAT GTTCCGTGGACGTTCGGTGGAGGCACCAAGCTGGAAATCAAAC |

3E1 (Heavy chain)

| | SEQ ID NO: | Sequence |
|---|---|---|
| CDRH1 | 45 | GFSFSDYW |
| CDRH2 | 46 | IRLKSSNYAT |

TABLE 2-continued

Summary of RON antibody sequences

| | SEQ ID NO: | Sequence |
|---|---|---|
| CDRH3 | 47 | TRGDY |
| FR1 | 48 | DVMLVESGGGLVQPGGSMKLSCVAS |
| FR2 | 49 | MNWVRQSPEKGLEWVAE |
| FR3 | 50 | HYAESVKGRFTISRDDSESSVYLQMNNLRPEDTGFYYC |
| FR4 | 7 | WGQGTSVTVSS |
| Heavy chain variable (amino acid) | 51 | DVMLVESGGGLVQPGGSMKLSCVASGFSFSDYWMNWVRQSPEKGLEW VAEIRLKSSNYATHYAESVKGRFTISRDDSESSVYLQMNNLRPEDTG FYYCTRGDYWGQGTSVTVSS |
| Heavy chain variable (nucleotide sequence) | 52 | GACGTGATGCTGGTGGAGTCTGGAGGAGGCTTGGTGCAACCTGGAGGAT CCATGAAACTCTCCTGTGTTGCCTCTGGATTCAGTTTCAGTGACTACTG GATGAACTGGGTCCGCCAGTCTCCAGAGAAGGGGCTTGAATGGGTTGCT GAGATTAGATTGAAATCTAGTAATTATGCAACACATTATGCGGAGTCTG TGAAAGGGAGGTTTACCATCTCAAGAGATGATTCCGAAAGTAGTGTCTA CCTGCAAATGAACAACTTAAGACCTGAAGACACTGGCTTTTATTACTGT ACCAGGGGGGACTATTGGGGTCAAGGAACCTCAGTCACCGTCTCTTCA |

3E1 (Kappa/light chain)

| | SEQ ID NO: | Sequence |
|---|---|---|
| CDRL1 | 18 | QSINNN |
| CDRL2 | 19 | FAS |
| CDRL3 | 20 | QQSNSWPLT |
| FR1 | 53 | DIVMTQSPATLSVTPGDGVSLSCRAS |
| FR2 | 22 | LHWYQQKSHESPRLLIK |
| FR3 | 23 | QSISGIPSRFSGSGSGTDFTLSINSVETEDFGMYFC |
| FR4 | 24 | FGAGTKLELK |
| Light chain variable (amino acid) | 54 | DIVMTQSPATLSVTPGDGVSLSCRASQSINNNLHWYQQKSHESPRLLIKF ASQSISGIPSRFSGSGSGTDFTLSINSVETEDFGMYFCQQSNSWPLTFGAG TKLELK |
| Light chain variable (nucleotide sequence) | 55 | GATATTGTGATGACCCAGTCTCCAGCCACCCTGTCTGTGACTCCAGGAG ATGGCGTCAGTCTTTCCTGCAGGGCCAGCCAAAGTATTAACAACAACCT ACACTGGTATCAACAAAAATCACATGAGTCTCCAAGACTTCTCATCAAG TTTGCTTCCCAGTCCATCTCTGGGATCCCCTCCAGGTTCAGTGGCAGTGG ATCAGGGACAGATTTCACTCTCAGTATCAACAGTGTGGAGACTGAAGAT TTTGGAATGTATTTCTGTCAACAGAGTAACAGCTGGCCTCTCACGTTCG GTGCTGGGACCAAGCTGGAGCTGAAAC |

3G4 (Heavy chain)

| | SEQ ID NO: | Sequence |
|---|---|---|
| CDRH1 | 56 | GYIFTSYW |
| CDRH2 | 57 | IYPGNSDT |
| CDRH3 | 58 | TRDGYYPFAY |
| FR1 | 59 | EVQLEESGTVLARPGASVKMSCKAS |
| FR2 | 60 | MHWIKQRPGQGLEWIGA |
| FR3 | 61 | STNQKFKDKAKLTAVTSTAYLELSSLTNEDSAVFYC |
| FR4 | 62 | WGQGTLVTVSA |
| Heavy chain variable (amino acid) | 63 | EVQLEESGTVLARPGASVKMSCKASGYIFTSYWMHWIKQRPGQGLEWI GAIYPGNSDTSTNQKFKDKAKLTAVTSTAYLELSSLTNEDSAVFYCTR DGYYPFAYWGQGTLVTVSA |
| Heavy chain variable (nucleotide sequence) | 64 | GAAGTGCAGCTGGAGGAGTCAGGGACTGTGCTGGCAAGGCCTGGGGCTT CAGTGAAGATGTCCTGCAAGGCTTCTGGCTACATTTTTACCAGCTACTG GATGCACTGGATAAAACAGAGGCCTGGACAGGGTCTGGAATGGATTGGC GCTATTTATCCTGGAAATAGTGATACTAGTACTAATCAGAAGTTCAAGG |

TABLE 2-continued

Summary of RON antibody sequences

| | SEQ ID NO: | Sequence |
|---|---|---|
| | | ACAAGGCCAAACTGACTGCAGTCACATCCACCAGCACTGCCTATTTGGA ACTCAGCAGCCTGACAAATGAGGACTCAGCGGTCTTTTACTGTACAAGA GATGGTTACTACCCGTTTGCTTACTGGGGCCAAGGGACTCTGGTCACTG TCTCTGCA |

3G4 (Kappa/light chain)

| | SEQ ID NO: | Sequence |
|---|---|---|
| CDRL1 | 65 | QSLVYINGDTY |
| CDRL2 | 66 | RVS |
| CDRL3 | 67 | SQTKHVPYT |
| FR1 | 68 | DIVLTQSPLSLPVSLGDQASISCRSS |
| FR2 | 69 | FHWYLQKPGQSPKLLIY |
| FR3 | 41 | NRFSGVPDRFSGSGSGTDFTLKISRVEAEDLGVYC |
| FR4 | 70 | FGGGTKLEMK |
| Light chain variable (amino acid) | 71 | DIVLTQSPLSLPVSLGDQASISCRSSQSLVYINGDTYFHWYLQKPGQSPKL LIYRVSNRFSGVPDRFSGSGSGTDFTLKISRVEAEDLGVYFCSQTKHVPY TFGGGTKLEMK |
| Light chain variable (nucleotide sequence) | 72 | GACATTGTGCTGACCCAATCTCCACTCTCCCTGCCTGTCAGTCTTGGAGA TCAAGCCTCCATCTCTTGCAGATCTAGTCAGAGCCTTGTATATATTAAT GGAGACACCTATTTTCATTGGTACTTGCAGAAGCCAGGCCAGTCTCCAA AGCTCCTGATCTACAGAGTTTCCAACCGATTTTCTGGGGTCCCAGACAG GTTCAGTGGCAGTGGATCAGGGACAGATTTCACACTCAAGATCAGCAGA GTGGAGGCTGAGGATCTGGGAGTTTATTTCTGCTCTCAAACTAAACATG TTCCGTACACGTTCGGAGGGGGGACCAAGCTGGAAATGAAACG |

5B9 (Heavy chain)

| | SEQ ID NO: | Sequence |
|---|---|---|
| CDRH1 | 73 | GYEFSKYW |
| CDRH2 | 74 | IFPGDGDI |
| CDRH3 | 75 | ARWYYGSNYAMDY |
| FR1 | 76 | EVQLQQPGAELVRPGSSVKISCKAS |
| FR2 | 77 | MNWVKQRPGQGLEWIGQ |
| FR3 | 78 | NYNGKFKGICATLTADKSSSTAYMQLSSLTSEESAVYFC |
| FR4 | 7 | WGQGTSVTVSS |
| Heavy chain variable (amino acid) | 79 | EVQLQQPGAELVRPGSSVKISCKASGYEFSKYWMNWVKQRPGQGLEWI GQIFPGDGDINYNGKFKGKATLTADKSSSTAYMQLSSLTSEESAVYFCAR WYYGSNYAMDYWGQGTSVTVSS |
| Heavy chain variable (nucleotide sequence) | 80 | GAGGTCCAGCTGCAGCAGCCTGGGGCTGAGCTGGTGAGGCCTGGGTCCT CAGTGAAGATTTCCTGCAAGGCTTCTGGCTATGAATTCAGTAAGTACTG GATGAACTGGGTGAAGCAGAGGCCTGACAGGGTCTTGAGTGGATTGGA CAGATTTTTCCAGGAGACGGTGATATTAATTACAATGGAAAATTCAAGG GTAAAGCCACACTGACTGCAGACAAATCCTCCAGCACAGCCTACATGCA GCTCAGCAGCCTAACATCTGAGGAATCTGCGGTCTATTTCTGTGCAAGA TGGTACTACGGTAGTAACTATGCTATGGACTACTGGGGTCAAGGAACCT CAGTCACCGTCTCCTCA |

5B9 (Kappa/light chain)

| | SEQ ID NO: | Sequence |
|---|---|---|
| CDRL1 | 81 | QSLLYSSNQKNY |
| CDRL2 | 82 | WAS |
| CDRL3 | 83 | QQYYAYRT |
| FR1 | 84 | DIVMTQTPSSLAVSVGEKITMSCKSS |
| FR2 | 85 | LAWYQQKPGQSPKLLIY |
| FR3 | 86 | TRESGVPDRFTGSGSGTDFTLTISSVKAEDLAVYYC |

TABLE 2-continued

Summary of RON antibody sequences

| | SEQ ID NO: | Sequence |
|---|---|---|
| FR4 | 42 | FGGGTKLEIK |
| Light chain variable (amino acid) | 87 | DIVMTQTPSSLAVSVGEKITMSCKSSQSLLYSSNQKNYLAWYQQKPGQSP KLLIYWASTRESGVPDRFTGSGSGTDFTLTISSVKAEDLAVYYCQQYYAY RTFGGGTKLEIK |
| Light chain variable (nucleotide sequence) | 88 | GACATTGTGATGACCCAGACTCCATCCTCCCTAGCTGTGTCAGTTGGAG AGAAGATTACTATGAGCTGCAAGTCCAGTCAGAGCCTTTTATATAGTAG CAATCAAAAGAACTACTTGGCCTGGTACCAGCAGAAACCAGGGCAGTCT CCTAAACTGCTGATTTACTGGGCATCCACTAGGGAATCTGGGGTCCCTG ATCGCTTCACAGGCAGTGGATCTGGGACAGATTTCACTCTCACCATCAG CAGTGTGAAGGCTGAAGACCTGGCAGTTTATTACTGTCAGCAATATTAT GCCTATCGGACGTTCGGTGGAGGCACCAAGCTGGAAATCAAAC |

6E6 (Heavy chain)

| | SEQ ID NO: | Sequence |
|---|---|---|
| CDRH1 | 89 | GYIFTSYW |
| CDRH2 | 90 | IYPGNNDT |
| CDRH3 | 91 | TRDGFYPFAY |
| FR1 | 92 | EVKLQQSGTVLARPGTSVKMSCKAS |
| FR2 | 93 | MHWIKERPGQGLEWIGA |
| FR3 | 94 | STNQKFKGKAKLTAVTSTSTAYLELSSLTNEDSAVYYC |
| FR4 | 62 | WGQGTLVTVSA |
| Heavy chain variable (amino acid) | 95 | EVKLQQSGTVLARPGTSVKMSCKASGYIFTSYWMHWIKERPGQGLEWI GAIYPGNNDTSTNQKFKGKAKLTAVTSTSTAYLELSSLTNEDSAVYYCTR DGFYPFAYWGQGTLVTVSA |
| Heavy chain variable (nucleotide sequence) | 96 | GAGGTTAAGCTGCAGCAGTCTGGGACTGTGCTGGCAAGGCCTGGGACTT CAGTGAAGATGTCTTGCAAGGCTTCTGGCTACATTTTTACCAGCTACTG GATGCATTGGATAAAAGAGAGGCCTGGACAGGGTCTGGAATGGATTGGC GCTATTTATCCTGGAAATAATGATACTAGTACTAATCAGAAGTTCAAGG GCAAGGCCAAACTGACTGCAGTCACATCCACCAGCACTGCCTATTTGGA ACTCAGCAGCCTGACAAATGAGGACTCAGCGGTCTATTACTGTACAAGA GATGGTTTTTACCCGTTTGCTTACTGGGGCCAAGGGACTCTGGTCACTG TCTCTGCA |

6E6 (Kappa/light chain)

| | SEQ ID NO: | Sequence |
|---|---|---|
| CDRL1 | 65 | QSLVYINGDTY |
| CDRL2 | 66 | RVS |
| CDRL3 | 67 | SQTKHVPYT |
| FR1 | 97 | DIVLTQTPLSLPVSLGDQASISCRSS |
| FR2 | 69 | FHWYLQKPGQSPKLLIY |
| FR3 | 41 | NRFSGVPDRFSGSGSGTDFTLKISRVEAEDLGVYFC |
| FR4 | 70 | FGGGTKLEMK |
| Light chain variable (amino acid) | 98 | DIVLTQTPLSLPVSLGDQASISCRSSQSLVYINGDTYFHWYLQKPGQSPKL LIYRVSNRFSGVPDRFSGSGSGTDFTLKISRVEAEDLGVYFCSQTKHVPY TFGGGTKLEMK |
| Light chain variable (nucleotide sequence) | 99 | GATATTGTGCTGACCCAGACTCCACTCTCCCTGCCTGTCAGTCTTGGAGA TCAAGCCTCCATCTCTTGCAGATCTAGTCAGAGCCTTGTATATATTAAT GGAGACACCTATTTTCATTGGTACCTGCAGAAGCCAGGCCAGTCTCCAA AGCTCCTGATCTACAGAGTTTCCAACCGATTTTCTGGGGTCCCAGACAG GTTCAGTGGCAGTGGATCAGGGACAGATTTCACACTCAAGATCAGCAGA GTGGAGGCTGAGGATCTGGGAGTTTATTTCTGCTCTCAAACTAAACATG TTCCGTACACGTTCGGAGGGGGGACCAAGCTGGAAATGAAACG |

TABLE 2-continued

Summary of RON antibody sequences

| | SEQ ID NO: | Sequence |
|---|---|---|
| 2B3 (Heavy chain) | | |
| CDRH1 | 100 | GYIFTSYY |
| CDRH2 | 101 | INPITGGT |
| CDRH3 | 102 | ARMGRDAMDY |
| FR1 | 103 | QVQLKQSGSELVKPGASVKLSCKAS |
| FR2 | 104 | MYWVKQRPGQGLEWIGG |
| FR3 | 105 | DFNEKFKDKATLTLAASSSTAYIQLSSLT S E D S A V Y F C |
| FR4 | 7 | WGQGTSVTVSS |
| Heavy chain variable (amino acid) | 106 | QVQLKQSGSELVKPGASVKLSCKASGYIFTSYYMYWVKQRPGQGLEWIGG INPITGGTDFNEKFKDKATLTLAASSSTAYIQLSSLTSEDSAVYFCARMGR DAMDYWGQGTSVTVSS |
| Heavychain variable (nucleotide sequence) | 107 | CAGGTGCAGCTGAAGCAGTCAGGGTCTGAACTGGTGAAACCTGGGGCTT CAGTGAAGTTGTCCTGCAAGGCTTCTGGCTACATCTTCACCAGCTACTA TATGTACTGGGTGAAGCAGAGGCCTGGACAAGGCCTTGAGTGGATTGGG GGGATTAATCCTATCACTGGTGGTACTGACTTCAATGAGAAGTTCAAGG ACAAGGCCACACTGACTCTGGCCGCATCCTCCAGCACAGCCTACATACA CTCAGCAGCCTGACATCTGAGGACTCTGCGGTCTATTTCTGTGCAAGAA TGGGACGGGATGCTATGGACTACTGGGGTCAAGGAACCTCAGTCACCGT CTCCTC |
| 2B3 (Kappa/light chain) | | |
| CDRL1 | 108 | KSVSTSGYSY |
| CDRL2 | 109 | LVS |
| CDRL3 | 110 | QHIRELYT |
| FR1 | 111 | DIVLTQSPASLAVSLGQRATISYRAS |
| FR2 | 112 | MHWNQQKPGQPPRLLIY |
| FR3 | 113 | NLESGVPARFSGSGSGTDFTLNIHPVEEEDAATYYC |
| FR4 | 42 | FGGGTKLEIK |
| Light chain variable (amino acid) | 114 | DIVLTQSPASLAVSLGQRATISYRASKSVSTSGYSYMHWNQQKPGQPPRL LIYLVSNLESGVPARFSGSGSGTDFTLNIHPVEEEDAATYYCQHIRELYTF GGGTKLEIK |
| Light chain variable (nucleotide sequence) | 115 | GACATTGTGCTGACACAGTCTCCTGCTTCCTTAGCTGTATCTCTGGGGCA GAGGGCCACCATCTCATACAGGGCCAGCAAAAGTGTCAGTACATCTGGC TATAGTTATATGCACTGGAACCAACAGAAACCAGGACAGCCACCCAGAC TCCTCATCTATCTTGTATCCAACCTAGAATCTGGGGTCCCTGCCAGGTTC AGTGGCAGTGGGTCTGGGACAGACTTCACCCTCAACATCCATCCTGTGG AGGAGGAGGATGCTGCAACCTATTACTGTCAGCACATTAGGGAGCTTTA CACGTTCGGAGGGGGGACCAAGCTGGAAATAAAACG |
| 2F1 (Heavy chain) | | |
| CDRH1 | 116 | GYTFTSYY |
| CDRH2 | 117 | INPTTGGT |
| CDRH3 | 102 | ARMGRDAMDY |
| FR1 | 118 | QVQLKESGAELVKPGTSVKLSCKAS |
| FR2 | 119 | MYWLKQRPGQGLEWIGG |
| FR3 | 120 | DFNENFKNKATLTLATSSSTAYIQLSSLTSEDSAVYFC |
| FR4 | 7 | WGQGTSVTVSS |
| Heavy chain | 121 | QVQLKESGAELVKPGTSVKLSCKASGYTFTSYYMYWLKQRPGQGLEWIG |

TABLE 2-continued

Summary of RON antibody sequences

| | SEQ ID NO: | Sequence |
|---|---|---|
| variable (amino acid) | | GINPTTGGTDFNENFKNKATLTLATSSSTAYIQLSSLTSEDSAVYFCARM GRDAMDYWGQGTSVTVSS |
| Heavy chain variable (nucleotide sequence) | 122 | CAGGTGCAGCTGAAGGAGTCAGGGGCTGAACTGGTGAAACCTGGGACTT CAGTGAAGTTGTCCTGCAAGGCTTCTGGCTACACCTTCACCAGCTACTA TATGTACTGGTTGAAGCAGAGGCCTGGACAAGGCCTTGAGTGGATTGGG GGGATTAATCCTACCACTGGTGGTACTGACTTCAATGAGAACTTCAAGA ACAAGGCCACACTGACTTTGGCCACATCCTCCAGCACAGCCTACATACAA CTCAGCAGCCTGACATCTGAGGACTCTGCGGTCTATTTCTGTGCAAGAA TGGGACGGGATGCTATGGACTACTGGGGTCAAGGAACCTCAGTCACCGT CTCCTCA |

2F1 (Kappa/light chain)

| | SEQ ID NO: | Sequence |
|---|---|---|
| CDRL1 | 108 | KSVSTSGYSY |
| CDRL2 | 109 | LVS |
| CDRL3 | 123 | QHIRELTR |
| FR1 | 124 | DIVLTQSPASLAVSLGQRATISYRAS |
| FR2 | 125 | MHWNQQKPGQPPRLLIY |
| FR3 | 126 | NLESGVPARFSGSGSGTDFTLNIHPVEEEDAATYYC |
| Light chain variable (amino acid) | 127 | DIVLTQSPASLAVSLGQRATISYRASKSVSTSGYSYMHWNQQKPGQPPRL LIYLVSNLESGVPARFSGSGSGTDFTLNIHPVEEEDAATYYCQHIRELTRS EGGPSWK |
| Light chain variable (nucleotide sequence) | 128 | GAC ATT GTG CTG ACA CAG TCT CCT GCT TCC TTA GCT GTA TCT CTG GGG CAG AGG GCC ACC ATC TCA TAC AGG GCC AGC AAA AGT GTC AGT ACA TCT GGG TAT AGT TAT ATG CAC TGG AAC CAA CAG AAA CCA GGA CAG CCA CCC AGA CTC CTC ATC TAT CTT GTA TCC AAC CTA GAA TCT GGG GTG CCT GCC AGG TTC AGT GGC AGT GGG TCT GGG ACA GAC TTG ACC CTC AAC ATC CAT CCT GTG GAG GAG GAG GAT GCT GCA ACC TAT TAC TGT CAG CAC ATT AGG GAG CTT ACA CGT TCG GAG GGG GGA CCA AGC TGG AAA |

1B9 (Heavy chain)

| | SEQ ID NO: | Sequence |
|---|---|---|
| CDRH1 | 116 | GYTFTSYY |
| CDRH2 | 117 | INPTTGGT |
| CDRH3 | 102 | ARMGRDAMDY |
| FR1 | 129 | EVQLQQSGAELVKPGTSVKLSCKAS |
| FR2 | 119 | MYWLKQRPGQGLEWIGG |
| FR3 | 120 | DFNENFKNKATLTLATSSSTAYIQLSSLTSEDSAVYFC |
| FR4 | 7 | WGQGTSVTVSS |
| Heavy chain variable (amino acid) | 130 | EVQLQQSGAELVKPGTSVKLSCKASGYTFTSYYMYWLKQRPGQGLEWIG GINPTTGGTDFNENFKNKATLTLATSSSTAYIQLSSLTSEDSAVYFCARM GRDAMDYWGQGTSVTVSS |
| Heavy chain variable (nucleotide sequence) | 131 | GAGGTTCAGCTGCAGCAGTCTGGGGCTGAACTGGTGAAACCTGGGACTT CAGTGAAGTTGTCCTGCAAGGCTTCTGGCTACACCTTCACCAGCTACTA TATGTACTGGTTGAAGCAGAGGCCTGGACAAGGCCTTGAGTGGATTGGG GGGATTAATCCTACCACTGGTGGTACTGACTTCAATGAGAACTTCAAGA ACAAGGCCACACTGACTTTGGCCACATCCTCCAGCACAGCCTACATACAA CTCAGCAGCCTGACATCTGAGGACTCTGCGGTCTATTTCTGTGCAAGAA TGGGACGGGATGCTATGGACTACTGGGGTCAAGGAACCTCAGTCACCGT CTCCTCA |

1D2 (Heavy chain)

| | SEQ ID NO: | Sequence |
|---|---|---|
| CDRH1 | 100 | GYIFTSYY |
| CDRH2 | 101 | INPITGGT |
| CDRH3 | 102 | ARMGRDAMDY |

TABLE 2-continued

Summary of RON antibody sequences

| | SEQ ID NO: | Sequence |
|---|---|---|
| FR1 | 129 | EVQLQQSGSELVKPGASVKLSCKAS |
| FR2 | 119 | MYWVKQRPGQGLEWIGG |
| FR3 | 120 | DFNEKFKNKATLTLATSSSTAYIHLSSLTSEDSAVYFC |
| FR4 | 132 | WGQGTSVTVS |
| Heavy chain variable (amino acid) | 133 | EVQLQQSGSELVKPGASVKLSCKASGYIFTSYYMYWVKQRPGQGLEWIG GINPITGGTDFNEKFKNKATLTLATSSSTAYIHLSSLTSEDSAVYFCARM GRDAMDYWGQGTSVTVS |
| Heavy chain variable (nucleotide sequence) | 134 | GAGGTTCAGCTGCAGCAGTCTGGGTCTGAACTGGTGAAACCTGGGGCTT CAGTGAAGTTGTCCTGCAAGGCTTCTGGCTACATCTTCACCAGCTACTA TATGTACTGGGTGAAGCAGAGGCCTGGACAAGGCCTTGAGTGGATTGGG GGGATTAATCCTATCACTGGTGGTACTGACTTCAATGAGAAGTTCAAGA ACAAGGCCACACTGACTCTGGCCACATCCTCCAGCACAGCCTACATACAT CTCAGCAGCCTGACATCTGAGGACTCTGCGGTCTATTTCTGTGCAAGAA TGGGACGGGATGCTATGGACTACTGGGGTCAAGGAACCTCAGTCACCGT CTCC |

5A5 (Heavy chain)

| | SEQ ID NO: | Sequence |
|---|---|---|
| CDRH1 | 135 | DYSITSDYA |
| CDRH2 | 136 | ILYSGST |
| CDRH3 | 137 | ASLGRGGS |
| FR1 | 138 | LEVKLEQSGPGLVKPSQSLSLTCTVT |
| FR2 | 139 | WNWIRQFPGNKLEWMGY |
| FR3 | 140 | TYNPSLKSRVSITRDTSKNQFFLHLDSVTTEDAATYYC |
| FR4 | 141 | WGQGTTLAVSS |
| Heavy chain variable (amino acid) | 142 | LEVKLEQSGPGLVKPSQSLSLTCTVTDYSITSDYAWNWIRQFPGNKLEW MGYILYSGSTTYNPSLKSRVSITRDTSKNQFFLHLDSVTTEDAATYYCASL GRGGSWGQGTTLAVSS |
| Heavy chain variable (nucleotide sequence) | 143 | CTTGAGGTTAAGCTGGAGCAGTCAGGACCTGGCCTGGTGAAACCTTCTC AGTCTCTGTCCCTCACCTGCACTGTCACTGACTACTCAATCACCAGTGAT TATGCCTGGAACTGGATCCGGCAATTTCCAGGAAACAAACTGGAGTGGA TGGGTTACATACTCTACAGTGGTTCCACTACGTACAATCCGTCTCTCAA AAGTCGAGTCTCTATCACTCGAGACACATCCAAGAACCAGTTCTTCCTG CACTTGGATTCTGTGACTACTGAGGACGCTGCCACATATTACTGTGCAA GCCTCGGGCGTGGGGGTCCTGGGGCAGGGCACCACTCTCGCAGTCTCC TCA |

5A5 (Kappa/light chain)

| | SEQ ID NO: | Sequence |
|---|---|---|
| CDRL1 | 144 | QSIVHSNGNTY |
| CDRL2 | 37 | KVS |
| CDRL3 | 145 | FQGSHAPWT |
| FR1 | 146 | DILMTQTPLSLPVSLGDQASISCRSS |
| FR2 | 147 | LEWYLQKPGQSPKLLIY |
| FR3 | 148 | NRFSGVPDRFTGSGSGTDFTLKISRVEAEDLGIYYC |
| FR4 | 149 | FGGGTKLEIR |
| Light chain variable (amino acid) | 150 | DILMTQTPLSLPVSLGDQASISCRSSQSIVHSNGNTYLEWYLQKPGQSPKL LIYKVSNRFSGVPDRFTGSGSGTDFTLKISRVEAEDLGIYYCFQGSHAPWT FGGGTKLEIR |
| Light chain variable (nucleotide sequence) | 17 | GATATTTTGATGACCCAAACTCCTCTCTCCCTGCCTGTCAGTCTTGGAGA TCAAGCCTCCATCTCTTGCAGATCTAGTCAGAGCATTGTACATAGTAAT GGAAACACCTATTTGGAATGGTACCTGCAGAAACCAGGCCAGTCTCCAA AGCTCCTTATCTACAAAGTTTCCAACCGATTTTCTGGGGTCCCAGACAG |

TABLE 2-continued

Summary of RON antibody sequences

| SEQ ID NO: | Sequence |
|---|---|
| | GTTCACTGGCAGTGGATCAGGGACAGATTTCACACTCAAGATCAGCAGA GTGGAGGCTGAGGATCTGGGAATTTATTACTGCTTTCAAGGTTCACATG CTCCGTGGACGTTCGGTGGAGGCACCAAGCTGGAAATCAGAC |

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred examples and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other examples are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1: Recombinant RON Antigen Design, Expression and Purification

The translated sequence for RON was analysed for antigenicity with Jameson-Wolf algorithm in Lasergene Protean v8.1 program (DNASTAR Inc., Madison, Wis.) to predict the antigenic index of RON. This algorithm integrates several parameters to calculate the antigenicity of the sequence based on the characteristics of its primary amino acid chain: hydrophilicity (Hopp-Woods), surface probability (Emini), flexibility of the protein backbone (Karplus-Schulz), and secondary structure prediction (Chou-Fasman and Garnier) (Jameson & Wolf, 1988).

The entry vector containing full length human RON cDNA in pCMV6 vector (RC212786) was obtained from Origene. Three truncated regions of RON were selected based on the most antigenic sequences in the extracellular regions and subcloned into pGEX-4T1 vector (GE Healthcare) using EcoRI and XhoI restriction sites. The recombinant plasmids were transformed into BL21 E. coli competent cells (Invitrogen) and plated on LB plate incubated at 37° C. overnight Single colonies were picked for prokaryotic expression. Transformed cells were grown in a 1 L culture until an OD 600 of 0.6-0.8 was reached. Protein expression was induced by addition of IPTG (isopropyl-β-D-thio-galactoside) to a final concentration of 300 μM. Cultures were then further allowed to grow for overnight at 18° C. Cells were recovered by centrifugation at 6000 rpm for 15 mins and resuspended in 20 ml of lysis buffer (20 mM Tris-HCl, pH 8.0, 1 M NaCl, 10% glycerol, 0.1% Triton-X 100 and 1 mM DTT). Cells were incubated in lysis buffer for 30 mins at 4° C., with constant swirling before sonication. Resuspended cells were lysed by sonication on ice using a sonicator (Sonics, Vibracell, USA) for 3 minutes. Sonication was performed for four cycles at 38% amplitude with 1 sec ON and 0.1 sec OFF. The resulting suspension was centrifuged at 18,000 rpm for 40 mins and the supernatant (pre-purified supernatant) obtained was used for protein purification. The supernatant of the bacterial lysate was loaded on a glutathione column, washed with 20 mM Tris-HCl, pH 8.0, 1 M NaCl, 10% glycerol, 0.1% Triton-X 100, and 1 mM DTT. The GST-tagged RON protein was eluted using a buffer of 20 mM Tris-HCl, pH 9.6, 100 mM NaCl, 1 mM DTT, and 10 mM glutathione. The eluted protein fractions were collected for analysis by SDS-PAGE.

Example 2: Immunization of Truncated RON into Mice

Five 8 weeks old Balb/c female mice were obtained from Biological Resource Center (Singapore) and inoculated with recombinant human protein RON immunogens. The first immunisation was performed intraperitoneally with Sigma Adjuvant System (Sigma) as adjuvant, followed by five intraperitoneal and subcutaneous injections at 3 weeks interval. One week after the fourth immunization, blood was drawn from each mouse via cheek bleed using a lancet (MEDIpoint International Inc.). Approximately 101 of blood was centrifuged for 10 min at 1600 rpm and serum was aspirated and stored at 4° C. Subsequently the antibody response was measured by enzyme-linked immunosorbent assay (ELISA) with the RON protein used for immunisation immobilized on the ELISA plate. The mouse with the highest serum antibody titer was selected as the spleen donor for fusion with myeloma cell line SP2/0.

Fusion of Mice Spleen with Myeloma Cells to Obtain Hybridoma Cells

The mice received a final boost by intravenous injection of the RON fusion protein without adjuvant Mouse myeloma SP2/0 cell line was used as the fusion partner. Thus, one week before fusion, cells were cultured in RPMI (Gibco) and 10% FBS until they attained >70% confluency in the logarithmic phase. The spleen cells of the immunised mouse were removed under sterile conditions. Generation, selection and cloning of hybridoma cells were performed using the ClonaCell-HY Hybridoma Cloning kit (STEM-CELL Technologies) following the manufacturer's protocol.

Example 3: Screening of Hybridoma Cells for RON Antibodies

ELISA

Hybridoma clones secreting mAbs targeting human RON were selected by ELISA assay with the use of 96-well Maxisorp plates (Nunc) coated separately with recombinant RON and GST. Supernatant collected from individual hybridoma wells were tested on ELISA plates. 10% fetal bovine serum (FBS) was used for blocking and antibody dilution. 1×PBS with 0.05% Tween 20 (PBST) was used for washes. After washing, IgGs were detected using 1:5000 goat anti-mouse IgG conjugated to HRP (Biorad) in PBST with 10% FBS. After washing, plates were developed with 1×TMB ELISA substrate solution (Sigma). Absorbance was measured at 650 nm with EnVision Plate Reader (Perkin Elmer).

Example 4: Immunofluorescence Staining

The 4% paraformaldehyde fixed HCT116 and TKO cells were subjected to permeabilization with 0.4% Triton X-100 for 20 minutes. After rinsing with PBS, cells were blocked with 5% BSA in PBSTritonX (PBSTX) for 20 min, followed by overnight incubation in hybridoma supernatant at 4° C. IgGs were detected using 1:1000 goat Alexaflor 488 Donkey anti-mouse IgG conjugated (Life technologies) in PBSTX with 1% BSA. Subsequently, cells were counterstained with DAPI, and viewed with Incell Analyzer (GE Healthcare).

Example 5: Immunohistochemical Staining of Paraffin-Embedded Sections

Tumour tissues from the HT29 xenograft mouse model were processed into paraffin blocks by the Advanced Molecular Pathology Laboratory (AMPL), Institute of Molecular and Cell Biology. Wax sections at 5 µm were then collected onto slides (Leica Biosystems) and dried on a 50° C. hot plate for 1 h.

Sections were deparaffinized in xylene (ChemTech Trading) and rehydrated through descending percentages of ethanol (ChemTech Trading) to water. Tissue sections were heated with Target Retrieval Solution, pH9 (Dako) in the 2100 Antigen Retriever (Aptum Biologics) to expose the antigens, then rinsed thrice in PBS. Endogenous peroxidase was blocked with 2% (v/v) hydrogen peroxide (Merck) in PBS for 30 min, rinsed with water then PBS. Sections were blocked with 10% (v/v) goat serum (Dako) in PBS for 1 h then incubated with primary antibodies 6D4 or 7G8 at 4° C. overnight Sections were washed in running tap water then rinsed in PBS before being incubated with EnVision peroxidase labeled polymer conjugated to goat anti-mouse or anti-rabbit immunoglobulins (Dako; neat concentrations) or 1:100 diluted peroxidase labeled goat anti-mouse or anti-mouse IgG (Fcγ fragment specific) (Jackson ImmunoResearch). Antigen-antibody interaction was then visualized using 3,3'-diaminobenzidine as a substrate, and the sections were lightly counterstained with hematoxylin before dehydrating and mounting in Cytoseal 60 synthetic resin (Richard-Allan Scientific™, Fisher Scientific). Slides were imaged under bright field using the AxioImager (Zeiss) light microscope and analyzed with AxioVision Rel 4.8 software (Carl Zeiss AG).

Example: 6 Ascites Fluid Production

BALB/c mice were given a single 0.25 mL intraperitoneal (IP) injection of Incomplete Freund's Adjuvant (Sigma Chemical Co.). Fourteen days later, mice were injected with a single IP injection of $4 \times 10^5$ in a volume of 0.5 mL of the hybridoma cells described above, after which they were examined daily for development of ascites fluid recognized by abdominal distention.

Seven to ten days after the injection of hybridoma cells, mice were anesthetized and the collection of ascites fluid was performed on all mice in all groups. Ascites fluid was collected aseptically from anesthetized mice by abdominal paracentesis with an 18-22 gauge needle by gravity flow into sterile centrifuge tubes. Digital pressure was gently applied to the abdomen and the position of the mouse was altered as needed to facilitate removal of the ascites fluid. Ascites was pooled for each separate cage of mice.

Example 7: Epitope Mapping of Obtained Antibodies

Pepscan

Overlapping (5 amino acids) 25-mer peptides, covering the extracellular human RON sequence, were ordered from Mimotopes, generating 93 biotinylated peptides in total. The peptides were resuspended in 100% DMSO to prepare a 30 mg/ml stock solution, which were then diluted to 10 ug/ml before adding into Streptavidin High Binding Capacity Coated 96-Well Plates (Pierce) for 1 hr at room temperature. ELISA was performed as per manufacturer's protocol. Briefly, 1 ug/ml purified antibody was added into the plate and incubated for 30 minutes at room temperature. After washing with PBST, IgGs were detected using 1:5000 goat anti-mouse IgG conjugated to HRP (Biorad) in PBST with 10% FBS. Subsequently, plates were stained with 1×TMB ELISA substrate solution (Sigma) and absorbance was measured at 650 nm with EnVision Plate Reader (Perkin Elmer).

Peptide Phage Display

An M13 phage library (Ph.D.-12, New England Biolabs) encoding random 12-mer peptides at the $NH_2$ terminus of pill coat protein ($2.7 \times 10^9$ sequences) was used. 50 nm purified antibody was coated on 96 well Maxisorp plates (Nunc). The wells were incubated with blocking buffer (1×PBS, 0.5% Tween20, 2% BSA) for 1 h at room temperature, washed with washing buffer (1×PBS, 1% Tween20, 2% BSA), and incubated in washing buffer at room temperature with $4 \times 10^{10}$ phages. Bound phages were eluted with 0.2 M glycine (pH 2.2) and neutralized with 1 M Tris (pH 9.1). The eluted phages were amplified as instructed by the manufacturer. The selection process was repeated for three cycles. Phage plaques from the final round were picked as described by the manufacturer and sequenced.

Example 8: Cell Proliferation Assay of Using Antibodies

RON expressing HCT116 cells were seeded in 96-well plates (Nunc) at 1000 cells each well. After an 8 h serum starvation period, specific concentrations of filter sterilized purified mAbs were added to the wells and the cells were incubated for an additional 3 days. IncuCyte system RON expressing HCT116 cells were transferred to a 96 well plate and imaged using the IncuCyte HD system (Essen BioScience). Frames were captured at 2 hrs intervals from 4 separate 950×760-µm$^2$ regions per well using a 20× objective. Seeded cells were serum starved for 8 hrs and filter-sterilized purified mAb were added into each treatment wells. IgGs Anti-Mouse IgG Fc-DM1 2°ADC (Moradec) were added to cells 30 minutes after anti-RON mAbs were added at 10 µg/ml. Cultures were maintained at 37° C. in a water jacketed C02 incubation chamber (Thermo Scientific) throughout and run in triplicates for 72 hrs. Cell confluency data was calculated by the IncuCyte software. Values from all three regions of each well were pooled and averaged across all three replicates.

Example 9: Receptor Mediated Endocytosis

Cells at $5 \times 10^4$ cells per well in a 96 well plate were treated with 10 ug/ml mAb overnight at 4° C. or for 37° C. for 1 hour followed by goat anti-mouse IgG coupled with FITC. Fixation was subsequently performed using 4% PFA for 20 minutes. Nuclear DNA was stained with 4'6-diamino-2-phenylindole (DAPI). Immunofluorescence was observed under an Olympus Confocal Microscope FV1000.

Example 10: Western Blot Assays

Lysis was performed using RIPA buffer (Thermo Scientific) supplemented with protease inhibitor cocktail (Roche). QuickStart Bradford protein assay (BioRad) was used to determine protein concentration with BSA as standard. Equal amounts of total protein were mixed with NuPAGE lithium dodecyl sulphate (LDS) and sample reducing buffer (Thermo Scientific), heated for 5 min at 95° C. and loaded into NuPAGE 10% or 12% Bis-Tris gels (Life Technologies) for electrophoresis. Separated proteins were transferred onto nitrocellulose membranes using iBlot 2 gel transfer device (Thermo Scientific). Blocking was performed with 5% milk or bovine serum albumin (BSA) in tris-buffered saline supplemented with 0.1% tween (TBST). AKT (4298S), ERK1/2 (4348S), p-AKT (9271S), and p-ERK (8544S) antibodies were from Cell Signaling Technology. RON antibody was made in-house and Actin-HRP (A3854) was from Sigma-Aldrich. Anti-rabbit (P0217) and anti-mouse (P0161) secondary antibodies were from Dako. The enhanced chemiluminescence (ECL) reagent used was SuperSignal West Dura Extended Duration Substrate (Thermo Scientific, #34076). Imaging and acquisition was performed with Licor Odyssey Fc and Image Studio (version 3.1).

Example 11: Cell Viability Assay

Cell viability assays were performed to quantitate ATP generated by metabolically active cells. Assays were performed using a CellTiter-Glo luminescent cell viability assay (Promega) as per the manufacturer's instruction. Briefly, $5 \times 10^3$ cells/ml was cultured in sterile 96-well plates in the presence of increasing concentrations of mAbs (0 to 20 µM) in complete McCoy 5A medium. The plates were then incubated for 72 h, and then 100 1 of CellTiter-Glo reagent was added to lyse the cells. After a 10-min incubation at room temperature, the luminescence was recorded in a luminometer with an integration time of 1 s per well on an Envision reader (PerkinElmer). The luminescence signals for the antibody-treated cells were normalized by the luminescence signal obtained from dimethyl sulfoxide (DMSO)-treated cells.

Example 12: Complement Dependent Cytotoxicity (CDC)

Target cells were labeled with DELFIA BATDA reagent (PerkinElmer) according to the manufacturer's instructions. After labeling, the cells were coated with antibodies for 60 min at 37° C. The cells were washed and then co-cultured with rabbit complement (10%) for 60 mins at 37° C. Cell supernatants were then reacted with DELFIA Europium solution, and the fluorescence was measured using the EnVision Plate Reader (Perkin Elmer). Specific lysis was calculated by a formula: (experimental lysis count minus spontaneous lysis count) divided by (maximum lysis count [by lysis buffer] minus spontaneous lysis count) times 100%.

Example 13: Antibody-Dependent Cell-Mediated Cytotoxicity (ADCC)

Target cells were labeled with DELFIA BATDA reagent (PerkinElmer) according to the manufacturer's instructions. After labeling, the cells were coated with antibodies for 60 min at 37° C. The cells were washed and then co-cultured with effector cells in a 150:1 ratio (effector to target) for overnight at 37° C. Cell supernatants were then reacted with DELFIA Europium solution, and the fluorescence was measured using the EnVision Plate Reader (Perkin Elmer). Specific lysis was calculated by a formula: (experimental lysis count minus spontaneous lysis count) divided by (maximum lysis count [by lysis buffer] minus spontaneous lysis count) times 100%.

Example 14: In Vivo Experimental Results and Animal Model

Antibodies inhibit tumour growth in HT29 human xenograft mouse model

Monoclonal antibodies have a huge role to play in targeting cancer immunotherapy. RON is identified as an ideal candidate to target for cancer therapy as it is over-expressed in cancer cells and minimally expressed in normal cells. Targeting RON has a good safety profile as RON is not expressed in fibroblasts, endothelial cells, and blood leukocytes. Anti-RON mouse mAbs 7G8 and 6D4 were tested for their abilities to inhibit tumour growth in-vivo in human xenograft mice models. For HT-29 cancer cell xenograft experiments, female nu/nu nude mice (ages 8 weeks; Biological Resource Centre) were inoculated subcutaneously with $5 \times 10^6$ HT-29-luc2 cells (Perkin Elmer) per mouse. Mice were randomized into different groups (5 mice per group). The study was performed by treating mice with antibodies at 10 mg/kg every 3-4 days for a total of 8 intravenous injections. Control group was injected intravenously with PBS. Bioluminescence from individual tumours was measured at Day 21 using Caliper IVIS image system (Perkin Elmer). Animals were euthanized when tumour volumes exceeded 2,000 mm3 or if tumours became necrotic or ulcerated through the skin.

Figure 31B:
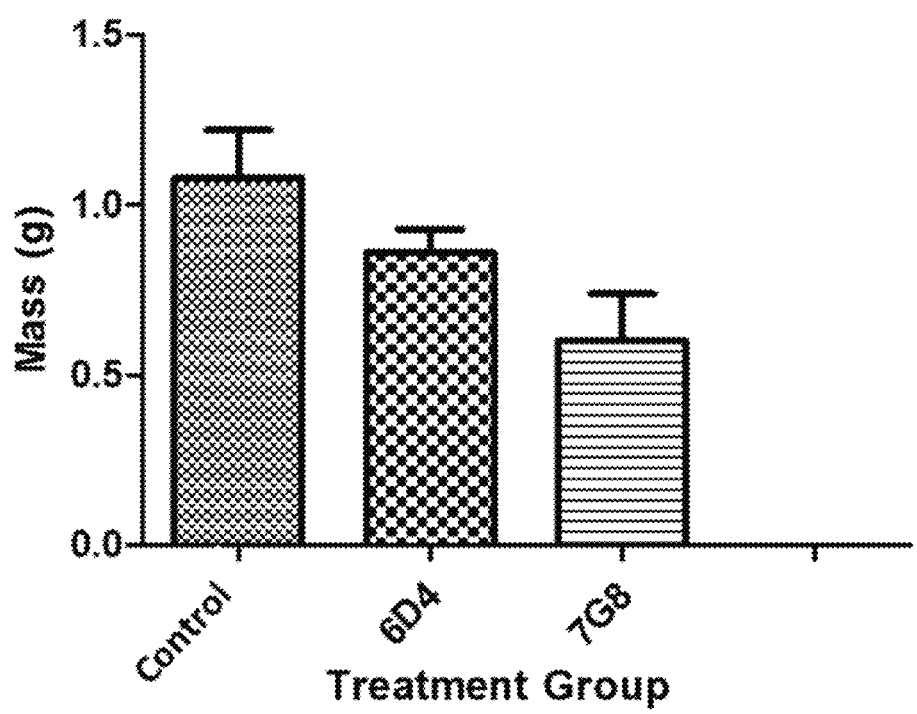
FIG. 31 (A) shows a timeline depicting the dosing and imaging protocol, and photographical images showing bioluminescence from individual tumors measured in the mice treated with antibodies 6D4 and 7G8; (B) shows bar graphs of the tumour weight at day 35 from the mouse xenograft model; (C) shows photographical images showing bioluminescence from individual tumors measured in the mice treated with antibody 6D4. Thus.
Figure 31C:
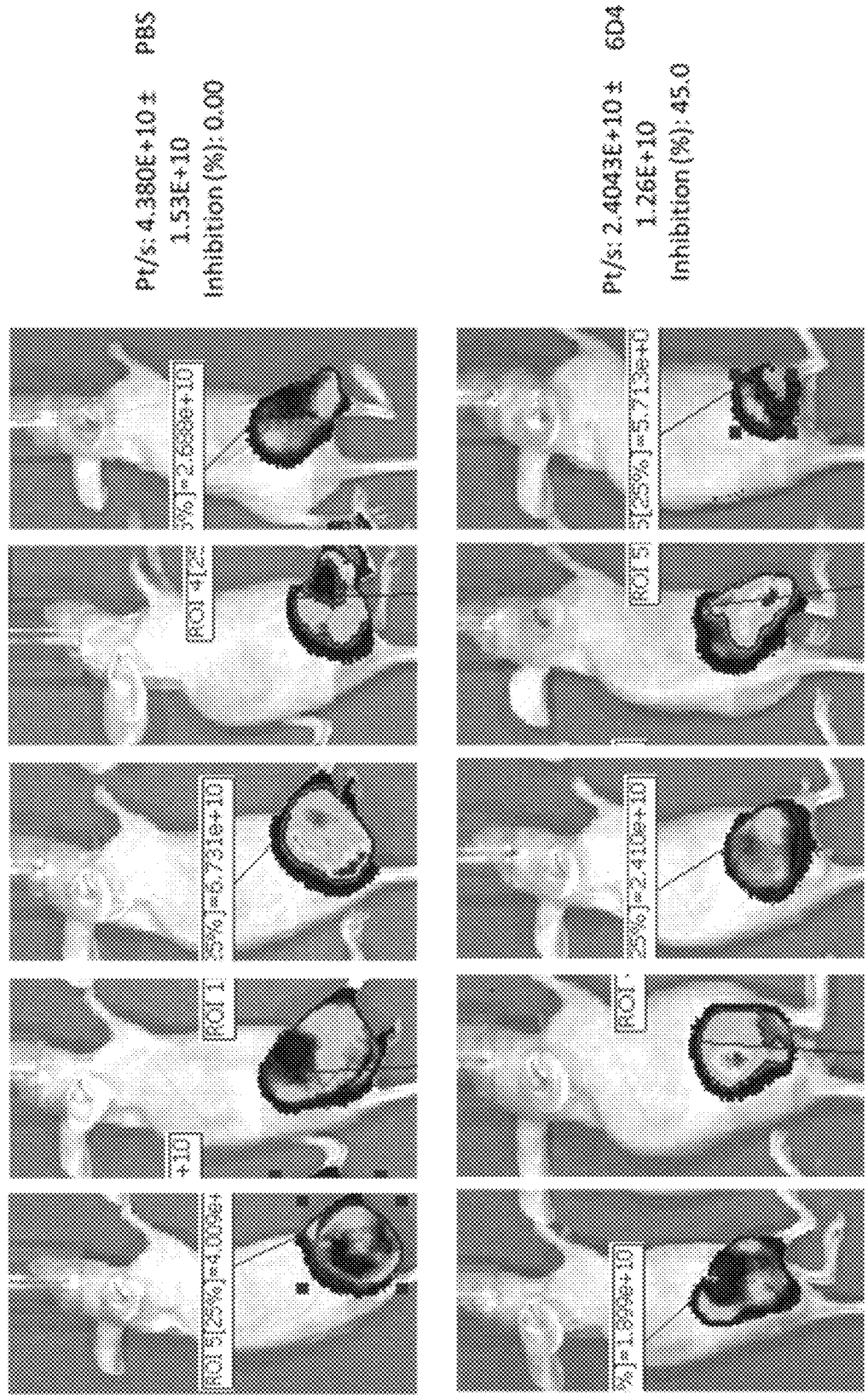
Figure 32:
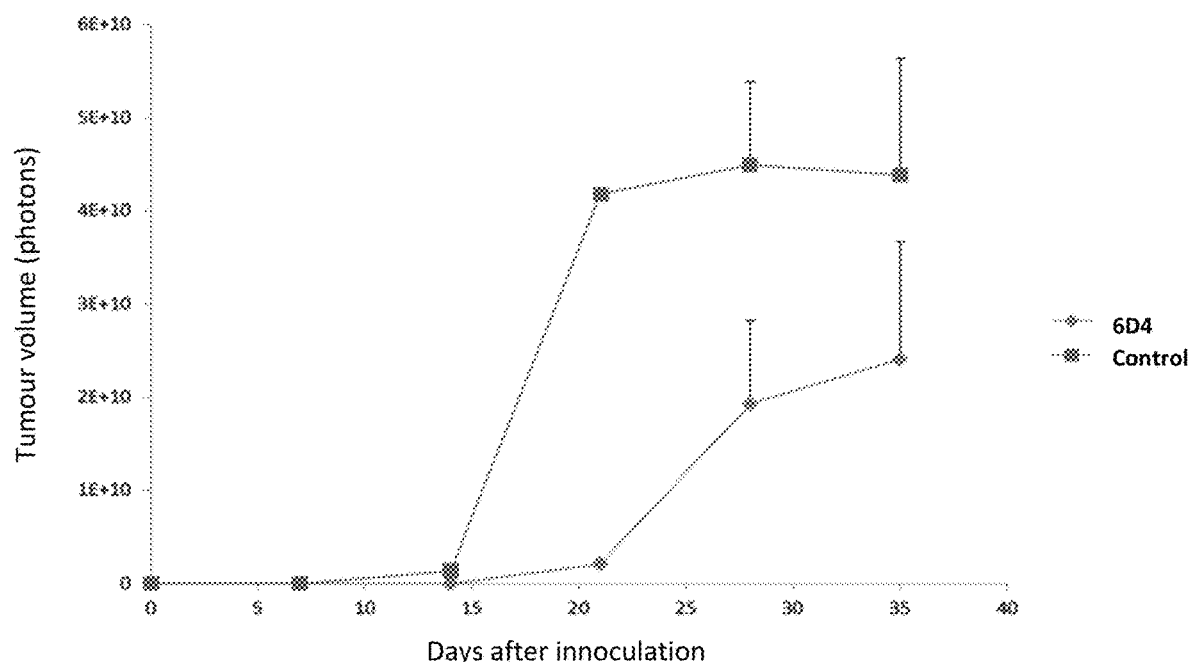
FIG. 32 shows a line graph showing an in vivo data on tumour volume in mice treated with antibody 6D4.
Figure 33:
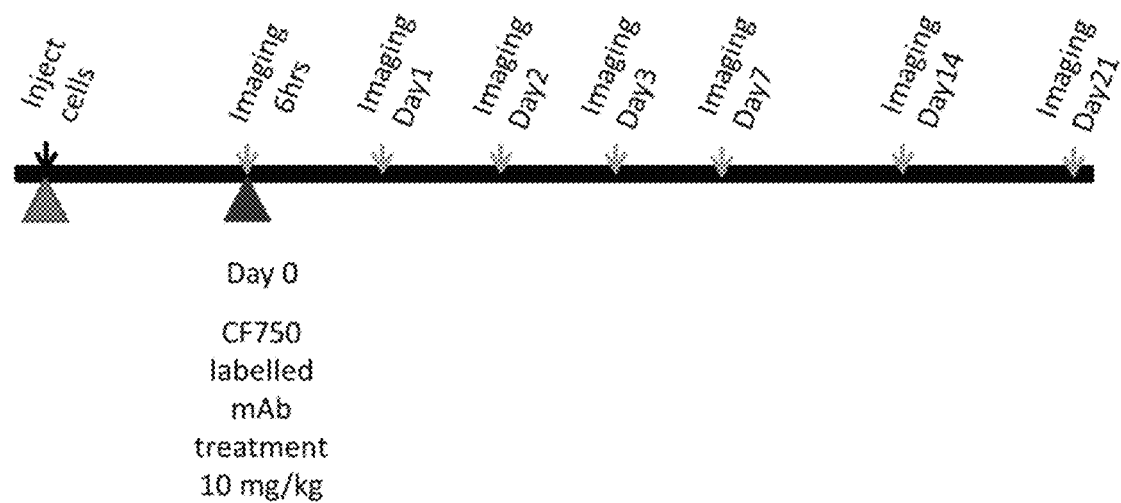
FIG. 33 shows a timeline for experiments employing 6D4 and 7G8 antibodies as in vivo imaging agents.
Figure 34:
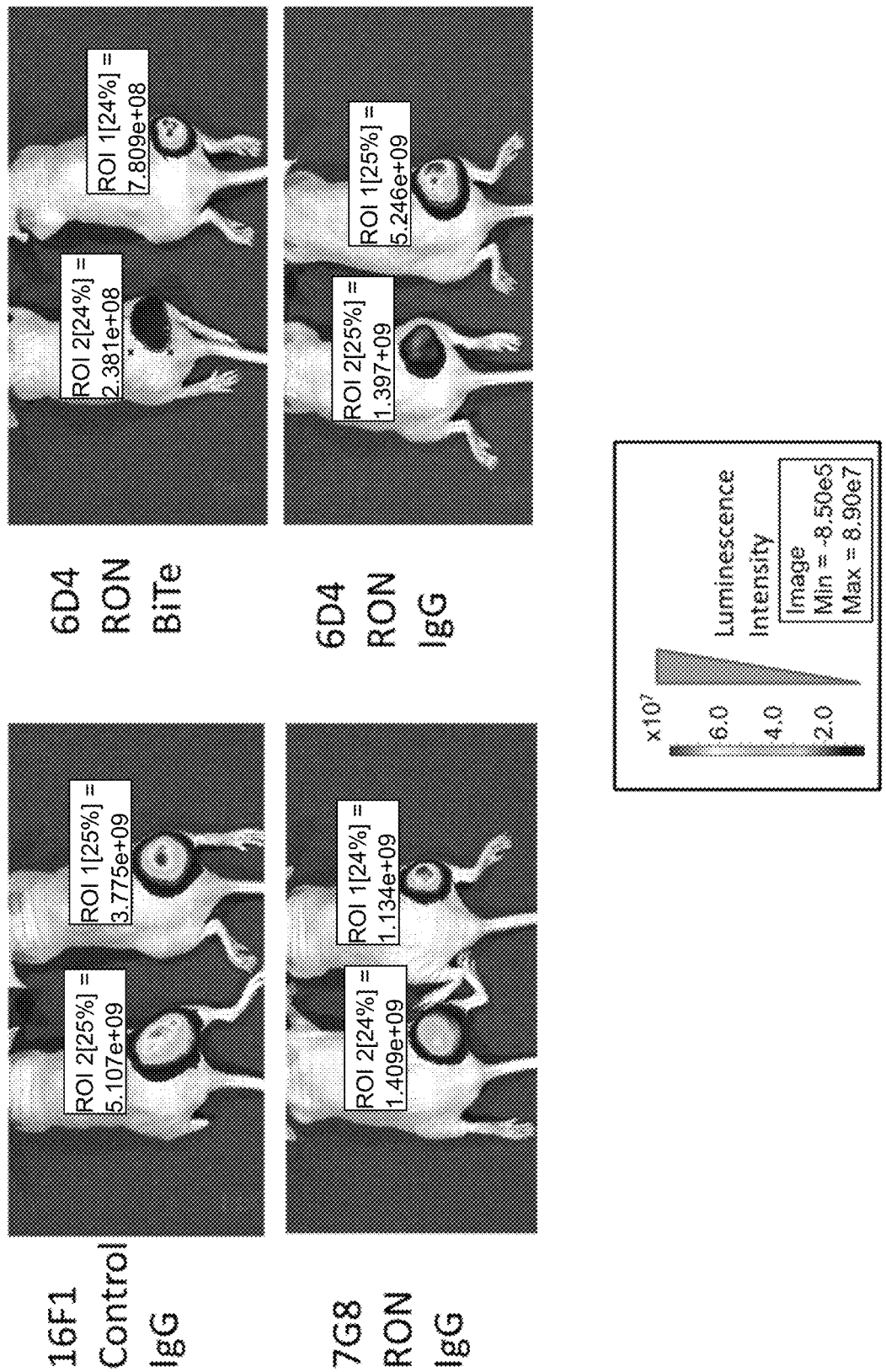
FIG. 34 shows photographical images of the results of experiments employing 6D4 and 7G8 antibodies as in vivo imaging agents.
Figure 35:
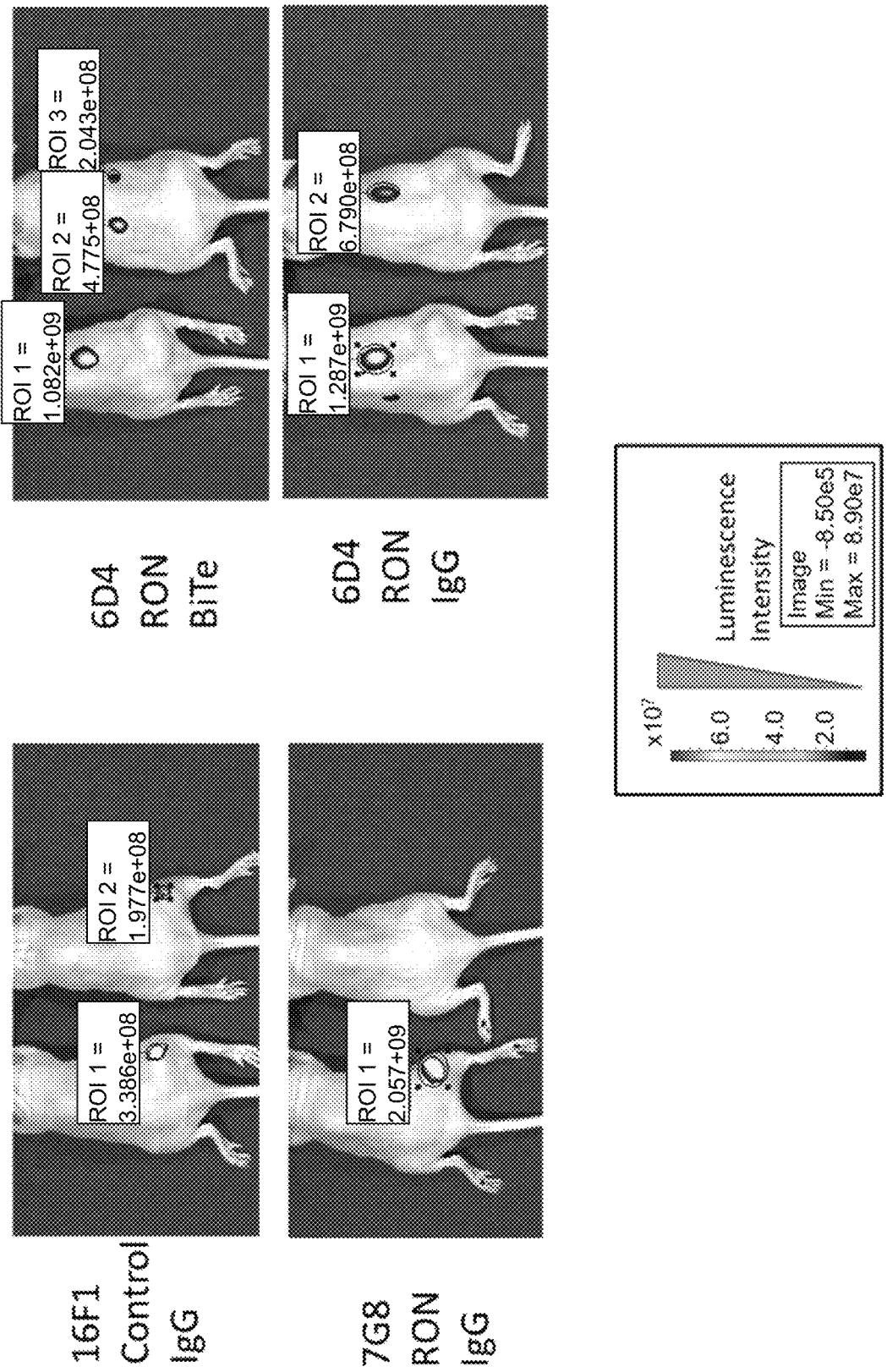
FIG. 35 shows photographical images of the results of experiments employing 6D4 and 7G8 antibodies as in vivo imaging agents 6 hours after administration.
Figure 36:
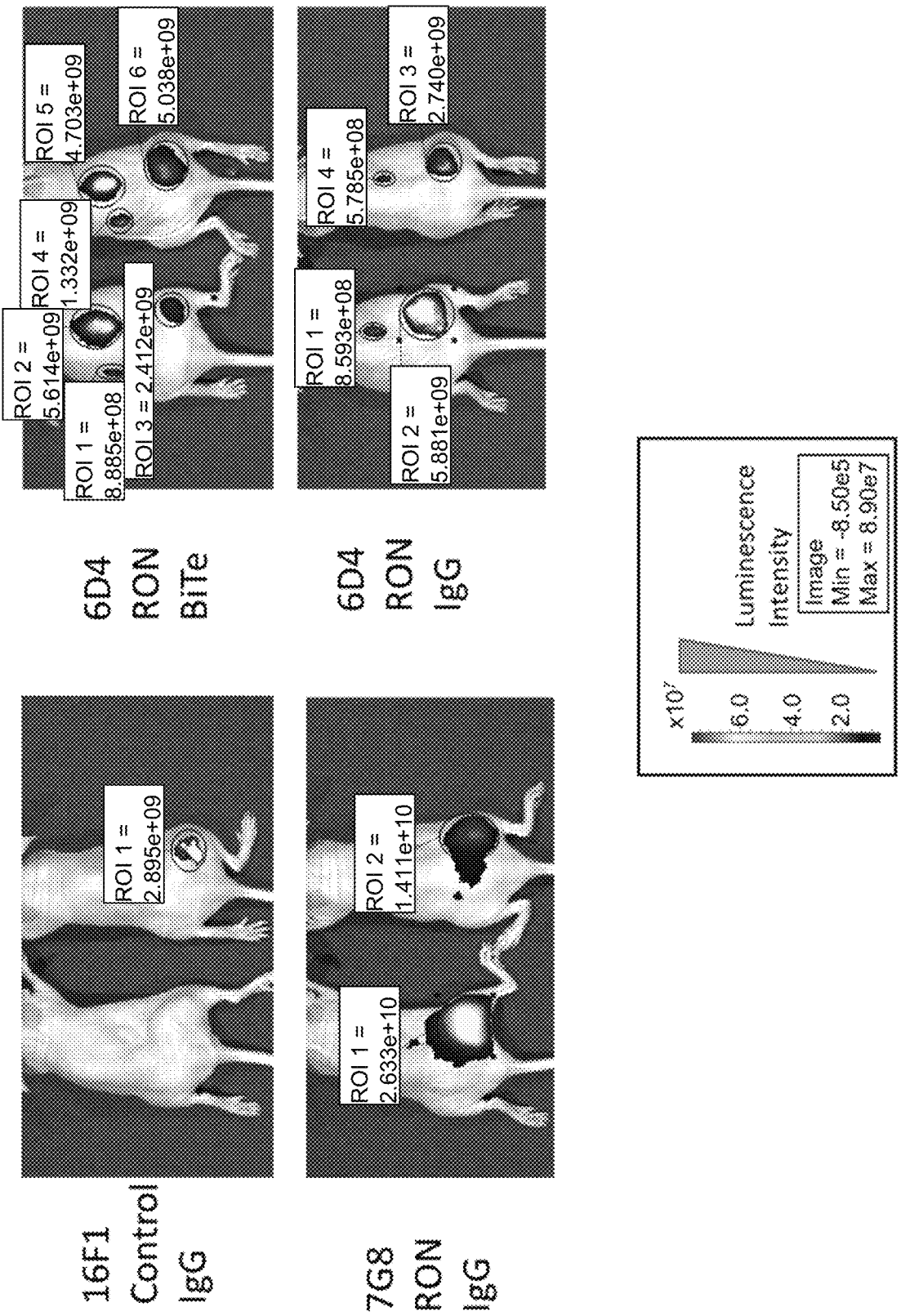
FIG. 36 shows photographical images of the results of experiments employing 6D4 and 7G8 antibodies as in vivo imaging agents 24 hours after administration.
Figure 37:
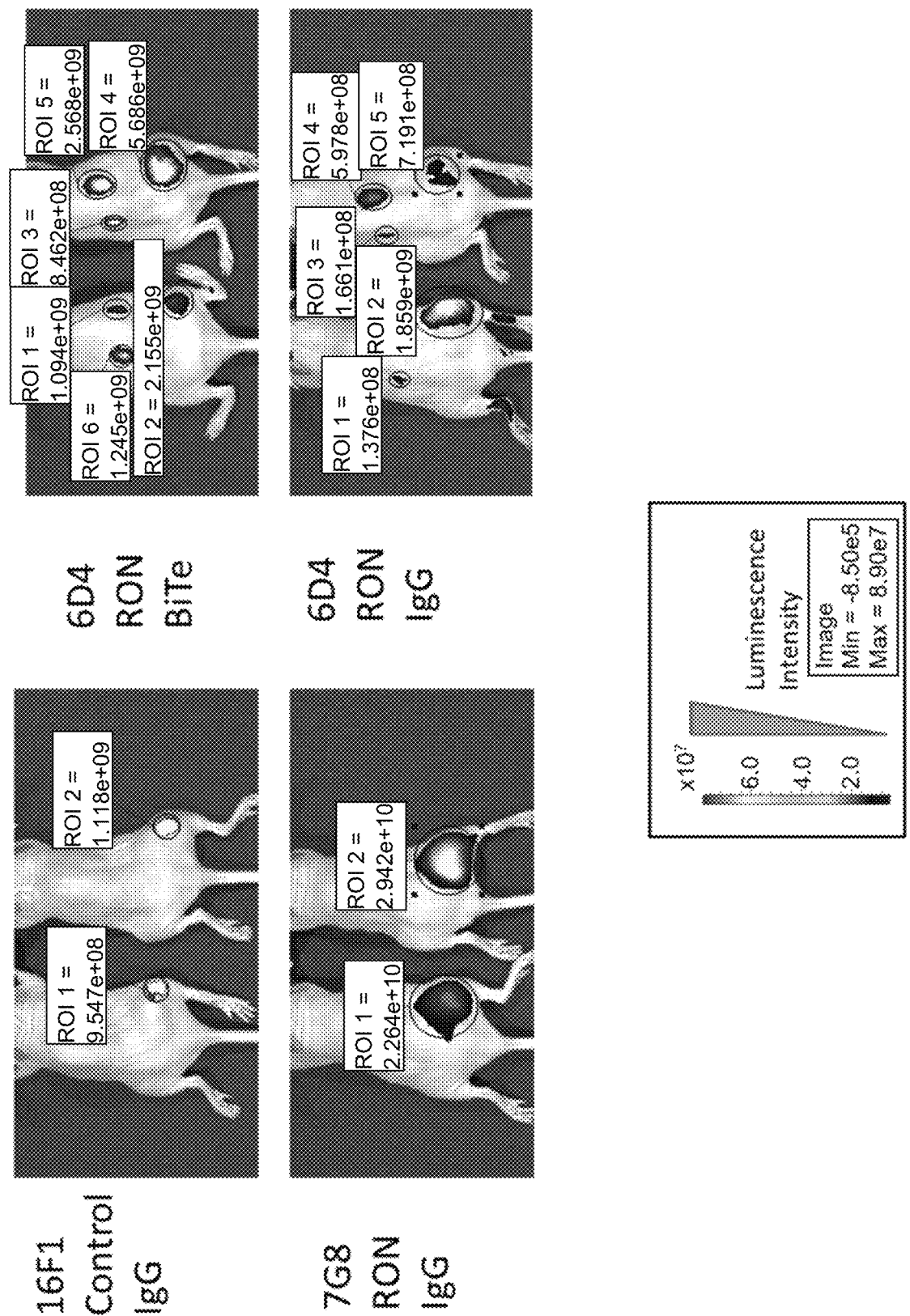
FIG. 37 shows photographical images of the results of experiments employing 6D4 and 7G8 antibodies as in vivo imaging agents 48 hours after administration.
Figure 38:
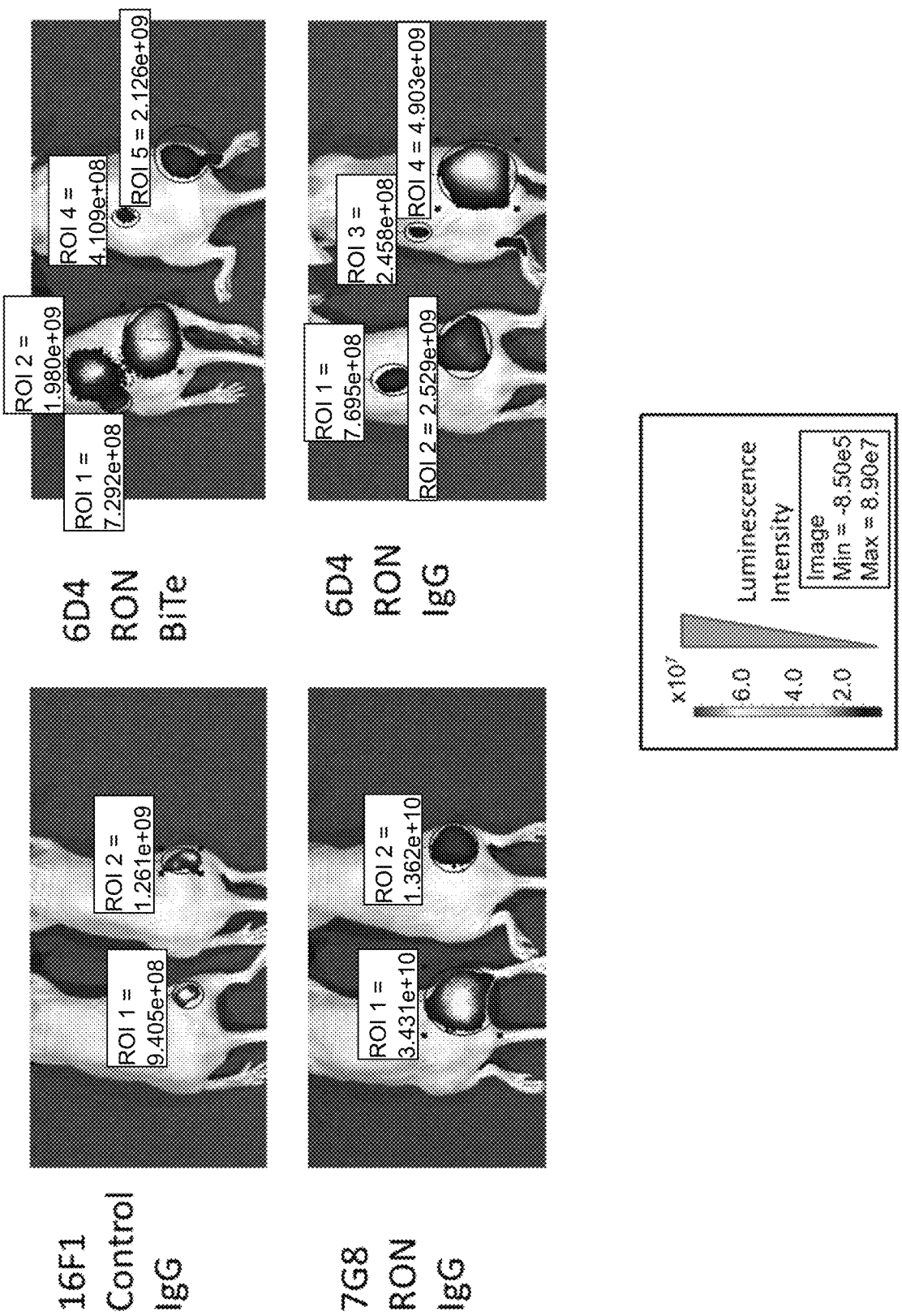
FIG. 38 shows photographical images of the results of experiments employing 6D4 and 7G8 antibodies as in vivo imaging agents 72 hours after administration.
Figure 39:
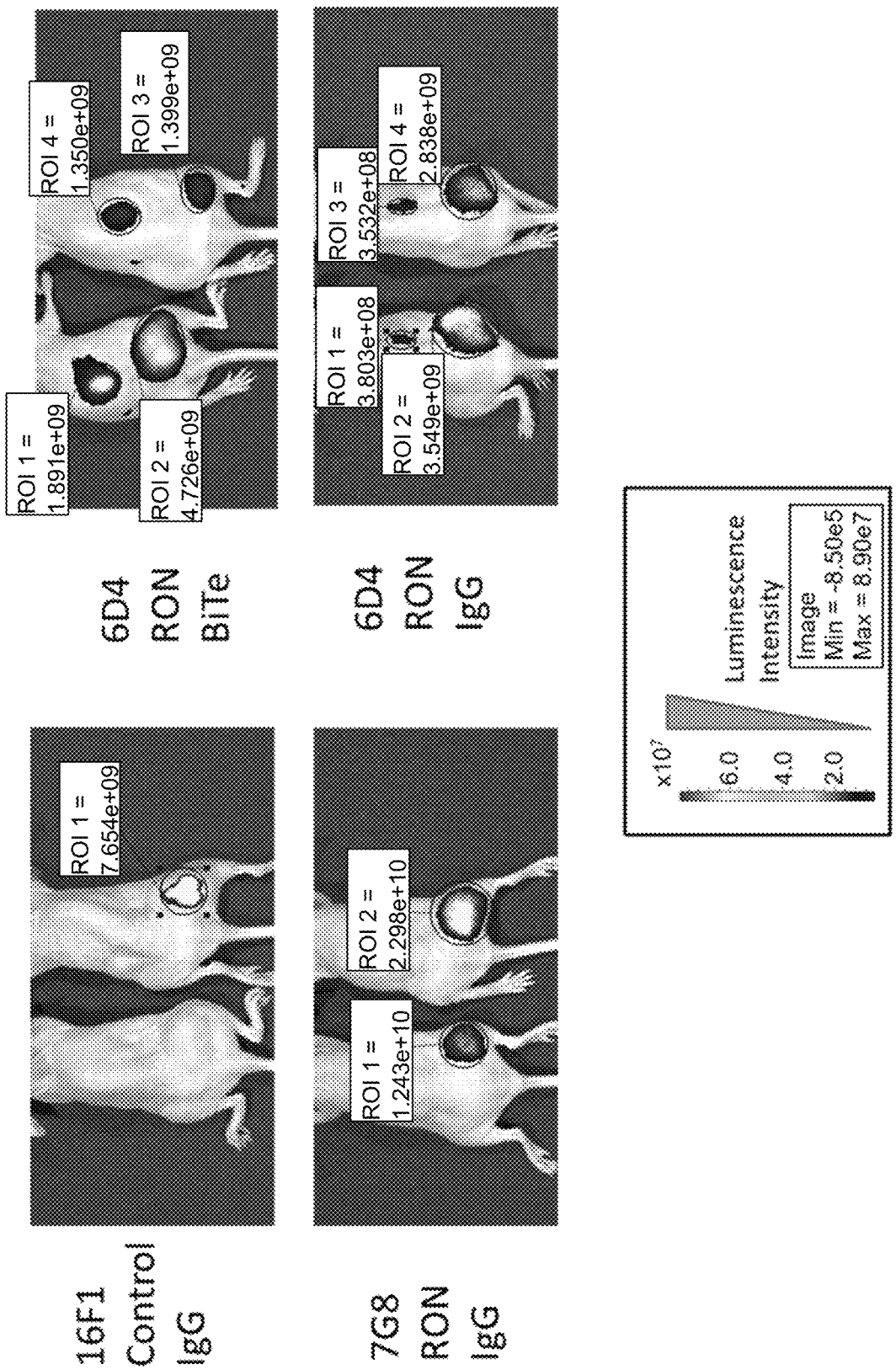
FIG. 39 shows photographical images of the results of experiments employing 6D4 and 7G8 antibodies as in vivo imaging agents 5 days after administration.
Figure 40:
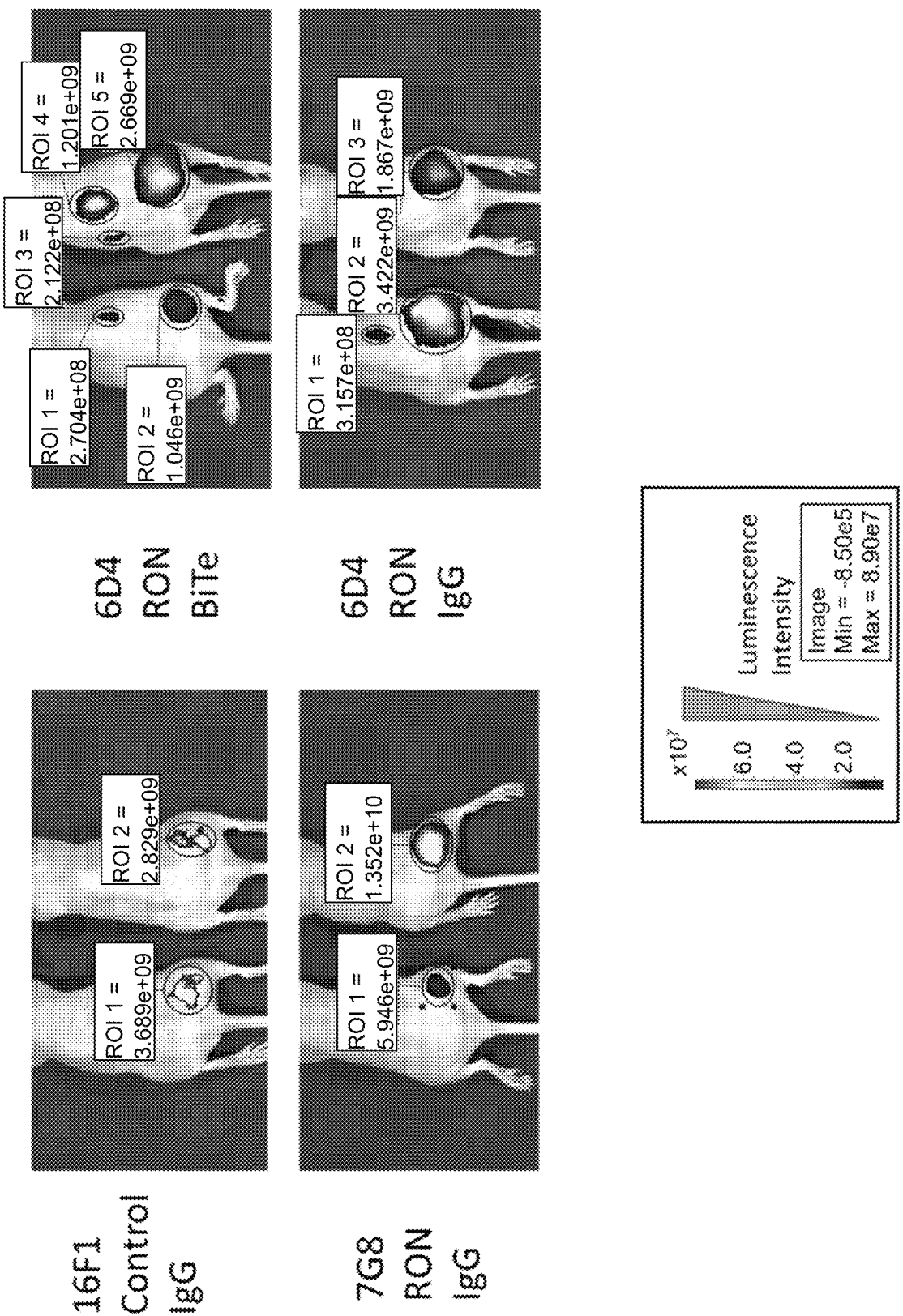
FIG. 40 shows photographical images of the results of experiments employing 6D4 and 7G8 antibodies as in vivo imaging agents 7 days after administration.
Figure 41:
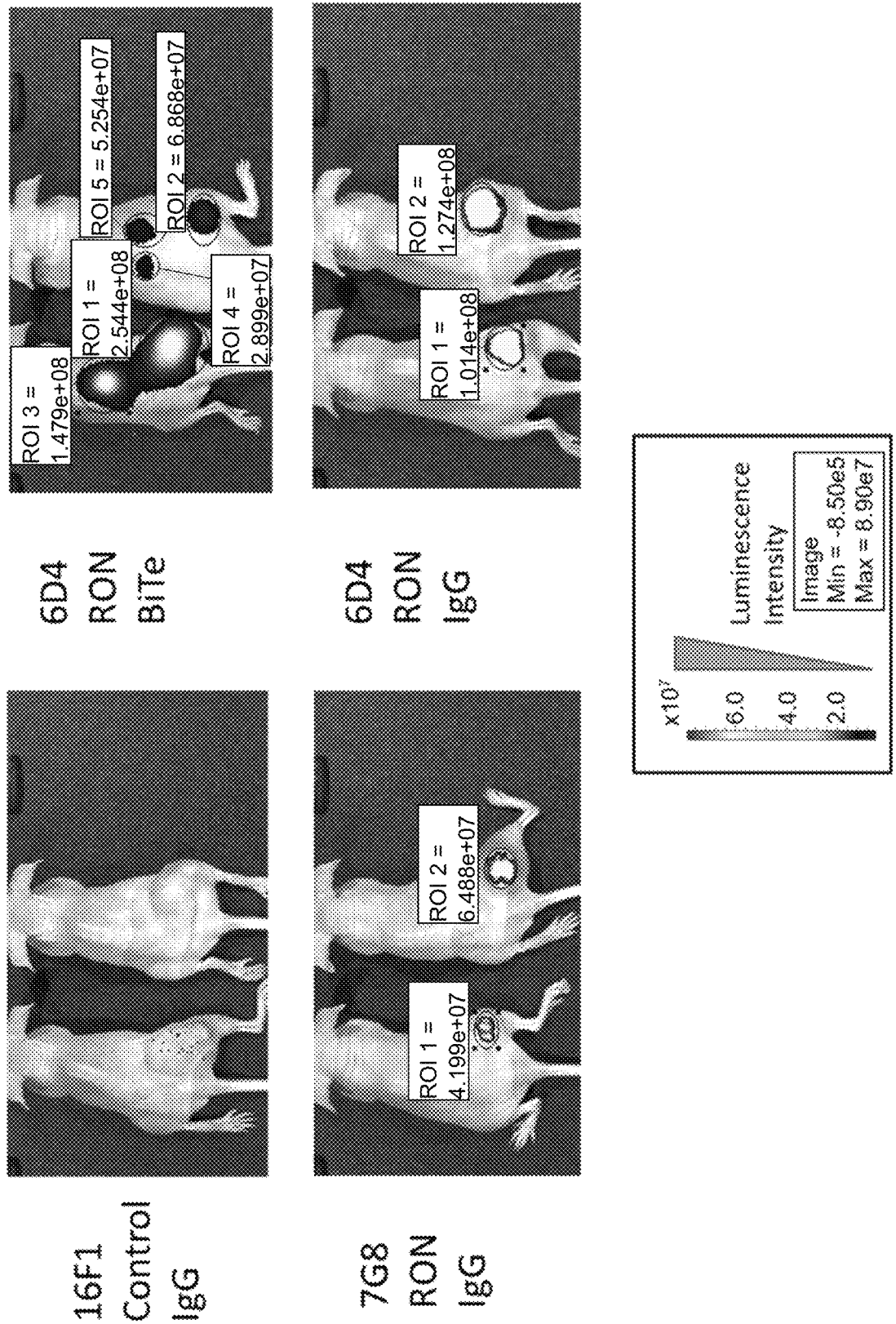
FIG. 41 shows photographical images of the results of experiments employing 6D4 and 7G8 antibodies as in vivo imaging agents 14 days after administration and measures the weight of the tumour at the end point.
Figure 43:
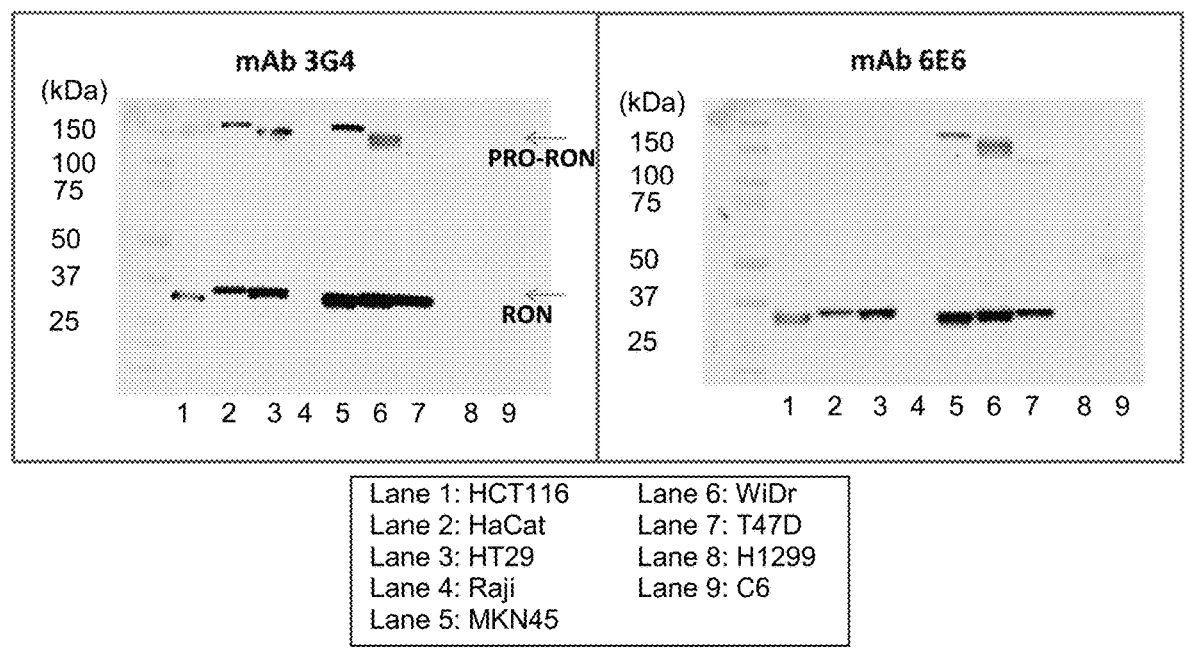
FIG. 43 shows Western Blots results demonstrating that antibodies 3G4 and 6E6 recognise different cancer cells lines expressing RON. Cell lines tested are human colorectal carcinoma cell line (e.g. HCT116), human keratinocyte cell line (e.g. HaCat), mouse hybridoma (e.g. HT29), human lymphoblast Burkitt's lymphoma cell line (e.g. Raji), human gastric cancer cells (e.g. MKN45), human colon colorectal adenocarcinoma cell line (e.g. WiDr), human breast cancer cell line (e.g. T47D), non-small cell lung cancer (e.g. H1299), and rat brain cancer cell line (e.g. C6).
Figure 44A:
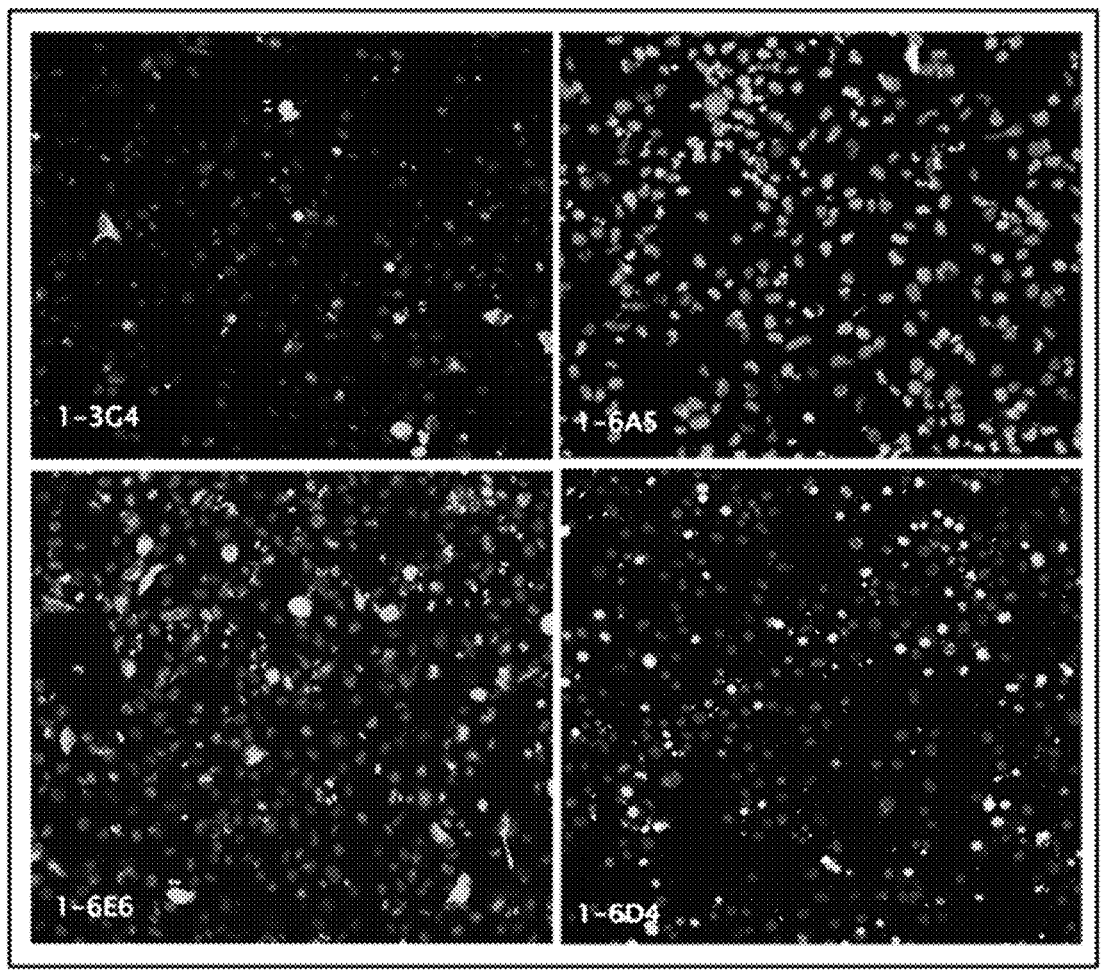
FIG. 44A shows immunofluorescence staining images showing that the antibodies of the present disclosure (3G4, 6A5, 6E6, and 6D4) recognise RON transfected H1299 cells.
Figure 44B:
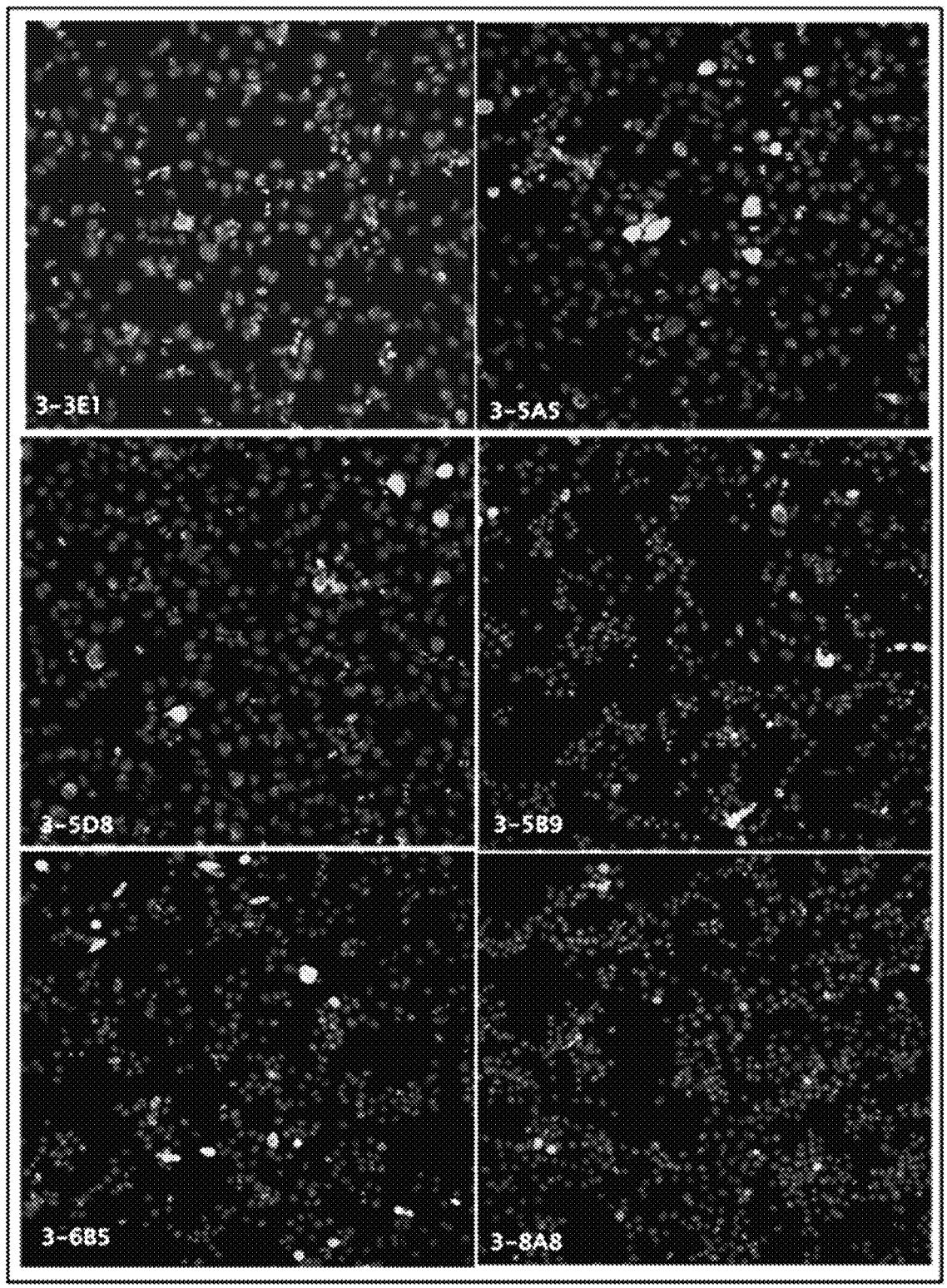
FIG. 44B shows immunofluorescence staining images showing that the antibodies of the present disclosure (3E1, 5A5, 5D8, 5B9, 6B5, and 8A8) recognise RON transfected H1299 cells.
Figure 47A:
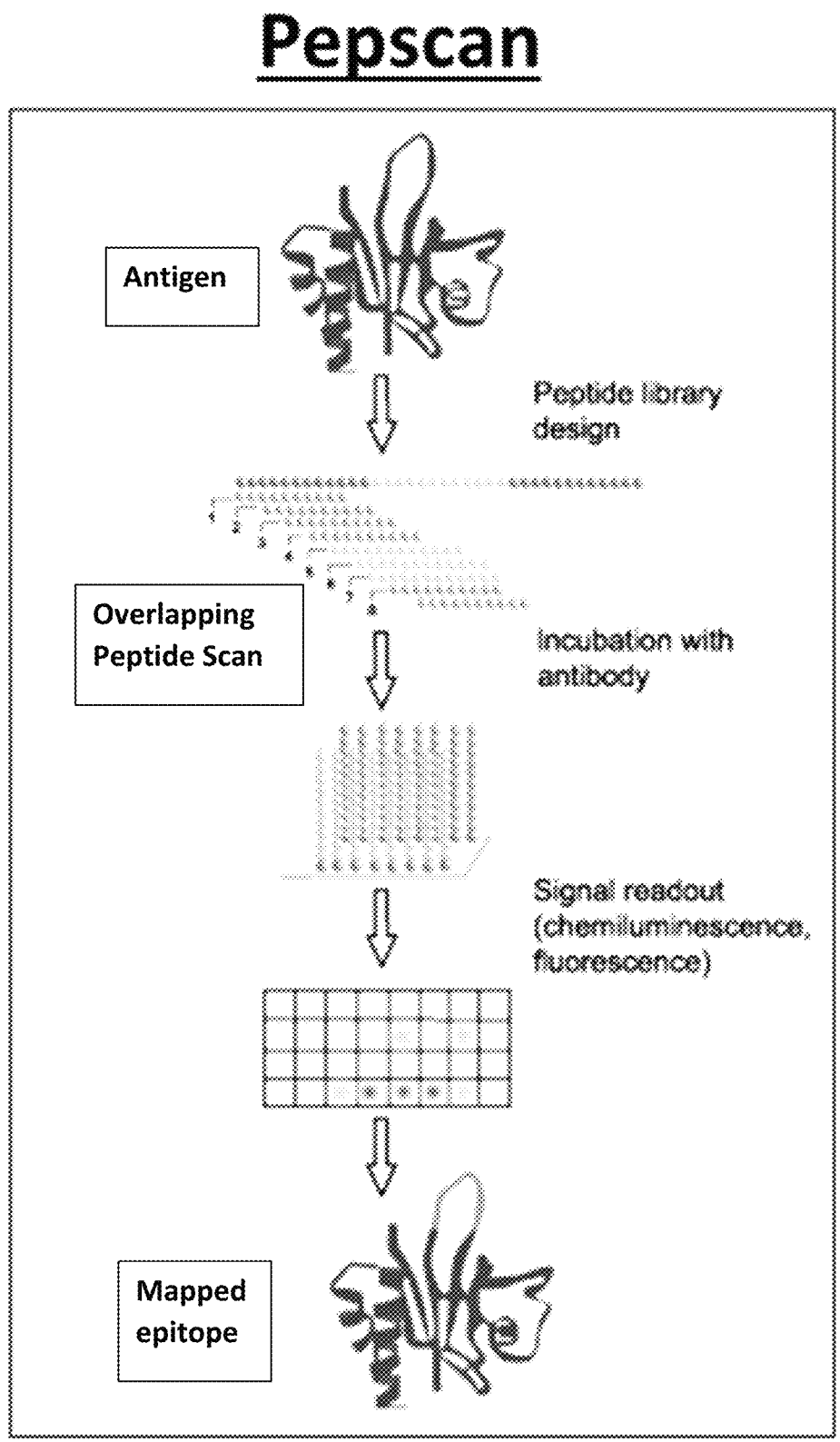
FIG. 47A shows a schematic showing Pepscan epitope mapping strategy.
Figure 47B:
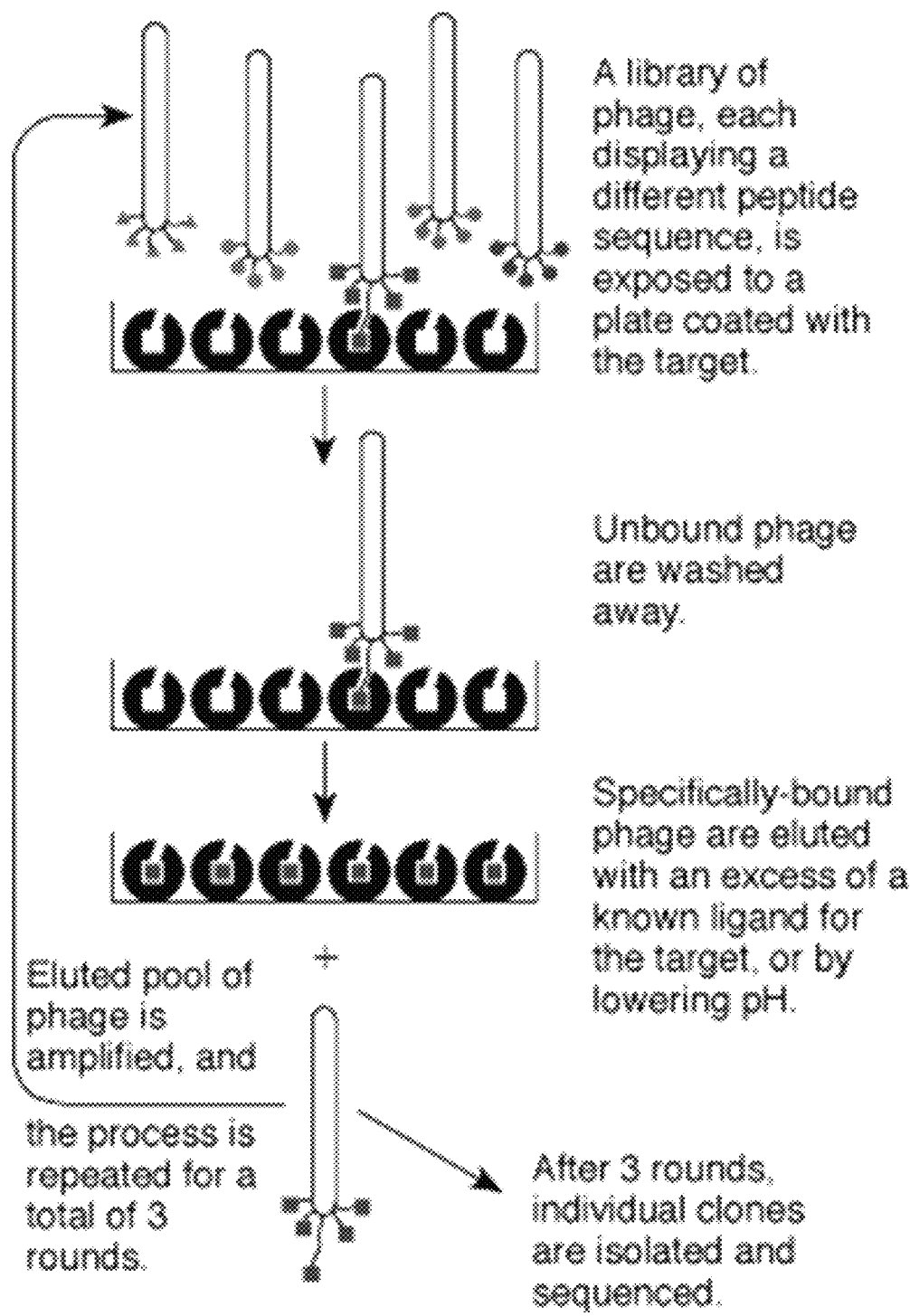
FIG. 47B shows schematic showing peptide phage display epitope mapping strategy.

Therapeutic effect of multiple doses (15 mg/kg) of mAbs 6D4 or 7G8 on human cell line HT29-luc derived tumours was investigated. Dosing was performed according to FIG. 31A. At Day 21, nude mice treated with mAb 7G8 showed an inhibition of 76.45% tumour size compared to control and mice treated with mAb 6D4 showed an inhibition of 50.19% tumour size compared to PBS control. Antibodies 7G8 and 6D4 both showed therapeutic abilities to inhibit HT29 tumour xenograft growth in nude mice (FIG. 31A).

Example 15: Human Xenograft Mouse Imaging

Monoclonal antibodies have a huge role to play in targeting cancer immunotherapy. RON is identified as an ideal candidate to target for cancer therapy as it is over-expressed in cancer cells and minimally expressed in normal cells. Targeting RON has a good safety profile as RON is not expressed in fibroblasts, endothelial cells, and blood leukocytes.

Anti-RON mouse mAbs 7G8 and 6D4 were tested for their abilities to inhibit tumour growth in vivo in human xenograft mice models. For HT-29 cancer cell xenograft experiments, female nu/nu nude mice (ages 8 weeks; Biological Resource Centre) were inoculated subcutaneously with $5 \times 10^6$ HT-29-luc2 cells (Perkin Elmer) per mouse.

Mice were randomized into different groups (5 mice per group). The study was performed by treating mice with antibodies at 10 mg/kg every 3-4 days for a total of 8 intravenous injections. Control group was injected intravenously with PBS.

Bioluminescence from individual tumours was measured at Day 21 using Caliper IVIS image system (Perkin Elmer). Animals were euthanized when tumour volumes exceeded 2,000 mm3 or if tumours became necrotic or ulcerated through the skin.

Therapeutic effect of multiple doses (15 mg/kg) of mAbs 6D4 or 7G8 on human cell line HT29-luc derived tumours was investigated. Dosing was performed according to FIGS. 31-42. At Day 21, nude mice treated with mAb 7G8 showed an inhibition of 76.45% tumour size compared to control and mice treated with mAb 6D4 showed an inhibition of 50.19% tumour size compared to PBS control. Antibodies 7G8 and 6D4 both showed therapeutic abilities to inhibit HT29 tumour xenograft growth in nude mice (FIGS. 31-42).

HT-29 tumour bearing nude mice were used for the imaging experiment. Investigation was performed to determine whether mAbs 6D4 and 7G8 could be used as in vivo molecules to detect RON expressing tumours in cancer. A fluorescent dye, (XenoLight CF750, Perkin Elmer), was conjugated via its reactive groups with 6D4 and 7G8. Detection of the fluorescent signal of CF750 was performed non-invasively using Caliper IVIS image system (Perkin Elmer), with excitation set at wavelength 710 nm and emission at 780 nm.

What is claimed is:

1. An antigen specific binding domain comprising the heavy chain CDRs of CDRH1, CDRH2, and CDRH3 and the light chain CDRs of CDRL1, CDRL2, and CDRL3, wherein
   (a) CDRH1 is SEQ ID NO: 89;
   (b) CDRH2 is SEQ ID NO: 90;
   (c) CDRH3 is SEQ ID NO: 91;
   (d) CDRL1 is SEQ ID NO: 65;
   (e) CDRL2 is SEQ ID NO: 66; and
   (f) CDRL3 is SEQ ID NO: 67;
   wherein the antigen is RON (Macrophage stimulating protein receptor or RON-Recepteur d' Origine Nantais).

2. The antigen specific binding domain according to claim 1, wherein the variable heavy domain has a sequence of SEQ ID NO: 95.

3. The antigen specific binding domain according to claim 1, wherein the variable light domain has a sequence of SEQ ID NO: 98.

4. An isolated antibody comprising an antigen specific binding domain comprising the heavy chain CDRs of CDRH1, CDRH2, and CDRH3 and the light chain CDRs of CDRL1, CDRL2, and CDRL3, wherein
   (a) CDRH1 is SEQ ID NO: 89;
   (b) CDRH2 is SEQ ID NO: 90;
   (c) CDRH3 is SEQ ID NO: 91;
   (d) CDRL1 is SEQ ID NO: 65;
   (e) CDRL2 is SEQ ID NO: 66; and
   (f) CDRL3 is SEQ ID NO: 67;
   wherein the antigen is RON.

5. The antibody according to claim 4, wherein the antibody molecule is selected from a full-length antibody or an antibody binding fragment.

6. The antibody according to claim 4, wherein the antibody is conjugated to a payload.

7. The antibody according to claim 6, wherein the payload is selected from a group consisting of toxin, a polymer, biologically active proteins, nucleic acids and fragments thereof-radionuclides chelated metals, nanoparticles and reporter groups.

8. The antibody according to claim 7, wherein the toxin is selected from a group consisting of an auristatin, MMAF (monomethyl auristatin F), pyrrolobenzodiazepine (PBD), doxorubicin, duocarmycin, a maytansinoid, calocheamicin, dolastatin, maytansine, α-amanitin, and a tubulysin.

9. A method of treating cancer in a patient comprising administering a therapeutically effective amount of an antigen specific binding domain to the patient in need thereof, wherein the antigen specific binding domain comprises the heavy chain CDRs of CDRH1, CDRH2, and CDRH3 and the light chain CDRs of CDRL1, CDRL2, and CDRL3, wherein
  (a) CDRH1 is SEQ ID NO: 89;
  (b) CDRH2 is SEQ ID NO: 90;
  (c) CDRH3 is SEQ ID NO: 91;
  (d) CDRL1 is SEQ ID NO: 65;
  (e) CDRL2 is SEQ ID NO: 66; and
   (f) CDRL3 is SEQ ID NO: 67,
wherein the antigen is RON, and wherein the cancer is a RON positive cancer.

10. The method of claim 9, wherein the patient has a RON positive and C-MET positive tumor.

11. The method of claim 9, wherein the method further comprises identifying the patient to have a RON positive tumor before treatment.

* * * * *

SEQUENCE LISTING

```
<160> NUMBER OF SEQ ID NOS: 150

<210> SEQ ID NO 1
<211> LENGTH: 8
<212> TYPE: PRT
<213> ORGANISM: Artificial Sequence
<220> FEATURE:
<223> OTHER INFORMATION: CDRH1

<400> SEQUENCE: 1

Gly Phe Thr Phe Asn Thr Tyr Thr
1               5

<210> SEQ ID NO 2
<211> LENGTH: 8
<212> TYPE: PRT
<213> ORGANISM: Artificial Sequence
<220> FEATURE:
<223> OTHER INFORMATION: CDRH2

<400> SEQUENCE: 2

Ile Ser Asn Gly Gly Gly Ser Thr
1               5

<210> SEQ ID NO 3
<211> LENGTH: 11
<212> TYPE: PRT
<213> ORGANISM: Artificial Sequence
<220> FEATURE:
<223> OTHER INFORMATION: CDRH3

<400> SEQUENCE: 3

Ala Arg Gly Tyr Arg Tyr Ala Ala Met Asp Tyr
1               5                   10

<210> SEQ ID NO 4
<211> LENGTH: 25
<212> TYPE: PRT
<213> ORGANISM: Artificial Sequence
<220> FEATURE:
<223> OTHER INFORMATION: FR1

<400> SEQUENCE: 4

Glu Val Gln Leu Glu Gln Ser Gly Gly Gly Leu Val Gln Pro Gly Gly
1               5                   10                  15
```

```
Ser Leu Lys Leu Ser Cys Ala Ala Ser
            20                  25

<210> SEQ ID NO 5
<211> LENGTH: 17
<212> TYPE: PRT
<213> ORGANISM: Artificial Sequence
<220> FEATURE:
<223> OTHER INFORMATION: FR2

<400> SEQUENCE: 5

Met Ser Trp Val Arg Gln Thr Pro Glu Lys Arg Leu Glu Trp Val Ala
1               5                   10                  15

Tyr

<210> SEQ ID NO 6
<211> LENGTH: 38
<212> TYPE: PRT
<213> ORGANISM: Artificial Sequence
<220> FEATURE:
<223> OTHER INFORMATION: FR3

<400> SEQUENCE: 6

Tyr Tyr Pro Asp Thr Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Met Tyr Tyr Cys
        35

<210> SEQ ID NO 7
<211> LENGTH: 11
<212> TYPE: PRT
<213> ORGANISM: Artificial Sequence
<220> FEATURE:
<223> OTHER INFORMATION: FR4

<400> SEQUENCE: 7

Trp Gly Gln Gly Thr Ser Val Thr Val Ser Ser
1               5                   10

<210> SEQ ID NO 8
<211> LENGTH: 118
<212> TYPE: PRT
<213> ORGANISM: Artificial Sequence
<220> FEATURE:
<223> OTHER INFORMATION: Heavy chain variable

<400> SEQUENCE: 8

Glu Val Gln Leu Glu Gln Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Thr Met Ser Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95
```

```
Ala Arg Gly Tyr Arg Tyr Ala Ala Met Asp Tyr Trp Gly Gln Gly Thr
            100                 105                 110

Ser Val Thr Val Ser Ser
        115
```

<210> SEQ ID NO 9
<211> LENGTH: 354
<212> TYPE: DNA
<213> ORGANISM: Artificial Sequence
<220> FEATURE:
<223> OTHER INFORMATION: Heavy chain variable

<400> SEQUENCE: 9

```
gaggtgcagc tggagcagtc tgggggaggt ttagtgcagc ctggagggtc cctgaaactc      60
tcctgtgcag cctctggatt cactttcaat acctatacca tgtcttgggt tcgccagact     120
ccagagaaga ggctggagtg ggtcgcatac attagtaatg gtggtggtag tacctactat     180
ccagacactg taaagggccg attcaccatc tccagagaca atgccaagaa caccctgtac     240
ctgcaaatga gcagtctgaa gtctgaggac acggccatgt attactgtgc aagaggctat     300
aggtacgctg ctatggacta ctggggtcaa ggaacctcag tcaccgtctc ctca            354
```

<210> SEQ ID NO 10
<211> LENGTH: 15
<212> TYPE: PRT
<213> ORGANISM: Artificial Sequence
<220> FEATURE:
<223> OTHER INFORMATION: Epitope; Peptide Number: 48

<400> SEQUENCE: 10

```
His Cys Pro Pro Lys Leu Thr Glu Phe His Pro His Ser Gly Pro
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: Epitope; Peptide Number: 49

<400> SEQUENCE: 11

```
Pro His Ser Gly Pro Leu Arg Gly Ser Thr Arg Leu Thr Leu Cys
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Epitope; Peptide Number: 67

<400> SEQUENCE: 12

```
Ala Gln Val Pro Gly Ser Trp Thr Phe Gln Tyr Arg Glu Asp Pro
1               5                   10                  15
```

<210> SEQ ID NO 13
<211> LENGTH: 15
<212> TYPE: PRT
<213> ORGANISM: Artificial Sequence
<220> FEATURE:
<223> OTHER INFORMATION: Epitope; Peptide Number: 68

<400> SEQUENCE: 13

```
Tyr Arg Glu Asp Pro Val Val Leu Ser Ile Ser Pro Asn Cys Gly
1               5                   10                  15
```

<210> SEQ ID NO 14
<211> LENGTH: 15
<212> TYPE: PRT
<213> ORGANISM: Artificial Sequence
<220> FEATURE:
<223> OTHER INFORMATION: Epitope; Peptide Number: 69

<400> SEQUENCE: 14

Leu His Thr Arg Leu Ala Arg Leu Ser Ala Thr Glu Pro Glu Leu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Epitope; Peptide Number: 29

<400> SEQUENCE: 15

Asp Pro Ala Leu Pro Ala Leu Val Ser Cys Gly Ser Ser Leu Gln
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Epitope; Peptide Number: 31

<400> SEQUENCE: 16

His Asp Leu Glu Pro Gln Gly Thr Ala Val His Leu Ala Ala Pro
1               5                   10                  15

<210> SEQ ID NO 17
<211> LENGTH: 337
<212> TYPE: DNA
<213> ORGANISM: Artificial Sequence
<220> FEATURE:
<223> OTHER INFORMATION: Light chain variable

<400> SEQUENCE: 17
gatattttga tgacccaaac tcctctctcc ctgcctgtca gtcttggaga tcaagcctcc      60
atctcttgca gatctagtca gagcattgta catagtaatg aaacaccta tttggaatgg     120 tacctgcaga aaccaggcca gtctccaaag ctccttatct acaaagtttc caaccgattt     180
tctggggtcc cagacaggtt cactggcagt ggatcaggga cagatttcac actcaagatc     240
agcagagtgg aggctgagga tctgggaatt tattactgct ttcaaggttc acatgctccg     300
tggacgttcg gtggaggcac caagctggaa atcagac                             337

<210> SEQ ID NO 18
<211> LENGTH: 6
<212> TYPE: PRT
<213> ORGANISM: Artificial Sequence
<220> FEATURE:
<223> OTHER INFORMATION: CDRL1

<400> SEQUENCE: 18

Gln Ser Ile Asn Asn Asn
1               5

<210> SEQ ID NO 19
<211> LENGTH: 3
<212> TYPE: PRT

```
<213> ORGANISM: Artificial Sequence
<220> FEATURE:
<223> OTHER INFORMATION: CDRL2

<400> SEQUENCE: 19

Phe Ala Ser
1

<210> SEQ ID NO 20
<211> LENGTH: 9
<212> TYPE: PRT
<213> ORGANISM: Artificial Sequence
<220> FEATURE:
<223> OTHER INFORMATION: CDRL3

<400> SEQUENCE: 20

Gln Gln Ser Asn Ser Trp Pro Leu Thr
1               5

<210> SEQ ID NO 21
<211> LENGTH: 26
<212> TYPE: PRT
<213> ORGANISM: Artificial Sequence
<220> FEATURE:
<223> OTHER INFORMATION: FR1

<400> SEQUENCE: 21

Asp Ile Val Met Thr Gln Thr Thr Ala Thr Leu Ser Val Thr Pro Gly
1               5                   10                  15

Asp Gly Val Ser Leu Ser Cys Arg Ala Ser
            20                  25

<210> SEQ ID NO 22
<211> LENGTH: 17
<212> TYPE: PRT
<213> ORGANISM: Artificial Sequence
<220> FEATURE:
<223> OTHER INFORMATION: FR2

<400> SEQUENCE: 22

Leu His Trp Tyr Gln Gln Lys Ser His Glu Ser Pro Arg Leu Leu Ile
1               5                   10                  15

Lys

<210> SEQ ID NO 23
<211> LENGTH: 36
<212> TYPE: PRT
<213> ORGANISM: Artificial Sequence
<220> FEATURE:
<223> OTHER INFORMATION: FR3

<400> SEQUENCE: 23

Gln Ser Ile Ser Gly Ile Pro Ser Arg Phe Ser Gly Ser Gly Ser Gly
1               5                   10                  15

Thr Asp Phe Thr Leu Ser Ile Asn Ser Val Glu Thr Glu Asp Phe Gly
            20                  25                  30

Met Tyr Phe Cys
        35

<210> SEQ ID NO 24
<211> LENGTH: 10
<212> TYPE: PRT
<213> ORGANISM: Artificial Sequence
<220> FEATURE:
<223> OTHER INFORMATION: FR4
```

<400> SEQUENCE: 24

Phe Gly Ala Gly Thr Lys Leu Glu Leu Lys
1               5                   10

<210> SEQ ID NO 25
<211> LENGTH: 107
<212> TYPE: PRT
<213> ORGANISM: Artificial Sequence
<220> FEATURE:
<223> OTHER INFORMATION: Light chain variable

<400> SEQUENCE: 25

Asp Ile Val Met Thr Gln Thr Thr Ala Thr Leu Ser Val Thr Pro Gly
1               5                   10                  15

Asp Gly Val Ser Leu Ser Cys Arg Ala Ser Gln Ser Ile Asn Asn Asn
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105

<210> SEQ ID NO 26
<211> LENGTH: 322
<212> TYPE: DNA
<213> ORGANISM: Artificial Sequence
<220> FEATURE:
<223> OTHER INFORMATION: Light chain variable

<400> SEQUENCE: 26
gatattgtga tgacccagac tacagccacc ctgtctgtga ctccaggaga tggcgtcagt      60
ctttcctgca gggccagcca agtattaac aacaacctac actggtatca acaaaaatca     120
catgagtctc caagacttct catcaagttt gcttcccagt ccatctctgg atcccctcc     180 aggttcagtg gcagtggatc agggacagat tcactctca gtatcaacag tgtggagact     240
gaagattttg gaatgtattt ctgtcaacag agtaacagct ggcctctcac gttcggtgct    300
gggaccaagc tggagctgaa ac                                              322

<210> SEQ ID NO 27
<211> LENGTH: 8
<212> TYPE: PRT
<213> ORGANISM: Artificial Sequence
<220> FEATURE:
<223> OTHER INFORMATION: CDRH1

<400> SEQUENCE: 27

Gly Phe Thr Phe Ser Asn Tyr Ala
1               5

<210> SEQ ID NO 28
<211> LENGTH: 7
<212> TYPE: PRT
<213> ORGANISM: Artificial Sequence
<220> FEATURE:
<223> OTHER INFORMATION: CDRH2

```
<400> SEQUENCE: 28

Ile Ser Ser Gly Gly Ser Thr
1               5

<210> SEQ ID NO 29
<211> LENGTH: 19
<212> TYPE: PRT
<213> ORGANISM: Artificial Sequence
<220> FEATURE:
<223> OTHER INFORMATION: CDRH3

<400> SEQUENCE: 29

Ala Arg Glu Gly Pro Leu Tyr Tyr Gly Pro Ser Tyr Gly Gly Tyr Tyr
1               5                   10                  15

Phe Asp Tyr

<210> SEQ ID NO 30
<211> LENGTH: 25
<212> TYPE: PRT
<213> ORGANISM: Artificial Sequence
<220> FEATURE:
<223> OTHER INFORMATION: FR1

<400> SEQUENCE: 30

Glu Val Gln Leu Leu Glu Thr Gly Gly Gly Leu Val Lys Pro Gly Gly
1               5                   10                  15

Ser Leu Lys Leu Ser Cys Ala Ala Ser
            20                  25

<210> SEQ ID NO 31
<211> LENGTH: 17
<212> TYPE: PRT
<213> ORGANISM: Artificial Sequence
<220> FEATURE:
<223> OTHER INFORMATION: FR2

<400> SEQUENCE: 31

Met Ser Trp Val Arg Gln Thr Pro Glu Lys Arg Leu Glu Trp Gly Ala
1               5                   10                  15

Ser

<210> SEQ ID NO 32
<211> LENGTH: 38
<212> TYPE: PRT
<213> ORGANISM: Artificial Sequence
<220> FEATURE:
<223> OTHER INFORMATION: FR3

<400> SEQUENCE: 32

Tyr Tyr Pro Asp Ser Val Lys Gly Arg Phe Thr Ile Ser Arg Asp Asn
1               5                   10                  15

Ala Arg Asn Ile Leu Tyr Leu Gln Met Ser Ser Leu Arg Ser Glu Asp
            20                  25                  30

Thr Ala Leu Tyr Tyr Cys
        35

<210> SEQ ID NO 33
<211> LENGTH: 11
<212> TYPE: PRT
<213> ORGANISM: Artificial Sequence
<220> FEATURE:
<223> OTHER INFORMATION: FR4
```

<400> SEQUENCE: 33

Trp Gly Gln Gly Thr Thr Leu Thr Val Ser Ser
1               5                   10

<210> SEQ ID NO 34
<211> LENGTH: 125
<212> TYPE: PRT
<213> ORGANISM: Artificial Sequence
<220> FEATURE:
<223> OTHER INFORMATION: Heavy chain variable

<400> SEQUENCE: 34

Glu Val Gln Leu Leu Glu Thr Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Gly
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Leu Tyr Tyr Cys Ala
                85                  90                  95

Arg Glu Gly Pro Leu Tyr Tyr Gly Pro Ser Tyr Gly Tyr Tyr Phe
            100                 105                 110

Asp Tyr Trp Gly Gln Gly Thr Thr Leu Thr Val Ser Ser
        115                 120                 125

<210> SEQ ID NO 35
<211> LENGTH: 375
<212> TYPE: DNA
<213> ORGANISM: Artificial Sequence
<220> FEATURE:
<223> OTHER INFORMATION: Heavy chain variable

<400> SEQUENCE: 35
gaagtgcagc tgttggagac tggggggaggc ttagtgaagc ctggagggtc cctgaaactc    60
tcctgtgcag cctctggatt cactttcagt aactatgcca tgtcttgggt tcgccagact   120
ccagagaaga ggctggagtg gggcgcatcc attagtagtg gtggtagcac ctactatcca   180
gacagtgtga aggggccgatt caccatctcc agagataatg ccaggaacat cctgtacctg   240
caaatgagca gtctgaggtc tgaggacacg gccctgtatt actgtgcaag agagggtccc   300
ctttactacg gtcctagcta cggagggtac tactttgact actggggcca aggcaccact   360
ctcacagtct cctca                                                    375

<210> SEQ ID NO 36
<211> LENGTH: 11
<212> TYPE: PRT
<213> ORGANISM: Artificial Sequence
<220> FEATURE:
<223> OTHER INFORMATION: CDRL1

<400> SEQUENCE: 36

Gln Arg Leu Val Tyr Ser Asn Gly Asn Thr Tyr
1               5                   10

<210> SEQ ID NO 37
<211> LENGTH: 3

```
<212> TYPE: PRT
<213> ORGANISM: Artificial Sequence
<220> FEATURE:
<223> OTHER INFORMATION: CDRL2

<400> SEQUENCE: 37

Lys Val Ser
1

<210> SEQ ID NO 38
<211> LENGTH: 9
<212> TYPE: PRT
<213> ORGANISM: Artificial Sequence
<220> FEATURE:
<223> OTHER INFORMATION: CDRL3

<400> SEQUENCE: 38

Ser Gln Ser Thr His Val Pro Trp Thr
1               5

<210> SEQ ID NO 39
<211> LENGTH: 26
<212> TYPE: PRT
<213> ORGANISM: Artificial Sequence
<220> FEATURE:
<223> OTHER INFORMATION: FR1

<400> SEQUENCE: 39

Asp Ile Val Met Thr Gln Ser Pro Leu Ser Leu Pro Val Ser Leu Gly
1               5                   10                  15

Asp Gln Ala Ser Ile Ser Cys Arg Ser Ser
            20                  25

<210> SEQ ID NO 40
<211> LENGTH: 17
<212> TYPE: PRT
<213> ORGANISM: Artificial Sequence
<220> FEATURE:
<223> OTHER INFORMATION: FR2

<400> SEQUENCE: 40

Leu His Trp Tyr Leu Gln Lys Pro Gly Gln Ser Pro Lys Leu Leu Ile
1               5                   10                  15

Tyr

<210> SEQ ID NO 41
<211> LENGTH: 36
<212> TYPE: PRT
<213> ORGANISM: Artificial Sequence
<220> FEATURE:
<223> OTHER INFORMATION: FR3

<400> SEQUENCE: 41

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 42
<211> LENGTH: 10
<212> TYPE: PRT
<213> ORGANISM: Artificial Sequence
<220> FEATURE:
```

<223> OTHER INFORMATION: FR4

<400> SEQUENCE: 42

Phe Gly Gly Gly Thr Lys Leu Glu Ile Lys
1               5                   10

<210> SEQ ID NO 43
<211> LENGTH: 112
<212> TYPE: PRT
<213> ORGANISM: Artificial Sequence
<220> FEATURE:
<223> OTHER INFORMATION: Light chain variable

<400> SEQUENCE: 43

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val Tyr Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 44
<211> LENGTH: 337
<212> TYPE: DNA
<213> ORGANISM: Artificial Sequence
<220> FEATURE:
<223> OTHER INFORMATION: Light chain variable

<400> SEQUENCE: 44
gacattgtga tgacacagtc tccactctcc ctgcctgtca gtcttggaga tcaagcctcc      60
atctcttgca gatctagtca gaggcttgta tacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaac                              337

<210> SEQ ID NO 45
<211> LENGTH: 8
<212> TYPE: PRT
<213> ORGANISM: Artificial Sequence
<220> FEATURE:
<223> OTHER INFORMATION: CDRH1

<400> SEQUENCE: 45

Gly Phe Ser Phe Ser Asp Tyr Trp
1               5

<210> SEQ ID NO 46
<211> LENGTH: 10
<212> TYPE: PRT
<213> ORGANISM: Artificial Sequence
<220> FEATURE:

<223> OTHER INFORMATION: CDRH2

<400> SEQUENCE: 46

Ile Arg Leu Lys Ser Ser Asn Tyr Ala Thr
1               5                   10

<210> SEQ ID NO 47
<211> LENGTH: 5
<212> TYPE: PRT
<213> ORGANISM: Artificial Sequence
<220> FEATURE:
<223> OTHER INFORMATION: CDRH3

<400> SEQUENCE: 47

Thr Arg Gly Asp Tyr
1               5

<210> SEQ ID NO 48
<211> LENGTH: 25
<212> TYPE: PRT
<213> ORGANISM: Artificial Sequence
<220> FEATURE:
<223> OTHER INFORMATION: FR1

<400> SEQUENCE: 48

Asp Val Met Leu Val Glu Ser Gly Gly Leu Val Gln Pro Gly Gly
1               5                   10                  15

Ser Met Lys Leu Ser Cys Val Ala Ser
            20                  25

<210> SEQ ID NO 49
<211> LENGTH: 17
<212> TYPE: PRT
<213> ORGANISM: Artificial Sequence
<220> FEATURE:
<223> OTHER INFORMATION: FR2

<400> SEQUENCE: 49

Met Asn Trp Val Arg Gln Ser Pro Glu Lys Gly Leu Glu Trp Val Ala
1               5                   10                  15

Glu

<210> SEQ ID NO 50
<211> LENGTH: 38
<212> TYPE: PRT
<213> ORGANISM: Artificial Sequence
<220> FEATURE:
<223> OTHER INFORMATION: FR3

<400> SEQUENCE: 50

His Tyr Ala Glu Ser Val Lys Gly Arg Phe Thr Ile Ser Arg Asp Asp
1               5                   10                  15

Ser Glu Ser Ser Val Tyr Leu Gln Met Asn Asn Leu Arg Pro Glu Asp
            20                  25                  30

Thr Gly Phe Tyr Tyr Cys
        35

<210> SEQ ID NO 51
<211> LENGTH: 114
<212> TYPE: PRT
<213> ORGANISM: Artificial Sequence
<220> FEATURE:
<223> OTHER INFORMATION: Heavy chain variable

<400> SEQUENCE: 51

Asp Val Met Leu Val Glu Ser Gly Gly Gly Leu Val Gln Pro Gly Gly
1               5                   10                  15

Ser Met Lys Leu Ser Cys Val Ala Ser Gly Phe Ser Phe Ser Asp Tyr
            20                  25                  30

Trp Met Asn Trp Val Arg Gln Ser Pro Glu Lys Gly Leu Glu Trp Val
            35                  40                  45

Ala Glu Ile Arg Leu Lys Ser Ser Asn Tyr Ala Thr His Tyr Ala Glu
        50                  55                  60

Ser Val Lys Gly Arg Phe Thr Ile Ser Arg Asp Asp Ser Glu Ser Ser
65                  70                  75                  80

Val Tyr Leu Gln Met Asn Asn Leu Arg Pro Glu Asp Thr Gly Phe Tyr
                85                  90                  95

Tyr Cys Thr Arg Gly Asp Tyr Trp Gly Gln Gly Thr Ser Val Thr Val
            100                 105                 110

Ser Ser

<210> SEQ ID NO 52
<211> LENGTH: 342
<212> TYPE: DNA
<213> ORGANISM: Artificial Sequence
<220> FEATURE:
<223> OTHER INFORMATION: Heavy chain variable

<400> SEQUENCE: 52
gacgtgatgc tggtggagtc tggaggaggc ttggtgcaac ctggaggatc catgaaactc      60
tcctgtgttg cctctggatt cagtttcagt gactactgga tgaactgggt ccgccagtct     120
ccagagaagg ggcttgaatg ggttgctgag attagattga aatctagtaa ttatgcaaca     180
cattatgcgg agtctgtgaa agggaggttt accatctcaa gagatgattc cgaaagtagt     240
gtctacctgc aaatgaacaa cttaagacct gaagacactg gcttttatta ctgtaccagg     300
ggggactatt ggggtcaagg aacctcagtc accgtctctt ca                        342

<210> SEQ ID NO 53
<211> LENGTH: 26
<212> TYPE: PRT
<213> ORGANISM: Artificial Sequence
<220> FEATURE:
<223> OTHER INFORMATION: FR1

<400> SEQUENCE: 53

Asp Ile Val Met Thr Gln Ser Pro Ala Thr Leu Ser Val Thr Pro Gly
1               5                   10                  15

Asp Gly Val Ser Leu Ser Cys Arg Ala Ser
            20                  25

<210> SEQ ID NO 54
<211> LENGTH: 107
<212> TYPE: PRT
<213> ORGANISM: Artificial Sequence
<220> FEATURE:
<223> OTHER INFORMATION: Light chain variable

<400> SEQUENCE: 54

Asp Ile Val Met Thr Gln Ser Pro Ala Thr Leu Ser Val Thr Pro Gly
1               5                   10                  15

Asp Gly Val Ser Leu Ser Cys Arg Ala Ser Gln Ser Ile Asn Asn Asn
            20                  25                  30

Leu His Trp Tyr Gln Gln Lys Ser His Glu Ser Pro Arg Leu Leu Ile

```
                35                  40                  45
Lys Phe Ala Ser Gln Ser Ile Ser Gly Ile Pro Ser Arg Phe Ser Gly
         50                  55                  60
Ser Gly Ser Gly Thr Asp Phe Thr Leu Ser Ile Asn Ser Val Glu Thr
 65                  70                  75                  80
Glu Asp Phe Gly Met Tyr Phe Cys Gln Gln Ser Asn Ser Trp Pro Leu
                 85                  90                  95
Thr Phe Gly Ala Gly Thr Lys Leu Glu Leu Lys
            100                 105
```

<210> SEQ ID NO 55
<211> LENGTH: 322
<212> TYPE: DNA
<213> ORGANISM: Artificial Sequence
<220> FEATURE:
<223> OTHER INFORMATION: Light chain variable

<400> SEQUENCE: 55

```
gatattgtga tgacccagtc tccagccacc ctgtctgtga ctccaggaga tggcgtcagt    60
ctttcctgca gggccagcca agtattaac aacaacctac actggtatca acaaaaatca   120
catgagtctc caagacttct catcaagttt gcttcccagt ccatctctgg gatcccctcc   180
aggttcagtg gcagtggatc agggacagat tcactctca gtatcaacag tgtggagact   240
gaagatttg aatgtatt ctgtcaacag agtaacagct ggcctctcac gttcggtgct   300
gggaccaagc tggagctgaa ac                                            322
```

<210> SEQ ID NO 56
<211> LENGTH: 8
<212> TYPE: PRT
<213> ORGANISM: Artificial Sequence
<220> FEATURE:
<223> OTHER INFORMATION: CDRH1

<400> SEQUENCE: 56

```
Gly Tyr Ile Phe Thr Ser Tyr Trp
 1               5
```

<210> SEQ ID NO 57
<211> LENGTH: 8
<212> TYPE: PRT
<213> ORGANISM: Artificial Sequence
<220> FEATURE:
<223> OTHER INFORMATION: CDRH2

<400> SEQUENCE: 57

```
Ile Tyr Pro Gly Asn Ser Asp Thr
 1               5
```

<210> SEQ ID NO 58
<211> LENGTH: 10
<212> TYPE: PRT
<213> ORGANISM: Artificial Sequence
<220> FEATURE:
<223> OTHER INFORMATION: CDRH3

<400> SEQUENCE: 58

```
Thr Arg Asp Gly Tyr Tyr Pro Phe Ala Tyr
 1               5                  10
```

<210> SEQ ID NO 59
<211> LENGTH: 25
<212> TYPE: PRT

```
<213> ORGANISM: Artificial Sequence
<220> FEATURE:
<223> OTHER INFORMATION: FR1

<400> SEQUENCE: 59

Glu Val Gln Leu Glu Glu Ser Gly Thr Val Leu Ala Arg Pro Gly Ala
1               5                   10                  15

Ser Val Lys Met Ser Cys Lys Ala Ser
            20                  25

<210> SEQ ID NO 60
<211> LENGTH: 17
<212> TYPE: PRT
<213> ORGANISM: Artificial Sequence
<220> FEATURE:
<223> OTHER INFORMATION: FR2

<400> SEQUENCE: 60

Met His Trp Ile Lys Gln Arg Pro Gly Gln Gly Leu Glu Trp Ile Gly
1               5                   10                  15

Ala

<210> SEQ ID NO 61
<211> LENGTH: 38
<212> TYPE: PRT
<213> ORGANISM: Artificial Sequence
<220> FEATURE:
<223> OTHER INFORMATION: FR3

<400> SEQUENCE: 61

Ser Thr Asn Gln Lys Phe Lys Asp Lys Ala Lys Leu Thr Ala Val Thr
1               5                   10                  15

Ser Thr Ser Thr Ala Tyr Leu Glu Leu Ser Ser Leu Thr Asn Glu Asp
            20                  25                  30

Ser Ala Val Phe Tyr Cys
        35

<210> SEQ ID NO 62
<211> LENGTH: 11
<212> TYPE: PRT
<213> ORGANISM: Artificial Sequence
<220> FEATURE:
<223> OTHER INFORMATION: FR4

<400> SEQUENCE: 62

Trp Gly Gln Gly Thr Leu Val Thr Val Ser Ala
1               5                   10

<210> SEQ ID NO 63
<211> LENGTH: 117
<212> TYPE: PRT
<213> ORGANISM: Artificial Sequence
<220> FEATURE:
<223> OTHER INFORMATION: Heavy chain variable

<400> SEQUENCE: 63

Glu Val Gln Leu Glu Glu Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Met His Trp Ile Lys Gln Arg Pro Gly Gln Gly Leu Glu Trp Ile
        35                  40                  45

Gly Ala Ile Tyr Pro Gly Asn Ser Asp Thr Ser Thr Asn Gln Lys Phe
```

```
                    50                  55                  60
Lys Asp Lys Ala Lys Leu Thr Ala Val Thr Ser Ser Thr Ala Tyr
 65                  70                  75                  80

Leu Glu Leu Ser Ser Leu Thr Asn Glu Asp Ser Ala Val Phe Tyr Cys
                 85                  90                  95

Thr Arg Asp Gly Tyr Tyr Pro Phe Ala Tyr Trp Gly Gln Gly Thr Leu
            100                 105                 110

Val Thr Val Ser Ala
        115

<210> SEQ ID NO 64
<211> LENGTH: 351
<212> TYPE: DNA
<213> ORGANISM: Artificial Sequence
<220> FEATURE:
<223> OTHER INFORMATION: Heavy chain variable

<400> SEQUENCE: 64
gaagtgcagc tggaggagtc agggactgtg ctggcaaggc ctggggcttc agtgaagatg       60
tcctgcaagg cttctggcta cattttacc  agctactgga tgcactggat aaaacagagg      120
cctggacagg gtctggaatg gattggcgct atttatcctg aaatagtga  actagtact       180 aatcagaagt tcaaggacaa ggccaaactg actgcagtca catccaccag cactgcctat      240
ttggaactca gcagcctgac aaatgaggac tcagcggtct tttactgtac aagagatggt      300
tactacccgt ttgcttactg gggccaaggg actctggtca ctgtctctgc a               351

<210> SEQ ID NO 65
<211> LENGTH: 11
<212> TYPE: PRT
<213> ORGANISM: Artificial Sequence
<220> FEATURE:
<223> OTHER INFORMATION: CDRL1

<400> SEQUENCE: 65

Gln Ser Leu Val Tyr Ile Asn Gly Asp Thr Tyr
 1               5                  10

<210> SEQ ID NO 66
<211> LENGTH: 3
<212> TYPE: PRT
<213> ORGANISM: Artificial Sequence
<220> FEATURE:
<223> OTHER INFORMATION: CDRL2

<400> SEQUENCE: 66

Arg Val Ser
 1

<210> SEQ ID NO 67
<211> LENGTH: 9
<212> TYPE: PRT
<213> ORGANISM: Artificial Sequence
<220> FEATURE:
<223> OTHER INFORMATION: CDRL3

<400> SEQUENCE: 67

Ser Gln Thr Lys His Val Pro Tyr Thr
 1               5

<210> SEQ ID NO 68
<211> LENGTH: 26
<212> TYPE: PRT
```

```
<213> ORGANISM: Artificial Sequence
<220> FEATURE:
<223> OTHER INFORMATION: FR1

<400> SEQUENCE: 68

Asp Ile Val Leu Thr Gln Ser Pro Leu Ser Leu Pro Val Ser Leu Gly
1               5                   10                  15

Asp Gln Ala Ser Ile Ser Cys Arg Ser Ser
            20                  25

<210> SEQ ID NO 69
<211> LENGTH: 17
<212> TYPE: PRT
<213> ORGANISM: Artificial Sequence
<220> FEATURE:
<223> OTHER INFORMATION: FR2

<400> SEQUENCE: 69

Phe His Trp Tyr Leu Gln Lys Pro Gly Gln Ser Pro Lys Leu Leu Ile
1               5                   10                  15

Tyr

<210> SEQ ID NO 70
<211> LENGTH: 10
<212> TYPE: PRT
<213> ORGANISM: Artificial Sequence
<220> FEATURE:
<223> OTHER INFORMATION: FR4

<400> SEQUENCE: 70

Phe Gly Gly Gly Thr Lys Leu Glu Met Lys
1               5                   10

<210> SEQ ID NO 71
<211> LENGTH: 112
<212> TYPE: PRT
<213> ORGANISM: Artificial Sequence
<220> FEATURE:
<223> OTHER INFORMATION: Light chain variable

<400> SEQUENCE: 71

Asp Ile Val Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val Tyr Ile
            20                  25                  30

Asn Gly Asp Thr Tyr Phe His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Lys His Val Pro Tyr Thr Phe Gly Gly Gly Thr Lys Leu Glu Met Lys
            100                 105                 110

<210> SEQ ID NO 72
<211> LENGTH: 338
<212> TYPE: DNA
<213> ORGANISM: Artificial Sequence
<220> FEATURE:
<223> OTHER INFORMATION: Light chain variable
```

-continued

```
<400> SEQUENCE: 72
gacattgtgc tgacccaatc tccactctcc ctgcctgtca gtcttggaga tcaagcctcc    60
atctcttgca gatctagtca gagccttgta tatattaatg gagacaccta ttttcattgg   120
tacttgcaga agccaggcca gtctccaaag ctcctgatct acagagtttc caaccgattt   180
tctggggtcc cagacaggtt cagtggcagt ggatcaggga cagatttcac actcaagatc   240
agcagagtgg aggctgagga tctgggagtt tatttctgct ctcaaactaa acatgttccg   300
tacacgttcg gaggggggac caagctggaa atgaaacg                           338

<210> SEQ ID NO 73
<211> LENGTH: 8
<212> TYPE: PRT
<213> ORGANISM: Artificial Sequence
<220> FEATURE:
<223> OTHER INFORMATION: CDRH1

<400> SEQUENCE: 73

Gly Tyr Glu Phe Ser Lys Tyr Trp
1               5

<210> SEQ ID NO 74
<211> LENGTH: 8
<212> TYPE: PRT
<213> ORGANISM: Artificial Sequence
<220> FEATURE:
<223> OTHER INFORMATION: CDRH2

<400> SEQUENCE: 74

Ile Phe Pro Gly Asp Gly Asp Ile
1               5

<210> SEQ ID NO 75
<211> LENGTH: 13
<212> TYPE: PRT
<213> ORGANISM: Artificial Sequence
<220> FEATURE:
<223> OTHER INFORMATION: CDRH3

<400> SEQUENCE: 75

Ala Arg Trp Tyr Tyr Gly Ser Asn Tyr Ala Met Asp Tyr
1               5                   10

<210> SEQ ID NO 76
<211> LENGTH: 25
<212> TYPE: PRT
<213> ORGANISM: Artificial Sequence
<220> FEATURE:
<223> OTHER INFORMATION: FR1

<400> SEQUENCE: 76

Glu Val Gln Leu Gln Gln Pro Gly Ala Glu Leu Val Arg Pro Gly Ser
1               5                   10                  15

Ser Val Lys Ile Ser Cys Lys Ala Ser
            20                  25

<210> SEQ ID NO 77
<211> LENGTH: 17
<212> TYPE: PRT
<213> ORGANISM: Artificial Sequence
<220> FEATURE:
<223> OTHER INFORMATION: FR2

<400> SEQUENCE: 77
```

```
Met Asn Trp Val Lys Gln Arg Pro Gly Gln Gly Leu Glu Trp Ile Gly
1               5                   10                  15

Gln
```

<210> SEQ ID NO 78
<211> LENGTH: 38
<212> TYPE: PRT
<213> ORGANISM: Artificial Sequence
<220> FEATURE:
<223> OTHER INFORMATION: FR3

<400> SEQUENCE: 78

```
Asn Tyr Asn Gly Lys Phe Lys Gly Lys Ala Thr Leu Thr Ala Asp Lys
1               5                   10                  15

Ser Ser Ser Thr Ala Tyr Met Gln Leu Ser Ser Leu Thr Ser Glu Glu
            20                  25                  30

Ser Ala Val Tyr Phe Cys
        35
```

<210> SEQ ID NO 79
<211> LENGTH: 120
<212> TYPE: PRT
<213> ORGANISM: Artificial Sequence
<220> FEATURE:
<223> OTHER INFORMATION: Heavy chain variable

<400> SEQUENCE: 79

```
Glu Val Gln Leu Gln Gln Pro Gly Ala Glu Leu Val Arg Pro Gly Ser
1               5                   10                  15

Ser Val Lys Ile Ser Cys Lys Ala Ser Gly Tyr Glu Phe Ser Lys Tyr
            20                  25                  30

Trp Met Asn Trp Val Lys Gln Arg Pro Gly Gln Gly Leu Glu Trp Ile
        35                  40                  45

Gly Gln Ile Phe Pro Gly Asp Gly Asp Ile Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Glu Ser Ala Val Tyr Phe Cys
            85                  90                  95

Ala Arg Trp Tyr Tyr Gly Ser Asn Tyr Ala Met Asp Tyr Trp Gly Gln
            100                 105                 110

Gly Thr Ser Val Thr Val Ser Ser
        115                 120
```

<210> SEQ ID NO 80
<211> LENGTH: 360
<212> TYPE: DNA
<213> ORGANISM: Artificial Sequence
<220> FEATURE:
<223> OTHER INFORMATION: Heavy chain variable

<400> SEQUENCE: 80

```
gaggtccagc tgcagcagcc tggggctgag ctggtgaggc ctgggtcctc agtgaagatt     60
tcctgcaagg cttctggcta tgaattcagt aagtactgga tgaactgggt gaagcagagg    120
cctggacagg gtcttgagtg gattggacag atttttccag agacggtga tattaattac     180 aatggaaaat tcaagggtaa agccacactg actgcagaca atcctccag cacagcctac     240 atgcagctca gcagcctaac atctgaggaa tctgcggtct atttctgtgc aagatggtac    300
tacggtagta actatgctat ggactactgg ggtcaaggaa cctcagtcac cgtctcctca    360
```

<210> SEQ ID NO 81
<211> LENGTH: 12
<212> TYPE: PRT
<213> ORGANISM: Artificial Sequence
<220> FEATURE:
<223> OTHER INFORMATION: CDRL1

<400> SEQUENCE: 81

Gln Ser Leu Leu Tyr Ser Ser Asn Gln Lys Asn Tyr
1               5                   10

<210> SEQ ID NO 82
<211> LENGTH: 3
<212> TYPE: PRT
<213> ORGANISM: Artificial Sequence
<220> FEATURE:
<223> OTHER INFORMATION: CDRL2

<400> SEQUENCE: 82

Trp Ala Ser
1

<210> SEQ ID NO 83
<211> LENGTH: 8
<212> TYPE: PRT
<213> ORGANISM: Artificial Sequence
<220> FEATURE:
<223> OTHER INFORMATION: CDRL3

<400> SEQUENCE: 83

Gln Gln Tyr Tyr Ala Tyr Arg Thr
1               5

<210> SEQ ID NO 84
<211> LENGTH: 26
<212> TYPE: PRT
<213> ORGANISM: Artificial Sequence
<220> FEATURE:
<223> OTHER INFORMATION: FR1

<400> SEQUENCE: 84

Asp Ile Val Met Thr Gln Thr Pro Ser Ser Leu Ala Val Ser Val Gly
1               5                   10                  15

Glu Lys Ile Thr Met Ser Cys Lys Ser Ser
            20                  25

<210> SEQ ID NO 85
<211> LENGTH: 17
<212> TYPE: PRT
<213> ORGANISM: Artificial Sequence
<220> FEATURE:
<223> OTHER INFORMATION: FR2

<400> SEQUENCE: 85

Leu Ala Trp Tyr Gln Gln Lys Pro Gly Gln Ser Pro Lys Leu Leu Ile
1               5                   10                  15

Tyr

<210> SEQ ID NO 86
<211> LENGTH: 36
<212> TYPE: PRT
<213> ORGANISM: Artificial Sequence
<220> FEATURE:
<223> OTHER INFORMATION: FR3

<400> SEQUENCE: 86

Thr Arg Glu Ser Gly Val Pro Asp Arg Phe Thr Gly Ser Gly Ser Gly
1               5                   10                  15

Thr Asp Phe Thr Leu Thr Ile Ser Ser Val Lys Ala Glu Asp Leu Ala
            20                  25                  30

Val Tyr Tyr Cys
        35

<210> SEQ ID NO 87
<211> LENGTH: 112
<212> TYPE: PRT
<213> ORGANISM: Artificial Sequence
<220> FEATURE:
<223> OTHER INFORMATION: Light chain variable

<400> SEQUENCE: 87

Asp Ile Val Met Thr Gln Thr Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ala Tyr Arg Thr Phe Gly Gly Gly Thr Lys Leu Glu Ile Lys
            100                 105                 110

<210> SEQ ID NO 88
<211> LENGTH: 337
<212> TYPE: DNA
<213> ORGANISM: Artificial Sequence
<220> FEATURE:
<223> OTHER INFORMATION: Light chain variable

<400> SEQUENCE: 88
gacattgtga tgacccagac tccatcctcc ctagctgtgt cagttggaga gaagattact      60
atgagctgca agtccagtca gagccttttg tatagtagca tcaaaagaa ctacttggcc     120 tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatgcctat    300
cggacgttcg gtggaggcac caagctggaa atcaaac                             337

<210> SEQ ID NO 89
<211> LENGTH: 8
<212> TYPE: PRT
<213> ORGANISM: Artificial Sequence
<220> FEATURE:
<223> OTHER INFORMATION: CDRH1

<400> SEQUENCE: 89

Gly Tyr Ile Phe Thr Ser Tyr Trp
1               5

<210> SEQ ID NO 90

-continued

```
<211> LENGTH: 8
<212> TYPE: PRT
<213> ORGANISM: Artificial Sequence
<220> FEATURE:
<223> OTHER INFORMATION: CDRH2

<400> SEQUENCE: 90

Ile Tyr Pro Gly Asn Asn Asp Thr
1               5

<210> SEQ ID NO 91
<211> LENGTH: 10
<212> TYPE: PRT
<213> ORGANISM: Artificial Sequence
<220> FEATURE:
<223> OTHER INFORMATION: CDRH3

<400> SEQUENCE: 91

Thr Arg Asp Gly Phe Tyr Pro Phe Ala Tyr
1               5                   10

<210> SEQ ID NO 92
<211> LENGTH: 25
<212> TYPE: PRT
<213> ORGANISM: Artificial Sequence
<220> FEATURE:
<223> OTHER INFORMATION: FR1

<400> SEQUENCE: 92

Glu Val Lys Leu Gln Gln Ser Gly Thr Val Leu Ala Arg Pro Gly Thr
1               5                   10                  15

Ser Val Lys Met Ser Cys Lys Ala Ser
            20                  25

<210> SEQ ID NO 93
<211> LENGTH: 17
<212> TYPE: PRT
<213> ORGANISM: Artificial Sequence
<220> FEATURE:
<223> OTHER INFORMATION: FR2

<400> SEQUENCE: 93

Met His Trp Ile Lys Glu Arg Pro Gly Gln Gly Leu Glu Trp Ile Gly
1               5                   10                  15

Ala

<210> SEQ ID NO 94
<211> LENGTH: 38
<212> TYPE: PRT
<213> ORGANISM: Artificial Sequence
<220> FEATURE:
<223> OTHER INFORMATION: FR3

<400> SEQUENCE: 94

Ser Thr Asn Gln Lys Phe Lys Gly Lys Ala Lys Leu Thr Ala Val Thr
1               5                   10                  15

Ser Thr Ser Thr Ala Tyr Leu Glu Leu Ser Ser Leu Thr Asn Glu Asp
            20                  25                  30

Ser Ala Val Tyr Tyr Cys
        35

<210> SEQ ID NO 95
<211> LENGTH: 117
<212> TYPE: PRT
<213> ORGANISM: Artificial Sequence
```

```
<220> FEATURE:
<223> OTHER INFORMATION: Heavy chain variable

<400> SEQUENCE: 95

Glu Val Lys Leu Gln Gln Ser Gly Thr Val Leu Ala Arg Pro Gly Thr
1               5                   10                  15

Ser Val Lys Met Ser Cys Lys Ala Ser Gly Tyr Ile Phe Thr Ser Tyr
            20                  25                  30

Trp Met His Trp Ile Lys Glu Arg Pro Gly Gln Gly Leu Glu Trp Ile
        35                  40                  45

Gly Ala Ile Tyr Pro Gly Asn Asn Asp Thr Thr Asn Gln Lys Phe
    50                  55                  60

Lys Gly Lys Ala Lys Leu Thr Ala Val Thr Ser Ser Thr Ala Tyr
65                  70                  75                  80

Leu Glu Leu Ser Ser Leu Thr Asn Glu Asp Ser Ala Val Tyr Tyr Cys
                85                  90                  95

Thr Arg Asp Gly Phe Tyr Pro Phe Ala Tyr Trp Gly Gln Gly Thr Leu
            100                 105                 110

Val Thr Val Ser Ala
        115

<210> SEQ ID NO 96
<211> LENGTH: 351
<212> TYPE: DNA
<213> ORGANISM: Artificial Sequence
<220> FEATURE:
<223> OTHER INFORMATION: Heavy chain variable

<400> SEQUENCE: 96
gaggttaagc tgcagcagtc tgggactgtg ctggcaaggc ctgggacttc agtgaagatg      60
tcttgcaagg cttctggcta cattttacc agctactgga tgcattggat aaaagagagg     120
cctggacagg gtctggaatg gattggcgct atttatcctg gaaataatga tactagtact    180
aatcagaagt tcaagggcaa ggccaaactg actgcagtca catccaccag cactgcctat    240
ttggaactca gcagcctgac aaatgaggac tcagcggtct attactgtac aagagatggt    300
ttttacccgt tgcttactg gggccaaggg actctggtca ctgtctctgc a              351

<210> SEQ ID NO 97
<211> LENGTH: 26
<212> TYPE: PRT
<213> ORGANISM: Artificial Sequence
<220> FEATURE:
<223> OTHER INFORMATION: FR1

<400> SEQUENCE: 97

Asp Ile Val Leu Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 98
<211> LENGTH: 112
<212> TYPE: PRT
<213> ORGANISM: Artificial Sequence
<220> FEATURE:
<223> OTHER INFORMATION: Light chain variable

<400> SEQUENCE: 98

Asp Ile Val Leu Thr Gln Thr Pro Leu Ser Leu Pro Val Ser Leu Gly
1               5                   10                  15
```

```
Asp Gln Ala Ser Ile Ser Cys Arg Ser Gln Ser Leu Val Tyr Ile
            20                  25                  30

Asn Gly Asp Thr Tyr Phe His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Lys His Val Pro Tyr Thr Phe Gly Gly Gly Thr Lys Leu Glu Met Lys
            100                 105                 110
```

<210> SEQ ID NO 99
<211> LENGTH: 338
<212> TYPE: DNA
<213> ORGANISM: Artificial Sequence
<220> FEATURE:
<223> OTHER INFORMATION: Light chain variable

<400> SEQUENCE: 99

```
gatattgtgc tgacccagac tccactctcc ctgcctgtca gtcttggaga tcaagcctcc      60
atctcttgca gatctagtca gagccttgta tatattaatg agacacccta ttttcattgg     120
tacctgcaga agccaggcca gtctccaaag ctcctgatct acagagtttc caaccgattt     180
tctggggtcc cagacaggtt cagtggcagt ggatcaggga cagatttcac actcaagatc    240
agcagagtgg aggctgagga tctgggagtt tatttctgct ctcaaactaa acatgttccg    300
tacacgttcg gaggggggac caagctggaa atgaaacg                             338
```

<210> SEQ ID NO 100
<211> LENGTH: 8
<212> TYPE: PRT
<213> ORGANISM: Artificial Sequence
<220> FEATURE:
<223> OTHER INFORMATION: CDRH1

<400> SEQUENCE: 100

```
Gly Tyr Ile Phe Thr Ser Tyr Tyr
1               5
```

<210> SEQ ID NO 101
<211> LENGTH: 8
<212> TYPE: PRT
<213> ORGANISM: Artificial Sequence
<220> FEATURE:
<223> OTHER INFORMATION: CDRH2

<400> SEQUENCE: 101

```
Ile Asn Pro Ile Thr Gly Gly Thr
1               5
```

<210> SEQ ID NO 102
<211> LENGTH: 10
<212> TYPE: PRT
<213> ORGANISM: Artificial Sequence
<220> FEATURE:
<223> OTHER INFORMATION: CDRH3

<400> SEQUENCE: 102

```
Ala Arg Met Gly Arg Asp Ala Met Asp Tyr
1               5                   10
```

<210> SEQ ID NO 103
<211> LENGTH: 25
<212> TYPE: PRT
<213> ORGANISM: Artificial Sequence
<220> FEATURE:
<223> OTHER INFORMATION: FR1

<400> SEQUENCE: 103

Gln Val Gln Leu Lys Gln Ser Gly Ser Glu Leu Val Lys Pro Gly Ala
1               5                   10                  15

Ser Val Lys Leu Ser Cys Lys Ala Ser
            20                  25

<210> SEQ ID NO 104
<211> LENGTH: 17
<212> TYPE: PRT
<213> ORGANISM: Artificial Sequence
<220> FEATURE:
<223> OTHER INFORMATION: FR2

<400> SEQUENCE: 104

Met Tyr Trp Val Lys Gln Arg Pro Gly Gln Gly Leu Glu Trp Ile Gly
1               5                   10                  15

Gly

<210> SEQ ID NO 105
<211> LENGTH: 38
<212> TYPE: PRT
<213> ORGANISM: Artificial Sequence
<220> FEATURE:
<223> OTHER INFORMATION: FR3

<400> SEQUENCE: 105

Asp Phe Asn Glu Lys Phe Lys Asp Lys Ala Thr Leu Thr Leu Ala Ala
1               5                   10                  15

Ser Ser Ser Thr Ala Tyr Ile Gln Leu Ser Ser Leu Thr Ser Glu Asp
            20                  25                  30

Ser Ala Val Tyr Phe Cys
        35

<210> SEQ ID NO 106
<211> LENGTH: 117
<212> TYPE: PRT
<213> ORGANISM: Artificial Sequence
<220> FEATURE:
<223> OTHER INFORMATION: Heavy chain variable

<400> SEQUENCE: 106

Gln Val Gln Leu Lys Gln Ser Gly Ser Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ile Thr Gly Gly Thr Asp Phe Asn Glu Lys Phe
    50                  55                  60

Lys Asp Lys Ala Thr Leu Thr Leu Ala Ala Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Met Gly Arg Asp Ala Met Asp Tyr Trp Gly Gln Gly Thr Ser
            100                 105                 110

Val Thr Val Ser Ser
        115

<210> SEQ ID NO 107
<211> LENGTH: 350
<212> TYPE: DNA
<213> ORGANISM: Artificial Sequence
<220> FEATURE:
<223> OTHER INFORMATION: Heavy chain variable

<400> SEQUENCE: 107
caggtgcagc tgaagcagtc agggtctgaa ctggtgaaac ctggggcttc agtgaagttg     60
tcctgcaagg cttctggcta catcttcacc agctactata tgtactgggt gaagcagagg    120
cctggacaag gccttgagtg gattgggggg attaatccta tcactggtgg tactgacttc    180
aatgagaagt tcaaggacaa ggccacactg actctggccg catcctccag cacagcctac    240
atacaactca gcagcctgac atctgaggac tctgcggtct atttctgtgc aagaatggga    300
cgggatgcta tggactactg gggtcaagga acctcagtca ccgtctcctc                350

<210> SEQ ID NO 108
<211> LENGTH: 10
<212> TYPE: PRT
<213> ORGANISM: Artificial Sequence
<220> FEATURE:
<223> OTHER INFORMATION: CDRL1

<400> SEQUENCE: 108

Lys Ser Val Ser Thr Ser Gly Tyr Ser Tyr
1               5                   10

<210> SEQ ID NO 109
<211> LENGTH: 3
<212> TYPE: PRT
<213> ORGANISM: Artificial Sequence
<220> FEATURE:
<223> OTHER INFORMATION: CDRL2

<400> SEQUENCE: 109

Leu Val Ser
1

<210> SEQ ID NO 110
<211> LENGTH: 8
<212> TYPE: PRT
<213> ORGANISM: Artificial Sequence
<220> FEATURE:
<223> OTHER INFORMATION: CDRL3

<400> SEQUENCE: 110

Gln His Ile Arg Glu Leu Tyr Thr
1               5

<210> SEQ ID NO 111
<211> LENGTH: 26
<212> TYPE: PRT
<213> ORGANISM: Artificial Sequence
<220> FEATURE:
<223> OTHER INFORMATION: FR1

<400> SEQUENCE: 111

Asp Ile Val Leu Thr Gln Ser Pro Ala Ser Leu Ala Val Ser Leu Gly
1               5                   10                  15

```
Gln Arg Ala Thr Ile Ser Tyr Arg Ala Ser
            20                  25
```

<210> SEQ ID NO 112
<211> LENGTH: 17
<212> TYPE: PRT
<213> ORGANISM: Artificial Sequence
<220> FEATURE:
<223> OTHER INFORMATION: FR2

<400> SEQUENCE: 112

```
Met His Trp Asn Gln Gln Lys Pro Gly Gln Pro Pro Arg Leu Leu Ile
1               5                   10                  15

Tyr
```

<210> SEQ ID NO 113
<211> LENGTH: 36
<212> TYPE: PRT
<213> ORGANISM: Artificial Sequence
<220> FEATURE:
<223> OTHER INFORMATION: FR3

<400> SEQUENCE: 113

```
Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
            20                  25                  30

Thr Tyr Tyr Cys
        35
```

<210> SEQ ID NO 114
<211> LENGTH: 110
<212> TYPE: PRT
<213> ORGANISM: Artificial Sequence
<220> FEATURE:
<223> OTHER INFORMATION: Light chain variable

<400> SEQUENCE: 114

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Tyr Thr Phe Gly Gly Gly Thr Lys Leu Glu Ile Lys
            100                 105                 110
```

<210> SEQ ID NO 115
<211> LENGTH: 332
<212> TYPE: DNA
<213> ORGANISM: Artificial Sequence
<220> FEATURE:
<223> OTHER INFORMATION: Light chain variable

<400> SEQUENCE: 115

```
gacattgtgc tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gctttacacg   300
ttcggagggg ggaccaagct ggaaataaaa cg                                 332
```

```
<210> SEQ ID NO 116
<211> LENGTH: 8
<212> TYPE: PRT
<213> ORGANISM: Artificial Sequence
<220> FEATURE:
<223> OTHER INFORMATION: CDRH1

<400> SEQUENCE: 116

Gly Tyr Thr Phe Thr Ser Tyr Tyr
1               5

<210> SEQ ID NO 117
<211> LENGTH: 8
<212> TYPE: PRT
<213> ORGANISM: Artificial Sequence
<220> FEATURE:
<223> OTHER INFORMATION: CDRH2

<400> SEQUENCE: 117

Ile Asn Pro Thr Thr Gly Gly Thr
1               5

<210> SEQ ID NO 118
<211> LENGTH: 25
<212> TYPE: PRT
<213> ORGANISM: Artificial Sequence
<220> FEATURE:
<223> OTHER INFORMATION: FR1

<400> SEQUENCE: 118

Gln Val Gln Leu Lys Glu Ser Gly Ala Glu Leu Val Lys Pro Gly Thr
1               5                   10                  15

Ser Val Lys Leu Ser Cys Lys Ala Ser
            20                  25

<210> SEQ ID NO 119
<211> LENGTH: 17
<212> TYPE: PRT
<213> ORGANISM: Artificial Sequence
<220> FEATURE:
<223> OTHER INFORMATION: FR2

<400> SEQUENCE: 119

Met Tyr Trp Leu Lys Gln Arg Pro Gly Gln Gly Leu Glu Trp Ile Gly
1               5                   10                  15

Gly

<210> SEQ ID NO 120
<211> LENGTH: 38
<212> TYPE: PRT
<213> ORGANISM: Artificial Sequence
<220> FEATURE:
<223> OTHER INFORMATION: FR3

<400> SEQUENCE: 120
```

Asp Phe Asn Glu Asn Phe Lys Asn Lys Ala Thr Leu Thr Leu Ala Thr
1               5                   10                  15

Ser Ser Ser Thr Ala Tyr Ile Gln Leu Ser Ser Leu Thr Ser Glu Asp
            20                  25                  30

Ser Ala Val Tyr Phe Cys
        35

<210> SEQ ID NO 121
<211> LENGTH: 117
<212> TYPE: PRT
<213> ORGANISM: Artificial Sequence
<220> FEATURE:
<223> OTHER INFORMATION: Heavy chain variable

<400> SEQUENCE: 121

Gln Val Gln Leu Lys Glu Ser Gly Ala Glu Leu Val Lys Pro Gly Thr
1               5                   10                  15

Ser Val Lys Leu Ser Cys Lys Ala Ser Gly Tyr Thr Phe Thr Ser Tyr
            20                  25                  30

Tyr Met Tyr Trp Leu Lys Gln Arg Pro Gly Gln Gly Leu Glu Trp Ile
        35                  40                  45

Gly Gly Ile Asn Pro Thr Thr Gly Gly Thr Asp Phe Asn Glu Asn Phe
    50                  55                  60

Lys Asn Lys Ala Thr Leu Thr Leu Ala Thr Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Met Gly Arg Asp Ala Met Asp Tyr Trp Gly Gln Gly Thr Ser
            100                 105                 110

Val Thr Val Ser Ser
        115

<210> SEQ ID NO 122
<211> LENGTH: 351
<212> TYPE: DNA
<213> ORGANISM: Artificial Sequence
<220> FEATURE:
<223> OTHER INFORMATION: Heavy chain variable

<400> SEQUENCE: 122
caggtgcagc tgaaggagtc agggctgaa ctggtgaaac ctgggacttc agtgaagttg      60
tcctgcaagg cttctggcta caccttcacc agctactata tgtactggtt gaagcagagg    120
cctggacaag ccttgagtg gattgggggg attaatccta ccactggtgg tactgacttc    180
aatgagaact tcaagaacaa ggccacactg actttggcca catcctccag cacagcctac    240
atacaactca gcagcctgac atctgaggac tctgcggtct atttctgtgc aagaatggga    300
cgggatgcta tggactactg gggtcaagga acctcagtca ccgtctcctc a             351

<210> SEQ ID NO 123
<211> LENGTH: 8
<212> TYPE: PRT
<213> ORGANISM: Artificial Sequence
<220> FEATURE:
<223> OTHER INFORMATION: CDRL3

<400> SEQUENCE: 123

Gln His Ile Arg Glu Leu Thr Arg
1               5

```
<210> SEQ ID NO 124
<211> LENGTH: 26
<212> TYPE: PRT
<213> ORGANISM: Artificial Sequence
<220> FEATURE:
<223> OTHER INFORMATION: FR1

<400> SEQUENCE: 124

Asp Ile Val Leu Thr Gln Ser Pro Ala Ser Leu Ala Val Ser Leu Gly
1               5                   10                  15
Gln Arg Ala Thr Ile Ser Tyr Arg Ala Ser
            20                  25

<210> SEQ ID NO 125
<211> LENGTH: 17
<212> TYPE: PRT
<213> ORGANISM: Artificial Sequence
<220> FEATURE:
<223> OTHER INFORMATION: FR2

<400> SEQUENCE: 125

Met His Trp Asn Gln Gln Lys Pro Gly Gln Pro Pro Arg Leu Leu Ile
1               5                   10                  15
Tyr

<210> SEQ ID NO 126
<211> LENGTH: 36
<212> TYPE: PRT
<213> ORGANISM: Artificial Sequence
<220> FEATURE:
<223> OTHER INFORMATION: FR3

<400> SEQUENCE: 126

Asn Leu Glu Ser Gly Val Pro Ala Arg Phe Ser Gly Ser Gly Ser Gly
1               5                   10                  15
Thr Asp Phe Thr Leu Asn Ile His Pro Val Glu Glu Glu Asp Ala Ala
            20                  25                  30
Thr Tyr Tyr Cys
        35

<210> SEQ ID NO 127
<211> LENGTH: 108
<212> TYPE: PRT
<213> ORGANISM: Artificial Sequence
<220> FEATURE:
<223> OTHER INFORMATION: Light chain variable

<400> SEQUENCE: 127

Asp Ile Val Leu Thr Gln Ser Pro Ala Ser Leu Ala Val Ser Leu Gly
1               5                   10                  15
Gln Arg Ala Thr Ile Ser Tyr Arg Ala Ser Lys Ser Val Ser Thr Ser
            20                  25                  30
Gly Tyr Ser Tyr Met His Trp Asn Gln Gln Lys Pro Gly Gln Pro Pro
        35                  40                  45
Arg Leu Leu Ile Tyr Leu Val Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ile Arg
                85                  90                  95
Glu Leu Thr Arg Ser Glu Gly Gly Pro Ser Trp Lys
            100                 105
```

<210> SEQ ID NO 128
<211> LENGTH: 324
<212> TYPE: DNA
<213> ORGANISM: Artificial Sequence
<220> FEATURE:
<223> OTHER INFORMATION: Light chain variable

<400> SEQUENCE: 128

```
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaa                                            324
```

<210> SEQ ID NO 129
<211> LENGTH: 25
<212> TYPE: PRT
<213> ORGANISM: Artificial Sequence
<220> FEATURE:
<223> OTHER INFORMATION: FR1

<400> SEQUENCE: 129

```
Glu Val Gln Leu Gln Gln Ser Gly Ala Glu Leu Val Lys Pro Gly Thr
1               5                   10                  15

Ser Val Lys Leu Ser Cys Lys Ala Ser
            20                  25
```

<210> SEQ ID NO 130
<211> LENGTH: 117
<212> TYPE: PRT
<213> ORGANISM: Artificial Sequence
<220> FEATURE:
<223> OTHER INFORMATION: Heavy chain variable

<400> SEQUENCE: 130

```
Glu Val Gln Leu Gln Gln Ser Gly Ala Glu Leu Val Lys Pro Gly Thr
1               5                   10                  15

Ser Val Lys Leu Ser Cys Lys Ala Ser Gly Tyr Thr Phe Thr Ser Tyr
            20                  25                  30

Tyr Met Tyr Trp Leu Lys Gln Arg Pro Gly Gln Gly Leu Glu Trp Ile
        35                  40                  45

Gly Gly Ile Asn Pro Thr Thr Gly Gly Thr Asp Phe Asn Glu Asn Phe
    50                  55                  60

Lys Asn Lys Ala Thr Leu Thr Leu Ala Thr Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Met Gly Arg Asp Ala Met Asp Tyr Trp Gly Gln Gly Thr Ser
            100                 105                 110

Val Thr Val Ser Ser
        115
```

<210> SEQ ID NO 131
<211> LENGTH: 351
<212> TYPE: DNA
<213> ORGANISM: Artificial Sequence
<220> FEATURE:

<223> OTHER INFORMATION: Heavy chain variable

<400> SEQUENCE: 131

```
gaggttcagc tgcagcagtc tggggctgaa ctggtgaaac ctgggacttc agtgaagttg     60
tcctgcaagg cttctggcta caccttcacc agctactata tgtactggtt gaagcagagg    120
cctggacaag gccttgagtg gattgggggg attaatccta ccactggtgg tactgacttc    180
aatgagaact tcaagaacaa ggccacactg actttggcca catcctccag cacagcctac    240
atacaactca gcagcctgac atctgaggac tctgcggtct atttctgtgc aagaatggga    300
cgggatgcta tggactactg gggtcaagga acctcagtca ccgtctcctc a             351
```

<210> SEQ ID NO 132
<211> LENGTH: 10
<212> TYPE: PRT
<213> ORGANISM: Artificial Sequence
<220> FEATURE:
<223> OTHER INFORMATION: FR4

<400> SEQUENCE: 132

Trp Gly Gln Gly Thr Ser Val Thr Val Ser
1               5                   10

<210> SEQ ID NO 133
<211> LENGTH: 116
<212> TYPE: PRT
<213> ORGANISM: Artificial Sequence
<220> FEATURE:
<223> OTHER INFORMATION: Heavy chain variable

<400> SEQUENCE: 133

Glu Val Gln Leu Gln Gln Ser Gly Ser Glu Leu Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Arg Pro Gly Gln Gly Leu Glu Trp Ile
            35                  40                  45

Gly Gly Ile Asn Pro Ile Thr Gly Gly Thr Asp Phe Asn Glu Lys Phe
        50                  55                  60

Lys Asn Lys Ala Thr Leu Thr Leu Ala Thr Ser Ser Ser Thr Ala Tyr
65                  70                  75                  80

Ile His Leu Ser Ser Leu Thr Ser Glu Asp Ser Ala Val Tyr Phe Cys
                85                  90                  95

Ala Arg Met Gly Arg Asp Ala Met Asp Tyr Trp Gly Gln Gly Thr Ser
            100                 105                 110

Val Thr Val Ser
        115

<210> SEQ ID NO 134
<211> LENGTH: 348
<212> TYPE: DNA
<213> ORGANISM: Artificial Sequence
<220> FEATURE:
<223> OTHER INFORMATION: Heavy chain variable

<400> SEQUENCE: 134

```
gaggttcagc tgcagcagtc tgggtctgaa ctggtgaaac ctggggcttc agtgaagttg     60
tcctgcaagg cttctggcta catcttcacc agctactata tgtactgggt gaagcagagg    120
cctggacaag gccttgagtg gattgggggg attaatccta tcactggtgg tactgacttc    180
```

```
aatgagaagt tcaagaacaa ggccacactg actctggcca catcctccag cacagcctac    240
atacatctca gcagcctgac atctgaggac tctgcggtct atttctgtgc aagaatggga    300
cgggatgcta tggactactg gggtcaagga acctcagtca ccgtctcc                348
```

<210> SEQ ID NO 135
<211> LENGTH: 9
<212> TYPE: PRT
<213> ORGANISM: Artificial Sequence
<220> FEATURE:
<223> OTHER INFORMATION: CDRH1

<400> SEQUENCE: 135

Asp Tyr Ser Ile Thr Ser Asp Tyr Ala
1               5

<210> SEQ ID NO 136
<211> LENGTH: 7
<212> TYPE: PRT
<213> ORGANISM: Artificial Sequence
<220> FEATURE:
<223> OTHER INFORMATION: CDRH2

<400> SEQUENCE: 136

Ile Leu Tyr Ser Gly Ser Thr
1               5

<210> SEQ ID NO 137
<211> LENGTH: 8
<212> TYPE: PRT
<213> ORGANISM: Artificial Sequence
<220> FEATURE:
<223> OTHER INFORMATION: CDRH3

<400> SEQUENCE: 137

Ala Ser Leu Gly Arg Gly Gly Ser
1               5

<210> SEQ ID NO 138
<211> LENGTH: 26
<212> TYPE: PRT
<213> ORGANISM: Artificial Sequence
<220> FEATURE:
<223> OTHER INFORMATION: FR1

<400> SEQUENCE: 138

Leu Glu Val Lys Leu Glu Gln Ser Gly Pro Gly Leu Val Lys Pro Ser
1               5                   10                  15
Gln Ser Leu Ser Leu Thr Cys Thr Val Thr
            20                  25

<210> SEQ ID NO 139
<211> LENGTH: 17
<212> TYPE: PRT
<213> ORGANISM: Artificial Sequence
<220> FEATURE:
<223> OTHER INFORMATION: FR2

<400> SEQUENCE: 139

Trp Asn Trp Ile Arg Gln Phe Pro Gly Asn Lys Leu Glu Trp Met Gly
1               5                   10                  15
Tyr

<210> SEQ ID NO 140
<211> LENGTH: 38

<212> TYPE: PRT
<213> ORGANISM: Artificial Sequence
<220> FEATURE:
<223> OTHER INFORMATION: FR3

<400> SEQUENCE: 140

Thr Tyr Asn Pro Ser Leu Lys Ser Arg Val Ser Ile Thr Arg Asp Thr
1               5                   10                  15

Ser Lys Asn Gln Phe Phe Leu His Leu Asp Ser Val Thr Thr Glu Asp
            20                  25                  30

Ala Ala Thr Tyr Tyr Cys
        35

<210> SEQ ID NO 141
<211> LENGTH: 11
<212> TYPE: PRT
<213> ORGANISM: Artificial Sequence
<220> FEATURE:
<223> OTHER INFORMATION: FR4

<400> SEQUENCE: 141

Trp Gly Gln Gly Thr Thr Leu Ala Val Ser Ser
1               5                   10

<210> SEQ ID NO 142
<211> LENGTH: 116
<212> TYPE: PRT
<213> ORGANISM: Artificial Sequence
<220> FEATURE:
<223> OTHER INFORMATION: Heavy chain variable

<400> SEQUENCE: 142

Leu Glu Val Lys Leu Glu Gln Ser Gly Pro Gly Leu Val Lys Pro Ser
1               5                   10                  15

Gln Ser Leu Ser Leu Thr Cys Thr Val Thr Asp Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Leu Tyr Ser Gly Ser Thr Thr Tyr Asn Pro Ser
    50                  55                  60

Leu Lys Ser Arg Val Ser Ile Thr Arg Asp Thr Ser Lys Asn Gln Phe
65                  70                  75                  80

Phe Leu His Leu Asp Ser Val Thr Thr Glu Asp Ala Ala Thr Tyr Tyr
                85                  90                  95

Cys Ala Ser Leu Gly Arg Gly Gly Ser Trp Gly Gln Gly Thr Thr Leu
            100                 105                 110

Ala Val Ser Ser
        115

<210> SEQ ID NO 143
<211> LENGTH: 348
<212> TYPE: DNA
<213> ORGANISM: Artificial Sequence
<220> FEATURE:
<223> OTHER INFORMATION: Heavy chain variable

<400> SEQUENCE: 143
cttgaggtta agctggagca gtcaggacct ggcctggtga aaccttctca gtctctgtcc      60
ctcacctgca ctgtcactga ctactcaatc accagtgatt atgcctggaa ctggatccgg     120
caatttccag gaaacaaact ggagtggatg ggttacatac tctacagtgg ttccactacg     180

```
tacaatccgt ctctcaaaag tcgagtctct atcactcgag acacatccaa gaaccagttc    240
ttcctgcact ggattctgt gactactgag gacgctgcca catattactg tgcaagcctc     300
gggcgtgggg ggtcctgggg ccagggcacc actctcgcag tctcctca                 348
```

```
<210> SEQ ID NO 144
<211> LENGTH: 11
<212> TYPE: PRT
<213> ORGANISM: Artificial Sequence
<220> FEATURE:
<223> OTHER INFORMATION: CDRL1

<400> SEQUENCE: 144

Gln Ser Ile Val His Ser Asn Gly Asn Thr Tyr
1               5                   10

<210> SEQ ID NO 145
<211> LENGTH: 9
<212> TYPE: PRT
<213> ORGANISM: Artificial Sequence
<220> FEATURE:
<223> OTHER INFORMATION: CDRL3

<400> SEQUENCE: 145

Phe Gln Gly Ser His Ala Pro Trp Thr
1               5

<210> SEQ ID NO 146
<211> LENGTH: 26
<212> TYPE: PRT
<213> ORGANISM: Artificial Sequence
<220> FEATURE:
<223> OTHER INFORMATION: FR1

<400> SEQUENCE: 146

Asp Ile Leu Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 147
<211> LENGTH: 17
<212> TYPE: PRT
<213> ORGANISM: Artificial Sequence
<220> FEATURE:
<223> OTHER INFORMATION: FR2

<400> SEQUENCE: 147

Leu Glu Trp Tyr Leu Gln Lys Pro Gly Gln Ser Pro Lys Leu Leu Ile
1               5                   10                  15

Tyr

<210> SEQ ID NO 148
<211> LENGTH: 36
<212> TYPE: PRT
<213> ORGANISM: Artificial Sequence
<220> FEATURE:
<223> OTHER INFORMATION: FR3

<400> SEQUENCE: 148

Asn Arg Phe Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30
```

```
Ile Tyr Tyr Cys
        35

<210> SEQ ID NO 149
<211> LENGTH: 10
<212> TYPE: PRT
<213> ORGANISM: Artificial Sequence
<220> FEATURE:
<223> OTHER INFORMATION: FR4

<400> SEQUENCE: 149

Phe Gly Gly Gly Thr Lys Leu Glu Ile Arg
1               5                   10

<210> SEQ ID NO 150
<211> LENGTH: 112
<212> TYPE: PRT
<213> ORGANISM: Artificial Sequence
<220> FEATURE:
<223> OTHER INFORMATION: Light chain variable

<400> SEQUENCE: 150

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Ala Pro Trp Thr Phe Gly Gly Gly Thr Lys Leu Glu Ile Arg
            100                 105                 110
```